United States Patent
Subramanian et al.

(10) Patent No.: US 10,570,129 B2
(45) Date of Patent: Feb. 25, 2020

(54) CARBOLINE ANTIPARASITICS

(71) Applicant: Zoetis Services LLC, Parsippany, NJ (US)

(72) Inventors: Govindan Subramanian, Belle Mead, NJ (US); Michael P. Curtis, Portage, MI (US); Jinxia (Nancy) Deng, Portage, MI (US); Richard Andrew Ewin, Kalamazoo, MI (US); Christopher Scott Knauer, Kalamazoo, MI (US); Graham M. Kyne, Portage, MI (US); Tomasz Respondek, Kalamazoo, MI (US); Susan Mary Kult Sheehan, Galesburg, MI (US); John Adam Wendt, Mattawan, MI (US)

(73) Assignee: Zoetis Services LLC, Parsippany, NJ (US)

( * ) Notice: Subject to any disclaimer, the term of this patent is extended or adjusted under 35 U.S.C. 154(b) by 294 days.

(21) Appl. No.: 15/735,686

(22) PCT Filed: Jun. 10, 2016

(86) PCT No.: PCT/US2016/036793
§ 371 (c)(1),
(2) Date: Dec. 12, 2017

(87) PCT Pub. No.: WO2016/209635
PCT Pub. Date: Dec. 29, 2016

(65) Prior Publication Data
US 2020/0031822 A1   Jan. 30, 2020

Related U.S. Application Data

(60) Provisional application No. 62/183,516, filed on Jun. 23, 2015.

(51) Int. Cl.
*C07D 471/04* (2006.01)
*A61K 31/437* (2006.01)
*A01N 47/38* (2006.01)

(52) U.S. Cl.
CPC .......... *C07D 471/04* (2013.01); *A01N 47/38* (2013.01)

(58) Field of Classification Search
CPC .......................... C07D 471/04; A61K 31/437
USPC ............................................ 546/87; 514/292
See application file for complete search history.

(56) References Cited

U.S. PATENT DOCUMENTS 5,530,008 A   6/1996  Azcona et al.

FOREIGN PATENT DOCUMENTS

| EP | 2184064 A2 | 5/2010 |
|---|---|---|
| WO | 02088123 A1 | 7/2002 |
| WO | 03014118 A1 | 2/2003 |
| WO | 2005058897 A1 | 6/2005 |
| WO | 2005061500 A1 | 7/2005 |
| WO | 2011038163 A1 | 3/2011 |
| WO | 2013017678 A1 | 2/2013 |

*Primary Examiner* — Charanjit Aulakh
(74) *Attorney, Agent, or Firm* — Paul M. Misiak

(57) ABSTRACT

The present invention provides Formula (1) compounds that are gamma-carbolines, Formula (1) wherein R1a, R1b, R1c, R1d, R2, R3, and "-" are as defined herein; veterinary acceptable salts thereof, and stereoisomers thereof, which act as parasiticides, in particular, endoparasiticides.

20 Claims, No Drawings

CARBOLINE ANTIPARASITICS

CROSS-REFERENCE TO RELATED APPLICATIONS

This application is the National Stage of International Application No. PCT/US2016/036793, filed Jun. 10, 2016, which application claims the benefit of U.S. Provisional Application No. 62/183,516, filed Jun. 23, 2015.

FIELD OF THE INVENTION

This invention relates to carboline derivatives having parasiticidal activity. The compounds of interest are gamma-carboline derivatives. The invention also relates to processes of making said gamma-carboline derivatives, compositions and methods of use thereof.

BACKGROUND

There is a continuing need to provide new agents for the control of parasitic infestations that present a threat to human and animal health. In particular, new agents are needed to manage endoparasitic infestations in animals due to the increasing prevalence of parasites, and in particular nematodes, that are resistant to many of the agents currently approved for this indication. The compounds currently available for endoparasitic treatment of animals do not always demonstrate good activity, good speed of action, or a long duration of action, and many are no longer efficacious as a result of genetic resistance. The gamma-carbolines of the instant invention have been shown to impart antiparasitic activity, particularly endoparasitic activity.

Beta-carboline derivatives have been described in publications WO2002/088123 and WO2011/038163. These β-derivatives reportedly modulate aminergic G protein-coupled receptors, 5-HT$_6$ receptors, and cGMP-specific PDE receptors for the treatment of cognitive disorders, cardiovascular disorders, erectile dysfunction, and other neurotransmitter mediated disorders, not parasiticidal activity. Publication WO2003/014118 generically describes hexahydro- and tetrahydro-1H-pyrido[4,3-b]indoles as 5-HT ligands capable of treating diseases modulated by 5-HT$_6$, for example, conditions which originate in the central nervous system (pain, dementia, neurodegenerative disorders, hypertension, sleeping, and others). However, this application publication does not describe or exemplify any piperidine substituted derivatives or amide substitutions (urea) of the indole moiety which were shown to impart nematocidal activity to the compounds of the instant invention. Other antiparasitic indoles have been described in application publication WO2005/061500, WO2005/058897, and WO2013/017678, however, these are all spiroindoline derivatives. The prior art citations do not exemplify the gamma-carboline derivatives of the instant invention, or processes of manufacturing the same, nor does the prior art indicate that such compounds would be useful against a spectrum of parasitic species, particularly endoparasites.

Despite the availability of effective, broad spectrum antiparasitic agents, there remains a need for a safer, convenient, efficacious, and environmentally friendly product(s) that will overcome the ever-present threat of resistance development.

The present invention overcomes one or more of the various disadvantages of, or improves upon, the properties of existing compounds. In particular the present invention develops new gamma-carboline derivatives that demonstrate such antiparasitic properties.

SUMMARY

The present invention provides Formula (1) compounds that are gamma-carbolines, veterinary acceptable salts thereof, and stereoisomers thereof, which act as parasiticides, in particular, endoparasiticides; therefore the Formula (1) compounds can be used to control and prevent endoparasitic infections in animals. The invention also contemplates the control and prevention of mosquito and sand fly born diseases, for example, heartworm infection and leishmaniasis, respectively.

Thus, according to the invention, there is provided a Formula (1) compound

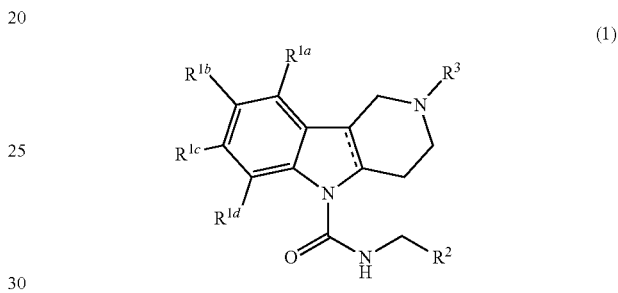

wherein $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NR$^a$R$^b$, cyano, —S(O)$_p$R, phenyl, pyridinyl, saturated or partially saturated 5- or 6-membered heterocyclic ring containing at least one heteroatom selected from the group consisting of N, S, and O, and wherein said heterocyclic ring, phenyl, or pyridinyl moiety are each optionally and independently substituted with at least one substituent selected from the group consisting of oxo, cyano, halo, and $C_1$-$C_6$alkyl; or $R^{1a}$ and $R^{1b}$ or $R^{1b}$ and $R^{1c}$ or $R^{1c}$ and $R^{1d}$ together form a tetrahydrofuran ring or phenyl ring;

$R^2$ is phenyl or a 5- or 6-membered heteroaryl ring containing at least one heteroatom selected from the group consisting of N, S, or O, and wherein said phenyl or heteroaryl ring is optionally and independently substituted with at least one $R^5$ substituent selected from the group consisting of halo, $C_1$-$C_6$alkyl, $C_1$-$C_6$haloalkyl, hydroxyl, $C_1$-$C_6$alkoxy, and $C_3$-$C_6$cycloalkyl;

$R^3$ is $C_1$-$C_4$alkylaryl, $C_1$-$C_4$alkylheteroaryl, $C_2$-$C_6$alkenylaryl, or $C_2$-$C_6$alkenylheteroaryl; and wherein each aryl and heteroaryl moiety is optionally and independently substituted with at least one $R^4$ substituent selected from the group consisting of halo, cyano, $C_1$-$C_6$alkoxy, $C_1$-$C_6$haloalkyl, $C_1$-$C_6$alkyl, $C_1$-$C_6$haloalkoxy, and —S(O)$_p$R; and wherein the alkenyl moiety is optionally substituted with halo;

$R^a$ and $R^b$ are each independently selected from the group consisting of H and $C_1$-$C_6$alkyl;

R is H or $C_1$-$C_6$alkyl;

p is the integer 0, 1, or 2; and wherein the solid line accompanied by the dotted line "- - - -" represents a single or double bond, and veterinary acceptable salts thereof, and stereoisomers thereof.

In yet another aspect, compounds of the present invention include a Formula (1.1) or Formula (1.2) compound of Formula (1)

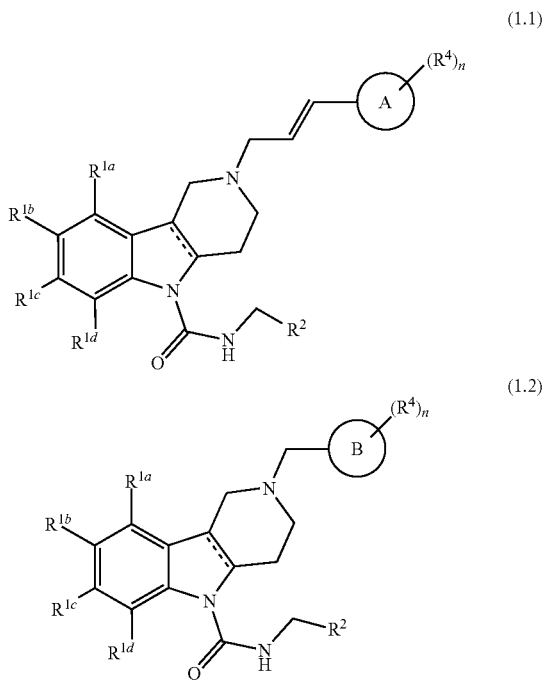

wherein $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NR$^a$R$^b$, cyano, —S(O)$_p$R, phenyl, pyridinyl, saturated or partially saturated 5- or 6-membered heterocyclic ring containing at least one heteroatom selected from the group consisting of N, S, and O, and wherein said heterocyclic ring, phenyl, or pyridinyl moiety are each optionally and independently substituted with at least one substituent selected from the group consisting of oxo, cyano, halo, and $C_1$-$C_6$alkyl; or $R^{1a}$ and $R^{1b}$ or $R^{1b}$ and $R^{1c}$ or $R^{1c}$ and $R^{1d}$ together form a tetrahydrofuran ring or phenyl ring; Ring A is phenyl or a 5- or 6-membered heteroaryl ring containing at least one heteroatom selected from the group consisting of N, S, or O; and wherein the alkenyl moiety is optionally substituted with halo; Ring B is naphthyl, quinolinyl, or isoquinolinyl; and wherein each of Ring A and Ring B moieties are each optionally and independently substituted with at least one $R^4$ substituent selected from the group consisting of halo, cyano, $C_1$-$C_6$alkoxy, $C_1$-$C_6$haloalkyl, $C_1$-$C_6$alkyl, $C_1$-$C_6$haloalkoxy, and —S(O)$_p$R; and $R^2$ is phenyl, pyridinyl, thiazolyl, pyridazinyl, or pyrrolyl, each optionally and independently substituted with at least one $R^5$ substituent selected from the group consisting of halo, $C_1$-$C_6$alkyl, $C_1$-$C_6$haloalkyl, $C_1$-$C_6$alkoxy, hydroxyl, and cyclopropyl. The variable n is an integer that is 0, 1, 2, 3, 4, or 5; and when n is 2 or more, then each $R^4$ can be the same or different from each other. A preferred n is the integer 1, 2, 3, or 4. Even more preferred, n is the integer 1, 2, or 3. The variable p is an integer that is 0, 1, or 2. A preferred p is the integer 0 or 2. The preferred $R^a$ and $R^b$ are each independently hydrogen and methyl. The more preferred $R^a$ and $R^b$ are each hydrogen. The preferred R is methyl.

In yet another aspect, compounds of the present invention include a Formula (1.1) or Formula (1.2) compound of Formula (1); $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NR$^a$R$^b$, cyano, and —S(O)$_p$R; Ring A is phenyl, pyridinyl, or thiophene; Ring B is naphthyl, quinolinyl, or isoquinolinyl; and wherein each of Ring A and Ring B is optionally and independently substituted with at least one $R^4$ substituent selected from halo, cyano, $C_1$-$C_6$haloalkyl, $C_1$-$C_6$alkyl, $C_1$-$C_6$alkoxy, $C_1$-$C_6$haloalkoxy, and —S(O)$_2$CH$_3$; and $R^2$ is phenyl, pyridinyl, thiazolyl, pyridazinyl, or pyrrolyl, each optionally and independently substituted with at least one $R^5$ substituent selected from the group consisting of halo, $C_1$-$C_6$alkyl, $C_1$-$C_6$haloalkyl, $C_1$-$C_6$alkoxy, hydroxyl, and cyclopropyl; and n is the integer 0, 1, 2, 3, 4, or 5; and when n is 2 or more, then each $R^4$ can be the same or different from each other; and veterinary acceptable salts thereof, and stereoisomers thereof. A preferred n is the integer 1, 2, 3, or 4. Even more preferred, n is the integer 1, 2, or 3. The variable p is an integer that is 0, 1, or 2. A preferred p is the integer 0 or 2. The preferred $R^a$ and $R^b$ are each independently hydrogen and methyl. The more preferred $R^a$ and $R^b$ are each hydrogen. The preferred R is methyl.

In yet another aspect, compounds of the present invention include a Formula (1.1) compound of Formula (1); $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NH$_2$, cyano, —S(O)$_2$CH$_3$; Ring A is phenyl, pyridinyl, or thiophene; each of which is optionally and independently substituted with at least one $R^4$ substituent selected from halo, cyano, $C_1$-$C_6$haloalkyl, $C_1$-$C_6$alkyl, $C_1$-$C_6$alkoxy, $C_1$-$C_6$haloalkoxy, and —S(O)$_2$CH$_3$; and $R^2$ is pyridinyl, thiazolyl, pyridazinyl, or pyrrolyl, each optionally and independently substituted with at least one $R^5$ substituent selected from the group consisting of halo, $C_1$-$C_6$alkyl, $C_1$-$C_6$haloalkyl, $C_1$-$C_6$alkoxy, hydroxyl, and cyclopropyl; and veterinary acceptable salts thereof, and stereoisomers thereof.

In yet another aspect, compounds of the present invention include a Formula (1.1) compound wherein $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NH$_2$, cyano, —S(O)$_2$CH$_3$; Ring A is phenyl optionally substituted with at least one $R^4$ substituent selected from the group consisting of halo, cyano, $C_1$-$C_6$alkoxy, $C_1$-$C_6$haloalkyl, $C_1$-$C_6$alkyl, $C_1$-$C_6$haloalkoxy, and —S(O)$_p$R; and wherein the alkenyl moiety is optionally substituted with halo; and $R^2$ is pyridinyl or thiazolyl, each optionally and independently substituted with at least one $R^5$ substituent selected from the group consisting of halo, methyl, —CF$_3$, —OCH$_3$, —OCH$_2$CH$_3$, hydroxyl, and cyclopropyl, and veterinary acceptable salts thereof, and stereoisomers thereof.

In yet another aspect, compounds of the present invention include a Formula (1.1) compound wherein $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NH$_2$, cyano, —S(O)$_2$CH$_3$; Ring A is phenyl substituted with at least one $R^4$ substituent selected from the group consisting of halo, cyano, $C_1$-$C_6$alkoxy, $C_1$-$C_6$haloalkyl, $C_1$-$C_6$alkyl, $C_1$-$C_6$haloalkoxy, and —S(O)$_2$CH$_3$; and wherein the alkenyl moiety is optionally substituted with fluoro; and $R^2$ is pyridinyl substituted with at least one $R^5$ substituent selected from the group consisting of halo, methyl, —$CF_3$, —$OCH_3$, hydroxyl, —$OCH_2CH_3$, and cyclopropyl, and veterinary acceptable salts thereof, and stereoisomers thereof.

In yet another aspect, compounds of the present invention include a Formula (1.1a) compound of Formula (1.1)

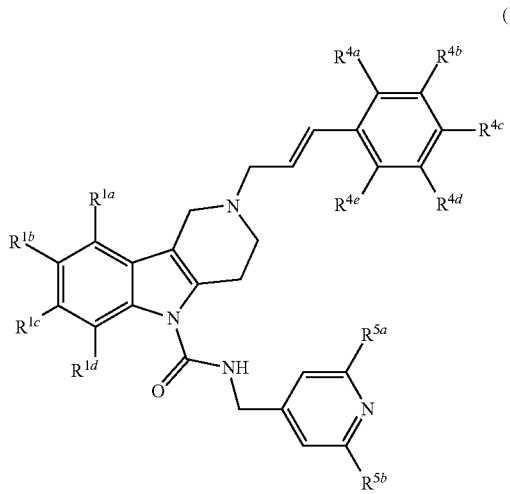

(1.1a)

$R^{1a}$, $R^{1b}$, $R^{1c}$, and $R^{1d}$ are each independently selected from the group consisting of H, chloro, fluoro, bromo, cyano, methyl, —$OCH_3$, —$OCH_2CH_3$, —$OCF_3$, —$CF_3$, —$SCH_3$, —$S(O)_2CH_3$, —$C(O)NH_2$, phenyl, pyridinyl, morpholinyl, azathienyl, and pyrrolidinyl; and wherein the phenyl and pyridinyl is optionally substituted with at least one substituent selected from halo, cyano, or oxo; $R^{4a}$, $R^{4b}$, $R^{4c}$, $R^{4d}$ and $R^{4e}$ are each independently selected from the group consisting of H, methyl, fluoro, chloro, bromo, —$CF_3$, cyano, —$OCF_3$, —$OCH_3$, and —$S(O)_2CH_3$; and $R^{5a}$ and $R^{5b}$ are each independently selected from the group consisting of H, chloro, fluoro, bromo, —$CF_3$, methyl, hydroxyl, cyclopropyl, —$OCH_3$, and —$OCH_2CH_3$; and veterinary acceptable salts thereof, and stereoisomers thereof.

In yet another aspect, compounds of the present invention include a Formula (1.1a) compound wherein $R^{1a}$, $R^{1b}$, $R^{1c}$, and $R^{1d}$ are each independently selected from the group consisting of H, chloro, fluoro, bromo, cyano, methyl, —$OCH_3$, —$OCH_2CH_3$, —$OCF_3$, —$CF_3$, —$SCH_3$, —$S(O)_2CH_3$, and —$C(O)NH_2$; each of $R^{4a}$, $R^{4b}$, $R^{4c}$, $R^{4d}$ and $R^{4e}$ are independently selected from the group consisting of H, fluoro, chloro, bromo, —$CF_3$, cyano, —$OCF_3$, —$OCH_3$, methyl, and —$S(O)_2CH_3$; and $R^{5a}$ and $R^{5b}$ are each independently selected from the group consisting of H, chloro, fluoro, bromo, —$CF_3$, methyl, hydroxyl, cyclopropyl, —$OCH_3$, and —$OCH_2CH_3$; and veterinary acceptable salts thereof, and stereoisomers thereof.

In yet another aspect, compounds of the present invention include a Formula (1.1a) compound wherein $R^{1a}$, $R^{1b}$, $R^{1c}$, and $R^{1d}$ are each independently selected from the group consisting of H, chloro, fluoro, bromo, cyano, methyl, —$OCH_3$, —$OCH_2CH_3$, —$OCF_3$, —$CF_3$, —$SCH_3$, —$S(O)_2CH_3$, and —$C(O)NH_2$; each of $R^{4a}$, $R^{4b}$, $R^{4c}$, $R^{4d}$ and $R^{4e}$ are independently selected from the group consisting of H, fluoro, chloro, bromo, —$CF_3$, methyl, cyano, —$CF_3$, —$OCH_3$, and —$S(O)_2CH_3$; and one of $R^{5a}$ or $R^{5b}$ is H and the other is fluoro, chloro, bromo, methyl, —$CF_3$, —$OCH_3$, —$OCH_2CH_3$, hydroxyl, or cyclopropyl, and veterinary acceptable salts thereof, and stereoisomers thereof.

In yet another aspect, compounds of the present invention include a Formula (1.1a) compound wherein at least one of $R^{1a}$, $R^{1b}$, $R^{1c}$, and $R^{1d}$ is H and the others are each independently selected from the group consisting of chloro, fluoro, bromo, cyano, methyl, —$OCH_3$, —$OCH_2CH_3$, —$OCF_3$, —$CF_3$, —$SCH_3$, —$S(O)_2CH_3$, and —$C(O)NH_2$; each of $R^{4a}$, $R^{4b}$, $R^{4c}$, $R^{4d}$ and $R^{4e}$ are independently selected from the group consisting of H, fluoro, chloro, bromo, —$CF_3$, methyl, cyano, —$OCF_3$, —$OCH_3$, and —$S(O)_2CH_3$; and one of $R^{5a}$ or $R^{5b}$ is H and the other is fluoro, chloro, bromo, methyl, —$CF_3$, —$OCH_3$, —$OCH_2CH_3$, hydroxyl, or cyclopropyl, and veterinary acceptable salts thereof, and stereoisomers thereof.

In yet another aspect, compounds of the present invention include a Formula (1.1a) compound wherein at least two of $R^{1a}$, $R^{1b}$, $R^{1c}$, and $R^{1d}$ is H and the others are each independently selected from the group consisting of chloro, fluoro, bromo, cyano, methyl, —$OCH_3$, —$OCH_2CH_3$, —$OCF_3$, —$CF_3$, —$SCH_3$, —$S(O)_2CH_3$, and —$C(O)NH_2$; each of $R^{4a}$, $R^{4b}$, $R^{4c}$, $R^{4d}$ and $R^{4e}$ are independently selected from the group consisting of H, fluoro, chloro, bromo, —$CF_3$, methyl, cyano, —$OCF_3$, —$OCH_3$, and —$S(O)_2CH_3$; and one of $R^{5a}$ or $R^{5b}$ is H and the other is fluoro, chloro, bromo, methyl, —$CF_3$, —$OCH_3$, —$OCH_2CH_3$, hydroxyl, or cyclopropyl, and veterinary acceptable salts thereof, and stereoisomers thereof.

In yet another aspect, compounds of the present invention include a Formula (1.1a) compound wherein at least two of $R^{1a}$, $R^{1b}$, $R^{1c}$, and $R^{1d}$ is H and the others are each independently selected from the group consisting of chloro, fluoro, cyano, and —$CF_3$; each of $R^{4a}$, $R^{4b}$, $R^{4c}$, $R^{4d}$ and $R^{4e}$ are independently selected from the group consisting of H, fluoro, chloro, bromo, —$CF_3$, and cyano; and one of $R^{5a}$ or $R^{5b}$ is H and the other is fluoro, chloro, bromo, methyl, —$CF_3$, —$OCH_3$, —$OCH_2CH_3$, hydroxyl, or cyclopropyl, and veterinary acceptable salts thereof, and stereoisomers thereof.

In yet another aspect, compounds of the present invention include a Formula (1.1a) compound selected from the group consisting of:
((E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide;
(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide;
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide; and
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, and veterinary acceptable salts thereof, and stereoisomers thereof.

In yet another aspect, compounds of the present invention include a Formula (1.1) compound wherein Ring A is pyridinyl optionally substituted with at least one R⁴ substituent independently selected from the group consisting of fluoro, chloro, bromo, —CF₃, cyano, —OCF₃, —OCH₃, methyl, and —S(O)₂CH₃; R² is pyridinyl optionally substituted with one or two R⁵ substituents each independently selected from the group consisting of chloro, fluoro, bromo, —CF₃, methyl, hydroxyl, cyclopropyl, —OCH₃, —OCH₂CH₃, and wherein $R^{1a}$, $R^{1b}$, $R^{1c}$, and $R^{1d}$ are each independently selected from the group consisting of H, chloro, fluoro, bromo, cyano, methyl, —OCH₃, —OCH₂CH₃, —OCF₃, —CF₃, —SCH₃, —S(O)₂CH₃, and —C(O)NH₂; and veterinary acceptable salts thereof, and stereoisomers thereof.

In yet another aspect, compounds of the present invention include a Formula (1.1) compound wherein Ring A is thiophene optionally substituted with one or two R⁴ substituents independently selected from the group consisting of fluoro, chloro, bromo, —CF₃, cyano, —OCF₃, —OCH₃, methyl, and —S(O)₂CH₃; R² is pyridinyl optionally substituted with one or two R⁵ substituents each independently selected from the group consisting of chloro, fluoro, bromo, —CF₃, methyl, hydroxyl, cyclopropyl, —OCH₃, —OCH₂CH₃, and wherein $R^{1a}$, $R^{1b}$, $R^{1c}$, and $R^{1d}$ are each independently selected from the group consisting of H, chloro, fluoro, bromo, cyano, methyl, —OCH₃, —OCH₂CH₃, —OCF₃, —CF₃, —SCH₃, —S(O)₂CH₃, and —C(O)NH₂; and veterinary acceptable salts thereof, and stereoisomers thereof.

In yet another aspect, compounds of the present invention include a compound of Formula (1.2a) of Formula (1.2)

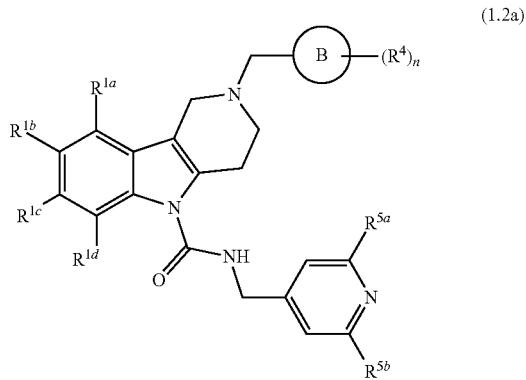

(1.2a)

wherein Ring B is naphthyl, quinolinyl, or isoquinolinyl, each optionally and independently substituted with at least one R⁴ substituent selected from the group consisting of H, fluoro, chloro, bromo, —CF₃, cyano, —OCF₃, —OCH₃, methyl, and —S(O)₂CH₃; $R^{1a}$, $R^{1b}$, $R^{1c}$, and $R^{1d}$ are each independently selected from the group consisting of H, chloro, fluoro, bromo, cyano, methyl, —OCH₃, —OCH₂CH₃, —OCF₃, —CF₃, —SCH₃, —S(O)₂CH₃, and —C(O)NH₂; and wherein $R^{5a}$ and $R^{5b}$ are each independently selected from the group consisting of H, chloro, fluoro, bromo, —CF₃, methyl, hydroxyl, cyclopropyl, —OCH₃, and —OCH₂CH₃; and n is the integer 0, 1, 2, 3, 4, or 5; and when n is 2 or more, then each R⁴ can be the same or different from each other; and veterinary acceptable salts thereof. In yet another aspect of the invention, Ring B is naphthyl and n is the integer 0 or 1. In yet another aspect of the invention, Ring B is quinolinyl and n is the integer 0 or 1. In yet another aspect of the invention, Ring B is isoquinolinyl and n is the integer 0 or 1.

In yet another aspect, compounds of the present invention include a Formula (1) compound that is selected from any one of Examples 1-517, veterinary acceptable salts thereof, and stereoisomers thereof.

In yet another aspect, the invention is a veterinary composition comprising a Formula (1) compound, veterinary acceptable salts thereof, and stereoisomers thereof. In yet another aspect of the invention is a veterinary composition comprising a Formula (1) compound and further comprising a veterinary acceptable carrier. In yet another aspect of the invention is a veterinary composition comprising a Formula (1) compound and further comprising a veterinary acceptable carrier, and optionally, at least one additional antiparasitic agent. In yet another aspect of the invention is a veterinary composition comprising a Formula (1) compound and further comprising a veterinary acceptable carrier, and at least one additional antiparasitic agent.

In yet another aspect, the invention is a veterinary composition comprising a Formula (1.1) compound, veterinary acceptable salts thereof, and stereoisomers thereof, or a Formula (1.2) compound, and veterinary acceptable salts thereof. In yet another aspect of the invention is a veterinary composition comprising a Formula (1.1) compound or Formula (1.2) compound, and further comprising a veterinary acceptable carrier. In yet another aspect of the invention is a veterinary composition comprising a Formula (1.1) or a Formula (1.2) compound, and further comprising a veterinary acceptable carrier, and optionally, at least one additional antiparasitic agent. In yet another aspect of the invention is a veterinary composition comprising a Formula (1.1) or a Formula (1.2) compound and further comprising a veterinary acceptable carrier, and at least one additional antiparasitic agent.

In yet another aspect, the invention is a veterinary composition comprising a Formula (1.1a) compound, veterinary acceptable salts thereof, and stereoisomers thereof. In yet another aspect of the invention is a veterinary composition comprising a Formula (1.1a) compound and further comprising a veterinary acceptable carrier. In yet another aspect of the invention is a veterinary composition comprising a Formula (1.1a) compound and further comprising a veterinary acceptable carrier, and optionally, at least one additional antiparasitic agent. In yet another aspect of the invention is a veterinary composition comprising a Formula (1.1a) compound and further comprising a veterinary acceptable carrier, and at least one additional antiparasitic agent.

In yet another aspect, the invention is a veterinary composition comprising a Formula (1.1a) compound selected from the group consisting of (E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide;

(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide;
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide; and
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, and veterinary acceptable salts thereof, and stereoisomers thereof, and further comprising a veterinary acceptable carrier, and optionally, at least one additional antiparsitic agent. In yet another aspect of the invention is a veterinary composition comprising one of these Formula (1.1a) compounds and further comprising a veterinary acceptable carrier, and at least one additional antiparsitic agent.

In yet another aspect, the invention is a veterinary composition comprising a Formula (1) compound selected from any one of Examples 1-517, veterinary acceptable salts thereof, and stereoisomers thereof. In yet another aspect of the invention is a veterinary composition comprising a Formula (1) compound selected from any one of Examples 1-517 and further comprising a veterinary acceptable carrier, and optionally, at least one additional antiparasitic agent. In yet another aspect of the invention is a veterinary composition comprising a Formula (1) compound selected from any one of Examples 1-517 and further comprising a veterinary acceptable carrier, and at least one additional antiparasitic agent.

In yet another aspect, the invention is a method for treating an animal with a parasitic infection comprising administering a therapeutically effective amount of a Formula (1) compound, veterinary acceptable salts thereof, and stereoisomers thereof, to an animal in need thereof. In yet another aspect of the invention is a method for treating an animal with a parasitic infection comprising administering a therapeutically effective amount of a Formula (1.1) or Formula (1.2) compound to an animal in need thereof. In yet another aspect of the invention is a method for treating an animal with a parasitic infection comprising administering a therapeutically effective amount of a Formula (1.1a) compound to an animal in need thereof, and optionally combining a Formula (1.1a) compound with at least one additional antiparasitic agent.

In yet another aspect of the invention is a method for treating an animal with a parasitic infection comprising administering a therapeutically effective amount of a Formula (1.1a) compound selected from the group consisting of
(E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide;
(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide;
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide; and
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, veterinary acceptable salts thereof, and stereoisomers thereof, to an animal in need thereof, and optionally, combining one of these Formula (1.1a) compounds with at least one additional antiparasitic agent. In yet another aspect of the invention is a method of treating an animal in need thereof with one of these Formula (1.1a) compounds and veterinary acceptable salts thereof, and stereoisomers thereof, combined with at least one additional antiparsitic agent.

In yet another aspect, the invention is a method for treating an animal for a parasitic infection comprising administering a Formula (1) compound selected from any one of Examples 1-517, veterinary acceptable salts thereof, and stereoisomers thereof. In yet another aspect of the invention is a method for treating an animal for a parasitic infection comprising administering a Formula (1) compound selected from any one of Examples 1-517 combined with at least one additional antiparasitic agent.

In yet another aspect, the invention, the animal is a companion animal or livestock and said parasitic infection is an endoparasitic infection, and wherein the Formula (1), Formula (1.1), Formula (1.2), Formula (1.1a), or Formula (1.2a) compound, veterinary acceptable salts thereof, and stereoisomers thereof, is administered orally, topically, or parenterally. A preferred companion animal is a dog and a preferred livestock animal is a cow. In one aspect of the invention, the compound is administered orally. In another aspect of the invention, the compound is administered parenterally. In yet another aspect of the invention, the compound is administered topically.

In yet another aspect, the invention is the use of a Formula (1), Formula (1.1), Formula (1.2), Formula (1.1a), or Formula (1.2a) compound, veterinary acceptable salts thereof, and stereoisomers thereof, for the manufacture of a medicament for the treatment of a parasitic infection in an animal in need thereof. The medicament can be administered to the animal orally, topically, or parenterally.

DETAILED DESCRIPTION

Definitions

For purposes of the present invention, as described and claimed herein, the following terms and phrases are herein defined:

"Additional antiparasitic agent(s)" as used herein, unless otherwise indicated, refers to other veterinary compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting alkoxy examples include: methoxy (—OCH$_3$), ethoxy (—OCH$_2$CH$_3$), n-propoxy, iso-propoxy, n-butoxy, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "$C_1$-$C_6$alkyl" refers to a monovalent, straight or branched aliphatic group containing 1 to 6 carbon atoms. Non-exclusive examples of $C_1$-$C_6$ alkyl groups include, but are not limited to methyl, ethyl, propyl, isopropyl, sec-butyl, t-butyl, n-propyl, n-butyl, i-butyl, s-butyl, n-pentyl, 1 methylbutyl, 2-methylbutyl, 3-methylbutyl, neopentyl, 3,3-dimethylpropyl, 2 methylpentyl, hexyl, and the like. The alkyl moiety may be attached to the chemical moiety by any one of the carbon atoms of the aliphatic chain. Alkyl groups are optionally substituted as described herein. Further when used in compound words such as haloalkyl, said alkyl moiety has the same meaning as herein defined and may be attached to the chemical moiety by any one of the carbon atoms of the aliphatic chain. Non-limiting examples of the compound word, haloalkyl include: difluoromethyl, trifluoromethyl, and the like. Further when used in compound words such as alkylaryl, said alkyl and aryl moieties have the same meaning as herein defined. Non-limiting examples of the compound word, alkylaryl include: benzyl, ethylbenzyl, propylbenzene, iso-butylbenzene, sec-butylbenzene, ethylnaphthalene, propylnaphthylene, 2,2-diphenylethyl, and the like.

"Alkenyl" as used herein, unless otherwise indicated, refers to a straight or branched aliphatic unsaturated hydrocarbon chain having at least one site of olefinic unsaturation (i.e., having at least one moiety of the formula C=C) and preferably having from 2- to 6-carbon atoms. Non-exclusive examples of alkenyl include: ethenyl, 1-propenyl, 2-propenyl, isopropenyl, 1-butenyl, 2-butenyl, 3-butenyl, 2-pentenyl, 1-methyl-1-propenyl, and the like. Further when used in compound words such as alkenylaryl or alkenylheteroaryl, said alkenyl, aryl, and heteroaryl moieties have the same meaning as herein defined and may be attached to the chemical moiety by any one of the carbon atoms of the aliphatic chain. Non-limiting examples of the compound word, alkenylaryl include: propenylbenzene, ethenylbenzene, butenylbenzene, and the like. Non-limiting examples of the compound word, alkenylheteroaryl include: propenylpyridine, propenylthiazole, butenylpyridine, ethenylimidazole, ethenylpyridine, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, and horse. A preferred companion animal is a dog. Non-exclusive examples of livestock include: swine, camel, rabbits, goat, sheep, deer, elk, and cattle. Preferred livestock is cattle and swine. More preferred is cattle. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Aryl", as used herein, unless otherwise indicated, refers to an aromatic 6- to 10-membered mono- or polycyclic ring containing 6 to 10 carbon atoms, respectively. Preferred aryls include phenyl and naphthyl. The aryl group may be attached to the chemical moiety by any one of the carbon atoms within the monocyclic or fused ring. Further when used in compound words such as alkylaryl or alkenylaryl, said alkyl, alkenyl, and aryl moieties have the same meaning as herein defined and may be attached to the chemical moiety by any one of the carbon atoms of the aliphatic chain. Non-exclusive examples of alkylaryl include: —C-phenyl, —C-naphthyl, and the like. Non-exclusive examples of alkenylaryl include: —C=C-phenyl, —C—C=C-phenyl, —C—C=C—C— phenyl, and the like. Aryls are optionally substituted as described herein.

"Compounds" and "Compounds of the present invention", as used herein, unless otherwise indicated, refers to a Formula (1), Formula (1.1), Formula (1.1a), Formula (1.2), and Formula (1.2a) compound, stereoisomer thereof, and veterinary acceptable salt thereof.

"Comprise(s)", as used herein, unless otherwise indicated, refers to an inclusive meaning, i.e., that it will be taken to mean an inclusion of not only the listed components it directly references, but also other non-specified components or elements. This rationale will also be used when the term "comprised" or "comprising" is used in relation to one or more Steps in a method or process.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings ($C_3$-$C_6$cycloalkyl) including cyclopropyl, cyclobutyl, cyclopentyl, and cyclohexyl. The cycloalkyl group may be attached to the chemical moiety by any one of the carbon atoms within the ring. Cycloalkyl groups are optionally substituted with at least one substituent as defined herein. Further when used in compound words such as alkylcycloalkyl, said alkyl and cycloalkyl moiety have the same meaning as herein defined and may be attached to the chemical moiety by any one of the carbon atoms of the aliphatic chain. Examples of $C_1$-$C_6$alkyl$C_3$-$C_6$cycloalkyl include, methylcyclopropane ($C_1$alkyl$C_3$cycloalkyl or $CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or $CH_2$cyclobutane), ethylcyclobutane ($C_2$alkyl$C_4$cycloalkyl or $CH_2CH_2$cyclobutane), methylcyclohexane ($C_1$alkyl$C_6$cycloalkyl or $CH_2$cyclohexane), and the like. Cycloalkyl moieties are optionally substituted as described herein "E/Z Notation" or "E and Z geometric isomer(s)", as used herein, unless otherwise indicated, refers to the International Union of Pure and Applied Chemistry (IUPAC) preferred method of describing the stereochemistry of double bonds in organic chemistry. It is an extension of cis/trans notation that can be used to describe double bonds having three or four substituents. Following a set of defined rules (Cahn-Ingold-Prelog priority rules), each substituent on a double-bond is assigned a priority. If the two groups of higher priority are on opposite sides of the double bond, the bond is assigned the configuration E (from entgegen, the German word for "opposite"). If the two groups of higher priority are on the same side of the double bond, the bond is assigned the configuration Z (from zusammen, the German word for "together").

"Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C—$, $ClCH_2—$, $CF_3CH_2—$ and $CF_3CCl_2—$, and the like. The term "haloalkoxy" is defined analogously to the term "haloalkyl". Examples of "haloalkoxy" include $CF_3O—$, $CCl_3CH_2O—$, $HCF_2CH_2CH_2O—$, $CF_3CH_2O—$, and the like. The term "haloalkenyl is defined analogously to the term "haloalkyl" except that the aliphatic chain contains at least one carbon-carbon double bond. Examples of "haloalkenyl" include $CF_3C=C—$, $CCl_3C=C—$, $HCF_2C=C—$, $CF_3C=CC—$, and the like. The term "haloalkynyl" is defined analogously to the term "haloalkyl" except that the aliphatic chain contains at least one carbon-carbon triple bond. Examples of "haloalkynyl" include $F_3CC≡C—$, $Cl_3CC≡C—$, $HF_2CC≡C—$, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophene, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophene, indolyl, benzimidazolyl, indazolyl, benzotriazolyl, thieno[2,3-c]pyridine, thieno[3,2-b]pyridine, benzo[1,2,5]thiadiazole, quinolinyl, isoquinolinyl, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. Non-exclusive examples of alkylheteroaryl include: $C_1$-heteroaryl (e.g., —C-pyridinyl; —C-quinolinyl; —C-isoquinolinyl), ethylpyridine, ethylpyrimidine, ethylpyridazine, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, morpholine, azathiane, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_1$alkylheterocycle is C-heterocycle, $C_2$alkylheterocycle is —C—C-heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from one up to a number of chemically available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Preferred endoparasites are gastrointestinal worms and heart worm. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxy-carbonyl (Boc, BOC), methoxycarbonyl, 9-fluorenyl-methoxycarbonyl, 2,2,2-trifluoroethoxy-carbonyl, 2-trimethylsilyl-ethxoycarbonyl, vinyloxycarbonyl, allyloxycarbonyl, 1,1 dimethyl-propynyloxycarbonyl, benzyloxy-carbonyl, p-nitrobenzyloxycarbonyl, 2,4-dichlorobenzyloxycarbonyl, and the like), diphenylmethane, and benzylcarbamates.

"$R^4$ substituent", as used herein, unless otherwise indicated, refers to a substituent that is further defined as $R^{4a}$, $R^{4b}$, $R^{4c}$, $R^{4d}$, and $R^{4e}$, each of which are defined herein, particularly for Formula (1.1a) and Formula (1.2a) compounds.

"$R^5$ substituent" as used herein, unless otherwise indicated, refers to a substituent that is further defined as $R^{5a}$ and $R^{5b}$, each of which are defined herein, particularly for Formula (1.1a) and Formula (1.2a) compounds.

"Therapeutically effective amount", as used herein, unless otherwise indicated, refers to a concentration of the active agent in a composition sufficient to elicit the desired biological response to the target parasite(s) after administration of the composition to the animal, as measured by methods known in the art and/or described in the examples herein. In some instances, an "effective amount" of the active agent in the composition will provide an efficacy of at least 70% against the target parasite compared to an untreated control. In other instances, "an effective amount" of the active agent will provide an efficacy of at least 80%, or at least 85% compared to untreated controls. More typically, "an effective amount" of the active agent will provide an efficacy of at least 90%, at least 93%, at least 95% or at least 97% against the target parasite. In certain instances, including the prevention of *Dirofilaria immitis*, the term "effective amount" may provide efficacy as high as 100%. As is understood in the art, a therapeutically effective amount may be in one or more doses, i.e., a single dose or multiple doses may be required to achieve the desired treatment endpoint, for example, (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate). Methods of treatment are synonomous with the use of the compound for treatment and use to prepare a medicament for treatment.

"Veterinary acceptable" as used herein, unless otherwise indicated, indicates that the substance or composition must be compatible chemically and/or toxicologically, with the other ingredients comprising a formulation, composition, and/or the animal being treated therewith.

"Veterinary acceptable salts" as used herein, unless otherwise indicated, are those salts which retain at least some of the biological activity of the free (non-salt) compound and which can be administered as drugs or pharmaceuticals to an animal. A veterinary acceptable salt intends ionic interactions and not a covalent bond. As such, an N-oxide is not considered a salt. Non-limiting examples of salts include acid addition salts, organic acids, and organic bases. Further examples of veterinary acceptable salts include those listed in Berge et. al., Pharmaceutical Salts, J. Pharm. Sci. (1977), 66(1):1-19. Veterinary acceptable salts can be prepared in-situ in the manufacturing process, or by separately reacting a purified compound of the invention in its free acid or base form with a suitable base or acid, respectively, and isolating the salt thus formed during subsequent purification.

The present invention provides Formula (1) compounds, stereoisomers thereof, particularly geometric isomers, veterinary acceptable salts thereof, as well as veterinary compositions that are useful as antiparasitic agents for animals, in particular, compounds that act as endoparasiticides in companion animals and livestock.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction Steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

The gamma-carbolines of the present invention described herein, exist in different stereoisomeric forms. Unless specified otherwise, it is intended that all stereoisomeric forms of the compounds of the present invention as well as mixtures thereof, including diastereomeric and geometric mixtures, form part of the present invention. Therefore, all of the "E" and "Z" isomers of the compounds of Formula (1), Formula (1.1), and Formula (1.1a) are contemplated.

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-4 outline the general procedures useful for the preparation and isolation of compounds of the present invention. It is to be understood, however, that the invention, as fully described herein and as recited in the claims, is not intended to be limited by the details of the following schemes or modes of preparation. In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc or BOC), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like. Similarly, diphenylmethane and benzylcarbamates can be used as amine protecting groups. The preferred amine protecting group is 1-tert-butyloxycarbonyl. Suitable protecting groups and their respective uses are readily determined by one skilled in the art. For a general description of protecting groups and their use, see T. W. Greene, Protective Groups in Organic Synthesis, John Wiley & Sons, New York, 1991.

In the Schemes and Examples below, the following catalysts/reactants and miscellaneous abbreviations include: mobile phase (MP); room temperature (RT); equivalent (eq); minute (min); hour (h or hr); round bottom flask (RBF); saturated (sat); N,N-dimethyl formamide (DMF); acetonitrile (ACN, Acn, or MeCN); dichloromethane (DCM); methyl tert-butyl ether (MTBE); triethylamine (TEA or Et₃N); methanol (MeOH), tetrahydrofuran (THF); ethyl acetate (EtOAc); trifluoroacetic acid (TFA); 4-dimethylaminopyridine (DMAP); isopropylmagnesium chloride (iPrMgCl); t-butyloxycarbonyl (BOC, boc); palladium (Pd); isopropyl alcohol (IPA); hydrochloric acid (HCl); dichloromethane (CH₂Cl₂); diethyl ether (Et₂O); dimethylsulfoxide (DMSO); 1,1'-Bis(diphenylphosphino)ferrocene (Pd (DPPF₂)Cl₂); zinc cyanide (Zn(CN₂)); zinc acetate (Zn (OAc)₂); dichloroethane (DCE); dimethyl acetamide (DMA); thin-layer chromatography (TLC); sodium triacetoxyborohydride (STAB); lithium diisopropylamide (LDA); n-butyllithium (n-BULi); di-tert-butyl pyrocarbonate (Boc₂O); and 2-dicyclohexylphosphino-2',4',6'-triisopropylbiphenyl (XPhos).

Scheme 1 - Fischer Indole Carboline Formation

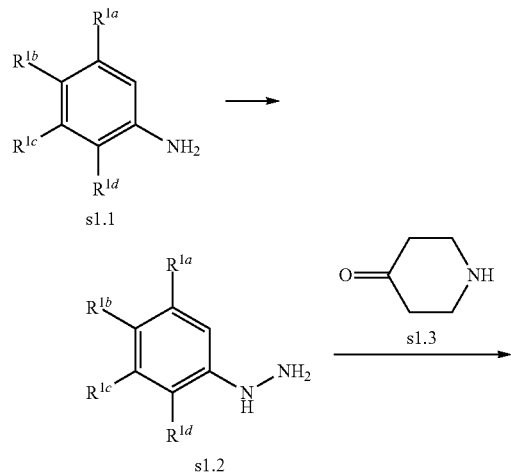

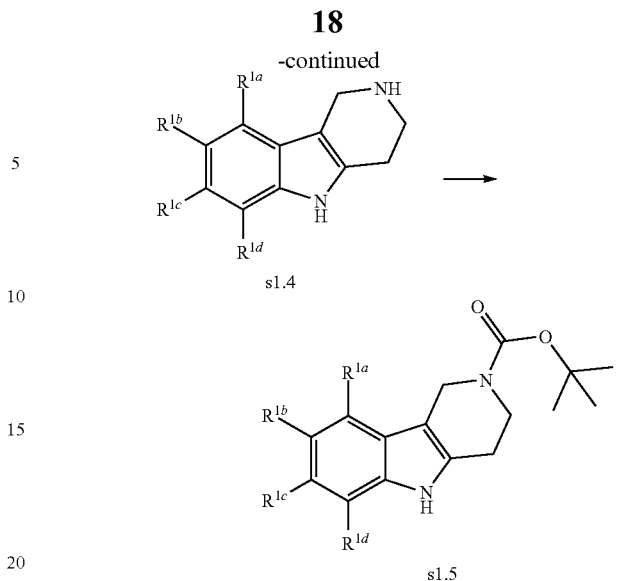

Scheme 1 describes the Fischer indole synthesis scheme. $R^{1a}$, $R^{1b}$, $R^{1c}$, and $R^{1d}$ are as defined herein. The ratio of isomeric products (analogs) varies depending on the aniline or hydrazine starting material. The commercially available aniline (s1.1) is converted to the corresponding hydrazine (s1.2) by diazotization at 0° C. using nitrous acid (prepared in situ from sodium nitrite and a mineral acid, typically hydrochloric acid), the intermediate diazonium salt is then reduced without isolation using stannous chloride dihydrate in concentrated hydrochloric acid at 0° C. Cyclization to the carboline (s1.4) is accomplished by the Fischer indole synthesis of the hydrazine (s1.2) and the commercially available piperidin-4-one (s1.3) in IPA with hydrochloric acid in dioxane at temperatures up to reflux. The piperidine (s1.5) moiety is BOC protected using commercially available di-tert-butyl dicarbonate, triethylamine as base in dichloromethane at 0° C. to room temperature.

Scheme 2 - Urea Formation

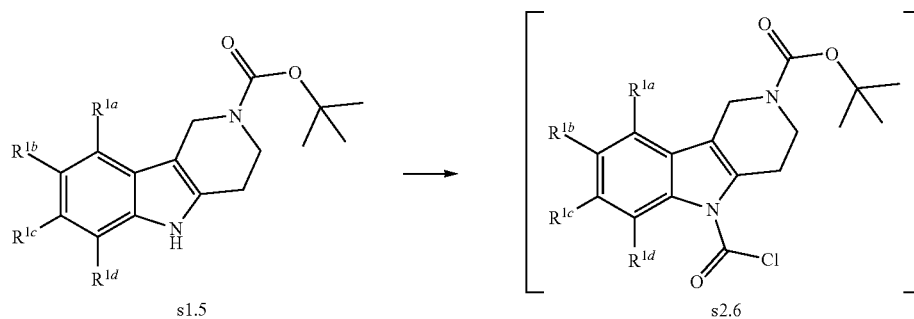

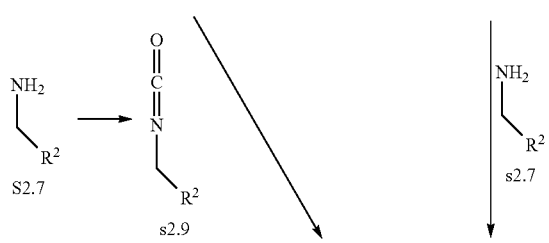

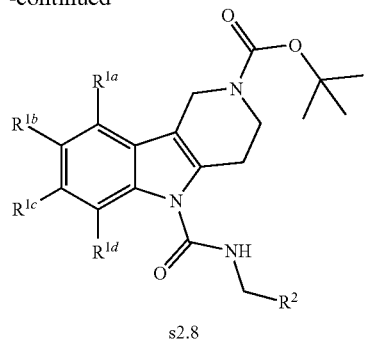

s2.8

$R^{1a}$, $R^{1b}$, $R^{1c}$, $R^{1d}$ and $R^2$ are as defined herein. The ureas (s2.8) are synthesized first by formation of an intermediate isocyanate (s2.9) from a commercially available methanamine (s2.7) using triphosgene and aqueous potassium carbonate or pyridine as base in dichloromethane as solvent at 0° C. Carboline (s1.5) is deprotonated using sodium hydride as base in THF as solvent at 0° C., followed by subsequent reaction with intermediate isocyanate (s2.9) to provide ureas (s2.8). Alternatively, the ureas (s2.8) can be synthesized by formation of an intermediate carbamoyl chloride (s2.6) using phosgene, triphosgene, or CDI and pyridine or triethylamine as base in dichloromethane or DCE as solvent at 0° C. followed by addition of a commercially available methanamine (s2.7) at 0° C. and then warming to room temperature.

Scheme 3 - Piperidine Substitution

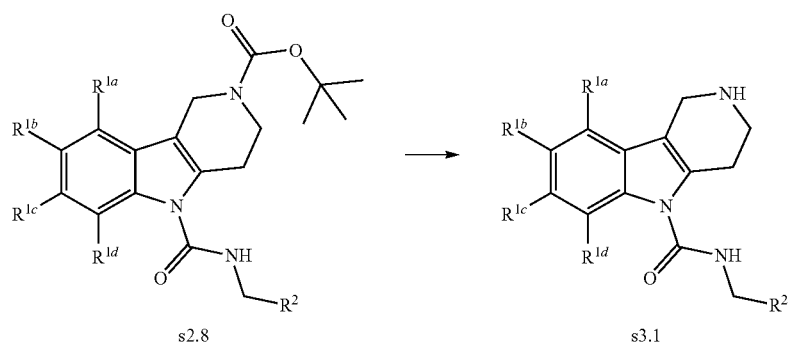

s2.8          s3.1

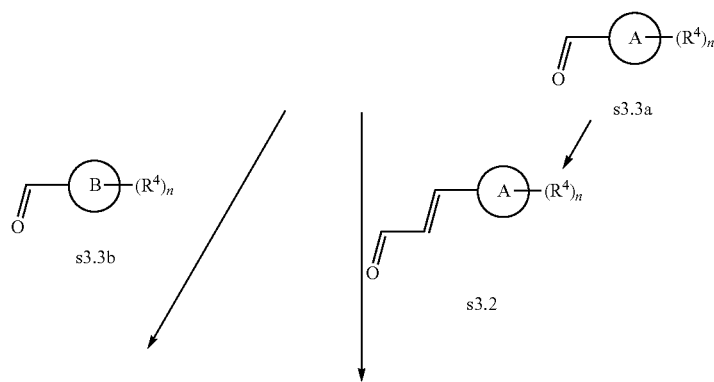

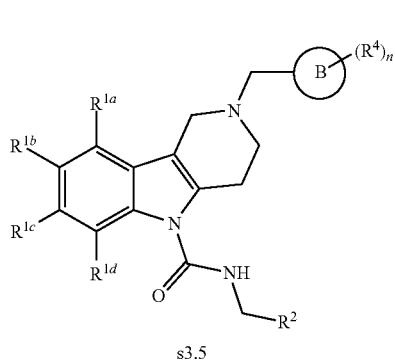

s3.5

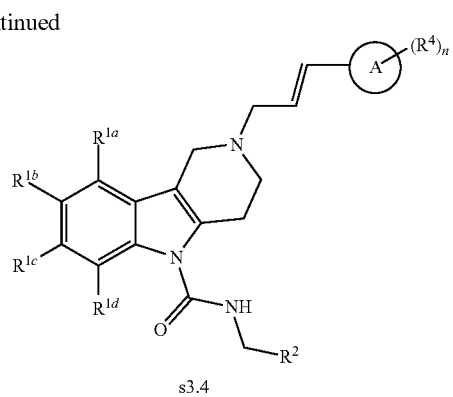

s3.4

$R^{1a}$, $R^{1b}$, $R^{1c}$, $R^{1d}$, $R^2$, $R^4$, n, ring A, and ring B are as defined herein. Deprotection of the BOC group on (s2.8) is accomplished by treatment with trifluoroacetic acid in dichloromethane at room temperature. The amine (s3.1) was then alkylated using a reductive amination procedure with either a readily prepared or commercially available aldehyde intermediate (s3.2). Mixing of the amine (s3.1) and the aldehyde (s3.2) with sodium triacetoxyborohydride and triethylamine in an organic solvent (typically dimethylformamide or dichloromethane) at room temperature affords the substituted piperidine (s3.4). The amine (s3.1) can be alternatively alkylated using a reductive alkylation procedure with a commercially available aldehyde (s3.3b) using sodium triacetoxyborohydride as reducing agent and triethylamine in an organic solvent (typically dimethylformamide or dichloromethane) at room temperature affords the substituted piperidine (s3.5).

Scheme 4 - Alternate Synthesis

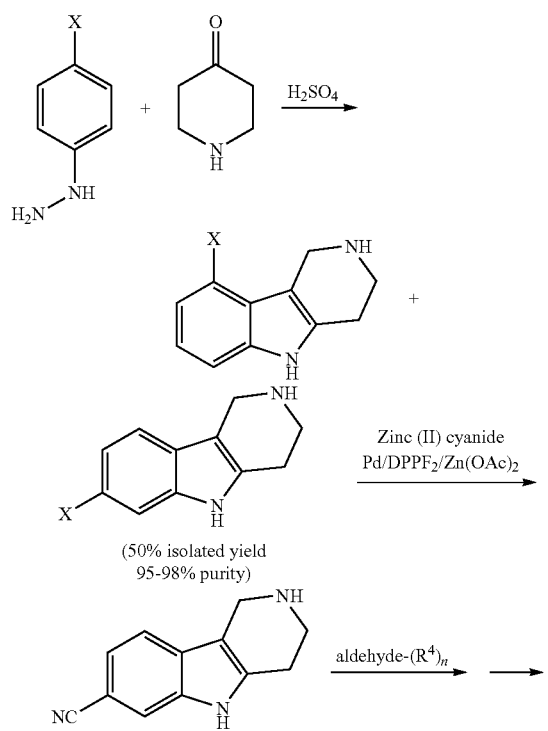

Alternatively, substituted gamma-carboline compounds can be prepared in 3 to 4 steps using the alternative reactive steps depicted in Scheme 4. The gamma-carboline core is prepared via standard Fischer-Indole chemistry, optionally followed by replacement of the halide X by other substituents (such as nitriles) through conventional palladium cross coupling chemistry.

The amine side chain is then added via reductive amination, by reacting excess aldehyde with the core gamma-carboline in the presence of a standard reducing agent (e.g., sodium triacetoxyborohydride, sodium cyanoborohydride, sodium borohydride, and the like (preferrably sodium triacetoxyborohydride)) in polar solvents such as THF, DCM, MeOH, iPrOH, DMF, DMA, and the like, preferably DMF or DMA. The urea tail piece is then inserted by reacting slight excess of isocyanate reagent in the presence of a base, such as trimethylamine, hunigg's base, or pyridine; in polar solvents such as THF, DMF, DMA, and the like, preferably DMF or DMA.

By reversing the order of the reductive amination step and the urea formation, the BOC protecting group can be omitted, thereby reducing the number of synthetic steps. $R^4$, $R^5$, and n are as defined herein. The letter "m" is an integer 0, 1, or 2.

It will be appreciated by those of skill in the art that certain compounds within the compositions of the invention may exist and be isolated as geometric isomers. The present invention encompasses the specific diastereomers of each compound as well as mixtures of different diastereomers of the compounds of the invention that possess the useful properties described herein.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Also contemplated within the scope of the invention are acid or base salts, where applicable, of the compounds of the invention provided for herein.

The term "acid" contemplates all veterinary acceptable inorganic or organic acids. Inorganic acids include inorganic acids such as hydrobromic acid and hydrochloric acid, sulfuric acid, phosphoric acids and nitric acid. Organic acids include all veterinary acceptable aliphatic, alicyclic and aromatic carboxylic acids, dicarboxylic acids, tricarboxylic acids, fatty acids and sulfonic acids. Non-limiting organic acids include: carbonic acid, formic acid, acetic acid, citric acid, propionic acid, isopropionic acid, valeric acid, glycolic acid, lactic acid, chloroacetic acid, benzoic acid, salicylic acid, oxalic acid, malic acid, succinic acid, tartaric acid, fumaric acid, and maleic acid, butyric acid, isobutyric acid, sec-butyric acid, lauric acid, palmitic acid, stearic acid, oleic acid, linoleic acid, linolenic acid, and phenylsteric acid, gluconic acid, glycoheptonic acid, and lactobionic acid, and the like.

The term "base" contemplates all veterinary acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, aluminum, magnesium or calcium salts. Salts formed with organic bases include the common hydrocarbon and heterocyclic amine salts, which include, for example, ammonium salts ($NH_4$), alkyl- and dialkylammonium salts, and salts of cyclic amines such as the morpholine and piperidine salts.

The free-base carbolines are converted to salt form by excess HCl gas addition in an ethereal and/or DCM solution and subsequent filtration or solvent evaporation. Alternatively, salts can also be formed by stoichiometric addition of HCl (4M solution in methanol or dioxane) or citric acid addition to a solution of the free-base in MeOH, DCM, EtOH, IPA, and the like, and mixtures thereof, followed by filtration or solvent evaporation.

One skilled in the art will recognize that, in some cases, after the introduction of a given reagent as it is depicted in the schemes, it may be necessary to perform additional routine synthetic Steps not described in detail to complete the synthesis of Formula (1) compounds.

The present invention includes all veterinary acceptable isotopically-labelled Formula (1) compounds wherein one or more atoms are replaced by atoms having the same atomic number, but an atomic mass or mass number different from the atomic mass or mass number usually found in nature. Examples of isotopes suitable for inclusion in the compounds of the present invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", RC Larock, Wiley-VCH (1999 or later editions).

The Formula (1) compounds are useful as antiparasitic agents, therefore, another aspect of the present invention is a veterinary composition comprising a therapeutically effective amount of a Formula (1) compound, stereoisomers thereof, and at least one veterinary acceptable carrier. The compounds of the present invention (including the compositions and processes used therein) may also be used in the manufacture of a medicament for the therapeutic applications described herein.

The compound of the present invention can be administered alone or in a formulation appropriate to the specific use envisaged, the particular species of host animal being treated and the parasite involved. Generally, it will be administered as a formulation in association with at least one veterinary acceptable carrier. The term "carrier" is used herein to describe any ingredient (e.g., excipient, diluents, and the like) other than the compound of the present invention or any additional veterinary (e.g., antiparasitic) agent. The choice of carrier will to a large extent depend on factors such as the particular mode of administration, the effect of the carrier on solubility and stability, and the nature of the dosage form. In addition to the carrier(s), the amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely.

In another aspect, the veterinary composition comprises a Formula (1) compound with at least one veterinary acceptable carrier. The concentration range will vary depending on the composition (e.g., oral, topical, or injectable). For an oral dose, the range of active (i.e., compound of the present invention) is about 0.1 to 50 mg/kg, preferably from about 0.2 to 25 mg/kg, and even more preferably from about 0.25 to 10 mg/kg, and most preferably from about 0.5 to 7 mg/kg or 1-5 mg/kg. For a topical solution, the range of active is about 0.1 to 1000 mg/mL, and preferably from about 0.5 to 500 mg/mL, and more preferably from about 1 to 250 mg/mL, and even more preferably from about 2 to 200 mg/mL. Depending upon the final volumes of the topical solution(s), the concentration of the active can change from that described above. Generally, injectable doses tend to be, but not always, lower in concentration.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a Formula (1) compound with at least one veterinary acceptable carrier. Suitable carriers are well known to those skilled in the art and include materials such as carbohydrates, waxes, water soluble and/or swellable polymers, starches, hydrophilic or hydrophobic materials, gelatin, oils, solvents, water, and the like. The particular carrier(s) will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament). The compound of the present invention will typically be formulated into veterinary dosage forms to provide an easily controllable dosage form for administration.

The methods by which the compound of the present invention may be administered include oral, topical, and injectable (e.g., parenteral and subcutaneous) administration. The particular route selected by the practitioner depends upon factors such as the physicochemical properties of the therapeutic agent, the condition of the host and economics. In certain cases, it is convenient and efficient to administer veterinary medicines orally by placing the therapeutic agent in a solid or liquid matrix that is suitable for oral delivery. These methods include chewable drug-delivery formulations. The problem associated with administering oral formulations to animals is that the therapeutic agent often provides an unpleasant taste, aroma, or texture, which causes the animals to reject the composition. This is further exacerbated by compositions that are hard and difficult to swallow.

The compound of the present invention can be administered orally by capsule, bolus, tablet, powders, lozenges, chews, multi and nanoparticulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise at least one veterinary acceptable carrier, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g. triethylene glycol, benzyl alcohol, and the like). The compound of the present invention can also be formulated with a food substance, e.g., a dietary admixture (food pellets or powder for birds).

The compound of the present invention can be administered topically to the skin or mucosa, that is dermally or transdermally. This is another preferred method of administration and as such it is desirable to develop the compound of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the compound of the present invention has increased persistence of action and is more durable, for example it may be more water-fast. Topical formulations contemplated herein can comprise from about 0.1 mg/kg to 50 mg/kg of a compound of the present invention, and more preferably from about 1 mg/kg to 10 mg/kg of a compound of the present invention, and even more preferably, from 1 mg/kg to 5 mg/kg.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinary acceptable amount of a compound of the present invention alone, or with at least one veterinary acceptable carrier, and optionally an additional antiparasitic agent, or veterinary acceptable salts thereof. Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal. The volume of the applied composition can be from about 0.2 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

The compounds of the present invention can also be administered by injection. Injectable (e.g., subcutaneous and parenteral) formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with at least one additional antiparasitic agent in the liquid carrier such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilization, may readily be accomplished using standard veterinary techniques well known to those skilled in the art. The solubility of a compound of the present invention used in the preparation of an injectable solution may be increased by the use of appropriate formulation techniques, such as the incorporation of solubility-enhancing agents.

Administration of the compound of the instant invention is contemplated to be once a month. However, an extended duration formulation may allow for dosing once every 2, 3, 4, 5, or 6 months.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

The composition of the present invention may be administered alone, as described above, or in combination with at least one other additional antiparasitic agent to form a multi-component parasiticide giving an even broader spectrum of veterinary utility. Thus, the present invention also envisions a combination veterinary composition comprising an effective amount of the compound of the present invention in combination with at least one other additional antiparasitic agent and can further comprise at least one veterinary acceptable carrier.

The following list of additional antiparasitic agents together with which the compound of the present invention can be used is intended to illustrate the possible combinations, but not to impose any limitation. Non-limiting examples of additional antiparasitic agents include: amitraz, aminoacetonitriles, albendazole, cambendazole, fenbendazole, flubendazole, thiabendazole, mebendazole, cyclic octadepsipeptides, oxfendazole, oxibendazole, paraherquamide, parbendazole, piperazines, praziquantel, thiabendazole, tetramisole, triclabendazole, levamisole, pyrantel (including the salt forms—pamoate, citrate, and tartrate), oxantel, morantel, abamectin, doramectin, emamectin, eprinomectin, ivermectin, moxidectin, selamectin, dimadectin, latidectin, lepimectin, milbemycin, milbemycin oxime, demiditraz, emodepside, fipronil, methoprene, diethylcarbamazine, hydroprene, kinoprene, lufenuron, metaflumizone, niclosamide, permethrin, pyrethrins, pyriproxyfen, closantel, clorsulon, novaluron, fluazuron, spinosad, sarolaner ((S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)-ethan-1-one), fluralaner (4-(5-(3,5-dichlorophenyl)-5-(trifluoromethyl)-4,5-dihydro-isoxazol-3-yl)-2-methyl-N-(2-oxo-2-((2,2,2-trifluoroethyl)amino)-ethyl)benzamide), afoxolaner (4-(5-(3-chloro-5-(trifluoromethyl)phenyl)-5-(trifluoromethyl)-4,5-dihydro-isoxazol-3-yl)-N-(2-oxo-2-((2,2,2-trifluoroethyl)amino)ethyl)-1-naphthamide), lotilaner (3-methyl-N-{2-oxo-2-[(2,2,2-trifluoroethyl)amino]ethyl}-5-[(5S)-5-(3,4,5-trichlorophenyl)-5-(trifluoromethyl)-4,5-dihydro-1,2-oxazol-3-yl]thiophene-2-carboxamide); and mixtures thereof. Preferred additional antiparasitic agents include moxidectin, doramectin, selamectin, abamectin, milbemycin, milbemycin oxime, pyrantel, praziquatel, and levamisole.

The veterinary composition for application to an animal may be packaged in a variety of ways depending upon the method used for administering the compound of the present invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) compound and at least one veterinary acceptable carrier are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish.

The compounds of the present invention are useful for the treatment of parasitic worms categorized as cestodes (tapeworms), nematodes (roundworms) and trematodes (flatworms or flukes). The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata, C. surnabada* (syn. mcmasteri), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylostoma caninum, A. tubaeforme, A. braziliense, Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the superfamily Filarioidea and the Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. repens, D. ursi, D. tenuis, D. spectans, D. lutrae*, and the like), *Dipetalonema* spp. (i.e., *D reconditum, D. repens*, and the like), *Onchocerca* spp. (i.e., *O. gibsoni, O. gutturosa, O. volvulus*, and the like), *Elaeophora* spp. (*E.*

*bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*). In another aspect of the invention, the compound of the present invention is useful for treating endoparasiticidal infection from filarial nematodes within the genus *Dirofilaria* (i.e., *D. immitis, D. repens, D. ursi, D. tenuis*, and the like).

The compounds of the present invention can also be used against ectoparasites, alone or in combination with at least one additional antiparasitic agent. Some non-limiting examples of ectoparasites include: ticks (e.g., *Ixodes* spp., (e.g., *I. ricinus, I. hexagonus*), *Rhipicephalus* spp., (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Sarcoptes* spp., (e.g., *S. scabiei*), *Psoroptes* spp., (e.g., *P/ bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*); and copepods (e.g., sea lice within the Order Siphonostomatoida, including genera *Lepeophtheirus* and *Caligus*).

The compounds of the present invention and compositions comprising compounds of the present invention in conjunction with at least one other antiparasitic agent are of particular value in the control of ectoparasites and endoparasites which are injurious to, or spread or act as vectors of diseases in companion animals, livestock, birds, and fish. The ectoparasites and endoparasites which can be treated with a combination of a Formula (1) compound and an additional antiparasitic agent include those as herein before described.

Any of the compounds of the present invention, or a suitable combination of a compound of the present invention and optionally, with at least one additional antiparasitic agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (1) compound, stereoisomers thereof, veterinary acceptable salts thereof, and combinations with at least one additional antiparasitic agent, as described herein, are of value for the treatment and control of the various lifecycle stages of parasites including egg, nymph, larvae, juvenile and adult stages.

The present invention also relates to a method of administering a compound of the present invention alone or in combination with at least one additional antiparasitic agent, and optionally at least one veterinary acceptable carrier, to animals in good health comprising the application to said animal to reduce or eliminate the potential for human parasitic infection or infestation from parasites carried by the animal and to improve the environment in which the animals inhabit.

The present invention also relates to a method of administering a compound of the present invention alone or in combination with at least one additional antiparasitic agent, and optionally at least one veterinary acceptable carrier, to a human in good or poor health comprising the application to said human to reduce or eliminate the potential for human parasitic infection or infestation from parasites carried by the human and to improve the environment in which the human inhabits.

The present invention also relates to a method of administering a compound of the present invention alone or in combination with at least one additional antiparasitic agent, and optionally at least one veterinary acceptable carrier, to a plant or soil to prevent parasitic infection to the plant.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., J. Org. Chem. 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (e.g., high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance (1H NMR) spectra were determined using a Bruker spectrometer operating at a field strength of 400 megahertz (MHz). Chemical shifts are reported in parts per million (ppm) downfield from an internal tetramethylsilane standard. Mass spectra (MS) data were obtained using Agilent mass spectrometer with atmospheric pressure chemical ionization. Method: Acquity UPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Certain aspects of the present invention are illustrated by the following Examples. It is to be understood, however, that the aspects of the invention are not limited to the specific details of these Examples, as other variations thereof will be known, or apparent in light of the instant disclosure, to one of ordinary skill in the art.

Compounds of this invention can exist as one or more stereoisomers. The various stereoisomers include diastereomers, e.g., cis/trans (E/Z) isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers.

EXAMPLES

The following examples were prepared according to the Schemes and preparations as presented herein. Example mass and NMR data is shown in Table 3.

Aldehyde Intermediates

Intermediate 1: (E)-3-(4-chloro-3,5-difluoro-phenyl)prop-2-enal; (E)-3-(4-chloro-3,5-difluorophenyl)acrylaldehyde

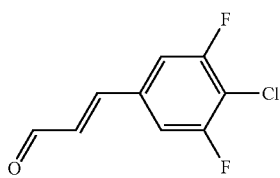 [SMILES: O=C/C=C/c1cc(F)c(Cl)c(F)c1]

Step 1: 4-chloro-3,5-difluoro-benzaldehyde

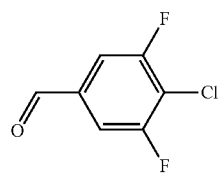 [SMILES: O=Cc1cc(F)c(Cl)c(F)c1]

To a solution of 5-bromo-2-chloro-1,3-difluoro-benzene (5.0 g, 21 mmol) in THF at −40° C. (dry ice/acetonitrile bath) was slowly added Isopropylmagnesium chloride-lithium chloride complex (1.3 mol/L) in THF (22 mL, 29 mmol). The reaction was stirred for 15 minutes. Next, DMF (3.1 mL, 40 mmol) was added. The reaction mixture was slowly allowed to warm to −20° C. while stirring over 2 hours. Citric acid was added and the reaction mixture was extracted with EtOAc (2×75 mL). The organic phase was washed with brine, dried ($Na_2SO_4$) and concentrated under vacuum. The crude material was chromatographed (80 g Redi-Sep column) eluting from 100% hexanes to 10:90 EtOAc:hexanes to afford the intermediate (3.25 g, 70%) as a solid. 1H NMR (400 MHz, $CDCl_3$) δ: 7.52-7.56 (m, 2H), 9.95 (t, 1H).

Step 2: Preparation of Intermediate 1.

To a solution of 4-chloro-3,5-difluoro-benzaldehyde (4.0 g, 22.6 mmol) in toluene (100 mL) was added (triphenylphosphoranylidene)acetaldehyde (7.7 g, 25.3 mmol). The reaction mixture was heated to 85° C. for 18 hours. Next, the reaction mixture was cooled and concentrated under vacuum. The crude material was chromatographed (220 g Redi-Sep column) eluting from 100% hexanes to 10:90 EtOAc:hexanes to afford the title compound (3.3 g, 72%) as a solid. 1H NMR (400 MHz, $CDCl_3$) δ: 6.66-6.72 (m, 1H), 7.19-7.23 (m, 2H), 7.37 (d, 1H), 9.75 (d, 1H).

The following aldehyde intermediates (I-2 to I-16 and I-19 to I-27) in Table 1 were prepared following the same procedure as Step 2 of Intermediate 1 but using one of the respective commercially available benzaldehydes: 4-methylsulfonylbenzaldehyde; 4-chloro-3-fluoro-benzaldehyde; 2,4-dichloro-benzaldehyde; 4-bromo-2-fluoro-benzaldehyde; 4-chloro-2,6-difluoro-benzaldehyde; 4-chloro-2-fluoro-benzaldehyde; 4-bromo-3-fluoro-benzaldehyde; 2,4,6-trifluorobenzaldehyde; 2-bromo-5-fluoro-benzaldehyde; 5-bromo-2-fluoro-benzaldehyde; 3-bromo-4-fluoro-benzaldehyde; 2,3,4-trifluorobenzaldehyde; 4-bromo-2,3-difluoro-benzaldehyde; 4-chloro-2,3-difluoro-benzaldehyde; pentafluoro-benzaldehyde; 3,5-dichloro-4-fluoro-benzaldehyde; 2-fluoro-5-formylbenzonitrile; 2-fluoro-4-formylbenzonitrile; 3-fluoro-5-(trifluoromethoxy)-benzaldehyde; 2,4-difluoro-5-bromo-benzaldehyde; 3,5-difluoro-4-methoxy-benzaldehyde; 4-chloro-2-fluoro-3-methoxy-benzaldehyde; 2-fluoro-3,6-dichloro-benzaldehyde; and 4-bromo-2,5-difluoro-benzaldehyde. Aldehyde intermediate 17 was synthesized using the procedure in Journal of Fluorine Chemistry (130 (2009) 175-196).

TABLE 1

| | Aldehyde Intermediates (I - #) Prepared from Commercially Available Benzaldehydes | |
|---|---|---|
| I - # | Structure | 1H NMR (400 MHz, $CDCl_3$, chloroform-d, DMSO-d6) δ |
| 2 | ![structure] | 3.02 (s, 3 H), 6.71-6.77 (m, 1H), 7.44-7.48 (m, 1 H), 7.67-7.72 (m, 2 H), 7.92-7.98 (m, 2 H), 9.70 (d, 1 H) |
| 3 | ![structure] | 6.67-6.73 (m, 1H), 7.30-7.51 (m, 4 H), 9.74 (d, 1 H) |
| 4 | ![structure] | 6.68-6.74 (m, 1H), 7.33-7.36 (m, 1 H), 7.52 (d, 1 H), 7.63 (d, 1 H), 7.86-7.90 (m, 1 H), 9.79 (d, 1 H) |

TABLE 1-continued
Aldehyde Intermediates (I - #) Prepared from Commercially Available Benzaldehydes
| I - # | Structure | 1H NMR (400 MHz, CDCl₃, chloroform-d, DMSO-d6) δ |
|---|---|---|
| 5 | 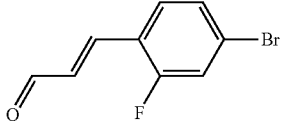 | 6.77-6.83 (m, 1H), 7.36-7.41 (m, 2 H), 7.46-7.50 (m, 1 H), 7.58-7.62 (m, 1 H), 9.74 (d, 1 H) |
| 6 | 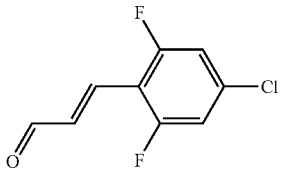 [SMILES: O=C/C=C/c1c(F)cc(Cl)cc1F] | 6.95-7.01 (m, 1H), 7.04-7.09 (m, 2 H), 7.49-7.54 (m, 1 H), 9.72 (d, 1 H). |
| 7 | 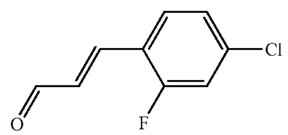 [SMILES: O=C/C=C/c1ccc(Cl)cc1F] | 6.76-6.82 (m, 1H), 7.20-7.27 (m, 2 H), 7.53-7.63 (m, 2 H), 9.74 (d, 1 H) |
| 8 | 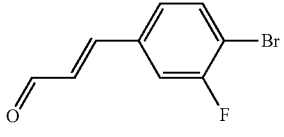 [SMILES: O=C/C=C/c1ccc(Br)c(F)c1] | 6.69-6.75 (m, 1H), 7.23-7.27 (m, 1 H), 7.32-7.43 (m, 2 H), 7.63-7.67 (m, 1 H), 9.74 (d, 1 H) |
| 9 | 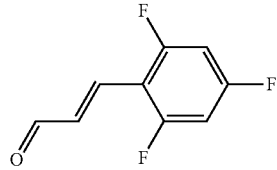 [SMILES: O=C/C=C/c1c(F)cc(F)cc1F] | 6.76-6.83 (m, 2 H), 6.95-6.99 (m, 1 H), 7.51 (m, 1 H), 9.72 (d, 1 H) |
| 10 | 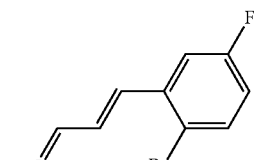 | 6.63-6.69 (m, 1 H), 7.02-7.09 (m, 1 H), 7.36-7.39 (m, 1 H), 7.63-7.67 (m, 1 H), 7.83-7.87 (m, 1 H), 9.81 (d, 1 H) |
| 11 | 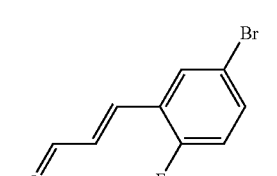 | 6.76-6.82 (m, 1 H), 7.05-7.09 (m, 1 H), 7.52-7.60 (m, 2 H), 7.72-7.74 (m, 1 H), 9.75 (d, 1 H) |
| 12 | 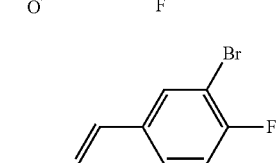 | 6.64-6.70 (m, 1 H), 7.19-7.24 (m, 1 H), 7.38-7.42 (m, 1 H), 7.51-7.55 (m, 1 H), 7.78-7.82 (m, 1 H), 9.72 (d, 1 H) |
| 13 | 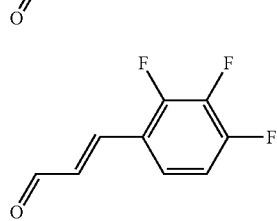 | 6.75-6.81 (m, 1 H), 7.05-7.11 (m, 1 H), 7.30-7.38 (m, 1 H), 7.55-7.59 (m, 1 H), 9.75 (d, 1 H) |

TABLE 1-continued
Aldehyde Intermediates (I - #) Prepared from Commercially Available Benzaldehydes
| I - # | Structure | 1H NMR (400 MHz, CDCl$_3$, chloroform-d, DMSO-d6) δ |
|---|---|---|
| 14 | 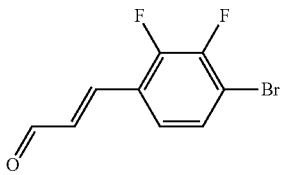 [SMILES: O=C/C=C/c1ccc(Br)c(F)c1F] | 6.79-6.85 (m, 1 H), 7.25-7.30 (m, 1 H), 7.39-7.45 (m, 1 H), 7.57-7.61 (m, 1 H), 9.76 (d, 1 H) |
| 15 | 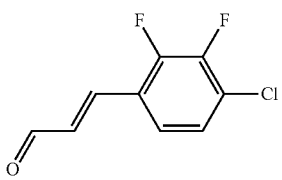 [SMILES: O=C/C=C/c1ccc(Cl)c(F)c1F] | 6.77-6.83 (m, 1 H), 7.25-7.35 (m, 2 H), 7.57-7.61 (m, 1 H), 9.76 (d, 1 H) |
| 16 | 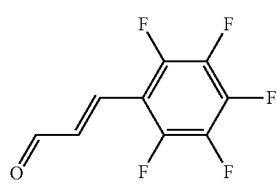 [SMILES: O=C/C=C/c1c(F)c(F)c(F)c(F)c1F] | 6.98-7.03 (m, 1 H), 7.46-7.50 (m, 1 H), 9.74-9.78 (m, 1 H) |
| 17 | 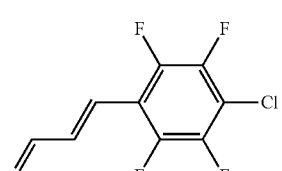 | 1H NMR (400 MHz, CDCl3) δ: 7.00-7.06 (m, 1 H), 7.48-7.53 (m, 1 H), 9.75-9.79 (m, 1 H) |
| 19 | 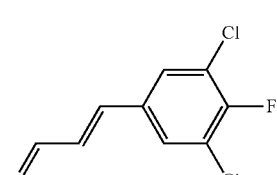 | 6.63-6.69 (m, 1 H), 7.32-7.36 (m, 1 H), 7.53-7.56 (m, 2 H), 9.73 (d, 1 H) |
| 20 | 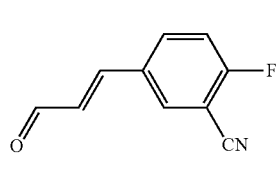 [SMILES: N#Cc1cc(/C=C/C=O)ccc1F] | 6.70 (dd, 1 H), 7.35 (t, 1 H), 7.43 (d, 2 H), 7.83 (2H, m), 9.73 (d, 1 H) |
| 21 | 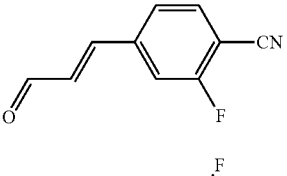 | 6.71-6.77 (dd, 1H), 7.38-7.45 (m, 3H), 7.67-7.71 (dd, 1H), 9.75 (d, 1H) |
| 22 | 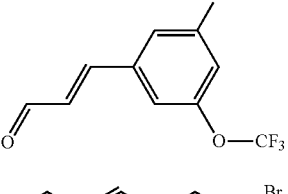 | 7.01-7.07 (dd, 1H), 7.52 (d, 1H), 7.69-7.81 (m, 3H), 9.69 (d, 1H) |
| 23 | 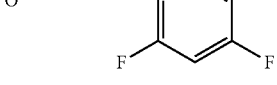 | .71 (d, 1H), 7.80 (m, 1H), 7.51 (d, 1H), 7.00 (m, 1H), 6.73 (m, 1H) |

TABLE 1-continued

Aldehyde Intermediates (I - #) Prepared from Commercially Available Benzaldehydes

| I - # | Structure | 1H NMR (400 MHz, CDCl₃, chloroform-d, DMSO-d6) δ |
|---|---|---|
| 24 | 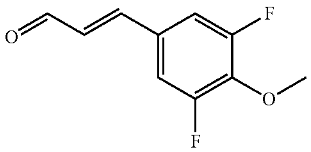 | 9.70 (br d, 1H), 7.33 (br d, 1H), 7.13 (br d, 2H), 6.60 (br m, 1H), 4.09 (s, 3H) |
| 25 | 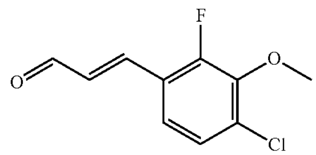 | 9.73 (br d, 1H), 7.60 (br d, 1H), 7.14-7.33 (m, 2H), 6.77 (br m, 1H), 4.01 (br s, 3H) |
| 26 | 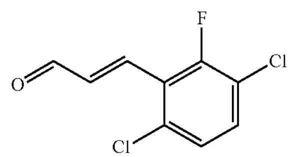 [SMILES: O=C/C=C/c1c(Cl)ccc(Cl)c1F] | 9.78 (m, 1H), 7.67 (d, 1H), 7.42 (m, 1H), 7.22-7.31 (m, 1H), 6.99 (m, 1H) |
| 27 | 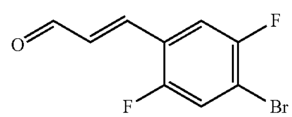 [SMILES: O=C/C=C/c1cc(F)c(Br)cc1F] | 9.73 (d, 1H), 7.47-7.61 (m, 1H), 7.30-7.44 (m, 2H), 6.75 (m, 1H) |

Intermediate 18: (E)-3-(5-(trifluoromethyl)pyridin-2-yl)prop-2-enal; (E)-3-(5-(trifluoromethyl)pyridin-2-yl)acrylaldehyde

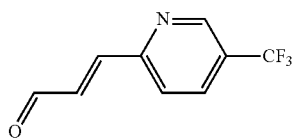

To commercially available 2-bromo-5-trifluoromethyl-pyridine (295 g, 1.3 mol) in DCM (4 L) at −2° C. was added iPrMgCl (2M in Et₂O, 750 ml, 1.5 mol) over 3 minutes then stirred at 0-60 for 40 minutes [jacket at 0° C., mild and gradual exotherm took pot temp to 6° C. maximum after about 15 minutes]. The mixture was cooled to −20° C. then DMF (200 ml, 2.6 mol) was added in one portion [exotherm to 6° C.]. The mixture was slowly re-cooled to 0° C. over 20 minutes then quenched by addition of 1.5 L saturated NaHCO₃ in one portion [temperature to 12° C.]. The mixture was stirred at 12° C. for 15 minutes then filtered through a celite pad. The layers were separated. The filtered solids were washed with 1 L DCM and this was then used to re-extract the aqueous layer. The combined organics were dried over MgSO₄, filtered through a pad of 1 kg silica, washed with 5 L DCM and evaporated (bath temp 35° C.). The brown oil was dissolved in 2 L hexane and washed with 2×1 L 12% brine to remove DMF. The organics were filtered through a pad of MgSO₄ and concentrated to low volume. This oil was distilled at 3500 and 20 inches Hg to remove hexane then at 56° C. and 26 inches Hg to afford the 5-(trifluoromethyl)-picolinaldehyde product (154 g, about 90% purity, 0.79 mol, 61%) as a pale yellow moist crystal. A solution of 5-(trifluoromethyl)picolinaldehyde (150 g, about 90% purity, 0.77 mol) in DCM (1.5 L) was bubbled with nitrogen for 5 minutes and cooled to 9° C. (Formylmethylene)triphenylphosphorane (257 g, 0.85 mol) was added in one portion [exotherm to 19° C.], and the reaction stirred at 20° C. for 60 minutes. The mixture was filtered through a pad of magnesol (100 g) and washed with DCM (400 ml). The filtrate was evaporated at 40° C. The residue was triturated with MTBE (150 ml) then diluted with hexane (300 ml) and filtered, washing with MTBE/hexane. The filtrate was diluted with DCM to solubilize a small amount of oil that had separated and then chromatographed (3 kg silica, 20-35% MTBE in hexane) to afford the desired product (60.3 g, 0.30 mol, 39%) as a dark red solid. ¹H NMR (500 MHz, CDCl₃) δ 9.85 (d, 1H), 8.95 (s, 1H), 8.02 (dd, 1H), 7.66 (d, 1H), 7.55 (d, 1H), 7.19 (dd, 1H).

Intermediate 28. (Z)-3-(4-chlorophenyl)-2-fluoroacrylaldehyde

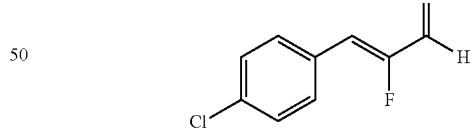

Step 1: Synthesis of (Z)-1-ethoxy-2-fluoro-2-trimethylsilanyl-1-trimethylsilanyloxy-ethene

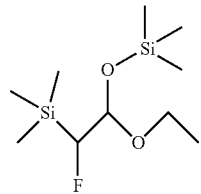

In a 250 mL round bottom flask, to a stirred solution of fluoro-acetic acid ethyl ester (7.5 gm, 70.68 mmol, 1 eq) and trimethysilyl chloride (19.73 mL, 155.51 mmol, 2.2 eq) in dry THF (23 mL) at −78° C. was added dropwise a solution of LDA (21.07 mL, 155.51 mmol, 2.2 eq, freshly prepared LDA by using n-BuLi (62.19 mL, 155.51 mmol, 2.2 eq and diisopropyl amine (21.8 mL, 155.51 mmol, 2.2 eq) in dry THF (52.5 mL) at −78° C. under nitrogen atmosphere. Resulting mass was stirred at −78° C. for 2 hours and then allowed to return to room temperature and then diluted with dry hexane (150 mL) and filtered. Filtrate was concentrated under reduced pressure to afford yellow liquid (18 gm, crude). Crude was used as such for next step. MW 250.46.

Step 2: Synthesis of (Z)-3-(4-chloro-phenyl)-2-fluoro-acrylic Acid Ethyl Ester

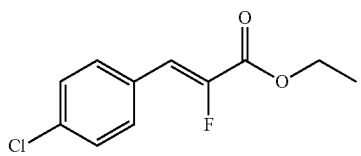

In a 500 mL round bottom flask to the stirred solution of 4-chloro-benzaldehyde (14 gm, 99.595 mmol, 1 eq) and tetrabutylammonium acetate (1.501 gm, 4.98 mmol, 0.05 eq) in dichloromethane (150 mL) was added (Z)-1-ethoxy-2-fluoro-2-trimethylsilanyl-1-trimethylsilanyloxy-ethene (34.922 gm, 139.43 mmol, 1.4 eq) at room temperature. Reaction mixture was stirred at room temperature for 1 hour. Progress of reaction was monitored by TLC. After completion of starting material, reaction mixture was quenched with aqueous (1 M) HCl (75 mL) and brine (75 mL). Aqueous layer was extracted with dichloromethane (75 mL×2). Combined organic layer was dried over sodium sulfate, filtered and concentrated under reduced pressure to afford yellow oil as crude compound 20g. Purification was done by combiflash column chromatography (120 gm Redisep column). Compound was eluted by 0.5% ethyl acetate in hexane to afford off white solid (17 g, 74.66%). 1H NMR (400 MHz, CDCl3) δ: 1.35-1.38 (m, 3H), 4.31-4.36 (q, 2H), 6.86 (d, 1H), 7.34-7.38 (m, 2H), 7.54-7.58 (m, 2H). LC-MS (m/z): Not ionized.

Step 3: Synthesis of (Z)-3-(4-Chloro-phenyl)-2-fluoro-prop-2-en-1-ol:

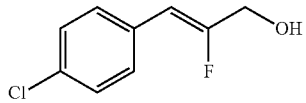 [SMILES: OC/C(F)=C/c1ccc(Cl)cc1]

In a 500 mL round bottom flask to the stirred solution of (Z)-3-(4-chloro-phenyl)-2-fluoro-acrylic acid ethyl ester (9 gm, 39.361 mmol, 1 eq) in dichloromethane (100 mL) was added diisobutylaluminium hydride (1M in THF) (5.598 gm, 39.36 ml, 39.361 mmol, 1 eq) at −78° C. After that reaction mixture was stirred at room temperature for 15 hours. Progress of reaction was monitored by TLC. After consumption of starting material, reaction mixture was quenched with aqueous tartarate salt solution (100 mL). Aqueous layer was extracted with dichloromethane (100 mL×3). Combined organic layer was dried over sodium sulfate, filtered and concentrated under reduced pressure to afford yellow semi solid crude compound 10g. 7.2 g crude compound of previous batch mixed and purified by combiflash (120 gm, Redisep column). Compound was eluted using 8% ethyl acetate in hexane to afford 8 g as yellow solid. 1H NMR (400 MHz, CDCl3) δ: 1.93 (t, 1H), 4.24-4.29 (dd, 2H), 5.74 (d, 1H), 7.21-7.31 (m, 2H), 7.40-7.44 (m, 2H). LC-MS (m/z): Not ionized.

Step 4: Synthesis of Intermediate 28.

In a 100 mL round bottom flask to a stirred solution of (Z)-3-(4-chloro-phenyl)-2-fluoro-prop-2-en-1-ol (4 gm, 21.43 mmol, 3.0 eq) in chloroform (50 mL) was added MnO$_2$ (9.31 gm, 107.17 mmol, 5.0 eq). Resulting reaction mixture was heated to 60° C. for 5 hours. Progress of reaction was monitored by TLC. TLC showed unreacted starting material on TLC so again MnO$_2$ (9.31 gm, 107.17 mmol, 5.0 eq) was added and continued the reaction at 60° C. for 15 hours. After maximum consumption of starting material, reaction mass was filtered on Buchner funnel and washed with DCM (50 mL×2). Filtrate was evaporated under reduced pressure to afford yellow oil (5 gm, crude). Purification was done by combiflash column chromatography (40 gm Redisep column). Compound was eluted by 2% ethyl acetate in hexane to afford off yellow solid (2.2 gm, 55.56%). 1H NMR (400 MHz, CDCl3) δ: 6.57 (d, 1H), 7.41 (d, 2H), 7.64 (d, 2H), 9.35 (d, 1H). LC-MS (m/z): Not ionized.

Commercially available aldehyde intermediates (I-#) were also used for preparing the compounds of the present invention and included: (E)-3-(2-chloro-4-fluorophenyl) acrylaldehyde (I-29); (E)-3-(2,4-difluorophenyl)-acrylaldehyde (I-30); (E)-3-(3-chloro-4-fluorophenyl)acrylaldehyde (I-31); (E)-3-(3,4-difluorophenyl)acrylaldehyde (I-32); (E)-3-(3,4,5-trifluorophenyl)acrylaldehyde (I-33); (E)-3-(3,5-difluorophenyl) acrylaldehyde (I-34); (E)-3-(3-chloro-2-fluoro-phenyl) acrylaldehyde (I-35); (E)-3-(2,3-difluorophenyl)acrylaldehyde (I-36); 4-[(E)-3-oxoprop-1-enyl]benzonitrile (I-37); (E)-3-(4-chlorophenyl) acrylaldehyde (I-38); (E)-3-(3,4-dichlorophenyl) acrylaldehyde (I-39); (E)-3-(4-fluorophenyl) acrylaldehyde (I-40); (E)-3-(pyridin-4-yl)acrylaldehyde (I-41); (E)-3-(2-bromo-4-fluorophenyl)acrylaldehyde (I-42); (E)-3-(4-bromothiophen-2-yl)acrylaldehyde (I-43); (E)-3-(4-methoxyphenyl)acrylaldehyde (I-44); (E)-3-(4-(trifluoromethoxy)-phenyl)acrylaldehyde (I-45); (E)-3-(4-(trifluoromethyl) phenyl)acrylaldehyde (I-46); 6-bromo-2-naphthaldehyde (I-47); 7-chloroisoquinoline-3-carbaldehyde (I-48); 6-fluoro-2-naphthaldehyde (I-49); 2-chloroquinoline-6-carbaldehyde (I-50); 6-chloro-2-naphthaldehyde (I-51); (E)-3-(3-chloro-5-fluorophenyl)acrylaldehyde (I-52); (E)-3-(4-fluoro-3-methoxyphenyl)acrylaldehyde (I-53); (E)-3-fluoro-5-(3-oxoprop-1-en-1-yl)benzonitrile (I-54); (E)-3-chloro-5-(3-oxoprop-1-en-1-yl)benzonitrile (I-55); (E)-3-(3-bromo-5-fluorophenyl)acrylaldehyde (I-56); (E)-3-(3,5-dichlorophenyl)acrylaldehyde (I-57); cinnamaldehyde (I-58), (E)-3-(4-chloro-3-methyl-phenyl)acrylaldehyde (I-59); and (E)-3-(3-bromo-4-chlorophenyl)acrylaldehyde (I-60).

For the reactions and Examples described herein, the Fischer-indole reaction of a meta-substituted hydrazine and a piperidinone produces regio-isomers that can be separated by chromatography to obtain the individual 7' and 9' gamma-carboline isomers. For example, the reaction of (3-bromophenyl)hydrazine and piperidin-4-one hydrochloride will produce 7-bromo-2,3,4,5-tetrahydro-1H-pyrido[4,3-b]indole and 9-bromo-2,3,4,5-tetrahydro-1H-pyrido[4,3-b]indole as shown in Step 1 of Example 1. Similar reactions occur for 3-chloro, -fluoro, -methyl, -methoxy, -trifluoromethyl, -trifluoromethoxy, and the like, meta-substituted phenyl hydrazines.

Non-limiting examples of commercially available hydrazines used to prepare the compounds of the present invention included: (3-bromophenyl)hydrazine, (4-bromophenyl) hydrazine, m-tolylhydrazine, (3-trifluorophenyl)hydrazine, (4-fluorophenyl) hydrazine, (3-chlorophenyl)hydrazine, 4-hydrazinyl-2-(trifluoromethyl)benzonitrile, 2-fluoro-5-hydrazinylbenzonitrile, 5-hydrazinyl-2-methylbenzonitrile, 2-chloro-4-hydrazinyl-benzonitrile, 2-fluoro-4-hydrazinyl-benzonitrile, (4-bromo-3-methylphenyl)hydrazine, (4-bromo-3-methoxyphenyl)hydrazine, (4-bromo-3-chlorophenyl)hydrazine, (4-bromo-3-fluorophenyl)hydrazine, (3,4-dibromophenyl)hydrazine, (4-chlorophenyl)hydrazine, (2-chlorophenyl)hydrazine, (3,4-dichlorophenyl)hydrazine, (3-chloro-4-fluorophenyl)-hydrazine, (3-fluoro-5-(trifluoromethyl)phenyl)hydrazine, (4-chloro-3-(trifluoromethyl)-phenyl)hydrazine, (4-methoxy-3-(trifluoromethyl)phenyl) hydrazine, (4-methyl-3-(trifluoromethyl)phenyl)hydrazine, (3-(trifluoromethoxy)phenyl)hydrazine, (4-(trifluoromethoxy)phenyl)hydrazine, (4-(trifluoromethyl)phenyl) hydrazine, p-tolylhydrazine, naphthalen-2-yl-hydrazine, (4-methylsulfanylphenyl)hydrazine, 2-chloro-5-hydrazinylbenzonitrile, (4-(methylsulfonyl)phenyl)hydrazine, 4-bromo-3-ethoxy-phenyl)-hydrazine, and the like.

The pyridyl-isocyanates were prepared according to Scheme 2 using the appropriate, commercially available, substituted pyridyl-methanamines, for example, (2,6-dichloropyridin-4-yl)methanamine, (2-chloropyridin-4-yl)methanamine, (2-fluoropyridin-4yl)methanamine, (2-cyclopropylpyridin-4-yl)methanamine, 2-trifluoropyridin-4yl) methanamine, (2-hydroxypyridin-4-yl)methanamine, (2-cyclopropylpyridin-4yl)methanamine, (2-methoxypyridin-4yl)methanamine, (2-chlorothiazol-5-yl)methanamine, and the like. Alternatively, substituted phenyl-methanamines, for example (4-fluorophenyl)methanamine, (4-chlorophenyl)-methanamine, and the like, can be used.

In the Examples described below, the respective substituted pyridyl-methanamine was used to prepare the respective pyridyl-isocyanate. For example, (2-chloropyridin-4-yl) methanamine was used to prepare 2-chloro-4-(isocyanatomethyl)pyridine, in Example 1. Similarly, (2,6-dichloropyridin-4-yl)methanamine was used instead of (2-chloropyridin-4-yl)methanamine to prepare 2,6-dichloro-4-(isocyanatomethyl)pyridine, in Example 187. Similar preparations were made for each of the respective urea's.
Example 1. (E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide HCl

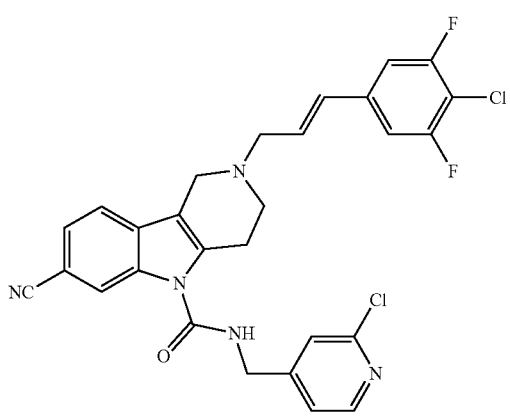 [SMILES: N#Cc1ccc2c3c(n(C(=O)NCc4ccnc(Cl)c4)c2c1)CCN(C/C=C/c1cc(F)c(Cl)c(F)c1)C3]

Step 1: 7-bromo-2,3,4,5-tetrahydro-1H-pyrido[4,3-b]indole and 9-bromo-2,3,4,5-tetrahydro-1H-pyrido[4,3-b]indole:

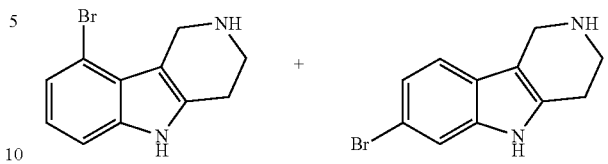

To a solution of (3-bromophenyl)hydrazine (10.0 g, 53.5 mmol) in IPA (100 mL) was added piperidin-4-one-HCl (7.9 g, 58.8 mmol) and HCl (40 mL of a 4.0M solution in dioxane). The reaction mixture was heated to reflux for 18 hours. The reaction mixture was cooled, filtered and rinsed with IPA to afford the intermediate HCl salt as a mixture of regio-isomers. LC-MS (m/z): [M+H]=251, 253.

Step 2: tert-butyl 7-bromo-1,3,4,5-tetrahydropyrido[4,3-b]indole-2-carboxylate

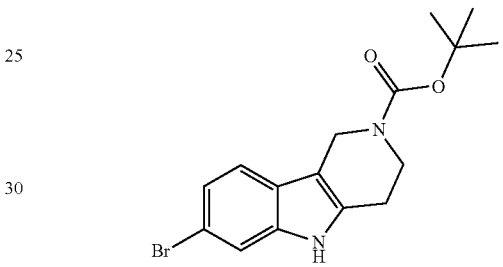

To a mixture of 7-bromo-2,3,4,5-tetrahydro-1H-pyrido[4, 3-b]indole and 9-bromo-2,3,4,5-tetrahydro-1H-pyrido[4,3-b]indole (12.5 g, 43.5 mmol) in CH$_2$Cl$_2$ (150 mL) was added triethylamine (18.4 mL, 130.0 mmol) followed by boc anhydride (8.3 g, 47.8 mmol). The reaction mixture was stirred at room temperature for 18 hours. Water was added to the reaction mixture and the organic phase was separated, washed with brine, dried (Na$_2$SO$_4$), and concentrated under vacuum. The crude mixture was chromatographed (220 g Redi-Sep column) eluting from 100% hexanes to 25:75 EtOAc:hexanes, collecting the title compound as first eluting peak. LC-Ms (m/z): [M+H-tbutyl]=295, 297. The second eluding peak constituted the 9' regio-isomer.

Step 3: tert-butyl 7-cyano-1,3,4,5-tetrahydropyrido[4,3-b]indole-2-carboxylate

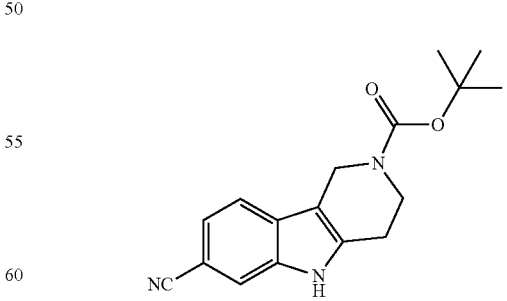

To a solution of tert-butyl 7-bromo-1,3,4,5-tetrahydropyrido[4,3-b]indole-2-carboxylate (6.4 g, 18 mmol) in DMF (100 mL) was added Zn(CN)$_2$ (1.5 g, 13 mmol), Zn(OAc)$_2$ (670 mg, 3.6 mmol), Pd(DPPF$_2$)Cl$_2$ (810 mg, 1.1 mmol), and zinc dust (480 mg, 7.3 mmol). The reaction mixture was purged with nitrogen and heated to 100° C. for 18 hours. The reaction mixture was cooled and poured onto ice water (100 mL). The resulting precipitate was filtered and washed with additional water. The precipitate was dissolved in CH$_2$Cl$_2$ (300 mL) dried (Na$_2$SO$_4$), and concentrated under vacuum. The crude material was chromatographed (120 g Redi-Sep column) eluting from 100% hexanes to 50:50 EtOAc: hexanes to afford the title compound as a solid. LC-MS (m/z): [M+H-t-butyl]=242.

Step 4: tert-butyl 5-[(2-chloro-4-pyridyl)methylcarbamoyl]-7-cyano-3,4-dihydro-1H-pyrido[4,3-b]indole-2-carboxylate.

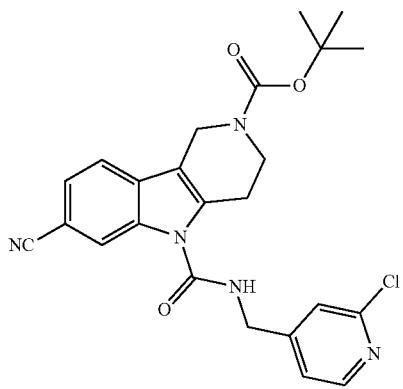 [SMILES: CC(C)(C)OC(=O)N1CCc2c(c3ccc(C#N)cc3n2C(=O)NCc2ccnc(Cl)c2)C1]

To a stirred solution of tert-butyl 7-cyano-1,3,4,5-tetrahydropyrido[4,3-b]indole-2-carboxylate (5.0 g, 16.8 mmol) in THF (75 ml) at 0° C. was added sodium hydride (1.2 g, 30.3 mmol). The reaction mixture was allowed to warm to room temperature while stirring for 30 minutes. Next, the mixture was cooled back to 0° C. in an ice bath and 2-chloro-4-(isocyanatomethyl)pyridine (3.4 g, 20.2 mmol) was added. The reaction was kept at 0° C. while stirring for 15 minutes. The reaction was quenched with 5 mL saturated NH$_4$Cl, then ice water was added to the reaction mixture and it was extracted with EtOAc (2×100 mL). The combined organic phases were washed with brine, dried (Na$_2$SO$_4$), and concentrated under vacuum. The crude product was chromatographed (120 g Redi-Sep column) eluting from 25:75 EtOAc:hexanes to 40:60 EtOAc:hexanes to afford title compound as a solid. LC-MS (m/z): [M+H-tbutyl]=410.

Step 5: N-[(2-chloro-4-pyridyl)methyl]-7-cyano-1,2,3,4-tetrahydropyrido[4,3-b]indole-5-carboxamide.

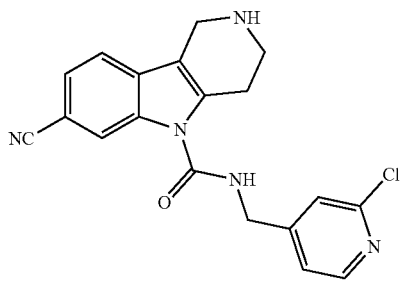 [SMILES: N#Cc1ccc2c3c(n(C(=O)NCc4ccnc(Cl)c4)c2c1)CCNC3]

To a solution of tert-butyl 5-[(2-chloro-4-pyridyl)methylcarbamoyl]-7-cyano-3,4-dihydro-1H-pyrido[4,3-b]indole-2-carboxylate (5.2 g, 11.0 mmol) in DCM (100 mL) at 0° C. was added TFA (8.4 mL, 110 mmol). The reaction was allowed to warm to room temperature and stirred for 18 hours. Toluene (35 mL) was added and the reaction was concentrated under vacuum. The resulting TFA salt was dissolved in EtOAc (175 mL) and saturated NaHCO$_3$ (75 mL) was added. The resulting precipitate was stirred at room temperature for 15 minutes, filtered, and dried under vacuum to afford the title compound as a solid (3.53 g, 86%): LC-Ms (m/z): [M+H]=366.

Step 6: Preparation of Example 1.

To a flask containing N-[(2-chloro-4-pyridyl)methyl]-7-cyano-1,2,3,4-tetrahydropyrido[4,3-b]indole-5-carboxamide (90 mg, 0.25 mmol) was added (E)-3-(4-chloro-3,5-difluoro-phenyl)prop-2-enal (Intermediate 1) (60 mg, 0.30 mmol), and CH$_2$Cl$_2$ (5 mL). The mixture was stirred at room temperature for 15 minutes and sodium triacetoxyborohydride (63 mg, 0.30 mmol) was added. The reaction mixture was stirred at room temperature for 18 hours; next, diluted with CH$_2$Cl$_2$ (50 mL), washed with saturated NaHCO$_3$, dried (Na$_2$SO$_4$), and concentrated under vacuum. The crude product was chromatographed (24 g Redi-Sep column) eluting from 50:50 EtOAc:hexanes to 100% EtOAc. The purified product was subsequently dissolved in CH$_2$Cl$_2$ (10 mL) and HCl gas was bubbled in slowly until a precipitate formed. The mixture was diluted with diethyl ether (10 mL), stirred for 5 minutes, filtered, washed with with additional diethyl ether, and dried under vacuum to afford the title compound as an HCl salt The following compounds were prepared similarly to Example 1 but using the respective aldehyde intermediate:

Example 2, (E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide (I-3);

Example 3, (E)-N-[(2-chloro-4-pyridyl)methyl]-7-cyano-2-[(E)-3-(2,4-dichlorophenyl)allyl]-3,4-dihydro-1H-pyrido[4,3-b]indole-5-carboxamide (I-4);

Example 4, (E)-N-((2-chloropyridin-4-yl)methyl)-9-cyano-2-(3-(2,4-dichlorophenyl)allyl)-1,2,3,4-tetrahydro-5H-pyrido[4,3-b]indole-5-carboxamide (I-4);

Example 5, (E)-2-(3-(4-bromo-2-fluorophenyl)allyl)-N-((2-chloropyridin-4-yl)methyl)-7-cyano-1,2,3,4-tetrahydro-5H-pyrido[4,3-b]indole-5-carboxamide (I-5);

Example 6, (E)-2-(3-(4-chloro-2,6-difluorophenyl)allyl)-N-((2-chloropyridin-4-yl)methyl)-7-cyano-1,2,3,4-tetrahydro-5H-pyrido[4,3-b]indole-5-carboxamide (I-6);

Example 7, (E)-2-(3-(4-chloro-2-fluorophenyl)allyl)-N-((2-chloropyridin-4-yl)methyl)-7-cyano-1,2,3,4-tetrahydro-5H-pyrido[4,3-b]indole-5-carboxamide (I-7);

Example 8, (E)-2-(3-(4-bromo-3-fluorophenyl)allyl)-N-((2-chloropyridin-4-yl)methyl)-7-cyano-1,2,3,4-tetrahydro-5H-pyrido[4,3-b]indole-5-carboxamide (I-8);

Example 9, (E)-N-((2-chloropyridin-4-yl)methyl)-7-cyano-2-(3-(2,4,6-trifluorophenyl)allyl)-1,2,3,4-tetrahydro-5H-pyrido[4,3-b]indole-5-carboxamide (I-9);

Example 10, (E)-2-(3-(2-bromo-5-fluorophenyl)allyl)-N-((2-chloropyridin-4-yl)methyl)-7-cyano-1,2,3,4-tetrahydro-5H-pyrido[4,3-b]indole-5-carboxamide (I-10);

Example 11, (E)-2-(3-(5-bromo-2-fluorophenyl)allyl)-N-((2-chloropyridin-4-yl)methyl)-7-cyano-1,2,3,4-tetrahydro-5H-pyrido[4,3-b]indole-5-carboxamide (I-11);

Example 12, (E)-2-(3-(3-bromo-4-fluorophenyl)allyl)-N-((2-chloropyridin-4-yl)methyl)-7-cyano-1,2,3,4-tetrahydro-5H-pyrido[4,3-b]indole-5-carboxamide (I-12);

Example 13, (E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide (I-13);

Example 14, (E)-2-(3-(4-bromo-2,3-difluorophenyl)allyl)-N-((2-chloropyridin-4-yl)methyl)-7-cyano-1,2,3,4-tetrahydro-5H-pyrido[4,3-b]indole-5-carboxamide (I-14);

Example 15, (E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide (I-15);
Example 16, (E)-N-((2-chloropyridin-4-yl)methyl)-7-cyano-2-(3-(perfluorophenyl)allyl)-1,2,3,4-tetrahydro-5H-pyrido[4,3-b]indole-5-carboxamide (I-16);
Example 17, (E)-2-(3-(4-chloro-2,3,5,6-tetrafluorophenyl)allyl)-N-((2-chloropyridin-4-yl)methyl)-7-cyano-1,2,3,4-tetrahydro-5H-pyrido[4,3-b]indole-5-carboxamide (I-17);
Example 18, N-[(2-chloro-4-pyridyl)methyl]-7-cyano-2-[(E)-3-(4-cyano-3-fluoro-phenyl)allyl]-3,4-dihydro-1H-pyrido[4,3-b]indole-5-carboxamide HCl (I-21);
Example 19, 2-[(E)-3-(5-bromo-2,4-difluoro-phenyl)allyl]-N-[(2-chloro-4-pyridyl)methyl]-7-cyano-3,4-dihydro-1H-pyrido[4,3-b]indole-5-carboxamide HCl (I-23);
Example 20, N-[(2-chloro-4-pyridyl)methyl]-7-cyano-2-[(E)-3-(3,5-difluoro-4-methoxy-phenyl)allyl]-3,4-dihydro-1H-pyrido[4,3-b]indole-5-carboxamide HCl (I-24);
Example 21, 2-[(E)-3-(4-chloro-2-fluoro-3-methoxy-phenyl)allyl]-N-[(2-chloro-4-pyridyl)methyl]-7-cyano-3,4-dihydro-1H-pyrido[4,3-b]indole-5-carboxamide HCl (I-25);
Example 22, N-[(2-chloro-4-pyridyl)methyl]-7-cyano-2-[(E)-3-(3,6-dichloro-2-fluoro-phenyl)allyl]-3,4-dihydro-1H-pyrido[4,3-b]indole-5-carboxamide HCl (I-26);
Example 23, 2-[(E)-3-(4-bromo-2,5-difluoro-phenyl)allyl]-N-[(2-chloro-4-pyridyl)methyl]-7-cyano-3,4-dihydro-1H-pyrido[4,3-b]indole-5-carboxamide HCl (I-27);
Example 24, (E)-2-(3-(2-chloro-4-fluorophenyl)allyl)-N-((2-chloropyridin-4-yl)methyl)-7-cyano-1,2,3,4-tetrahydro-5H-pyrido[4,3-b]indole-5-carboxamide (I-29);
Example 25, (E)-2-(3-(2-chloro-4-fluorophenyl)allyl)-N-((2-chloropyridin-4-yl)methyl)-9-cyano-1,2,3,4-tetrahydro-5H-pyrido[4,3-b]indole-5-carboxamide (I-29);
Example 26, (E)-N-((2-chloropyridin-4-yl)methyl)-7-cyano-2-(3-(2,4-difluorophenyl)allyl)-1,2,3,4-tetrahydro-5H-pyrido[4,3-b]indole-5-carboxamide (I-30);
Example 27, (E)-2-(3-(3-chloro-4-fluorophenyl)allyl)-N-((2-chloropyridin-4-yl)methyl)-7-cyano-1,2,3,4-tetrahydro-5H-pyrido[4,3-b]indole-5-carboxamide (I-31);
Example 28, (E)-N-((2-chloropyridin-4-yl)methyl)-7-cyano-2-(3-3,4-difluorophenyl)allyl)-1,2,3,4-tetrahydro-5H-pyrido[4,3-b]indole-5-carboxamide (I-32);
Example 29, (E)-N-((2-chloropyridin-4-yl)methyl)-7-cyano-2-(3-(3,4,5-trifluorophenyl)allyl)-1,2,3,4-tetrahydro-5H-pyrido[4,3-b]indole-5-carboxamide (I-33);
Example 30, (E)-N-((2-chloropyridin-4-yl)methyl)-7-cyano-2-(3-(3,5-difluorophenyl)allyl)-1,2,3,4-tetrahydro-5H-pyrido[4,3-b]indole-5-carboxamide (I-34);
Example 31, (E)-2-(3-(3-chloro-2-fluorophenyl)allyl)-N-((2-chloropyridin-4-yl)methyl)-7-cyano-1,2,3,4-tetrahydro-5H-pyrido[4,3-b]indole-5-carboxamide (I-35);
Example 32, (E)-N-((2-chloropyridin-4-yl)methyl)-7-cyano-2-(3-(2,3-difluorophenyl)allyl)-1,2,3,4-tetrahydro-5H-pyrido[4,3-b]indole-5-carboxamide (I-36);
Example 33, (E)-N-((2-chloropyridin-4-yl)methyl)-7-cyano-2-(3-(4-cyanophenyl)allyl)-1,2,3,4-tetrahydro-5H-pyrido[4,3-b]indole-5-carboxamide (I-37);
Example 34, (E)-2-(3-(4-chlorophenyl)allyl)-N-((2-chloropyridin-4-yl)methyl)-7-cyano-1,2,3,4-tetrahydro-5H-pyrido[4,3-b]indole-5-carboxamide (I-38);
Example 35, (E)-N-((2-chloropyridin-4-yl)methyl)-7-cyano-2-(3-(3,4-dichlorophenyl)allyl)-1,2,3,4-tetrahydro-5H-pyrido[4,3-b]indole-5-carboxamide (I-39);
Example 36, (E)-N-((2-chloropyridin-4-yl)methyl)-7-cyano-2-(3-(4-fluorophenyl)allyl)-1,2,3,4-tetrahydro-5H-pyrido[4,3-b]indole-5-carboxamide (I-40);
Example 37, (E)-N-((2-chloropyridin-4-yl)methyl)-7-cyano-2-(3-(pyridin-4-yl)allyl)-1,2,3,4-tetrahydro-5H-pyrido[4,3-b]indole-5-carboxamide (I-41); and
Example 38, N-[(2-chloro-4-pyridyl)methyl]-7-cyano-2-[(E)-3-(4-fluoro-3-methoxy-phenyl)allyl]-3,4-dihydro-1H-pyrido[4,3-b]indole-5-carboxamide HCl (I-53).
Example 39, (E)-2-(3-(4-chloro-3-fluorophenyl)allyl)-7-cyano-N-((2,6-dichloropyridin-4-yl)methyl)-1,2,3,4-tetrahydro-5H-pyrido[4,3-b]indole-5-carboxamide HCl, was prepared similarly to Example 1 but using (2,6-dichloropyridin-4-yl)methanamine and aldehyde intermediate, I-3.

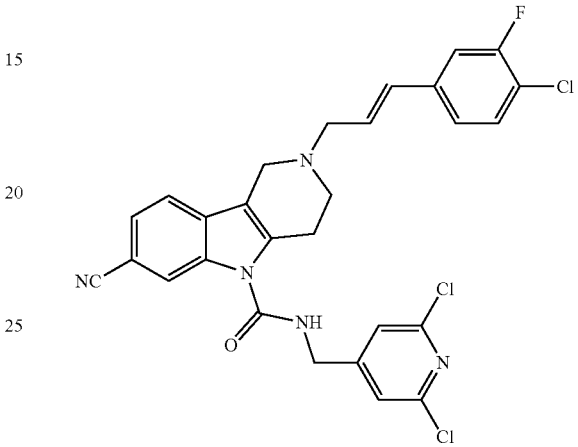

The following compounds were prepared similarly to Example 1 but using (2-bromopyridin-4-yl)methanamine and the respective aldehyde intermediate:
Example 40, (E)-N-((2-bromopyridin-4-yl)methyl)-2-(3-(4-chloro-3,5-difluorophenyl)allyl)-7-cyano-1,2,3,4-tetrahydro-5H-pyrido[4,3-b]indole-5-carboxamide HCl (I-1)

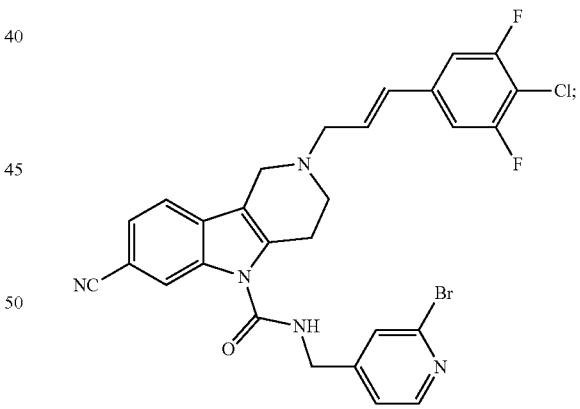

Example 41, (E)-N-((2-bromopyridin-4-yl)methyl)-2-(3-(4-chloro-3-fluorophenyl)allyl)-7-cyano-1,2,3,4-tetrahydro-5H-pyrido[4,3-b]indole-5-carboxamide (I-3);
Example 42, (E)-N-((2-bromopyridin-4-yl)methyl)-2-(3-(4-chloro-2-fluorophenyl)allyl)-7-cyano-1,2,3,4-tetrahydro-5H-pyrido[4,3-b]indole-5-carboxamide, HCl, (I-7);
Example 43, (E)-N-((2-bromopyridin-4-yl)methyl)-7-cyano-2-(3-(2,3,4-trifluorophenyl)allyl)-1,2,3,4-tetrahydro-5H-pyrido[4,3-b]indole-5-carboxamide HCl (I-13);
Example 44, (E)-N-((2-bromopyridin-4-yl)methyl)-7-cyano-2-(3-(2,4-difluorophenyl)allyl)-1,2,3,4-tetrahydro-5H-pyrido[4,3-b]indole-5-carboxamide, HCl (I-30);

Example 45, (E)-N-((2-bromopyridin-4-yl)methyl)-7-cyano-2-(3-(3,4-difluorophenyl)allyl)-1,2,3,4-tetrahydro-5H-pyrido[4,3-b]indole-5-carboxamide HCl, (I-32);

Example 46, (E)-N-((2-bromopyridin-4-yl)methyl)-7-cyano-2-(3-(3,4,5-trifluorophenyl)-allyl)-1,2,3,4-tetrahydro-5H-pyrido[4,3-b]indole-5-carboxamide, HCl (I-33);

Example 47, (E)-N-((2-bromopyridin-4-yl)methyl)-7-cyano-2-(3-(3,5-difluorophenyl)allyl)-1,2,3,4-tetrahydro-5H-pyrido[4,3-b]indole-5-carboxamide HCl, (I-34);

Example 48, (E)-N-((2-bromopyridin-4-yl)methyl)-2-(3-(4-chlorophenyl)allyl)-7-cyano-1,2,3,4-tetrahydro-5H-pyrido[4,3-b]indole-5-carboxamide HCl. (I-38); and Example 49, (E)-N-((2-bromopyridin-4-yl)methyl)-7-cyano-2-(3-(4-fluorophenyl)allyl)-1,2,3,4-tetrahydro-5H-pyrido[4,3-b]indole-5-carboxamide, HCl (I-40).

The following compounds were prepared similarly to Example 1 but using (2-fluoropyridin-4-yl)methanamine and the respective aldehyde intermediate:

Example 50, (E)-2-(3-(4-chloro-3,5-difluorophenyl)allyl)-7-cyano-N-((2-fluoropyridin-4-yl)methyl)-1,2,3,4-tetrahydro-5H-pyrido[4,3-b]indole-5-carboxamide (I-1)

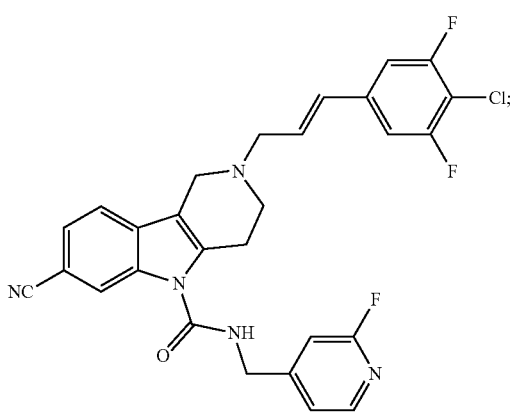 [SMILES: N#Cc1ccc2c3c(n(C(=O)NCc4ccnc(F)c4)c2c1)CCN(C/C=C/c1cc(F)c(Cl)c(F)c1)C3]

Example 51, (E)-2-(3-(4-chloro-3-fluorophenyl)allyl)-7-cyano-N-((2-fluoropyridin-4-yl)methyl)-1,2,3,4-tetrahydro-5H-pyrido[4,3-b]indole-5-carboxamide (I-3);

Example 52, (E)-2-(3-(4-chloro-2-fluorophenyl)allyl)-7-cyano-N-((2-fluoropyridin-4-yl)methyl)-1,2,3,4-tetrahydro-5H-pyrido[4,3-b]indole-5-carboxamide (I-7);

Example 53, (E)-2-(3-(4-chloro-2,3-difluorophenyl)allyl)-7-cyano-N-((2-fluoropyridin-4-yl)methyl)-1,2,3,4-tetrahydro-5H-pyrido[4,3-b]indole-5-carboxamide (I-15);

Example 54, (E)-7-cyano-2-(3-(3-fluoro-5-(trifluoromethoxy)phenyl)allyl)-N-((2-fluoro-pyridin-4-yl)methyl)-1,2,3,4-tetrahydro-5H-pyrido[4,3-b]indole-5-carboxamide (I-22); and Example 55, (E)-2-(3-(4-chlorophenyl)allyl)-7-cyano-N-((2-fluoropyridin-4-yl)methyl)-1,2,3,4-tetrahydro-5H-pyrido[4,3-b]indole-5-carboxamide (I-38).

Example 56, (E)-2-(3-(4-chloro-3-fluorophenyl)allyl)-7-cyano-N-(pyridin-4-ylmethyl)-1,2,3,4-tetrahydro-5H-pyrido[4,3-b]indole-5-carboxamide HCl was prepared similarly to Example 1 but using pyridin-3-yl-methanamine and aldehyde intermediate, I-3

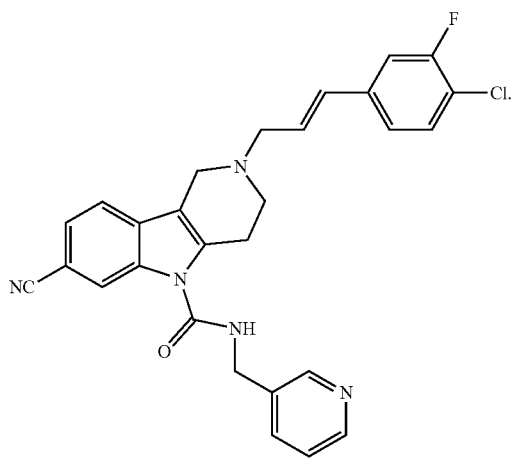 [SMILES: N#Cc1ccc2c3c(n(C(=O)NCc4cccnc4)c2c1)CCN(C/C=C/c1ccc(Cl)c(F)c1)C3]

Example 57, (E)-2-(3-(4-chloro-3-fluorophenyl)allyl)-7-cyano-N-((2-methylpyridin-4-yl)methyl)-1,2,3,4-tetrahydro-5H-pyrido[4,3-b]indole-5-carboxamide HCl was prepared similarly to Example 1 but using (2-methylpyridin-4-yl)methanamine and aldehyde intermediate, I-3

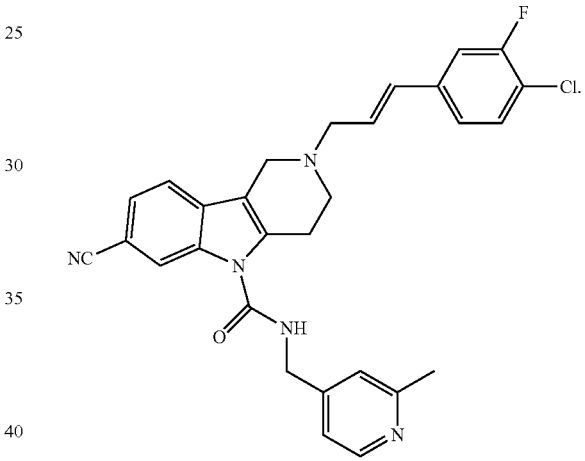

Example 58, (E)-2-(3-(4-chloro-3-fluorophenyl)allyl)-7-cyano-N-((2,6-dimethylpyridin-4-yl)methyl)-1,2,3,4-tetrahydro-5H-pyrido[4,3-b]indole-5-carboxamide HCl was prepared similarly to Example 1 but using (2,6-dimethylpyridin-4-yl)methanamine and aldehyde intermediate I-3

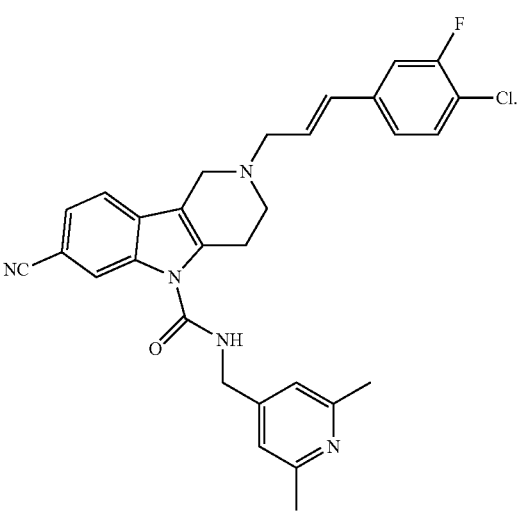 [SMILES: Cc1cc(CNC(=O)n2c3c(c4ccc(C#N)cc42)CN(C/C=C/c2ccc(Cl)c(F)c2)CC3)cc(C)n1]

Example 59, (E)-2-(3-(4-chloro-3-fluorophenyl)allyl)-7-cyano-N-((2-methoxypyridin-4-yl)methyl)-1,2,3,4-tetrahydro-5H-pyrido[4,3-b]indole-5-carboxamide, was prepared similarly to Example 1 but using (2-methoxypyridin-4yl)methanamine and aldehyde intermediate, I-3

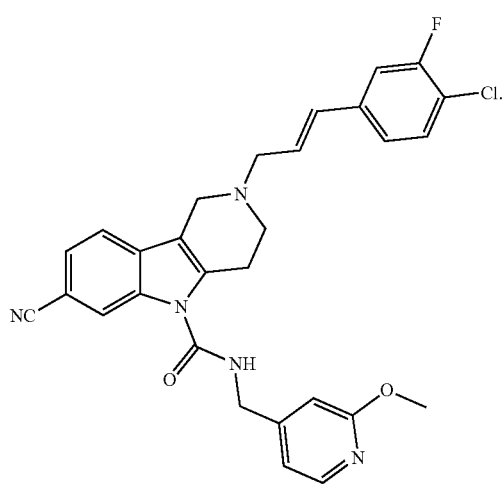 [SMILES: COc1cc(CNC(=O)n2c3c(c4ccc(C#N)cc42)CN(C/C=C/c2ccc(Cl)c(F)c2)CC3)ccn1]

Example 60. (E)-2-(3-(4-chloro-3-fluorophenyl)allyl)-7-cyano-N-((2-(trifluoromethyl)pyridin-4-yl)methyl)-1,2,3,4-tetrahydro-5H-pyrido[4,3-b]indole-5-carboxamide was prepared similarly to Example 1 but using (2-trifluoromethyl-pyridin-4yl)methanamine and aldehyde intermediate, I-3

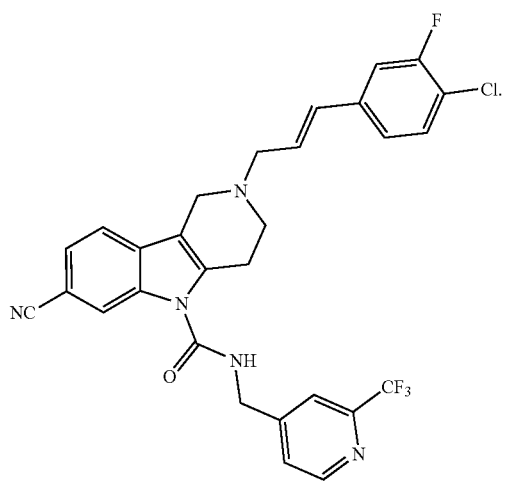 [SMILES: N#Cc1ccc2c3c(n(C(=O)NCc4ccnc(C(F)(F)F)c4)c2c1)CCN(C/C=C/c1ccc(Cl)c(F)c1)C3]

Example 61, (E)-2-(3-(4-chloro-3-fluorophenyl)allyl)-7-cyano-N-(pyridazin-4-ylmethyl)-1,2,3,4-tetrahydro-5H-pyrido[4,3-b]indole-5-carboxamide HCl, was prepared similarly to Example 1 but using pyridazin-4-yl-methanamine and aldehyde intermediate, I-3

Example 62, (E)-2-(3-(4-chloro-3-fluorophenyl)allyl)-7-cyano-N-((1-methyl-4,5-dihydro-1H-pyrrol-3-yl)methyl)-1,2,3,4-tetrahydro-5H-pyrido[4,3-b]indole-5-carboxamide HCl was prepared similarly to Example 1 but using (1-methyl-1H-pyrazol-4-yl)methanamine and aldehyde intermediate, I-3

Example 63. (E)-8-cyano-N-((2-methoxypyridin-4-yl)methyl)-2-(3-(3,4,5-trifluorophenyl)allyl)-1,2,3,4-tetrahydro-5H-pyrido[4,3-b]indole-5-carboxamide HCl

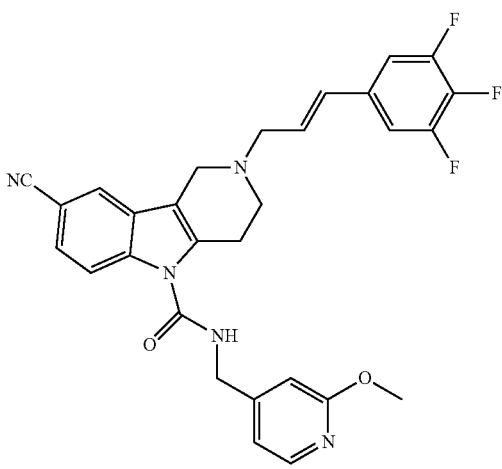 [SMILES: COc1cc(CNC(=O)n2c3c(c4cc(C#N)ccc42)CN(C/C=C/c2cc(F)c(F)c(F)c2)CC3)ccn1]

Step 1: 8-bromo-2,3,4,5-tetrahydro-1H-pyrido[4,3-b]indole hydrochloride

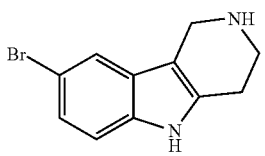 [SMILES: Brc1ccc2[nH]c3c(c2c1)CNCC3]

In a 350 mL pressure flask, (4-bromophenyl)hydrazine hydrochloride (10.64 g, 47.61 mmol) and piperidin-4-one hydrochloride (7.39 g, 48.08 mmol) were suspended in 200 mL isopropanol. HCl in Dioxane (4.0 mol/L, 23.8 mL, 95.21 mmol) was added, the flask was capped and the resulting solution was stirred at 80° C. overnight. Progress of the reaction was monitored by LCMS. After consumption of all starting materials the solids were stirred at 1000 RPM at 0° C. for 2 hours. The solids were then filtered, dried under reduced pressure and used in the next step without further purification LC-Ms (m/z): [M+H]=251.1.

Step 2: tert-butyl 8-bromo-1,3,4,5-tetrahydro-2H-pyrido[4,3-b]indole-2-carboxylate

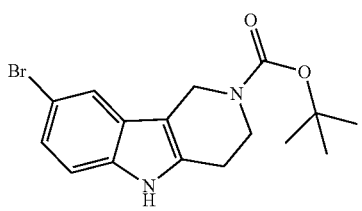 [SMILES: CC(C)(C)OC(=O)N1CCc2[nH]c3ccc(Br)cc3c2C1]

In a 500 mL round bottom flask, 8-bromo-2,3,4,5-tetrahydro-1H-pyrido[4,3-b]indole hydrochloride (13.82 g, 48.06 mmol) was suspended in 200 mL DCM at 0° C., TEA (14.8 mL, 105.72 mmol) was added and the resulting solution was maintained at 0° C. for 15 minutes. Boc$_2$O (10.8 g, 49.02 mmol) was then added in one portion and the ice bath removed. The solution was stirred at 0° C. to room temperature for 1.5 hours. Progress of the reaction was monitored by LCMS. After consumption of all starting materials 200 mL of saturated NaHCO$_3$ was added and the resulting biphasic solution was vigorously stirred for 30 minutes. The solution was transferred into a separatory funnel and the aqueous layer was extracted 3 times with DCM. The organic layers were combined, dried over MgSO$_4$ and the volatiles removed under reduced pressure. The crude was purified on silica using flash chromatography using 0-50% EtOAc in Hexanes on 340 g column to give the desired product as a pale yellow solid. LC-Ms (m/z): [M+H]=351.1.

For reactions wherein the bromo substitution is to be converted to cyano, the following Step (3) can be performed as described below, or alternatively, similarly to the cyanation step described in Example 1. If cyanation is not required, for example, to retain the bromo substitution (or other substituted moiety, e.g., Cl, F, methyl, methoxy, and the like) then the cyanation step(s) can be bypassed.

Step 3: tert-butyl 8-cyano-1,3,4,5-tetrahydropyrido[4,3-b]indole-2-carboxylate

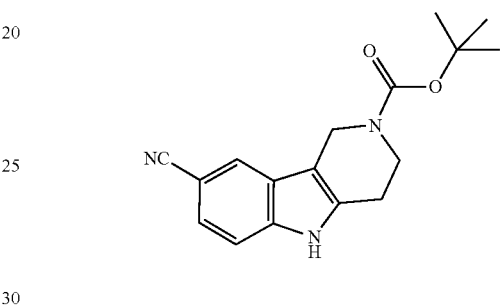

tert-butyl 8-bromo-1,3,4,5-tetrahydropyrido[4,3-b]indole-2-carboxylate (6.4 g, 18 mmol) in DMF (100 mL) was added Zn(CN)$_2$ (1.5 g, 13 mmol), Zn(OAc)$_2$ (670 mg, 3.6 mmol), Pd(DPPF$_2$)Cl$_2$ (810 mg, 1.1 mmol), and zinc dust (480 mg, 7.3 mmol). The reaction mixture was purged with nitrogen and heated to 100° C. for 18 hours. The reaction mixture was cooled and poured onto ice water (100 mL). The resulting precipitate was filtered and washed with additional water. The precipitate was dissolved in CH$_2$Cl$_2$ (300 mL) dried (Na$_2$SO$_4$), and concentrated under vacuum. The crude material was chromatographed (120 g Redi-Sep column) eluting from 100% hexanes to 50:50 EtOAc: hexanes to afford the title compound as a solid (This procedure can be used to synthesize subsequent cyano compounds from bromo precursors).

Step 4: tert-butyl 8-cyano-5-(((2-methoxypyridin-4-yl)methyl)carbamoyl)-1,3,4,5-tetrahydro-2H-pyrido[4,3-b]indole-2-carboxylate

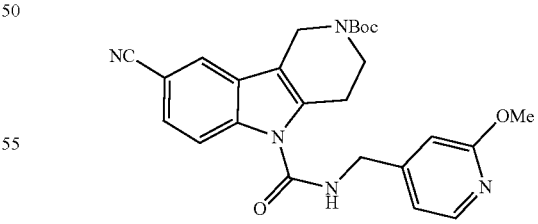

A 100 mL Schlenk flask was charged with tert-butyl 8-cyano-1,3,4,5-tetrahydro-2H-pyrido[4,3-b]indole-2-carboxylate (1000 mg, 3.36 mmol) and anhydrous THF (40 mL). The resulting suspension was cooled to 0° C. with an ice bath and NaH (404 mg, 60% disp, 10.09 mmol) was added in small portions. Gas slowly evolves and the reaction mixture turned from an off white suspension to a rose pinkish-red suspension. The ice bath was removed after 2 hours, and the reaction was allowed to warm to room temperature for 10 minutes. Next, the mixture was cooled back to 0° C. In a separate 25 mL round bottom flask, (2-methoxy-4-pyridyl)methanamine (0.69 g, 5.044 mmol) was dissolved in 10 mL DCM at 0° C. Triphosgene (1.56 g, 5.212 mmol) and triethylamine (4.71 mL, 33.6 mmol) were added and the resulting solution stirred at 0° C. for 30 minutes. The two solutions were mixed together by pouring the (2-methoxy-4-pyridyl)-methanamine solution into the indole solution quickly and in one portion. After stirring for 5 minutes at 0° C., the reaction mixture was carefully quenched with addition of HCl (10 mL, 1.0 M) at 0° C. The reaction mixture diluted with water (20 mL) and saturated NaHCO$_3$ (20 mL) and extracted with EtOAc (2×30 mL). The combined organic phases were washed with brine, dried over MgSO$_4$, and concentrated under reduced pressure. The crude was purified by flash chromatography using EtOAc in Hexanes (0 to 70%) to give the desired compound as an amorphous off yellow solid. LC-Ms (m/z): [M+Na]=484.2.

Step 5: Preparation of Example 63.

In a 8 mL vial 110 mg of tert-butyl 8-cyano-5-(((2-methoxypyridin-4-yl)methyl)carbamoyl)-1,3,4,5-tetrahydro-2H-pyrido[4,3-b]indole-2-carboxylate was dissolved in 5.0 mL of DCM and 183 μL of TFA was added at room temperature. The resulting solution was stirred at room temperature for two hours. Upon completion of the reaction the volatiles were removed under reduced pressure. The crude was dissolved in 2.0 mL of DCM and 0.2 mL of MeOH after which 100 μL of TEA was added. The resulting solution was cooled to 0° C. and 53 mg of commercially available (E)-3-(3,4,5-trifluorophenyl)acrylaldehyde was added. After stirring for 15 minutes at 0° C., 155 mg of sodium triacetoxyborohydride was added and the resulting solution was stirred for 3 hours. Upon completion of the reaction as monitored by LCMS, 3 mL of saturated NaHCO$_3$ solution were added and the resulting solution stirred for 1 hour at room temperature. The biphasic solution was passed through a phase separator cartridge and the aqueous layer washed with DCM. The organic volatiles were removed under a flow of N$_2$, and the crude material was dissolved in 2.0 mL of EtOAc and placed in the freezer at −20° C. overnight. The resulting crystals were isolated by filtration and washed with cold EtOAc and Et$_2$O and dried under high vacuum. The crystals were dissolved in DCM and Et$_2$O and a stream of HCl gas was passed through the solution to prepare title compound (HCl salt).

The following compounds were prepared similarly to Example 63 but using the respective aldehyde intermediate:
Example 64, (E)-2-(3-(4-chloro-3-fluorophenyl)allyl)-8-cyano-N-((2-methoxypyridin-4-yl)methyl)-1,2,3,4-tetrahydro-5H-pyrido[4,3-b]indole-5-carboxamide HCl (I-3);
Example 65, (E)-8-cyano-2-(3-(2,4-dichlorophenyl)allyl)-N-((2-methoxypyridin-4-yl)methyl)-1,2,3,4-tetrahydro-5H-pyrido[4,3-b]indole-5-carboxamide HCl (I-4);
Example 66, (E)-2-(3-(4-bromo-2-fluorophenyl)allyl)-8-cyano-N-((2-methoxypyridin-4-yl)methyl)-1,2,3,4-tetrahydro-5H-pyrido[4,3-b]indole-5-carboxamide HCl (I-5);
Example 67, (E)-8-cyano-2-(3-(2,4-difluorophenyl)allyl)-N-((2-methoxypyridin-4-yl)methyl)-1,2,3,4-tetrahydro-5H-pyrido[4,3-b]indole-5-carboxamide HCl (I-30);
Example 68, (E)-2-(3-(3-chloro-4-fluorophenyl)allyl)-8-cyano-N-((2-methoxypyridin-4-yl)methyl)-1,2,3,4-tetrahydro-5H-pyrido[4,3-b]indole-5-carboxamide HCl (I-31); and
Example 69, (E)-8-cyano-2-(3-(3,4-dichlorophenyl)allyl)-N-((2-methoxypyridin-4-yl)methyl)-1,2,3,4-tetrahydro-5H-pyrido[4,3-b]indole-5-carboxamide HCl (I-39).

Example 70, (E)-2-(3-(4-chloro-3-fluorophenyl)allyl)-8-cyano-N-((2-ethoxypyridin-4-yl)methyl)-1,2,3,4-tetrahydro-5H-pyrido[4,3-b]indole-5-carboxamide, (I-3) was prepared similarly to Example 63 but using (2-ethoxypyridin-4-yl)methanamine and aldehyde intermediate, I-3

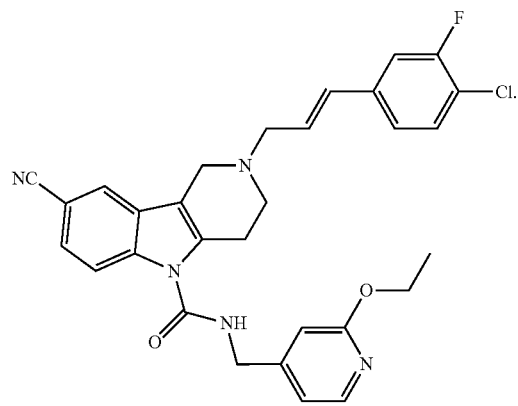 [SMILES: CCOc1cc(CNC(=O)n2c3c(c4cc(C#N)ccc42)CN(C/C=C/c2ccc(Cl)c(F)c2)CC3)ccn1]

The following compounds were prepared similarly to Example 63 but using (2-chloropyridin-4-yl)methanamine and the respective aldehyde intermediate:
Example 71, (E)-2-(3-(4-chloro-3,5-difluorophenyl)allyl)-N-((2-chloropyridin-4-yl)methyl)-8-cyano-1,2,3,4-tetrahydro-5H-pyrido[4,3-b]indole-5-carboxamide HCl (I-1)

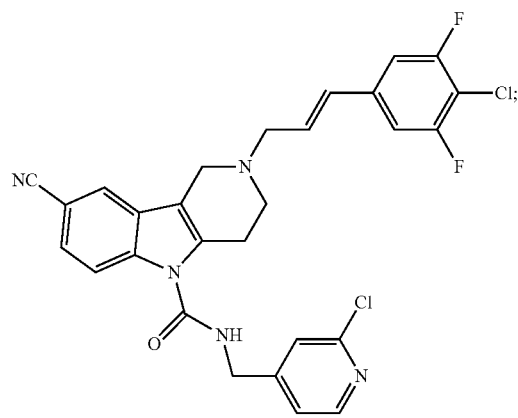 [SMILES: N#Cc1ccc2c(c1)c1c(n2C(=O)NCc2ccnc(F)c2)CCN(C/C=C/c2cc(F)c(Cl)c(F)c2)C1]

Example 72, (E)-2-(3-(4-chloro-3-fluorophenyl)allyl)-N-((2-chloropyridin-4-yl)methyl)-8-cyano-1,2,3,4-tetrahydro-5H-pyrido[4,3-b]indole-5-carboxamide (I-3);
Example 73, (E)-2-(3-(4-bromo-2-fluorophenyl)allyl)-N-((2-chloropyridin-4-yl)methyl)-8-cyano-1,2,3,4-tetrahydro-5H-pyrido[4,3-b]indole-5-carboxamide HCl (I-5);
Example 74, (E)-2-(3-(4-chloro-2,6-difluorophenyl)allyl)-N-((2-chloropyridin-4-yl)methyl)-8-cyano-1,2,3,4-tetrahydro-5H-pyrido[4,3-b]indole-5-carboxamide HCl (I-6);
Example 75, (E)-2-(3-(4-chloro-2-fluorophenyl)allyl)-N-((2-chloropyridin-4-yl)methyl)-8-cyano-1,2,3,4-tetrahydro-5H-pyrido[4,3-b]indole-5-carboxamide (I-7);
Example 76, (E)-N-((2-chloropyridin-4-yl)methyl)-8-cyano-2-(3-(2,4,6-trifluorophenyl)allyl)-1,2,3,4-tetrahydro-5H-pyrido[4,3-b]indole-5-carboxamide HCl (I-9);
Example 77, (E)-2-(3-(2-bromo-5-fluorophenyl)allyl)-N-((2-chloropyridin-4-yl)methyl)-8-cyano-1,2,3,4-tetrahydro-5H-pyrido[4,3-b]indole-5-carboxamide HCl, (I-10);

Example 78, (E)-2-(3-(5-bromo-2-fluorophenyl)allyl)-N-((2-chloropyridin-4-yl)methyl)-8-cyano-1,2,3,4-tetrahydro-5H-pyrido[4,3-b]indole-5-carboxamide HCl (I-11);
Example 79, (E)-2-(3-(3-bromo-4-fluorophenyl)allyl)-N-((2-chloropyridin-4-yl)methyl)-8-cyano-1,2,3,4-tetrahydro-5H-pyrido[4,3-b]indole-5-carboxamide HCl (I-12);
Example 80, (E)-N-((2-chloropyridin-4-yl)methyl)-8-cyano-2-(3-(2,3,4-trifluorophenyl)allyl)-1,2,3,4-tetrahydro-5H-pyrido[4,3-b]indole-5-carboxamide HCl (I-13);
Example 81, (E)-2-(3-(4-bromo-2,3-difluorophenyl)allyl)-N-((2-chloropyridin-4-yl)methyl)-8-cyano-1,2,3,4-tetrahydro-5H-pyrido[4,3-b]indole-5-carboxamide HCl (I-14);
Example 82, (E)-2-(3-(4-chloro-2,3-difluorophenyl)allyl)-N-((2-chloropyridin-4-yl)methyl)-8-cyano-1,2,3,4-tetrahydro-5H-pyrido[4,3-b]indole-5-carboxamide HCl) (I-15);
Example 83, (E)-N-((2-chloropyridin-4-yl)methyl)-8-cyano-2-(3-(perfluorophenyl)allyl)-1,2,3,4-tetrahydro-5H-pyrido[4,3-b]indole-5-carboxamide HCl (I-16);
Example 84, (E)-2-(3-(4-chloro-2,3,5,6-tetrafluorophenyl)allyl)-N-((2-chloropyridin-4-yl)methyl)-8-cyano-1,2,3,4-tetrahydro-5H-pyrido[4,3-b]indole-5-carboxamide HCl (I-17);
Example 85, (E)-2-(3-(4-bromo-3-fluorophenyl)allyl)-N-((2-chloropyridin-4-yl)methyl)-8-cyano-1,2,3,4-tetrahydro-5H-pyrido[4,3-b]indole-5-carboxamide HCl (I-18);
Example 86, (E)-N-((2-chloropyridin-4-yl)methyl)-8-cyano-2-(3-(3-fluoro-5-(trifluoro-methoxy)phenyl)allyl)-1,2,3,4-tetrahydro-5H-pyrido[4,3-b]indole-5-carboxamide (I-22);
Example 87, (E)-2-(3-(2-chloro-4-fluorophenyl)allyl)-N-((2-chloropyridin-4-yl)methyl)-8-cyano-1,2,3,4-tetrahydro-5H-pyrido[4,3-b]indole-5-carboxamide (I-29);
Example 88, (E)-N-((2-chloropyridin-4-yl)methyl)-8-cyano-2-(3-(2,4-difluorophenyl)allyl)-1,2,3,4-tetrahydro-5H-pyrido[4,3-b]indole-5-carboxamide (I-30);
Example 89, (E)-N-((2-chloropyridin-4-yl)methyl)-8-cyano-2-(3-(3,4,5-trifluorophenyl)allyl)-1,2,3,4-tetrahydro-5H-pyrido[4,3-b]indole-5-carboxamide (I-33);
Example 90, (E)-N-((2-chloropyridin-4-yl)methyl)-8-cyano-2-(3-(3,5-difluorophenyl)allyl)-1,2,3,4-tetrahydro-5H-pyrido[4,3-b]indole-5-carboxamide (I-34);
Example 91, (E)-N-((2-chloropyridin-4-yl)methyl)-8-cyano-2-(3-(4-cyanophenyl)allyl)-1,2,3,4-tetrahydro-5H-pyrido[4,3-b]indole-5-carboxamide (I-37);
Example 92, (E)-2-(3-(4-chlorophenyl)allyl)-N-((2-chloropyridin-4-yl)methyl)-8-cyano-1,2,3,4-tetrahydro-5H-pyrido[4,3-b]indole-5-carboxamide (I-38);
Example 93, (E)-N-((2-chloropyridin-4-yl)methyl)-8-cyano-2-(3-(3,4-dichlorophenyl)allyl)-1,2,3,4-tetrahydro-5H-pyrido[4,3-b]indole-5-carboxamide (I-39);
Example 94, (E)-2-(3-(2-bromo-4-fluorophenyl)allyl)-N-((2-chloropyridin-4-yl)methyl)-8-cyano-1,2,3,4-tetrahydro-5H-pyrido[4,3-b]indole-5-carboxamide HCL (I-42);
Example 95, (E)-2-(3-(3-chloro-5-cyanophenyl)allyl)-N-((2-chloropyridin-4-yl)methyl)-8-cyano-1,2,3,4-tetrahydro-5H-pyrido[4,3-b]indole-5-carboxamide (I-55);
Example 96, (E)-2-(3-(4-chloro-3-methylphenyl)allyl)-N-((2-chloropyridin-4-yl)methyl)-8-cyano-1,2,3,4-tetrahydro-5H-pyrido[4,3-b]indole-5-carboxamide HCl (I-59);
Example 97, (E)-2-(3-(3-bromo-4-chlorophenyl)allyl)-N-((2-chloropyridin-4-yl)methyl)-8-cyano-1,2,3,4-tetrahydro-5H-pyrido[4,3-b]indole-5-carboxamide HCl (I-60); and
Example 98, (E)-N-((2-chloropyridin-4-yl)methyl)-8-cyano-2-(3-(3-cyano-4-fluorophenyl)allyl)-1,2,3,4-tetrahydro-5H-pyrido[4,3-b]indole-5-carboxamide HCl (I-20).

The following compounds were prepared similarly to Example 63 but using (2-fluoropyridin-4-yl)methanamine and the respective aldehyde intermediate:
Example 99, (E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide HCl (I-1)

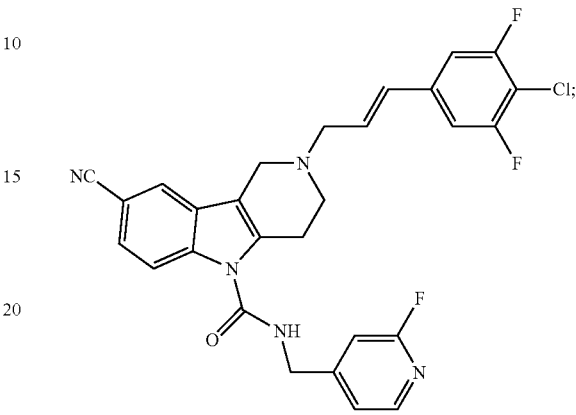

Example 100, (E)-8-cyano-N-((2-fluoropyridin-4-yl)methyl)-2-(3-(4-(methylsulfonyl)-phenyl)allyl)-1,2,3,4-tetrahydro-5H-pyrido[4,3-b]indole-5-carboxamide HCl (I-2);
Example 101, (E)-8-cyano-2-(3-(2,4-dichlorophenyl)allyl)-N-((2-fluoropyridin-4-yl)methyl)-1,2,3,4-tetrahydro-5H-pyrido[4,3-b]indole-5-carboxamide (I-4);
Example 102, (E)-2-(3-(4-bromo-2-fluorophenyl)allyl)-8-cyano-N-((2-fluoropyridin-4-yl)methyl)-1,2,3,4-tetrahydro-5H-pyrido[4,3-b]indole-5-carboxamide (I-5);
Example 103, (E)-2-(3-(4-chloro-2,6-difluorophenyl)allyl)-8-cyano-N-((2-fluoropyridin-4-yl)methyl)-1,2,3,4-tetrahydro-5H-pyrido[4,3-b]indole-5-carboxamide (I-6);
Example 104, (E)-2-(3-(4-chloro-2-fluorophenyl)allyl)-8-cyano-N-((2-fluoropyridin-4-yl)methyl)-1,2,3,4-tetrahydro-5H-pyrido[4,3-b]indole-5-carboxamide (I-7);
Example 105, (E)-2-(3-(4-bromo-3-fluorophenyl)allyl)-8-cyano-N-((2-fluoropyridin-4-yl)methyl)-1,2,3,4-tetrahydro-5H-pyrido[4,3-b]indole-5-carboxamide (I-8);
Example 106, (E)-8-cyano-N-((2-fluoropyridin-4-yl)methyl)-2-(3-(2,4,6-trifluorophenyl)allyl)-1,2,3,4-tetrahydro-5H-pyrido[4,3-b]indole-5-carboxamide (I-9);
Example 107, (E)-2-(3-(2-bromo-5-fluorophenyl)allyl)-8-cyano-N-((2-fluoropyridin-4-yl)methyl)-1,2,3,4-tetrahydro-5H-pyrido[4,3-b]indole-5-carboxamide (I-10);
Example 108, (E)-2-(3-(5-bromo-2-fluorophenyl)allyl)-8-cyano-N-((2-fluoropyridin-4-yl)methyl)-1,2,3,4-tetrahydro-5H-pyrido[4,3-b]indole-5-carboxamide (I-11);
Example 109, (E)-2-(3-(3-bromo-4-fluorophenyl)allyl)-8-cyano-N-((2-fluoropyridin-4-yl)methyl)-1,2,3,4-tetrahydro-5H-pyrido[4,3-b]indole-5-carboxamide HCl (I-12);
Example 110, (E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide HCl (I-13);
Example 111, (E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide HCl (I-14);
Example 112, (E)-8-cyano-2-(3-(3,5-dichloro-4-fluorophenyl)allyl)-N-((2-fluoropyridin-4-yl)methyl)-1,2,3,4-tetrahydro-5H-pyrido[4,3-b]indole-5-carboxamide (I-19);
Example 113, (E)-8-cyano-2-(3-(3-cyano-4-fluorophenyl)allyl)-N-((2-fluoropyridin-4-yl)methyl)-1,2,3,4-tetrahydro-5H-pyrido[4,3-b]indole-5-carboxamide (I-20).

Example 114, (E)-2-(3-(2-chloro-4-fluorophenyl)allyl)-8-cyano-N-((2-fluoropyridin-4-yl)methyl)-1,2,3,4-tetrahydro-5H-pyrido[4,3-b]indole-5-carboxamide (I-29);
Example 115, (E)-8-cyano-2-(3-(2,4-difluorophenyl)allyl)-N-((2-fluoropyridin-4-yl)methyl)-1,2,3,4-tetrahydro-5H-pyrido[4,3-b]indole-5-carboxamide (I-30);
Example 116, (E)-8-cyano-N-((2-fluoropyridin-4-yl)methyl)-2-(3-(3,4,5-trifluorophenyl)allyl)-1,2,3,4-tetrahydro-5H-pyrido[4,3-b]indole-5-carboxamide (I-33);
Example 117, (E)-8-cyano-2-(3-(3,5-difluorophenyl)allyl)-N-((2-fluoropyridin-4-yl)methyl)-1,2,3,4-tetrahydro-5H-pyrido[4,3-b]indole-5-carboxamide (I-34);
Example 118, (E)-2-(3-(3-chloro-2-fluorophenyl)allyl)-8-cyano-N-((2-fluoropyridin-4-yl)methyl)-1,2,3,4-tetrahydro-5H-pyrido[4,3-b]indole-5-carboxamide (I-35);
Example 119, (E)-8-cyano-2-(3-(2,3-difluorophenyl)allyl)-N-((2-fluoropyridin-4-yl)methyl)-1,2,3,4-tetrahydro-5H-pyrido[4,3-b]indole-5-carboxamide (I-36);
Example 120, (E)-8-cyano-2-(3-(4-cyanophenyl)allyl)-N-((2-fluoropyridin-4-yl)methyl)-1,2,3,4-tetrahydro-5H-pyrido[4,3-b]indole-5-carboxamide (I-37);
Example 121, (E)-2-(3-(4-chlorophenyl)allyl)-8-cyano-N-((2-fluoropyridin-4-yl)methyl)-1,2,3,4-tetrahydro-5H-pyrido[4,3-b]indole-5-carboxamide (I-38);
Example 122, (E)-8-cyano-2-(3-(3,4-dichlorophenyl)allyl)-N-((2-fluoropyridin-4-yl)methyl)-1,2,3,4-tetrahydro-5H-pyrido[4,3-b]indole-5-carboxamide (I-39);
Example 123, (E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide HCl (I-40);
Example 124, (E)-8-cyano-N-((2-fluoropyridin-4-yl)methyl)-2-(3-(pyridin-4-yl)allyl)-1,2,3,4-tetrahydro-5H-pyrido[4,3-b]indole-5-carboxamide HCl (I-41);
Example 125, (E)-2-(3-(2-bromo-4-fluorophenyl)allyl)-8-cyano-N-((2-fluoropyridin-4-yl)methyl)-1,2,3,4-tetrahydro-5H-pyrido[4,3-b]indole-5-carboxamide (I-42);
Example 126, (E)-2-(3-(4-bromothiophen-2-yl)allyl)-8-cyano-N-((2-fluoropyridin-4-yl)methyl)-1,2,3,4-tetrahydro-5H-pyrido[4,3-b]indole-5-carboxamide (I-43); and
Example 127, (E)-8-cyano-2-(3-(3-cyano-5-fluorophenyl)allyl)-N-((2-fluoropyridin-4-yl)methyl)-1,2,3,4-tetrahydro-5H-pyrido[4,3-b]indole-5-carboxamide, (I-54).

The following compounds were prepared similarly to Example 63 but using (2-trifluoromethylpyridin-4-yl)methanamine and the respective aldehyde intermediate:
Example 128, (E)-2-(3-(4-chloro-2-fluorophenyl)allyl)-8-cyano-N-((2-(trifluoromethyl)pyridin-4-yl)methyl)-1,2,3,4-tetrahydro-5H-pyrido[4,3-b]indole-5-carboxamide (I-7)

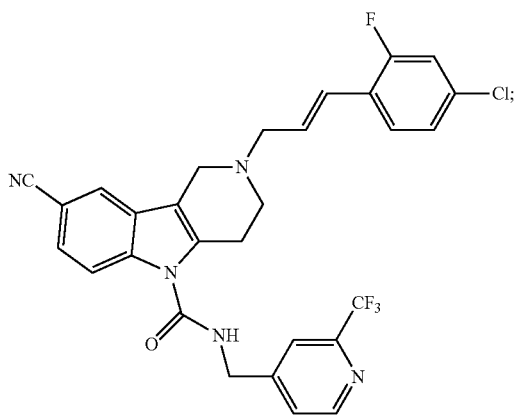 [SMILES: N#Cc1ccc2c(c1)c1c(n2C(=O)NCc2ccnc(C(F)(F)F)c2)CCN(C/C=C/c2ccc(Cl)cc2F)C1]

and
Example 129, (E)-8-cyano-2-(3-(2,4-difluorophenyl)allyl)-N-((2-(trifluoromethyl)pyridin-4-yl)methyl)-1,2,3,4-tetrahydro-5H-pyrido[4,3-b]indole-5-carboxamide (I-30).

The following compounds were prepared similarly to Example 63 but using (2-bromopyridin-4-yl)methanamine and the respective aldehyd intermediate:
Example 130, (E)-N-((2-bromopyridin-4-yl)methyl)-2-(3-(4-chloro-3,5-difluorophenyl)-allyl)-8-cyano-1,2,3,4-tetrahydro-5H-pyrido[4,3-b]indole-5-carboxamide (I-1)

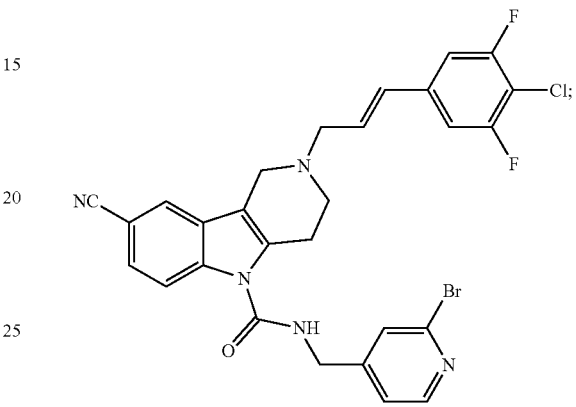

Example 131, (E)-N-((2-bromopyridin-4-yl)methyl)-2-(3-(4-chloro-3-fluorophenyl)allyl)-8-cyano-1,2,3,4-tetrahydro-5H-pyrido[4,3-b]indole-5-carboxamide (I-3);
Example 132, (E)-N-((2-bromopyridin-4-yl)methyl)-2-(3-(4-chloro-2-fluorophenyl)allyl)-8-cyano-1,2,3,4-tetrahydro-5H-pyrido[4,3-b]indole-5-carboxamide (I-7);
Example 133, (E)-N-((2-bromopyridin-4-yl)methyl)-8-cyano-2-(3-(2,3,4-trifluorophenyl)allyl)-1,2,3,4-tetrahydro-5H-pyrido[4,3-b]indole-5-carboxamide (I-13);
Example 134, (E)-N-((2-bromopyridin-4-yl)methyl)-8-cyano-2-(3-(4-cyano-3-fluorophenyl)allyl)-1,2,3,4-tetrahydro-5H-pyrido[4,3-b]indole-5-carboxamide (I-21);
Example 135. (E)-N-((2-bromopyridin-4-yl)methyl)-2-(3-(2-chloro-4-fluorophenyl)allyl)-8-cyano-1,2,3,4-tetrahydro-5H-pyrido[4,3-b]indole-5-carboxamide (I-29);
Example 136, (E)-N-((2-bromopyridin-4-yl)methyl)-8-cyano-2-(3-(2,4-difluorophenyl)allyl)-1,2,3,4-tetrahydro-5H-pyrido[4,3-b]indole-5-carboxamide (I-30);
Example 137, (E)-N-((2-bromopyridin-4-yl)methyl)-2-(3-(3-chloro-4-fluorophenyl)allyl)-8-cyano-1,2,3,4-tetrahydro-5H-pyrido[4,3-b]indole-5-carboxamide HCL (I-31);
Example 138, (E)-N-((2-bromopyridin-4-yl)methyl)-8-cyano-2-(3-(3,4-difluorophenyl)allyl)-1,2,3,4-tetrahydro-5H-pyrido[4,3-b]indole-5-carboxamide (I-32);
Example 139, (E)-N-((2-bromopyridin-4-yl)methyl)-8-cyano-2-(3-(3,4,5-trifluorophenyl)allyl)-1,2,3,4-tetrahydro-5H-pyrido[4,3-b]indole-5-carboxamide (I-33);
Example 140, (E)-N-((2-bromopyridin-4-yl)methyl)-8-cyano-2-(3-(3,5-difluorophenyl)allyl)-1,2,3,4-tetrahydro-5H-pyrido[4,3-b]indole-5-carboxamide (I-34);
Example 141, (E)-N-((2-bromopyridin-4-yl)methyl)-2-(3-(4-chlorophenyl)allyl)-8-cyano-1,2,3,4-tetrahydro-5H-pyrido[4,3-b]indole-5-carboxamide (I-38); and
Example 142, (E)-N-((2-bromopyridin-4-yl)methyl)-8-cyano-2-(3-(4-fluorophenyl)allyl)-1,2,3,4-tetrahydro-5H-pyrido[4,3-b]indole-5-carboxamide (I-40).
Example 143, (Z)-2-(3-(4-chlorophenyl)-2-fluoroallyl)-8-cyano-N-((2-chloropyridin-4-yl)methyl)-1,2,3,4-tetrahydro-5H-

5H-pyrido[4,3-b]indole-5-carboxamide HCl was prepared similarly to Example 63 but using (2-chloropyridin-4-yl)methanamine and aldehyde intermediate, I-28

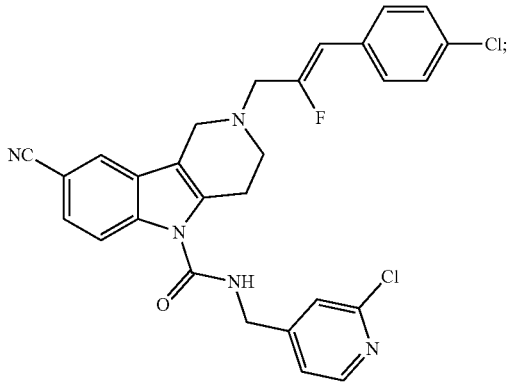 [SMILES: N#Cc1ccc2c(c1)c1c(n2C(=O)NCc2ccnc(Cl)c2)CCN(C/C(F)=C/c2ccc(Cl)cc2)C1]

Example 144, (Z)-2-(3-(4-chlorophenyl)-2-fluoroallyl)-8-cyano-N-((2-fluoropyridin-4-yl)methyl)-1,2,3,4-tetrahydro-5H-pyrido[4,3-b]indole-5-carboxamide HCl was prepared similarly to Example 63 but using (2-fluoropyridin-4-yl)methanamine and aldehyde intermediate, I-28

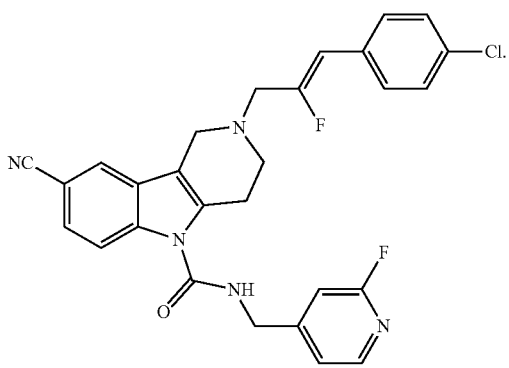 [SMILES: N#Cc1ccc2c(c1)c1c(n2C(=O)NCc2ccnc(F)c2)CCN(C/C(F)=C/c2ccc(Cl)cc2)C1]

Example 145, (E)-N-((2-chloropyridin-4-yl)methyl)-2-(3-(3,4-dichlorophenyl)allyl)-7-methyl-1,2,3,4-tetrahydro-5H-pyrido[4,3-b]indole-5-carboxamide (I-39)

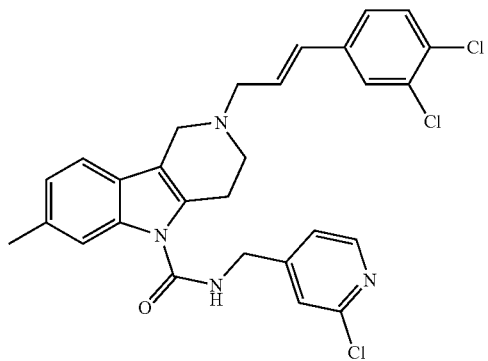 [SMILES: Cc1ccc2c3c(n(C(=O)NCc4ccnc(Cl)c4)c2c1)CCN(C/C=C/c1ccc(Cl)c(Cl)c1)C3]

Step 1: tert-butyl 7-methyl-1,3,4,5-tetrahydropyrido[4,3-b]indole-2-carboxylate; tert-butyl 9-methyl-i 1,3,4,5-tetrahydropyrido[4,3-b]indole-2-carboxylate.

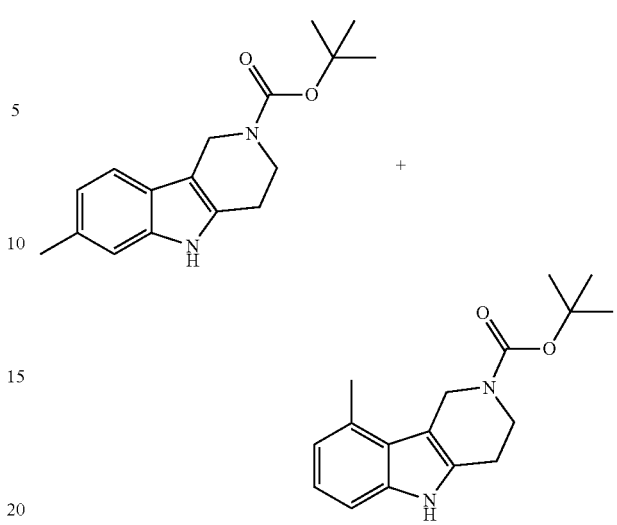

To a solution of m-tolylhydrazine (4.0 g, 32.7 mmol) in IPA (40 mL) was added tert-butyl 4-oxopiperidine-1-carboxylate (6.5 g, 32.6 mmol) and HCl (9.0 mL of a 4.0M solution in dioxane). The reaction mixture was heated to reflux for 18 hours. Next, the reaction mixture was cooled and concentrated under vacuum to afford the crude intermediate as a mixture of regio-isomers. The mixture was purified by SFC chromatography (Berger multigram, column=2-EP 30×250 mm 5 um, MP A=$CO_2$ MP B=0.1% $NH_4$ in MeOH, 15% B, 100 mL/minute, 100bar, 40° C.) to afford tert-butyl 7-methyl-1,3,4,5-tetrahydropyrido[4,3-b]indole-2-carboxylate (1.53 g, 16%) as the first eluting isomer and 9-methyl-i 1,3,4,5-tetrahydropyrido[4,3-b]indole-2-carboxylate (1.9 g, 20%) as the second eluting isomer. $1^{st}$ eluting isomer: LC-Ms (m/z): [M+H-tbutyl]=231. $2^{nd}$ eluting isomer isomer: LC-Ms (m/z): [M+H-tbutyl]=231.

Step 2: tert-butyl 5-[(2-chloro-4-pyridyl)methylcarbamoyl]-7-methyl-3,4-dihydro-1H-pyrido[4,3-b]indole-2-carboxylate.

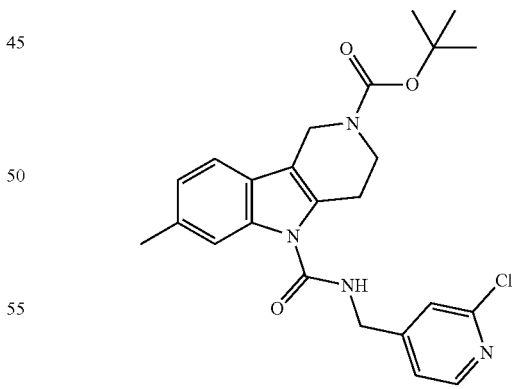

To a stirred solution of 7-methyl-1,3,4,5-tetrahydropyrido[4,3-b]indole-2-carboxylate (500 mg, 1.75 mmol) in THF (25 ml) at 0° C. was added NaH (210 mg, 5.2 mmol). The reaction mixture was allowed to warm to room temperature while stirring for 1 hour. Next, the mixture was cooled back to 0° C. in an ice bath and 2-chloro-4-(isocyanatomethyl)pyridine (590 mg, 3.5 mmol) was added. The reaction was allowed to warm to room temperature while stirring for an additional 1 hour. Ice water was added and the reaction was extracted with EtOAc (2×100 mL). The combined organic phase was washed with brine, dried (Na₂SO₄), and concentrated under vacuum. The crude product was chromatographed (40 g Redi-Sep column) eluting from 25:75 EtOAc: hexanes to 50:50 EtOAc:hexanes to afford title compound (341 mg, 43%) as a solid. LC-MS (m/z): [M+H-tbutyl]=399.
Step 3: N-[(2-chloro-4-pyridyl)methyl]-7-methyl-1,2,3,4-tetrahydropyrido[4,3-b]indole-5-carboxamide

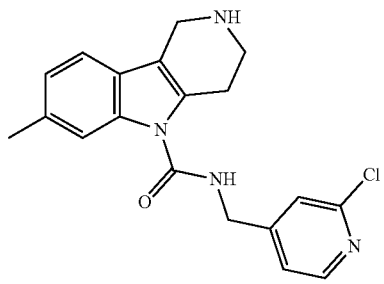 [SMILES: Cc1ccc2c3c(n(C(=O)NCc4ccnc(Cl)c4)c2c1)CCNC3]

To a solution of tert-butyl 5-[(2-chloro-4-pyridyl)methylcarbamoyl]-7-methyl-3,4-dihydro-1H-pyrido[4,3-b]indole-2-carboxylate (330 mg, 7.3 mmol) in DCM (15 mL) at 0° C. was added TFA (1 mL). The reaction was allowed to warm to room temperature and stir for 2 hours. Toluene (35 mL) was added and the reaction was concentrated under vacuum. The resulting TFA salt was dissolved in CH₂Cl₂ (100 mL) and washed with saturated NaHCO₃ (50 mL). The organic phase was separated, dried (Na2SO4), and concentrated under vacuum to afford the free-base intermediate (215 mg, 84%) as a solid. LC-Ms (m/z): [M+H]=355.
Step 4: Preparation of Example 145.

To a flask containing N-[(2-chloro-4-pyridyl)methyl]-7-methyl-1,2,3,4-tetrahydropyrido[4,3-b]indole-5-carboxamide (70 mg, 0.19 mmol) was added aldehyde intermediate I-39 (40 mg, 0.24 mmol), and CH₂Cl₂ (5 mL). The mixture was stirred at room temperature for 15 minutes and sodium triacetoxyborohydride (63 mg, 0.30 mmol) was added. The reaction mixture was stirred at room temperature for 2 hours; next, diluted with CH₂Cl₂ (50 mL), washed with saturated NaHCO₃, dried (Na₂SO₄), and concentrated under vacuum. The crude product was chromatographed (24 g Redi-Sep column) eluting from 50:50 EtOAc:hexanes to 90:10 EtOAc:MeOH to afford the title compound (72 mg, 67%) as a solid.

The following compounds were prepared similarly to Example 145 but using the respective aldehyde intermediate:
Example 146, (E)-2-(3-(4-chlorophenyl)allyl)-N-((2-chloropyridin-4-yl)methyl)-7-methyl-1,2,3,4-tetrahydro-5H-pyrido[4,3-b]indole-5-carboxamide (I-38);
Example 147, (E)-2-(3-(4-chlorophenyl)allyl)-N-((2-chloropyridin-4-yl)methyl)-9-methyl-1,2,3,4-tetrahydro-5H-pyrido[4,3-b]indole-5-carboxamide (I-38);
Example 148, (E)-N-((2-chloropyridin-4-yl)methyl)-2-(3-(3,4-dichlorophenyl)allyl)-9-methyl-1,2,3,4-tetrahydro-5H-pyrido[4,3-b]indole-5-carboxamide (I-39);
Example 149, (E)-N-((2-chloropyridin-4-yl)methyl)-2-(3-(4-fluorophenyl)allyl)-9-methyl-1,2,3,4-tetrahydro-5H-pyrido[4,3-b]indole-5-carboxamide (I-40); and
Example 150, (E)-N-((2-chloropyridin-4-yl)methyl)-7-methyl-2-(3-(4-(trifluoromethyl)-phenyl)allyl)-1,2,3,4-tetrahydro-5H-pyrido[4,3-b]indole-5-carboxamide, (I-46).

The following compounds were prepared similarly to Example 145 but using [3-(trifluoromethyl)phenyl]hydrazine and the respective aldehyde intermediate:
Example 151, (E)-N-((2-chloropyridin-4-yl)methyl)-2-(3-(4-(methylsulfonyl)phenyl)allyl)-7-(trifluoromethyl)-1,2,3,4-tetrahydro-5H-pyrido[4,3-b]indole-5-carboxamide (I-2)

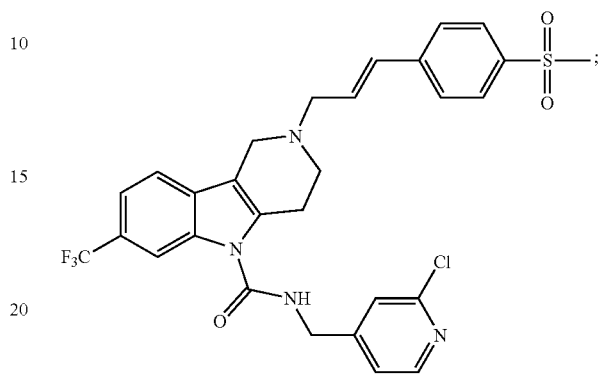

Example 152, (E)-2-(3-(4-chloro-3-fluorophenyl)allyl)-N-((2-chloropyridin-4-yl)methyl)-7-(trifluoromethyl)-1,2,3,4-tetrahydro-5H-pyrido[4,3-b]indole-5-carboxamide (I-3);
Example 153, (E)-N-((2-chloropyridin-4-yl)methyl)-2-(3-(4-cyano-3-fluorophenyl)allyl)-7-(trifluoromethyl)-1,2,3,4-tetrahydro-5H-pyrido[4,3-b]indole-5-carboxamide (I-21);
Example 154, (E)-N-((2-chloropyridin-4-yl)methyl)-2-(3-(3,4-difluorophenyl)allyl)-7-(trifluoromethyl)-1,2,3,4-tetrahydro-5H-pyrido[4,3-b]indole-5-carboxamide (I-32);
Example 155, (E)-N-((2-chloropyridin-4-yl)methyl)-2-(3-(4-cyanophenyl)allyl)-7-(trifluoromethyl)-1,2,3,4-tetrahydro-5H-pyrido[4,3-b]indole-5-carboxamide, (I-37);
Example 156, (E)-2-(3-(4-chlorophenyl)allyl)-N-((2-chloropyridin-4-yl)methyl)-7-(trifluoromethyl)-1,2,3,4-tetrahydro-5H-pyrido[4,3-b]indole-5-carboxamide (I-38);
Example 157, (E)-2-(3-(4-chlorophenyl)allyl)-N-((2-chloropyridin-4-yl)methyl)-9-(trifluoromethyl)-1,2,3,4-tetrahydro-5H-pyrido[4,3-b]indole-5-carboxamide (I-38);
Example 158, (E)-N-((2-chloropyridin-4-yl)methyl)-2-(3-(3,4-dichlorophenyl)allyl)-7-(trifluoromethyl)-1,2,3,4-tetrahydro-5H-pyrido[4,3-b]indole-5-carboxamide (I-39);
Example 159, (E)-N-((2-chloropyridin-4-yl)methyl)-2-(3-(3,4-dichlorophenyl)allyl)-9-(trifluoromethyl)-1,2,3,4-tetrahydro-5H-pyrido[4,3-b]indole-5-carboxamide (I-39);
Example 160, (E)-N-((2-chloropyridin-4-yl)methyl)-2-(3-(4-fluorophenyl)allyl)-7-(trifluoromethyl)-1,2,3,4-tetrahydro-5H-pyrido[4,3-b]indole-5-carboxamide (I-40);
Example 161, (E)-N-((2-chloropyridin-4-yl)methyl)-2-(3-(4-fluorophenyl)allyl)-9-(trifluoromethyl)-1,2,3,4-tetrahydro-5H-pyrido[4,3-b]indole-5-carboxamide (I-40); and
Example 162, (E)-N-((2-chloropyridin-4-yl)methyl)-9-(trifluoromethyl)-2-(3-(4-(trifluoromethyl)-phenyl)allyl)-1,2,3,4-tetrahydro-5H-pyrido[4,3-b]indole-5-carboxamide (I-46).

The following compounds were prepared similarly to Example 145 but using [3-(trifluoromethyl)phenyl]hydrazine, (2-fluoropyridin-4-yl)methanamine, and the respective aldehyde intermediate:
Example 163, (E)-2-(3-(4-chloro-3-fluorophenyl)allyl)-N-((2-fluoropyridin-4-yl)methyl)-7-(trifluoromethyl)-1,2,3,4-tetrahydro-5H-pyrido[4,3-b]indole-5-carboxamide (I-3)

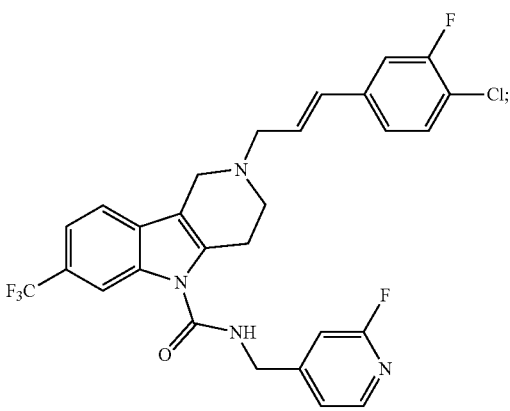 [SMILES: O=C(NCc1ccnc(F)c1)n1c2c(c3ccc(C(F)(F)F)cc31)CN(C/C=C/c1ccc(Cl)c(F)c1)CC2]

Example 164, (E)-2-(3-(4-cyanophenyl)allyl)-N-((2-fluoropyridin-4-yl)methyl)-7-(trifluoromethyl)-1,2,3,4-tetrahydro-5H-pyrido[4,3-b]indole-5-carboxamide (I-37);
Example 165, (E)-2-(3-(4-chlorophenyl)allyl)-N-((2-fluoropyridin-4-yl)methyl)-7-(trifluoromethyl)-1,2,3,4-tetrahydro-5H-pyrido[4,3-b]indole-5-carboxamide (I-38); and
Example 166, (E)-2-(3-(3,4-dichlorophenyl)allyl)-N-((2-fluoropyridin-4-yl)methyl)-7-(trifluoromethyl)-1,2,3,4-tetrahydro-5H-pyrido[4,3-b]indole-5-carboxamide (I-39).
Example 167, (E)-N-((2-chloropyridin-4-yl)methyl)-2-(3-(3,4-dichlorophenyl)allyl)-8-fluoro-1,2,3,4-tetrahydro-5H-pyrido[4,3-b]indole-5-carboxamide (I-39)

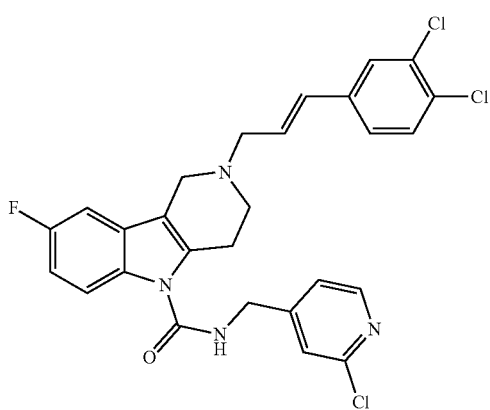 [SMILES: O=C(NCc1ccnc(Cl)c1)n1c2c(c3cc(F)ccc31)CN(C/C=C/c1ccc(Cl)c(Cl)c1)CC2]

Step 1: tert-butyl 5-[(2-chloro-4-pyridyl)methylcarbamoyl]-8-fluoro-3,4-dihydro-1H-pyrido[4,3-b]indole-2-carboxylate.

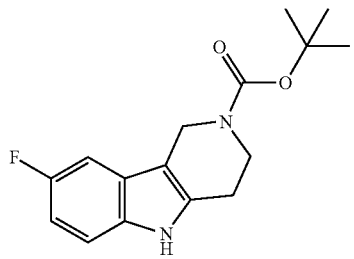 [SMILES: CC(C)(C)OC(=O)N1CCc2[nH]c3ccc(F)cc3c2C1]

To a solution of 8-fluoro-2,3,4,5-tetrahydro-1H-pyrido[4,3-b]indole HCl (1.0 g, 5.3 mmol) in CH₂Cl₂ (50 mL) was added N,N-diisopropylamine (2.3 mL, 13.0 mmol) followed by BOC anhydride (1.0 g, 5.8 mmol). The reaction mixture was stirred at room temperature for 18 hours. Water was added to the reaction mixture and the organic phase was separated, washed with brine, dried (Na₂SO₄), and concentrated under vacuum. The crude mixture was chromatographed (40 g Redi-Sep column) eluting from 100% hexanes to 40:60 EtOAc:hexanes to afford the title compound (1.49 g, 98%) as a solid. LC-Ms (m/z): [M+H-tbutyl]=235.

Step 2: tert-butyl 5-[(2-chloro-4-pyridyl)methylcarbamoyl]-8-fluoro-3,4-dihydro-1H-pyrido[4,3-b]indole-2-carboxylate.

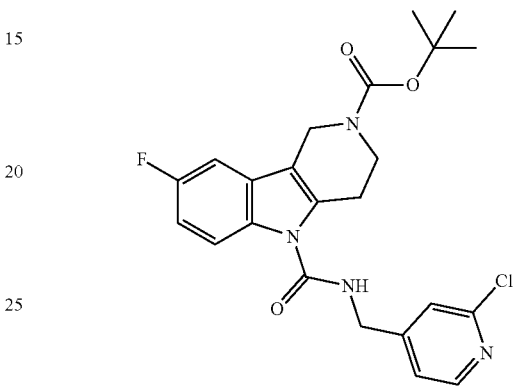

The title compound was synthesized following the same procedure as Step 2 of Example 145 using tert-butyl 5-[(2-chloro-4-pyridyl)methylcarbamoyl]-8-fluoro-3,4-dihydro-1H-pyrido[4,3-b]indole-2-carboxylate in place of tert-butyl 7-methyl-1,3,4,5-tetrahydropyrido[4,3-b]indole-2-carboxylate. LC-MS (m/z): [M+H-tbutyl]=403.

Step 3: N-[(2-chloro-4-pyridyl)methyl]-8-fluoro-1,2,3,4-tetrahydropyrido[4,3-b]indole-5-carboxamide.

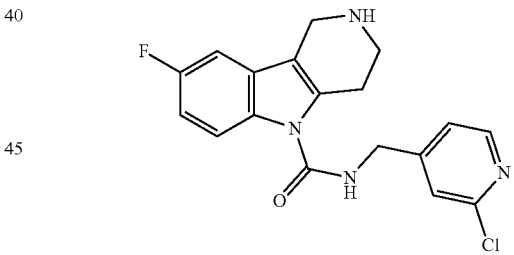

The title compound was synthesized following the same procedure as Step 3 of Example 145 using tert-butyl 5-[(2-chloro-4-pyridyl)methylcarbamoyl]-8-fluoro-3,4-dihydro-1H-pyrido[4,3-b]indole-2-carboxylate in place of tert-butyl 5-[(2-chloro-4-pyridyl)methylcarbamoyl]-7-methyl-3,4-dihydro-1H-pyrido[4,3-b]indole-2-carboxylate. LC-MS (m/z): [M+H]=359.

Step 4: Preparation of Example 167.

The title compound was synthesized following the same procedure as Step 4 of Example 145 using N-[(2-chloro-4-pyridyl)methyl]-8-fluoro-1,2,3,4-tetrahydropyrido[4,3-b]indole-5-carboxamide in place of of N-[(2-chloro-4-pyridyl)methyl]-7-methyl-1,2,3,4-tetrahydropyrido[4,3-b]indole-5-carboxamide.

The following compounds were prepared similarly to Example 167 but using the respective aldehyde intermediate.

Example 168, (E)-N-((2-chloropyridin-4-yl)methyl)-2-(3-(4-cyanophenyl)allyl)-8-fluoro-1,2,3,4-tetrahydro-5H-pyrido[4,3-b]indole-5-carboxamide (I-37); and Example 169, (E)-2-(3-(4-chlorophenyl)allyl)-N-((2-chloro-pyridin-4-yl)methyl)-8-fluoro-1,2,3,4-tetrahydro-5H-pyrido[4,3-b]indole-5-carboxamide (I-38).

Example 170, (E)-2-(3-(4-chlorophenyl)allyl)-8-fluoro-N-(4-fluorobenzyl)-1,2,3,4-tetrahydro-5H-pyrido[4,3-b]indole-5-carboxamide, was prepared similarly to Example 167 but using (4-fluorophenyl)methanamine and aldehyde intermediate, I-38

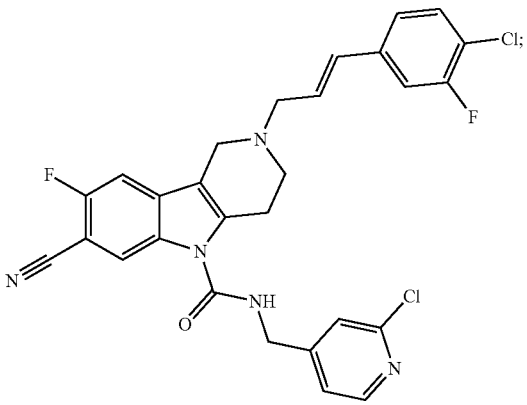

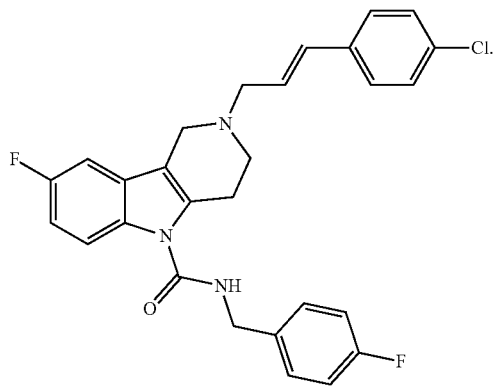 [SMILES: O=C(NCc1ccc(F)cc1)n1c2c(c3cc(F)ccc31)CN(C/C=C/c1ccc(Cl)cc1)CC2]

Example 173, (E)-N-((2-chloropyridin-4-yl)methyl)-7-cyano-2-(3-(4-cyanophenyl)allyl)-8-fluoro-1,2,3,4-tetrahydro-5H-pyrido[4,3-b]indole-5-carboxamide (I-37);

Example 174, (E)-2-(3-(4-chlorophenyl)allyl)-7-cyano-8-fluoro-N-((2-fluoropyridin-4-yl)methyl)-1,2,3,4-tetrahydro-5H-pyrido[4,3-b]indole-5-carboxamide (I-38); and Example 175, (E)-N-((2-chloropyridin-4-yl)methyl)-7-cyano-8-fluoro-2-(3-(4-fluorophenyl)allyl)-1,2,3,4-tetrahydro-5H-pyrido[4,3-b]indole-5-carboxamide (I-40).

Example 176, (E)-2-(3-(4-chlorophenyl)allyl)-N-((2-chloropyridin-4-yl)methyl)-7-cyano-8-methyl-1,2,3,4-tetrahydro-5H-pyrido[4,3-b]indole-5-carboxamide was prepared similarly to Example 145 but using 5-hydrazinyl-2-methylbenzonitrile and aldehyde intermediate, I-38

Example 171, (E)-2-(3-(4-chlorophenyl)allyl)-N-((2-chloro-pyridin-4-yl)methyl)-8-cyano-7-(trifluoromethyl)-1,2,3,4-tetrahydro-5H-pyrido[4,3-b]indole-5-carboxamide, was prepared similarly to Example 145 but using 4-hydrazinyl-2-(trifluoromethyl)benzonitrile and aldehyde intermediate, I-38

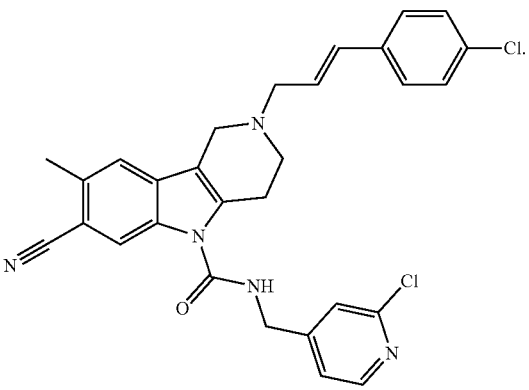

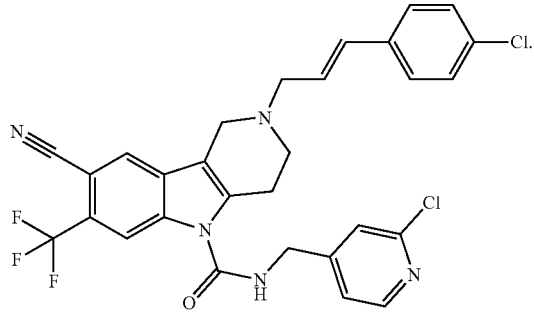 [SMILES: N#Cc1cc2c3c(n(C(=O)NCc4ccnc(Cl)c4)c2cc1C(F)(F)F)CCN(C/C=C/c1ccc(Cl)cc1)C3]

The following compounds were prepared similarly to Example 145 but using 2-fluoro-5-hydrazinylbenzonitrile and the respective aldehyde intermediate:

Example 172, (E)-2-(3-(4-chloro-3-fluorophenyl)allyl)-N-((2-chloropyridin-4-yl)methyl)-7-cyano-8-fluoro-1,2,3,4-tetrahydro-5H-pyrido[4,3-b]indole-5-carboxamide (I-3)

Example 177, (E)-7-chloro-2-(3-(4-chlorophenyl)allyl)-N-((2-chloropyridin-4-yl)methyl)-8-cyano-1,2,3,4-tetrahydro-5H-pyrido[4,3-b]indole-5-carboxamide, was prepared similarly to Example 145 but using 2-chloro-4-hydrazinylbenzonitrile and aldehyde intermediate, I-38

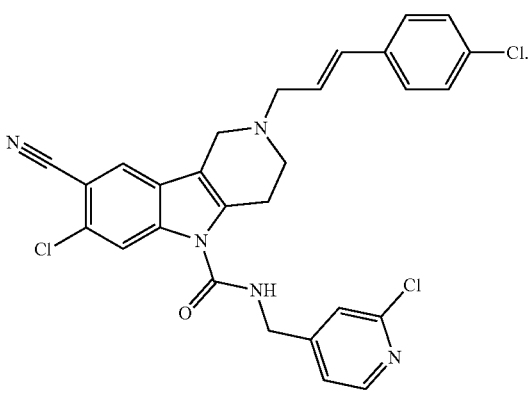 [SMILES: N#Cc1cc2c3c(n(C(=O)NCc4ccnc(Cl)c4)c2cc1Cl)CCN(C/C=C/c1ccc(Cl)cc1)C3]

Example 178, (E)-2-(3-(4-chlorophenyl)allyl)-N-((2-chloropyridin-4-yl)methyl)-8-cyano-7-fluoro-1,2,3,4-tetrahydro-5H-pyrido[4,3-b]indole-5-carboxamide was prepared similarly to Example 145 but using 2-fluoro-4-hydrazinylbenzonitrile and aldehyde intermediate, I-38

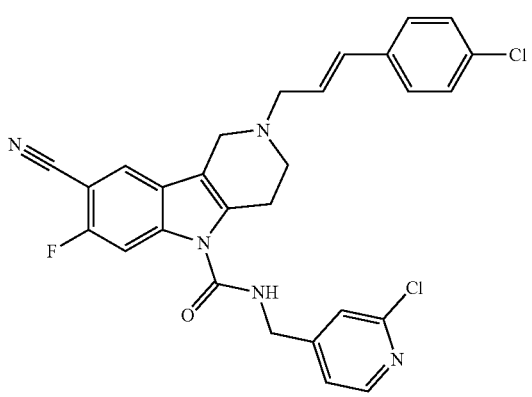 [SMILES: N#Cc1cc2c3c(n(C(=O)NCc4ccnc(Cl)c4)c2cc1F)CCN(C/C=C/c1ccc(Cl)cc1)C3]

The following compounds were prepared similarly to Example 63, but without Step 3 (cyanation), and the respective aldehyde intermediate:

Example 179, (E)-8-bromo-2-(3-(4-chloro-3-fluorophenyl)allyl)-N-((2-chloropyridin-4-yl)methyl)-1,2,3,4-tetrahydro-5H-pyrido[4,3-b]indole-5-carboxamide (I-3)

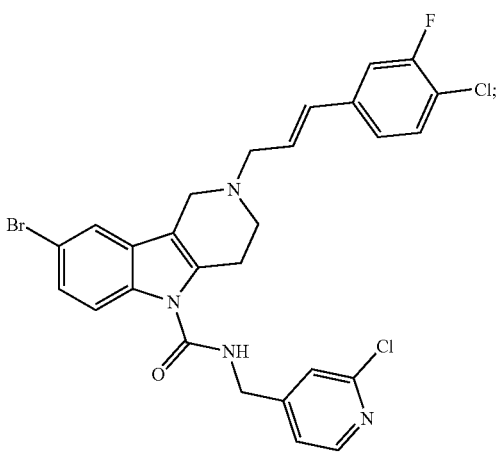 [SMILES: O=C(NCc1ccnc(Cl)c1)n1c2c(c3cc(Br)ccc31)CN(C/C=C/c1ccc(Cl)c(F)c1)CC2]

Example 180, (E)-8-bromo-N-((2-chloropyridin-4-yl)methyl)-2-(3-(4-cyano-3-fluorophenyl)allyl)-1,2,3,4-tetrahydro-5H-pyrido[4,3-b]indole-5-carboxamide HCl (I-21);

Example 181, (E)-8-bromo-N-((2-chloropyridin-4-yl)methyl)-2-(3-(2,4-difluorophenyl)allyl)-1,2,3,4-tetrahydro-5H-pyrido[4,3-b]indole-5-carboxamide (I-30);

Example 182, (E)-8-bromo-2-(3-(3-chloro-4-fluorophenyl)allyl)-N-((2-chloropyridin-4-yl)methyl)-1,2,3,4-tetrahydro-5H-pyrido[4,3-b]indole-5-carboxamide (I-31);

Example 183, (E)-8-bromo-N-((2-chloropyridin-4-yl)methyl)-2-(3-(3,4-difluorophenyl)allyl)-1,2,3,4-tetrahydro-5H-pyrido[4,3-b]indole-5-carboxamide HCl (I-32);

Example 184, (E)-8-bromo-N-((2-chloropyridin-4-yl)methyl)-2-(3-(4-cyanophenyl)allyl)-1,2,3,4-tetrahydro-5H-pyrido[4,3-b]indole-5-carboxamide (I-37);

Example 185, (E)-8-bromo-2-(3-(4-chlorophenyl)allyl)-N-((2-chloropyridin-4-yl)methyl)-1,2,3,4-tetrahydro-5H-pyrido[4,3-b]indole-5-carboxamide (I-38);

Example 186, (E)-8-bromo-N-((2-chloropyridin-4-yl)methyl)-2-(3-(3,4-dichlorophenyl)allyl)-1,2,3,4-tetrahydro-5H-pyrido[4,3-b]indole-5-carboxamide (I-39); and Example 187, (E)-8-bromo-N-((2-chloropyridin-4-yl)methyl)-2-(3-(4-(trifluoromethoxy)phenyl)allyl)-1,2,3,4-tetrahydro-5H-pyrido[4,3-b]indole-5-carboxamide (I-45).

The following compounds were prepared similarly to Example 63, but without Step 3 (cyanation), and using (2-fluoropyridin-4-yl)methanamine and the respective aldehyde intermediate:

Example 188, (E)-8-bromo-2-(3-(4-chloro-3-fluorophenyl)allyl)-N-((2-fluoropyridin-4-yl)methyl)-1,2,3,4-tetrahydro-5H-pyrido[4,3-b]indole-5-carboxamide (I-3)

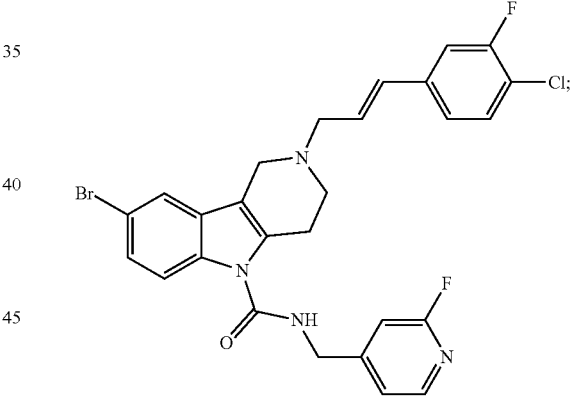

Example 189, (E)-8-bromo-2-(3-(4-cyano-3-fluorophenyl)allyl)-N-((2-fluoropyridin-4-yl)methyl)-1,2,3,4-tetrahydro-5H-pyrido[4,3-b]indole-5-carboxamide (I-21);

Example 190, (E)-8-bromo-2-(3-(3-chloro-4-fluorophenyl)allyl)-N-((2-fluoropyridin-4-yl)methyl)-1,2,3,4-tetrahydro-5H-pyrido[4,3-b]indole-5-carboxamide (I-31);

Example 191, (E)-8-bromo-2-(3-(3,4-difluorophenyl)allyl)-N-((2-fluoropyridin-4-yl)methyl)-1,2,3,4-tetrahydro-5H-pyrido[4,3-b]indole-5-carboxamide (I-32); and Example 192, (E)-8-bromo-2-(3-(4-chlorophenyl)allyl)-N-((2-fluoropyridin-4-yl)methyl)-1,2,3,4-tetrahydro-5H-pyrido[4,3-b]indole-5-carboxamide (I-38).

Example 193, (E)-8-bromo-2-(3-(4-chlorophenyl)allyl)-N-((2-chlorothiazol-5-yl)methyl)-1,2,3,4-tetrahydro-5H-pyrido[4,3-b]indole-5-carboxamide, was prepared similarly to Example 63, but without Step 3 (cyanation), and using (2-chlorothiazol-5-yl)methanamine and aldehyde intermediate, I-38

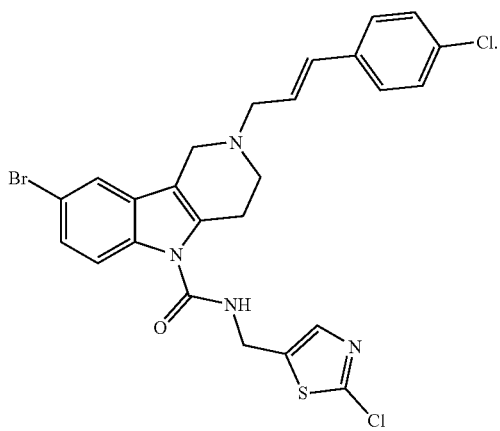 [SMILES: O=C(NCc1cnc(Cl)s1)n1c2c(c3cc(Br)ccc31)CN(C/C=C/c1ccc(Cl)cc1)CC2]

Example 194, (E)-8-bromo-2-(3-(4-chlorophenyl)allyl)-N-((2-chloropyridin-4-yl)methyl)-7-methyl-1,2,3,4-tetrahydro-5H-pyrido[4,3-b]indole-5-carboxamide was prepared similarly to Example 145 but using (4-bromo-3-methylphenyl)hydrazine and aldehyde intermediate, I-38

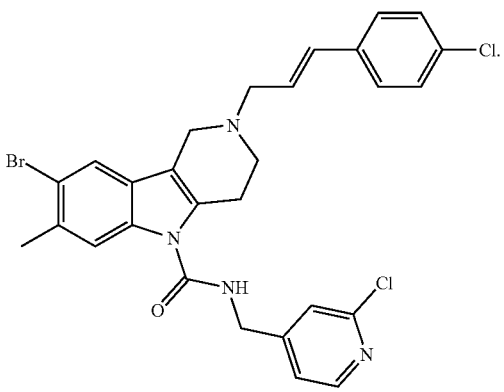 [SMILES: Cc1cc2c(cc1Br)c1c(n2C(=O)NCc2ccnc(Cl)c2)CCN(C/C=C/c2ccc(Cl)cc2)C1]

Example 195, (E)-8-bromo-2-(3-(4-chlorophenyl)allyl)-N-((2-chloropyridin-4-yl)methyl)-7-methoxy-1,2,3,4-tetrahydro-5H-pyrido[4,3-b]indole-5-carboxamide, was prepared similarly to Example 145 but using (4-bromo-3-methoxyphenyl)hydrazine and aldehyde intermediate, I-38

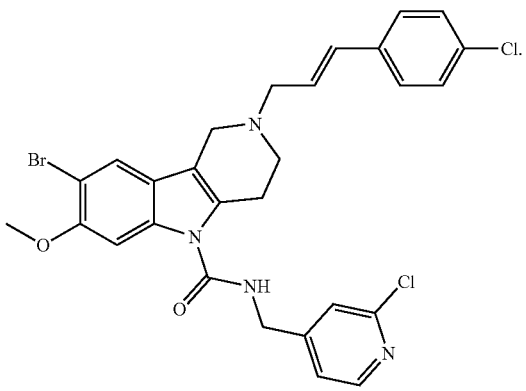 [SMILES: COc1cc2c(cc1Br)c1c(n2C(=O)NCc2ccnc(Cl)c2)CCN(C/C=C/c2ccc(Cl)cc2)C1]

Example 196, (E)-8-bromo-7-chloro-2-(3-(4-chlorophenyl)allyl)-N-((2-chloropyridin-4-yl)methyl)-1,2,3,4-tetrahydro-5H-pyrido[4,3-b]indole-5-carboxamide, was prepared similarly to Example 145 but using (4-bromo-3-chlorophenyl)hydrazine and aldehyde intermediate, I-38

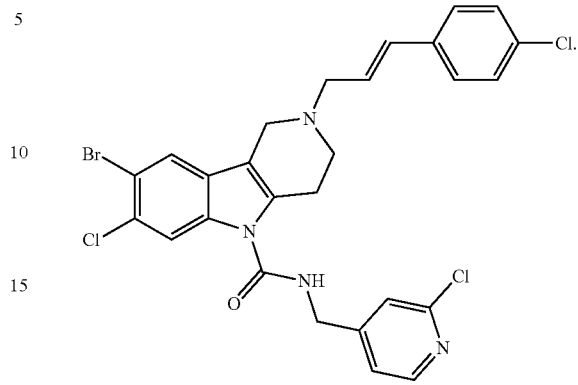

Example 197, (E)-8-bromo-2-(3-(4-chlorophenyl)allyl)-N-((2-chloropyridin-4-yl)methyl)-7-fluoro-1,2,3,4-tetrahydro-5H-pyrido[4,3-b]indole-5-carboxamide, was prepared similarly to Example 145 but using (4-bromo-3-fluorophenyl)hydrazine and aldehyde intermediate, I-38

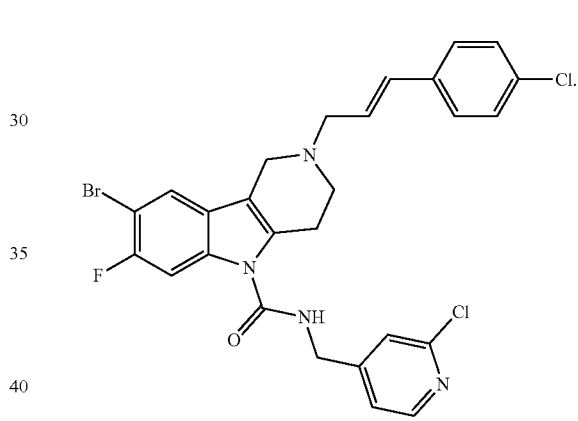

Example 198, (E)-7,8-dibromo-2-(3-(4-chlorophenyl)allyl)-N-((2-chloropyridin-4-yl)methyl)-1,2,3,4-tetrahydro-5H-pyrido[4,3-b]indole-5-carboxamide, was prepared similarly to Example 145 but using (3,4-dibromophenyl)hydrazine and aldehyde intermediate, I-38

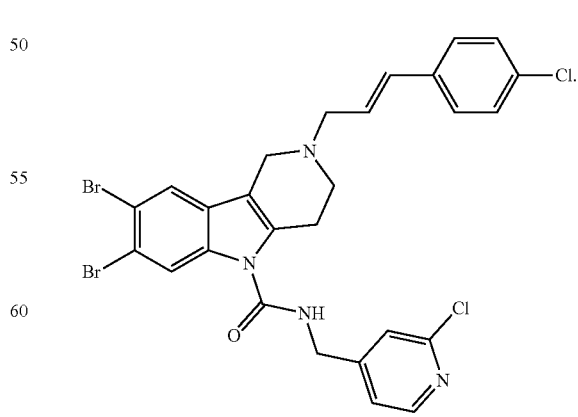

Example 199, (E)-7-bromo-N-((2-chloropyridin-4-yl)methyl)-2-(3-(2,4-difluorophenyl)allyl)-1,2,3,4-tetrahydro- 5H-pyrido[4,3-b]indole-5-carboxamide, was prepared similarly to Example 145 but using (3-bromophenyl)hydrazine and aldehyde intermediate, I-30

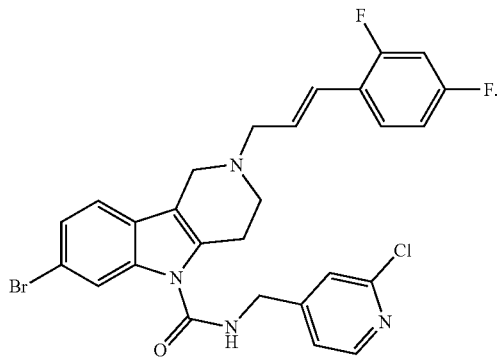 [SMILES: O=C(NCc1ccnc(Cl)c1)n1c2c(c3ccc(Br)cc31)CN(C/C=C/c1ccc(F)cc1F)CC2]

The following compounds were prepared similarly to Example 145 but using (3-bromophenyl)hydrazine, (2-fluoropyridin-4-yl)methanamine, and the respective aldehyde intermediate:

Example 200, (E)-7-bromo-2-(3-(4-chloro-3-fluorophenyl)allyl)-N-((2-fluoropyridin-4-yl)methyl)-1,2,3,4-tetrahydro-5H-pyrido[4,3-b]indole-5-carboxamide (I-3)

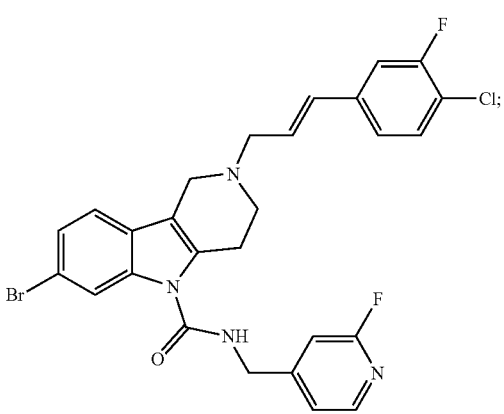 [SMILES: O=C(NCc1ccnc(F)c1)C1C2=C(CN(C/C=C/c3ccc(Cl)c(F)c3)CC2)c2ccc(Cl)cc21]

Example 201, (E)-7-bromo-2-(3-(4-cyano-3-fluorophenyl)allyl)-N-((2-fluoropyridin-4-yl)methyl)-1,2,3,4-tetrahydro-5H-pyrido[4,3-b]indole-5-carboxamide (I-21);

Example 202, (E)-7-bromo-2-(3-(2,4-difluorophenyl)allyl)-N-((2-fluoropyridin-4-yl)methyl)-1,2,3,4-tetrahydro-5H-pyrido[4,3-b]indole-5-carboxamide HCl (I-30);

Example 203, (E)-7-bromo-2-(3-(3-chloro-4-fluorophenyl)allyl)-N-((2-fluoropyridin-4-yl)methyl)-1,2,3,4-tetrahydro-5H-pyrido[4,3-b]indole-5-carboxamide HCl (I-31); and Example 204, (E)-7-bromo-2-(3-(3,4-difluorophenyl)allyl)-N-((2-fluoropyridin-4-yl)methyl)-1,2,3,4-tetrahydro-5H-pyrido[4,3-b]indole-5-carboxamide HCl (I-32).

The following compounds were prepared similarly to Example 145 but using (3-chlorophenyl)hydrazine and the respective aldehyde intermediate:

Example 205, (E)-7-chloro-2-(3-(4-chloro-3-fluorophenyl)allyl)-N-((2-chloropyridin-4-yl)methyl)-1,2,3,4-tetrahydro-5H-pyrido[4,3-b]indole-5-carboxamide (I-3)

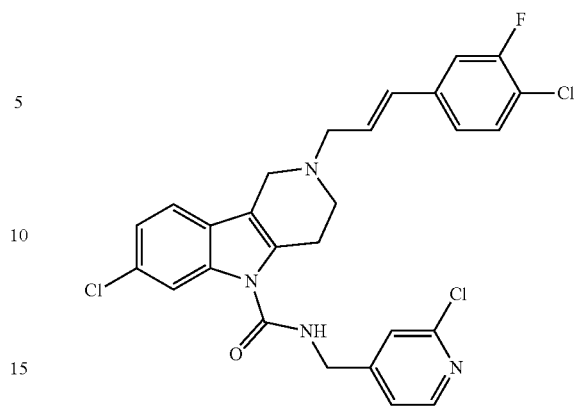

Example 206, (E)-7-chloro-N-((2-chloropyridin-4-yl)methyl)-2-(3-(5-(trifluoromethyl)-pyridin-2-yl)allyl)-1,2,3,4-tetrahydro-5H-pyrido[4,3-b]indole-5-carboxamide (I-18);
Example 207, (E)-9-chloro-N-((2-chloropyridin-4-yl)methyl)-2-(3-(5-(trifluoromethyl)-pyridin-2-yl)allyl)-1,2,3,4-tetrahydro-5H-pyrido[4,3-b]indole-5-carboxamide (I-18);
Example 208, (E)-7-chloro-N-((2-chloropyridin-4-yl)methyl)-2-(3-(4-cyano-3-fluorophenyl)allyl)-1,2,3,4-tetrahydro-5H-pyrido[4,3-b]indole-5-carboxamide (I-21);
Example 209, (E)-7-chloro-N-((2-chloropyridin-4-yl)methyl)-2-(3-(2,4-difluorophenyl)-allyl)-1,2,3,4-tetrahydro-5H-pyrido[4,3-b]indole-5-carboxamide (I-30);
Example 210, (E)-7-chloro-2-(3-(3-chloro-4-fluorophenyl)allyl)-N-((2-chloropyridin-4-yl)methyl)-1,2,3,4-tetrahydro-5H-pyrido[4,3-b]indole-5-carboxamide (I-31);
Example 211, (E)-7-chloro-N-((2-chloropyridin-4-yl)methyl)-2-(3-(3,4-difluorophenyl)allyl)-1,2,3,4-tetrahydro-5H-pyrido[4,3-b]indole-5-carboxamide (I-32);
Example 212, (E)-7-chloro-N-((2-chloropyridin-4-yl)methyl)-2-(3-(4-cyanophenyl)allyl)-1,2,3,4-tetrahydro-5H-pyrido[4,3-b]indole-5-carboxamide (I-37);
Example 213, (E)-7-chloro-2-(3-(4-chlorophenyl)allyl)-N-((2-chloropyridin-4-yl)methyl)-1,2,3,4-tetrahydro-5H-pyrido[4,3-b]indole-5-carboxamide (I-38);
Example 214, (E)-9-chloro-2-(3-(4-chlorophenyl)allyl)-N-((2-chloropyridin-4-yl)methyl)-1,2,3,4-tetrahydro-5H-pyrido[4,3-b]indole-5-carboxamide (I-38);
Example 215, (E)-7-chloro-N-((2-chloropyridin-4-yl)methyl)-2-(3-(3,4-dichlorophenyl)allyl)-1,2,3,4-tetrahydro-5H-pyrido[4,3-b]indole-5-carboxamide (I-39);
Example 216, (E)-9-chloro-N-((2-chloropyridin-4-yl)methyl)-2-(3-(3,4-dichlorophenyl)allyl)-1,2,3,4-tetrahydro-5H-pyrido[4,3-b]indole-5-carboxamide (I-39);
Example 217, (E)-7-chloro-N-((2-chloropyridin-4-yl)methyl)-2-(3-(4-fluorophenyl)allyl)-1,2,3,4-tetrahydro-5H-pyrido[4,3-b]indole-5-carboxamide (I-40);
Example 218, (E)-9-chloro-N-((2-chloropyridin-4-yl)methyl)-2-(3-(4-fluorophenyl)allyl)-1,2,3,4-tetrahydro-5H-pyrido[4,3-b]indole-5-carboxamide (I-40);
Example 219, (E)-7-chloro-N-((2-chloropyridin-4-yl)methyl)-2-(3-(4-methoxyphenyl)allyl)-1,2,3,4-tetrahydro-5H-pyrido[4,3-b]indole-5-carboxamide (I-44);
Example 220, (E)-9-chloro-N-((2-chloropyridin-4-yl)methyl)-2-(3-(4-methoxyphenyl)allyl)-1,2,3,4-tetrahydro-5H-pyrido[4,3-b]indole-5-carboxamide (I-44);
Example 221, (E)-7-chloro-N-((2-chloropyridin-4-yl)methyl)-2-(3-(4-(trifluoromethoxy)-phenyl)allyl)-1,2,3,4-tetrahydro-5H-pyrido[4,3-b]indole-5-carboxamide (I-45);

Example 222, (E)-9-chloro-N-((2-chloropyridin-4-yl)methyl)-2-(3-(4-(trifluoromethoxy)-phenyl)allyl)-1,2,3,4-tetrahydro-5H-pyrido[4,3-b]indole-5-carboxamide (I-45); and Example 223, (E)-7-chloro-N-((2-chloropyridin-4-yl)methyl)-2-(3-(4-(trifluoromethyl)-phenyl)allyl)-1,2,3,4-tetrahydro-5H-pyrido[4,3-b]indole-5-carboxamide (I-46).

The following compounds were prepared similarly to Example 145 but using 3-chlorophenyl)hydrazine, (2-fluoropyridin-4-yl)methanamine, and the respective aldehyde intermediate:

Example 224, (E)-7-chloro-2-(3-(4-chloro-3-fluorophenyl)allyl)-N-((2-fluoropyridin-4-yl)methyl)-1,2,3,4-tetrahydro-5H-pyrido[4,3-b]indole-5-carboxamide (I-3)

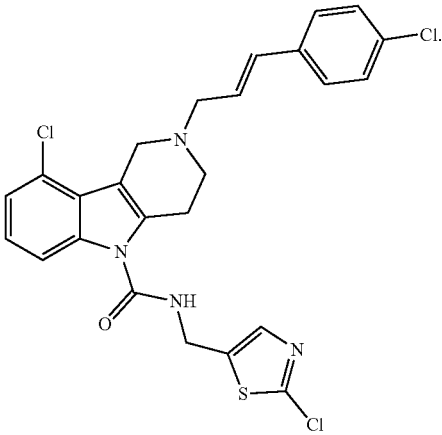 [SMILES: O=C(NCc1cnc(Cl)s1)n1c2c(c3c(Cl)cccc31)CN(C/C=C/c1ccc(Cl)cc1)CC2]

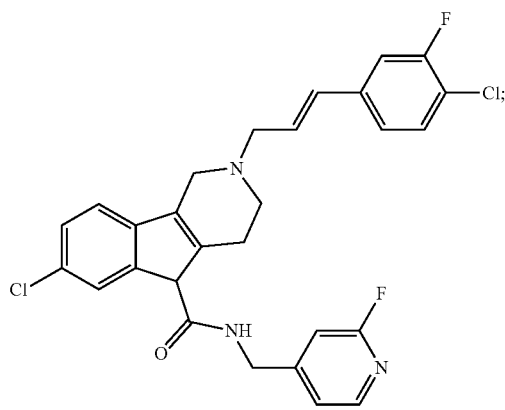

Example 225, (E)-7-chloro-2-(3-(4-cyano-3-fluorophenyl)allyl)-N-((2-fluoropyridin-4-yl)methyl)-1,2,3,4-tetrahydro-5H-pyrido[4,3-b]indole-5-carboxamide (I-21);

Example 226, (E)-7-chloro-2-(3-(2,4-difluorophenyl)allyl)-N-((2-fluoropyridin-4-yl)methyl)-1,2,3,4-tetrahydro-5H-pyrido[4,3-b]indole-5-carboxamide (I-30);

Example 227, (E)-7-chloro-2-(3-(3-chloro-4-fluorophenyl)allyl)-N-((2-fluoropyridin-4-yl)methyl)-1,2,3,4-tetrahydro-5H-pyrido[4,3-b]indole-5-carboxamide (I-31);

Example 228, (E)-7-chloro-2-(3-(3,4-difluorophenyl)allyl)-N-((2-fluoropyridin-4-yl)methyl)-1,2,3,4-tetrahydro-5H-pyrido[4,3-b]indole-5-carboxamide (I-32);

Example 229, (E)-7-chloro-2-(3-(4-chlorophenyl)allyl)-N-((2-fluoropyridin-4-yl)methyl)-1,2,3,4-tetrahydro-5H-pyrido[4,3-b]indole-5-carboxamide (I-38); and Example 230, (E)-9-chloro-2-(3-(4-chlorophenyl)allyl)-N-((2-fluoropyridin-4-yl)methyl)-1,2,3,4-tetrahydro-5H-pyrido[4,3-b]indole-5-carboxamide (I-38).

Example 231, (E)-9-chloro-2-(3-(4-chlorophenyl)allyl)-N-((2-chlorothiazol-5-yl)methyl)-1,2,3,4-tetrahydro-5H-pyrido[4,3-b]indole-5-carboxamide was prepared similarly to Example 145 but using (3-chlorophenyl)hydrazine, (2-chlorothiazol-5-yl)methanamine, and aldehyde intermediate, I-38

The following compounds were prepared similarly to Example 167 but using (4-chlorophenyl)hydrazine and the respective aldehyde intermediate:

Example 232, (E)-8-chloro-2-(3-(4-chloro-3-fluorophenyl)allyl)-N-((2-chloropyridin-4-yl)methyl)-1,2,3,4-tetrahydro-5H-pyrido[4,3-b]indole-5-carboxamide (I-3)

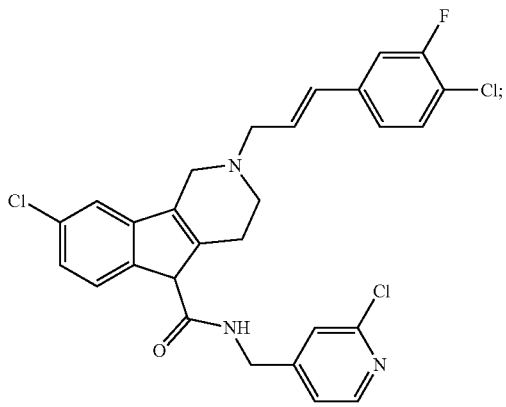 [SMILES: O=C(NCc1ccnc(Cl)c1)C1C2=C(CN(C/C=C/c3ccc(Cl)c(F)c3)CC2)c2cc(Cl)ccc21]

Example 233, (E)-8-chloro-2-(3-(4-chloro-2-fluorophenyl)allyl)-N-((2-chloropyridin-4-yl)methyl)-1,2,3,4-tetrahydro-5H-pyrido[4,3-b]indole-5-carboxamide (I-7);

Example 234, (E)-8-chloro-N-((2-chloropyridin-4-yl)methyl)-2-(3-(3-cyano-4-fluorophenyl)allyl)-1,2,3,4-tetrahydro-5H-pyrido[4,3-b]indole-5-carboxamide (I-20);

Example 235, (E)-8-chloro-N-((2-chloropyridin-4-yl)methyl)-2-(3-(4-cyano-3-fluorophenyl)allyl)-1,2,3,4-tetrahydro-5H-pyrido[4,3-b]indole-5-carboxamide (I-21);

Example 236, (E)-8-chloro-N-((2-chloropyridin-4-yl)methyl)-2-(3-(3-fluoro-5-(trifluoromethoxy)phenyl)allyl)-1,2,3,4-tetrahydro-5H-pyrido[4,3-b]indole-5-carboxamide HCl (I-22);

Example 237, (E)-8-chloro-2-(3-(2-chloro-4-fluorophenyl)allyl)-N-((2-chloropyridin-4-yl)methyl)-1,2,3,4-tetrahydro-5H-pyrido[4,3-b]indole-5-carboxamide (I-29);

Example 238, (E)-8-chloro-N-((2-chloropyridin-4-yl)methyl)-2-(3-(2,4-difluorophenyl)allyl)-1,2,3,4-tetrahydro-5H-pyrido[4,3-b]indole-5-carboxamide (I-30);

Example 239, (E)-8-chloro-2-(3-(3-chloro-4-fluorophenyl)allyl)-N-((2-chloropyridin-4-yl)methyl)-1,2,3,4-tetrahydro-5H-pyrido[4,3-b]indole-5-carboxamide (I-31);

Example 240, (E)-8-chloro-N-((2-chloropyridin-4-yl)methyl)-2-(3-(3,4-difluorophenyl)allyl)-1,2,3,4-tetrahydro-5H-pyrido[4,3-b]indole-5-carboxamide (I-32);

Example 241, (E)-8-chloro-N-((2-chloropyridin-4-yl)methyl)-2-(3-(4-cyanophenyl)allyl)-1,2,3,4-tetrahydro-5H-pyrido[4,3-b]indole-5-carboxamide (I-37);
Example 242, (E)-8-chloro-2-(3-(4-chlorophenyl)allyl)-N-((2-chloropyridin-4-yl)methyl)-1,2,3,4-tetrahydro-5H-pyrido[4,3-b]indole-5-carboxamide (I-38);
Example 243, (E)-8-chloro-N-((2-chloropyridin-4-yl)methyl)-2-(3-(3,4-dichlorophenyl)allyl)-1,2,3,4-tetrahydro-5H-pyrido[4,3-b]indole-5-carboxamide (I-39);
Example 244, (E)-8-chloro-N-((2-chloropyridin-4-yl)methyl)-2-(3-(4-fluorophenyl)allyl)-1,2,3,4-tetrahydro-5H-pyrido[4,3-b]indole-5-carboxamide (I-40);
Example 245, (E)-8-chloro-N-((2-chloropyridin-4-yl)methyl)-2-(3-(4-(trifluoromethoxy)-phenyl)allyl)-1,2,3,4-tetrahydro-5H-pyrido[4,3-b]indole-5-carboxamide (I-45);
Example 246, (E)-8-chloro-N-((2-chloropyridin-4-yl)methyl)-2-(3-(4-(trifluoromethyl)-phenyl)allyl)-1,2,3,4-tetrahydro-5H-pyrido[4,3-b]indole-5-carboxamide (I-46);
Example 247, 8-chloro-N-((2-chloropyridin-4-yl)methyl)-2-((6-chloroquinolin-2-yl)methyl)-1,2,3,4-tetrahydro-5H-pyrido[4,3-b]indole-5-carboxamide HCl (I-48);
Example 248, (E)-8-chloro-N-((2-chloropyridin-4-yl)methyl)-2-(3-(pyridin-4-yl)allyl)-1,2,3,4-tetrahydro-5H-pyrido[4,3-b]indole-5-carboxamide (I-41);
Example 249, (E)-8-chloro-2-(3-(3-chloro-5-fluorophenyl)allyl)-N-((2-chloropyridin-4-yl)methyl)-1,2,3,4-tetrahydro-5H-pyrido[4,3-b]indole-5-carboxamide HCl (I-52);
Example 250, (E)-8-chloro-N-((2-chloropyridin-4-yl)methyl)-2-(3-(3-cyano-5-fluorophenyl)allyl)-1,2,3,4-tetrahydro-5H-pyrido[4,3-b]indole-5-carboxamide HCl (I-54);
Example 251, (E)-8-chloro-2-(3-(3-chloro-5-cyanophenyl)allyl)-N-((2-chloropyridin-4-yl)methyl)-1,2,3,4-tetrahydro-5H-pyrido[4,3-b]indole-5-carboxamide HCl (I-55);
Example 252, (E)-2-(3-(3-bromo-5-fluorophenyl)allyl)-8-chloro-N-((2-chloropyridin-4-yl)methyl)-1,2,3,4-tetrahydro-5H-pyrido[4,3-b]indole-5-carboxamide HCl (I-56); and
Example 253, (E)-8-chloro-N-((2-chloropyridin-4-yl)methyl)-2-(3-(3,5-dichlorophenyl)allyl)-1,2,3,4-tetrahydro-5H-pyrido[4,3-b]indole-5-carboxamide (I-57).

The following compounds were prepared similarly to Example 167 but using (4-chlorophenyl)hydrazine, (2-fluoropyridin-4-yl)methanamine, and the respective aldehyde intermediate:
Example 254, (E)-8-chloro-2-(3-(4-chloro-3-fluorophenyl)allyl)-N-((2-fluoropyridin-4-yl)methyl)-1,2,3,4-tetrahydro-5H-pyrido[4,3-b]indole-5-carboxamide (I-3)

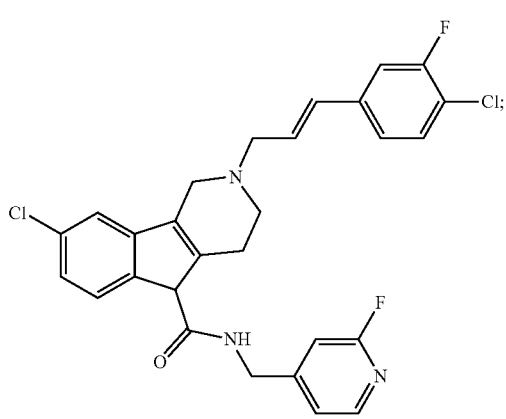 [SMILES: O=C(NCc1ccnc(F)c1)C1C2=C(CN(C/C=C/c3ccc(Cl)c(F)c3)CC2)c2cc(Cl)ccc21]

Example 255, (E)-8-chloro-2-(3-(4-chloro-2-fluorophenyl)allyl)-N-((2-fluoropyridin-4-yl)methyl)-1,2,3,4-tetrahydro-5H-pyrido[4,3-b]indole-5-carboxamide (I-7);
Example 256, (E)-8-chloro-2-(3-(2-chloro-4-fluorophenyl)allyl)-N-((2-fluoropyridin-4-yl)methyl)-1,2,3,4-tetrahydro-5H-pyrido[4,3-b]indole-5-carboxamide (I-29);
Example 257, (E)-8-chloro-2-(3-(2,4-difluorophenyl)allyl)-N-((2-fluoropyridin-4-yl)methyl)-1,2,3,4-tetrahydro-5H-pyrido[4,3-b]indole-5-carboxamide (I-30);
Example 258, (E)-8-chloro-2-(3-(3-chloro-4-fluorophenyl)allyl)-N-((2-fluoropyridin-4-yl)methyl)-1,2,3,4-tetrahydro-5H-pyrido[4,3-b]indole-5-carboxamide (I-31);
Example 259, (E)-8-chloro-2-(3-(3,4-difluorophenyl)allyl)-N-((2-fluoropyridin-4-yl)methyl)-1,2,3,4-tetrahydro-5H-pyrido[4,3-b]indole-5-carboxamide (I-32);
Example 260, (E)-8-chloro-2-(3-(4-chlorophenyl)allyl)-N-((2-fluoropyridin-4-yl)methyl)-1,2,3,4-tetrahydro-5H-pyrido[4,3-b]indole-5-carboxamide (I-38);
Example 261, (E)-8-chloro-2-(3-(3,4-dichlorophenyl)allyl)-N-((2-fluoropyridin-4-yl)methyl)-1,2,3,4-tetrahydro-5H-pyrido[4,3-b]indole-5-carboxamide (I-39);
Example 262, (E)-8-chloro-2-(3-(3-chloro-5-fluorophenyl)allyl)-N-((2-fluoropyridin-4-yl)methyl)-1,2,3,4-tetrahydro-5H-pyrido[4,3-b]indole-5-carboxamide HCl (I-52);
Example 263, (E)-8-chloro-2-(3-(3-cyano-5-fluorophenyl)allyl)-N-((2-fluoropyridin-4-yl)methyl)-1,2,3,4-tetrahydro-5H-pyrido[4,3-b]indole-5-carboxamide HCl (I-54);
Example 264, (E)-2-(3-(3-bromo-5-fluorophenyl)allyl)-8-chloro-N-((2-fluoropyridin-4-yl)methyl)-1,2,3,4-tetrahydro-5H-pyrido[4,3-b]indole-5-carboxamide HCl (I-56); and
Example 265, (E)-8-chloro-2-(3-(3,5-dichlorophenyl)allyl)-N-((2-fluoropyridin-4-yl)methyl)-1,2,3,4-tetrahydro-5H-pyrido[4,3-b]indole-5-carboxamide HCl (I-57).

The following compounds were prepared similarly to Example 167 but using (2-chlorophenyl)hydrazine and the respective aldehyde intermediate:
Example 266, (E)-6-chloro-N-((2-chloropyridin-4-yl)methyl)-2-(3-(5-(trifluoromethyl)-pyridin-2-yl)allyl)-1,2,3,4-tetrahydro-5H-pyrido[4,3-b]indole-5-carboxamide (I-18)

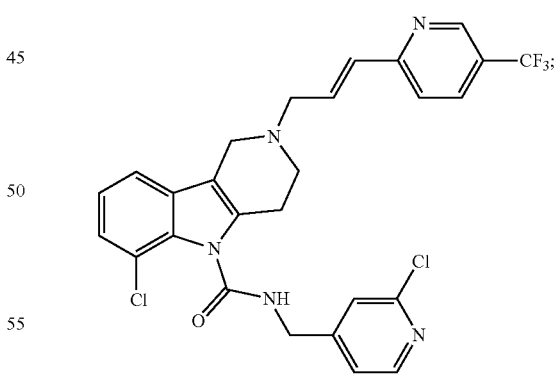

Example 267, (E)-6-chloro-2-(3-(4-chlorophenyl)allyl)-N-((2-chloropyridin-4-yl)methyl)-1,2,3,4-tetrahydro-5H-pyrido[4,3-b]indole-5-carboxamide (I-38);
Example 268, (E)-6-chloro-N-((2-chloropyridin-4-yl)methyl)-2-(3-(3,4-dichlorophenyl)allyl)-1,2,3,4-tetrahydro-5H-pyrido[4,3-b]indole-5-carboxamide (I-39);
Example 269, (E)-6-chloro-N-((2-chloropyridin-4-yl)methyl)-2-(3-(4-fluorophenyl)allyl)-1,2,3,4-tetrahydro-5H-pyrido[4,3-b]indole-5-carboxamide (I-40);

Example 270, (E)-6-chloro-N-((2-chloropyridin-4-yl) methyl)-2-(3-(4-methoxyphenyl)allyl)-1,2,3,4-tetrahydro-5H-pyrido[4,3-b]indole-5-carboxamide (I-44);
Example 271, (E)-6-chloro-N-((2-chloropyridin-4-yl) methyl)-2-(3-(4-(trifluoromethoxy)-phenyl)allyl)-1,2,3,4-tetrahydro-5H-pyrido[4,3-b]indole-5-carboxamide (I-45); and
Example 272, (E)-6-chloro-N-((2-chloropyridin-4-yl) methyl)-2-(3-(4-(trifluoromethyl)-phenyl)allyl)-1,2,3,4-tetrahydro-5H-pyrido[4,3-b]indole-5-carboxamide (I-46).
Example 273, (E)-6-chloro-2-(3-(4-chlorophenyl)allyl)-N-((2-chlorothiazol-5-yl)methyl)-1,2,3,4-tetrahydro-5H-pyrido[4,3-b]indole-5-carboxamide, was prepared similarly to Example 167 but using (2-chlorophenyl)hydrazine, (2-chlorothiazol-5-yl)methanamine, and aldehyde intermediate, I-38

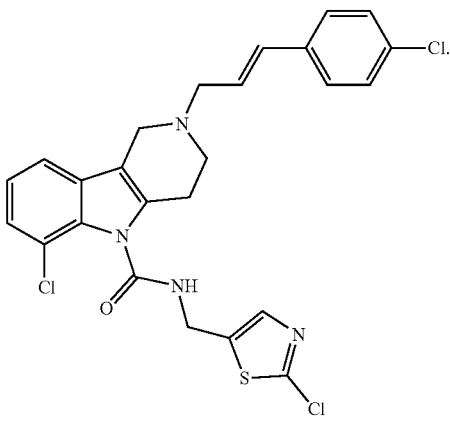 [SMILES: O=C(NCc1cnc(Cl)s1)n1c2c(c3cccc(Cl)c31)CN(C/C=C/c1ccc(Cl)cc1)CC2]

The following compounds were prepared similarly to Example 145 but using (3,4-dichlorophenyl)hydrazine, and the respective aldehyde intermediate:
Example 274, (E)-7,8-dichloro-2-(3-(4-chloro-3-fluorophenyl)allyl)-N-((2-chloropyridin-4-yl)methyl)-1,2,3,4-tetrahydro-5H-pyrido[4,3-b]indole-5-carboxamide (I-3)

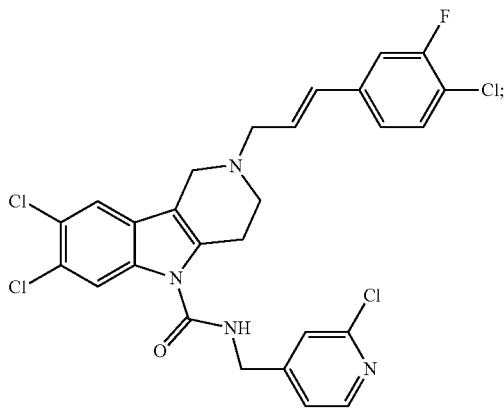 [SMILES: O=C(NCc1ccnc(Cl)c1)n1c2c(c3cc(Cl)c(Cl)cc31)CN(C/C=C/c1ccc(Cl)c(F)c1)CC2]

Example 275, (E)-7,8-dichloro-N-((2-chloropyridin-4-yl) methyl)-2-(3-(4-cyano-3-fluorophenyl)allyl)-1,2,3,4-tetrahydro-5H-pyrido[4,3-b]indole-5-carboxamide (I-21);
Example 276, (E)-7,8-dichloro-N-((2-chloropyridin-4-yl) methyl)-2-(3-(2,4-difluorophenyl)allyl)-1,2,3,4-tetrahydro-5H-pyrido[4,3-b]indole-5-carboxamide (I-30);
Example 277, (E)-7,8-dichloro-2-(3-(3-chloro-4-fluorophenyl)allyl)-N-((2-chloropyridin-4-yl)methyl)-1,2,3,4-tetrahydro-5H-pyrido[4,3-b]indole-5-carboxamide (I-31);
Example 278, (E)-7,8-dichloro-N-((2-chloropyridin-4-yl) methyl)-2-(3-(3,4-difluorophenyl)allyl)-1,2,3,4-tetrahydro-5H-pyrido[4,3-b]indole-5-carboxamide (I-32);
Example 279, (E)-7,8-dichloro-N-((2-chloropyridin-4-yl) methyl)-2-(3-(4-cyanophenyl)allyl)-1,2,3,4-tetrahydro-5H-pyrido[4,3-b]indole-5-carboxamide (I-37);
Example 280, (E)-7,8-dichloro-2-(3-(4-chlorophenyl)allyl)-N-((2-chloropyridin-4-yl)methyl)-1,2,3,4-tetrahydro-5H-pyrido[4,3-b]indole-5-carboxamide (I-38);
Example 281, (E)-7,8-dichloro-N-((2-chloropyridin-4-yl) methyl)-2-(3-(3,4-dichlorophenyl)allyl)-1,2,3,4-tetrahydro-5H-pyrido[4,3-b]indole-5-carboxamide (I-39);
Example 282, (E)-7,8-dichloro-N-((2-chloropyridin-4-yl) methyl)-2-(3-(4-fluorophenyl)allyl)-1,2,3,4-tetrahydro-5H-pyrido[4,3-b]indole-5-carboxamide (I-40);
Example 283, (E)-7,8-dichloro-N-((2-chloropyridin-4-yl) methyl)-2-(3-(4-methoxyphenyl)allyl)-1,2,3,4-tetrahydro-5H-pyrido[4,3-b]indole-5-carboxamide (I-44);
Example 284, (E)-7,8-dichloro-N-((2-chloropyridin-4-yl) methyl)-2-(3-(4-(trifluoro-methoxy)phenyl)allyl)-1,2,3,4-tetrahydro-5H-pyrido[4,3-b]indole-5-carboxamide (I-45); and
Example 285, (E)-7,8-dichloro-N-((2-chloropyridin-4-yl) methyl)-2-(3-(4-(trifluoromethyl)-phenyl)allyl)-1,2,3,4-tetrahydro-5H-pyrido[4,3-b]indole-5-carboxamide (I-46).
The following compounds were prepared similarly to Example 145 but using (3,4-dichlorophenyl)hydrazine, (2-fluoropyridin-4-yl)methanamine, and the respective aldehyde intermediate:
Example 286, (E)-7,8-dichloro-2-(3-(4-chloro-3-fluorophenyl)allyl)-N-((2-fluoropyridin-4-yl)methyl)-1,2,3,4-tetrahydro-5H-pyrido[4,3-b]indole-5-carboxamide HCl (I-3)

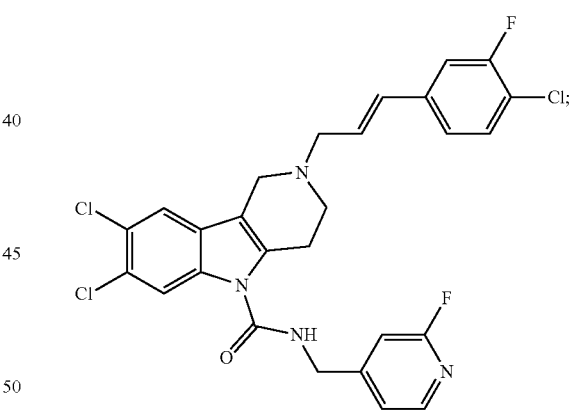

Example 287, (E)-7,8-dichloro-N-((2-fluoropyridin-4-yl) methyl)-2-(3-(5-(trifluoromethyl)pyridin-2-yl)allyl)-1,2,3,4-tetrahydro-5H-pyrido[4,3-b]indole-5-carboxamide (I-18);
Example 288, (E)-7,8-dichloro-2-(3-(4-cyano-3-fluorophenyl)allyl)-N-((2-fluoropyridin-4-yl)methyl)-1,2,3,4-tetrahydro-5H-pyrido[4,3-b]indole-5-carboxamide HCl (I-21);
Example 289, (E)-7,8-dichloro-2-(3-(2,4-difluorophenyl)allyl)-N-((2-fluoropyridin-4-yl)methyl)-1,2,3,4-tetrahydro-5H-pyrido[4,3-b]indole-5-carboxamide HCl (I-30);
Example 290, (E)-7,8-dichloro-2-(3-(3-chloro-4-fluorophenyl)allyl)-N-((2-fluoropyridin-4-yl)methyl)-1,2,3,4-tetrahydro-5H-pyrido[4,3-b]indole-5-carboxamide HCl (I-31);
Example 291, (E)-7,8-dichloro-2-(3-(3,4-difluorophenyl)allyl)-N-((2-fluoropyridin-4-yl)methyl)-1,2,3,4-tetrahydro-5H-pyrido[4,3-b]indole-5-carboxamide HCl (I-32);

Example 292, (E)-7,8-dichloro-2-(3-(4-chlorophenyl)allyl)-N-((2-fluoropyridin-4-yl)methyl)-1,2,3,4-tetrahydro-5H-pyrido[4,3-b]indole-5-carboxamide (I-38); and Example 293, (E)-8,9-dichloro-2-(3-(4-chlorophenyl)allyl)-N-((2-fluoropyridin-4-yl)methyl)-1,2,3,4-tetrahydro-5H-pyrido[4,3-b]indole-5-carboxamide (I-38).

The following compounds were prepared similarly to Example 145 but using (3,4-dichlorophenyl)hydrazine, (2-chlorothiazol-5-yl)methanamine, and the respective aldehyde intermediate:

Example 294, (E)-7,8-dichloro-2-(3-(4-chlorophenyl)allyl)-N-((2-chlorothiazol-5-yl)methyl)-1,2,3,4-tetrahydro-5H-pyrido[4,3-b]indole-5-carboxamide (I-38)

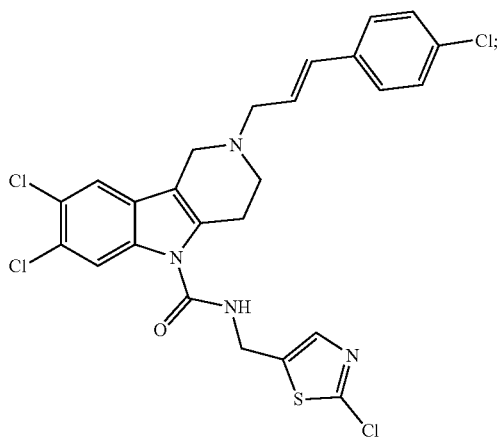 [SMILES: O=C(NCc1cnc(Cl)s1)n1c2c(c3cc(Cl)c(Cl)cc31)CN(C/C=C/c1ccc(Cl)cc1)CC2]

and

Example 295, (E)-8,9-dichloro-2-(3-(4-chlorophenyl)allyl)-N-((2-chlorothiazol-5-yl)methyl)-1,2,3,4-tetrahydro-5H-pyrido[4,3-b]indole-5-carboxamide (I-38).

Example 296, (E)-8-chloro-2-(3-(4-chlorophenyl)allyl)-N-((2-chloropyridin-4-yl)methyl)-7-cyano-1,2,3,4-tetrahydro-5H-pyrido[4,3-b]indole-5-carboxamide, was prepared similarly to Example 145 but using 2-chloro-5-hydrazinylbenzonitrile and aldehyde intermediate, I-38

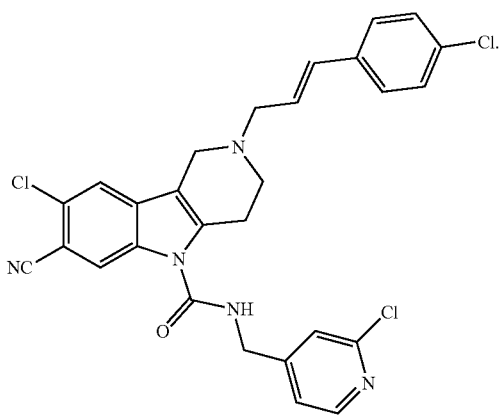 [SMILES: N#Cc1cc2c(cc1Cl)c1c(n2C(=O)NCc2ccnc(Cl)c2)CCN(C/C=C/c2ccc(Cl)cc2)C1]

The following compounds were prepared similarly to Example 145 but using (3-chloro-4-fluorophenyl)hydrazine and the respective aldehyde intermediate:

Example 297, (E)-7-chloro-2-(3-(4-chloro-3-fluorophenyl)allyl)-N-((2-chloropyridin-4-yl)methyl)-8-fluoro-1,2,3,4-tetrahydro-5H-pyrido[4,3-b]indole-5-carboxamide (I-3)

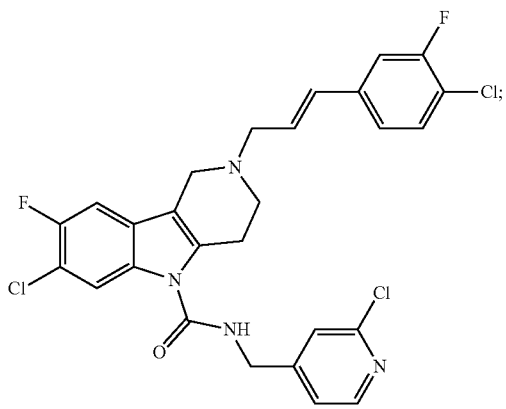 [SMILES: O=C(NCc1ccnc(Cl)c1)n1c2c(c3cc(F)c(Cl)cc31)CN(C/C=C/c1ccc(Cl)c(F)c1)CC2]

Example 298, (E)-7-chloro-N-((2-chloropyridin-4-yl)methyl)-2-(3-(4-cyano-3-fluoro-phenyl)allyl)-8-fluoro-1,2,3,4-tetrahydro-5H-pyrido[4,3-b]indole-5-carboxamide (I-21);

Example 299, (E)-7-chloro-N-((2-chloropyridin-4-yl)methyl)-2-(3-(2,4-difluorophenyl)-allyl)-8-fluoro-1,2,3,4-tetrahydro-5H-pyrido[4,3-b]indole-5-carboxamide (I-30);

Example 300, (E)-7-chloro-N-((2-chloropyridin-4-yl)methyl)-2-(3-(3,4-difluorophenyl)-allyl)-8-fluoro-1,2,3,4-tetrahydro-5H-pyrido[4,3-b]indole-5-carboxamide (I-32);

Example 301, (E)-7-chloro-N-((2-chloropyridin-4-yl)methyl)-8-fluoro-2-(3-(3,4,5-trifluorophenyl)allyl)-1,2,3,4-tetrahydro-5H-pyrido[4,3-b]indole-5-carboxamide (I-33);

Example 302, (E)-7-chloro-N-((2-chloropyridin-4-yl)methyl)-2-(3-(3,5-difluorophenyl)-allyl)-8-fluoro-1,2,3,4-tetrahydro-5H-pyrido[4,3-b]indole-5-carboxamide (I-34);

Example 303, (E)-9-chloro-N-((2-chloropyridin-4-yl)methyl)-2-(3-(4-cyanophenyl)allyl)-8-fluoro-1,2,3,4-tetrahydro-5H-pyrido[4,3-b]indole-5-carboxamide (I-37);

Example 304, (E)-7-chloro-2-(3-(4-chlorophenyl)allyl)-N-((2-chloropyridin-4-yl)methyl)-8-fluoro-1,2,3,4-tetrahydro-5H-pyrido[4,3-b]indole-5-carboxamide (I-38);

Example 305, (E)-9-chloro-2-(3-(4-chlorophenyl)allyl)-N-((2-chloropyridin-4-yl)methyl)-8-fluoro-1,2,3,4-tetrahydro-5H-pyrido[4,3-b]indole-5-carboxamide (I-38);

Example 306, (E)-7-chloro-N-((2-chloropyridin-4-yl)methyl)-8-fluoro-2-(3-(4-fluorophenyl)allyl)-1,2,3,4-tetrahydro-5H-pyrido[4,3-b]indole-5-carboxamide (I-40);

Example 307, (E)-9-chloro-N-((2-chloropyridin-4-yl)methyl)-8-fluoro-2-(3-(4-fluorophenyl)allyl)-1,2,3,4-tetrahydro-5H-pyrido[4,3-b]indole-5-carboxamide (I-40); and Example 308, (E)-9-chloro-N-((2-chloropyridin-4-yl)methyl)-8-fluoro-2-(3-(4-(trifluoro-methyl)phenyl)allyl)-1,2,3,4-tetrahydro-5H-pyrido[4,3-b]indole-5-carboxamide (I-46).

The following compounds were prepared similarly to Example 145 but using (3-chloro-4-fluorophenyl)hydrazine, (2-fluoropyridin-4-yl)methanamine, and the respective aldehyde intermediate:

Example 309, (E)-7-chloro-2-(3-(4-chloro-3-fluorophenyl)allyl)-8-fluoro-N-((2-fluoropyridin-4-yl)methyl)-1,2,3,4-tetrahydro-5H-pyrido[4,3-b]indole-5-carboxamide (I-3)

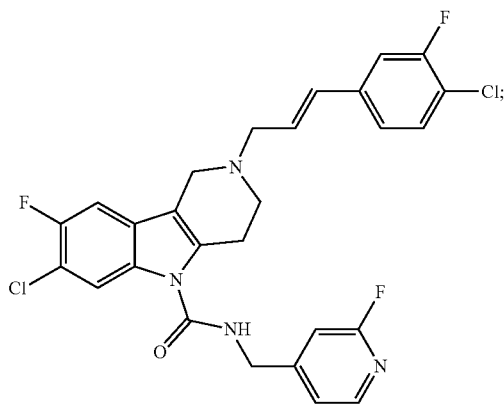 [SMILES: O=C(NCc1ccnc(F)c1)n1c2c(c3cc(F)c(Cl)cc31)CN(C/C=C/c1ccc(Cl)c(F)c1)CC2]

Example 310, (E)-7-chloro-2-(3-(4-chloro-2-fluorophenyl) allyl)-8-fluoro-N-((2-fluoropyridin-4-yl)methyl)-1,2,3,4-tetrahydro-5H-pyrido[4,3-b]indole-5-carboxamide (I-7);

Example 311, (E)-7-chloro-2-(3-(4-cyano-3-fluorophenyl) allyl)-8-fluoro-N-((2-fluoro-pyridin-4-yl)methyl)-1,2,3,4-tetrahydro-5H-pyrido[4,3-b]indole-5-carboxamide (I-21);

Example 312, (E)-7-chloro-2-(3-(2,4-difluorophenyl)allyl)-8-fluoro-N-((2-fluoropyridin-4-yl)methyl)-1,2,3,4-tetrahydro-5H-pyrido[4,3-b]indole-5-carboxamide (I-30);

Example 313, (E)-7-chloro-2-(3-(3-chloro-4-fluorophenyl) allyl)-8-fluoro-N-((2-fluoro-pyridin-4-yl)methyl)-1,2,3,4-tetrahydro-5H-pyrido[4,3-b]indole-5-carboxamide (I-31);

Example 314, (E)-7-chloro-2-(3-(3,4-difluorophenyl)allyl)-8-fluoro-N-((2-fluoropyridin-4-yl)methyl)-1,2,3,4-tetrahydro-5H-pyrido[4,3-b]indole-5-carboxamide (I-32);

Example 315, (E)-7-chloro-8-fluoro-N-((2-fluoropyridin-4-yl)methyl)-2-(3-(3,4,5-trifluorophenyl)allyl)-1,2,3,4-tetrahydro-5H-pyrido[4,3-b]indole-5-carboxamide (I-33);

Example 316, (E)-7-chloro-2-(3-(3,5-difluorophenyl)allyl)-8-fluoro-N-((2-fluoropyridin-4-yl)methyl)-1,2,3,4-tetrahydro-5H-pyrido[4,3-b]indole-5-carboxamide (I-34);

Example 317, (E)-7-chloro-2-(3-(4-chlorophenyl)allyl)-8-fluoro-N-((2-fluoropyridin-4-yl)methyl)-1,2,3,4-tetrahydro-5H-pyrido[4,3-b]indole-5-carboxamide (I-38);

Example 318, (E)-9-chloro-2-(3-(4-chlorophenyl)allyl)-N-((2-chloropyridin-4-yl)methyl)-8-fluoro-1,2,3,4-tetrahydro-5H-pyrido[4,3-b]indole-5-carboxamide (I-38); and Example 319, (E)-7-chloro-8-fluoro-2-(3-(4-fluorophenyl) allyl)-N-((2-fluoropyridin-4-yl)methyl)-1,2,3,4-tetrahydro-5H-pyrido[4,3-b]indole-5-carboxamide (I-40).

The following compounds were prepared similarly to Example 145 but using (3-fluoro-5-(trifluoromethyl)phenyl) hydrazine instead of m-tolylhydrazine and the respective aldehyde intermediate:

Example 320, (E)-N-((2-chloropyridin-4-yl)methyl)-2-(3-(4-cyanophenyl)allyl)-7-fluoro-9-(trifluoromethyl)-1,2,3,4-tetrahydro-5H-pyrido[4,3-b]indole-5-carboxamide (I-37)

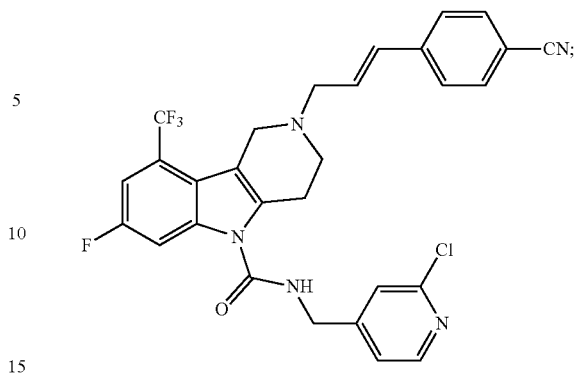

Example 321, (E)-N-((2-chloropyridin-4-yl)methyl)-2-(3-(4-cyanophenyl)allyl)-9-fluoro-7-(trifluoromethyl)-1,2,3,4-tetrahydro-5H-pyrido[4,3-b]indole-5-carboxamide (I-37);

Example 322, (E)-2-(3-(4-chlorophenyl)allyl)-N-((2-chloropyridin-4-yl)methyl)-7-fluoro-9-(trifluoromethyl)-1,2,3,4-tetrahydro-5H-pyrido[4,3-b]indole-5-carboxamide (I-38);

Example 323, (E)-2-(3-(4-chlorophenyl)allyl)-N-((2-chloropyridin-4-yl)methyl)-9-fluoro-7-(trifluoromethyl)-1,2,3,4-tetrahydro-5H-pyrido[4,3-b]indole-5-carboxamide (I-38);

Example 324, (E)-N-((2-chloropyridin-4-yl)methyl)-7-fluoro-2-(3-(4-fluorophenyl)allyl)-9-(trifluoromethyl)-1,2,3,4-tetrahydro-5H-pyrido[4,3-b]indole-5-carboxamide (I-40); and Example 325, (E)-N-((2-chloropyridin-4-yl)methyl)-9-fluoro-2-(3-(4-fluorophenyl)allyl)-7-(trifluoromethyl)-1,2,3,4-tetrahydro-5H-pyrido[4,3-b]indole-5-carboxamide (I-40).

The following compounds were prepared similarly to Example 145 but using (3-fluoro-5-(trifluoromethyl)phenyl) hydrazine instead of m-tolylhydrazine, (2-fluoropyridin-4-yl)methanamine instead of (2-chloropyridin-4-yl)methanamine, and the respective aldehyde intermediate:

Example 326, (E)-2-(3-(4-chlorophenyl)allyl)-7-fluoro-N-((2-fluoropyridin-4-yl)methyl)-9-(trifluoromethyl)-1,2,3,4-tetrahydro-5H-pyrido[4,3-b]indole-5-carboxamide (I-38)

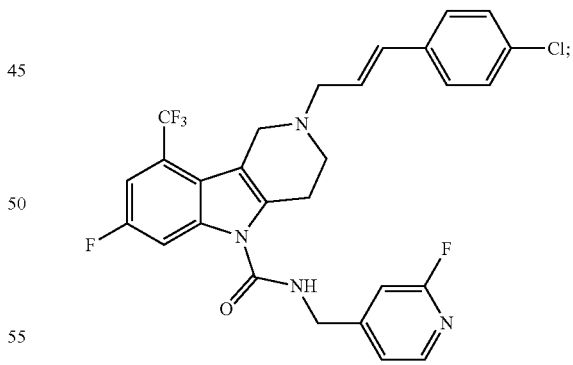

and

Example 327, (E)-2-(3-(4-chlorophenyl)allyl)-9-fluoro-N-((2-fluoropyridin-4-yl)methyl)-7-(trifluoromethyl)-1,2,3,4-tetrahydro-5H-pyrido[4,3-b]indole-5-carboxamide (I-38).

Example 328, (E)-8-chloro-2-(3-(4-chlorophenyl)allyl)-N-((2-chloropyridin-4-yl)methyl)-7-(trifluoromethyl)-1,2,3,4-tetrahydro-5H-pyrido[4,3-b]indole-5-carboxamide, was prepared similarly to Example 145 but using (4-chloro-3-(trifluoromethyl)phenyl)-hydrazine and aldehyde intermediate, I-38

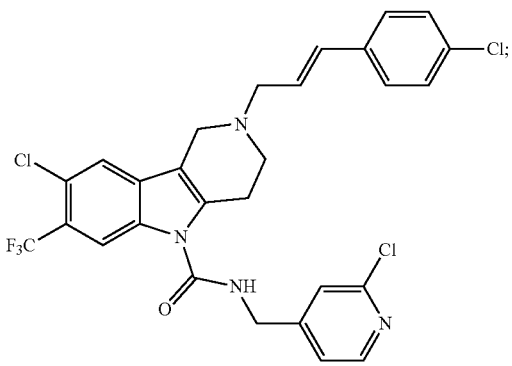 [SMILES: O=C(NCc1ccnc(Cl)c1)n1c2c(c3cc(Cl)c(C(F)(F)F)cc31)CN(C/C=C/c1ccc(Cl)cc1)CC2]

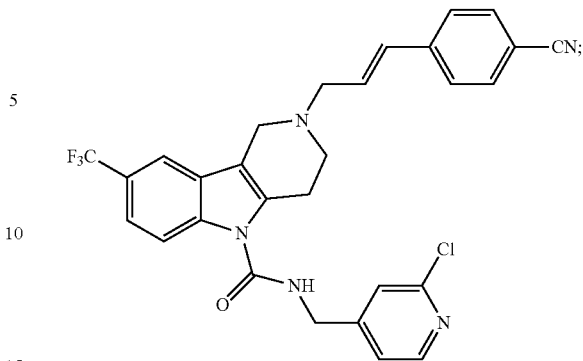

Example 329, (E)-2-(3-(4-chlorophenyl)allyl)-N-((2-chloropyridin-4-yl)methyl)-8-methoxy-7-(trifluoromethyl)-1,2,3,4-tetrahydro-5H-pyrido[4,3-b]indole-5-carboxamide, was prepared similarly to Example 145 but using (4-methoxy-3-(trifluoromethyl)-phenyl)hydrazine and aldehyde intermediate, I-38

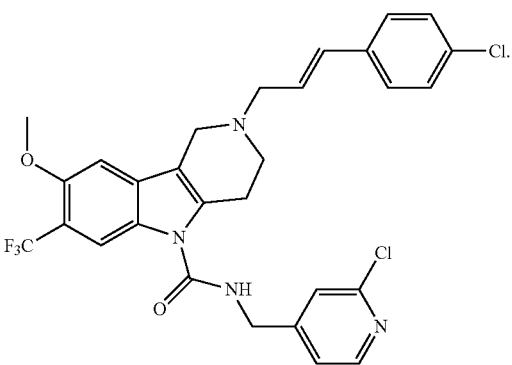 [SMILES: COc1cc2c3c(n(C(=O)NCc4ccnc(Cl)c4)c2cc1C(F)(F)F)CCN(C/C=C/c1ccc(Cl)cc1)C3]

Example 330, (E)-2-(3-(4-chlorophenyl)allyl)-N-((2-chloropyridin-4-yl)methyl)-8-methyl-7-(trifluoromethyl)-1,2,3,4-tetrahydro-5H-pyrido[4,3-b]indole-5-carboxamide, was prepared similarly to Example 145 but using (4-methyl-3-(trifluoromethyl)phenyl)-hydrazine and aldehyde intermediate, I-38

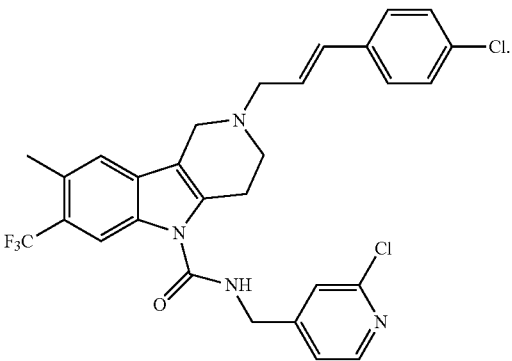 [SMILES: Cc1cc2c3c(n(C(=O)NCc4ccnc(Cl)c4)c2cc1C(F)(F)F)CCN(C/C=C/c1ccc(Cl)cc1)C3]

The following compounds were prepared similarly to Example 167 but using (4-(trifluoromethyl)phenyl)-hydrazine and the respective aldehyde intermediate:
Example 331, (E)-N-((2-chloropyridin-4-yl)methyl)-2-(3-(4-cyanophenyl)allyl)-8-(trifluoromethyl)-1,2,3,4-tetrahydro-5H-pyrido[4,3-b]indole-5-carboxamide (I-37)

Example 332, (E)-2-(3-(4-chlorophenyl)allyl)-N-((2-chloropyridin-4-yl)methyl)-8-(trifluoromethyl)-1,2,3,4-tetrahydro-5H-pyrido[4,3-b]indole-5-carboxamide (I-38);
Example 333, (E)-N-((2-chloropyridin-4-yl)methyl)-2-(3-(3,4-dichlorophenyl)allyl)-8-(trifluoromethyl)-1,2,3,4-tetrahydro-5H-pyrido[4,3-b]indole-5-carboxamide (I-39);
Example 334, (E)-N-((2-chloropyridin-4-yl)methyl)-2-(3-(4-fluorophenyl)allyl)-8-(trifluoromethyl)-1,2,3,4-tetrahydro-5H-pyrido[4,3-b]indole-5-carboxamide (I-40); and
Example 335, (E)-N-((2-chloropyridin-4-yl)methyl)-2-(3-(4-(trifluoromethoxy)phenyl)allyl)-8-(trifluoromethyl)-1,2,3,4-tetrahydro-5H-pyrido[4,3-b]indole-5-carboxamide (I-45).

The following compounds were prepared similarly to Example 145 but using (3-(trifluoromethoxy)phenyl)hydrazine and the respective aldehyde intermediate:
Example 336, (E)-2-(3-(4-chloro-3-fluorophenyl)allyl)-N-((2-chloropyridin-4-yl)methyl)-7-(trifluoromethoxy)-1,2,3,4-tetrahydro-5H-pyrido[4,3-b]indole-5-carboxamide (I-3)

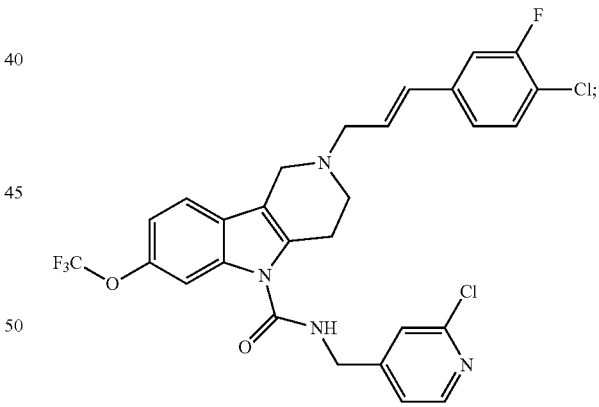

Example 337, (E)-N-((2-chloropyridin-4-yl)methyl)-2-(3-(2,4-dichlorophenyl)allyl)-7-(trifluoromethoxy)-1,2,3,4-tetrahydro-5H-pyrido[4,3-b]indole-5-carboxamide (I-4);
Example 338, (E)-2-(3-(4-bromo-2-fluorophenyl)allyl)-N-((2-chloropyridin-4-yl)methyl)-7-(trifluoromethoxy)-1,2,3,4-tetrahydro-5H-pyrido[4,3-b]indole-5-carboxamide (I-5);
Example 339, (E)-2-(3-(4-chloro-2,6-difluorophenyl)allyl)-N-((2-chloropyridin-4-yl)-methyl)-7-(trifluoromethoxy)-1,2,3,4-tetrahydro-5H-pyrido[4,3-b]indole-5-carboxamide (I-6);
Example 340, (E)-2-(3-(4-chloro-2-fluorophenyl)allyl)-N-((2-chloropyridin-4-yl)methyl)-7-(trifluoromethoxy)-1,2,3,4-tetrahydro-5H-pyrido[4,3-b]indole-5-carboxamide (I-7);

Example 341, (E)-N-((2-chloropyridin-4-yl)methyl)-7-(trifluoromethoxy)-2-(3-(2,4,6-trifluorophenyl)allyl)-1,2,3,4-tetrahydro-5H-pyrido[4,3-b]indole-5-carboxamide (I-9);
Example 342, (E)-N-((2-chloropyridin-4-yl)methyl)-7-(trifluoromethoxy)-2-(3-(5-(trifluoromethyl)pyridin-2-yl)allyl)-1,2,3,4-tetrahydro-5H-pyrido[4,3-b]indole-5-carboxamide (I-18);
Example 343, (E)-N-((2-chloropyridin-4-yl)methyl)-9-(trifluoromethoxy)-2-(3-(5-(trifluoromethyl)pyridin-2-yl)allyl)-1,2,3,4-tetrahydro-5H-pyrido[4,3-b]indole-5-carboxamide (I-18);
Example 344, (E)-N-((2-chloropyridin-4-yl)methyl)-2-(3-(3-cyano-4-fluorophenyl)allyl)-7-(trifluoromethoxy)-1,2,3,4-tetrahydro-5H-pyrido[4,3-b]indole-5-carboxamide (I-20);
Example 345, (E)-N-((2-chloropyridin-4-yl)methyl)-2-(3-(4-cyano-3-fluorophenyl)allyl)-7-(trifluoromethoxy)-1,2,3,4-tetrahydro-5H-pyrido[4,3-b]indole-5-carboxamide (I-21);
Example 346, (E)-2-(3-(2-chloro-4-fluorophenyl)allyl)-N-((2-chloropyridin-4-yl)methyl)-7-(trifluoromethoxy)-1,2,3,4-tetrahydro-5H-pyrido[4,3-b]indole-5-carboxamide (I-29);
Example 347, (E)-N-((2-chloropyridin-4-yl)methyl)-2-(3-(2,4-difluorophenyl)allyl)-7-(trifluoromethoxy)-1,2,3,4-tetrahydro-5H-pyrido[4,3-b]indole-5-carboxamide (I-30);
Example 348, (E)-2-(3-(3-chloro-4-fluorophenyl)allyl)-N-((2-chloropyridin-4-yl)methyl)-7-(trifluoromethoxy)-1,2,3,4-tetrahydro-5H-pyrido[4,3-b]indole-5-carboxamide (I-31);
Example 349, (E)-N-((2-chloropyridin-4-yl)methyl)-2-(3-(3,4-difluorophenyl)allyl)-7-(trifluoromethoxy)-1,2,3,4-tetrahydro-5H-pyrido[4,3-b]indole-5-carboxamide (I-32);
Example 350, (E)-N-((2-chloropyridin-4-yl)methyl)-7-(trifluoromethoxy)-2-(3-(3,4,5-trifluorophenyl)allyl)-1,2,3,4-tetrahydro-5H-pyrido[4,3-b]indole-5-carboxamide (I-33);
Example 351, (E)-N-((2-chloropyridin-4-yl)methyl)-2-(3-(4-cyanophenyl)allyl)-7-(trifluoromethoxy)-1,2,3,4-tetrahydro-5H-pyrido[4,3-b]indole-5-carboxamide (I-37);
Example 352, (E)-N-((2-chloropyridin-4-yl)methyl)-2-(3-(4-cyanophenyl)allyl)-9-(trifluoromethoxy)-1,2,3,4-tetrahydro-5H-pyrido[4,3-b]indole-5-carboxamide (I-37).
Example 353, (E)-2-(3-(4-chlorophenyl)allyl)-N-((2-chloropyridin-4-yl)methyl)-7-(trifluoromethoxy)-1,2,3,4-tetrahydro-5H-pyrido[4,3-b]indole-5-carboxamide (I-38);
Example 354, (E)-2-(3-(4-chlorophenyl)allyl)-N-((2-chloropyridin-4-yl)methyl)-9-(trifluoromethoxy)-1,2,3,4-tetrahydro-5H-pyrido[4,3-b]indole-5-carboxamide (I-38);
Example 355, (E)-N-((2-chloropyridin-4-yl)methyl)-2-(3-(3,4-dichlorophenyl)allyl)-7-(trifluoromethoxy)-1,2,3,4-tetrahydro-5H-pyrido[4,3-b]indole-5-carboxamide (I-39);
Example 356, (E)-N-((2-chloropyridin-4-yl)methyl)-2-(3-(4-fluorophenyl)allyl)-7-(trifluoromethoxy)-1,2,3,4-tetrahydro-5H-pyrido[4,3-b]indole-5-carboxamide (I-40);
Example 357, (E)-N-((2-chloropyridin-4-yl)methyl)-2-(3-(4-fluorophenyl)allyl)-9-(trifluoromethoxy)-1,2,3,4-tetrahydro-5H-pyrido[4,3-b]indole-5-carboxamide (I-40);
Example 358, (E)-N-((2-chloropyridin-4-yl)methyl)-2-(3-(4-methoxyphenyl)allyl)-7-(trifluoromethoxy)-1,2,3,4-tetrahydro-5H-pyrido[4,3-b]indole-5-carboxamide (I-44);
Example 359, (E)-N-((2-chloropyridin-4-yl)methyl)-2-(3-(4-methoxyphenyl)allyl)-9-(trifluoromethoxy)-1,2,3,4-tetrahydro-5H-pyrido[4,3-b]indole-5-carboxamide (I-44);
Example 360, (E)-N-((2-chloropyridin-4-yl)methyl)-7-(trifluoromethoxy)-2-(3-(4-(trifluoro-methoxy)phenyl)allyl)-1,2,3,4-tetrahydro-5H-pyrido[4,3-b]indole-5-carboxamide (I-45);
Example 361, (E)-N-((2-chloropyridin-4-yl)methyl)-9-(trifluoromethoxy)-2-(3-(4-(trifluoro-methoxy)phenyl)allyl)-1,2,3,4-tetrahydro-5H-pyrido[4,3-b]indole-5-carboxamide (I-45);
Example 362, (E)-N-((2-chloropyridin-4-yl)methyl)-7-(trifluoromethoxy)-2-(3-(4-(trifluoro-methyl)phenyl)allyl)-1,2,3,4-tetrahydro-5H-pyrido[4,3-b]indole-5-carboxamide (I-46);
Example 363, (E)-N-((2-chloropyridin-4-yl)methyl)-9-(trifluoromethoxy)-2-(3-(4-(trifluoro-methyl)phenyl)allyl)-1,2,3,4-tetrahydro-5H-pyrido[4,3-b]indole-5-carboxamide (I-46);
Example 364, 2-((6-bromonaphthalen-2-yl)methyl)-N-((2-chloropyridin-4-yl)methyl)-7-(trifluoromethoxy)-1,2,3,4-tetrahydro-5H-pyrido[4,3-b]indole-5-carboxamide (I-47);
Example 365, 2-((7-chloroisoquinolin-3-yl)methyl)-N-((2-chloropyridin-4-yl)methyl)-7-(trifluoromethoxy)-1,2,3,4-tetrahydro-5H-pyrido[4,3-b]indole-5-carboxamide (I-48);
Example 366, N-((2-chloropyridin-4-yl)methyl)-2-((6-fluoronaphthalen-2-yl)methyl)-7-(trifluoromethoxy)-1,2,3,4-tetrahydro-5H-pyrido[4,3-b]indole-5-carboxamide (I-49);
Example 367, N-((2-chloropyridin-4-yl)methyl)-2-((2-chloroquinolin-6-yl)methyl)-7-(trifluoromethoxy)-1,2,3,4-tetrahydro-5H-pyrido[4,3-b]indole-5-carboxamide (I-50); and
Example 368, 2-((6-chloronaphthalen-2-yl)methyl)-N-((2-chloropyridin-4-yl)methyl)-7-(trifluoromethoxy)-1,2,3,4-tetrahydro-5H-pyrido[4,3-b]indole-5-carboxamide (I-51).

The following compounds were prepared similarly to Example 145 but using (3-(trifluoromethoxy)phenyl)hydrazine, (2-fluoropyridin-4-yl)methanamine, and the respective aldehyde intermediate:
Example 369, (E)-2-(3-(4-chloro-3-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-3)

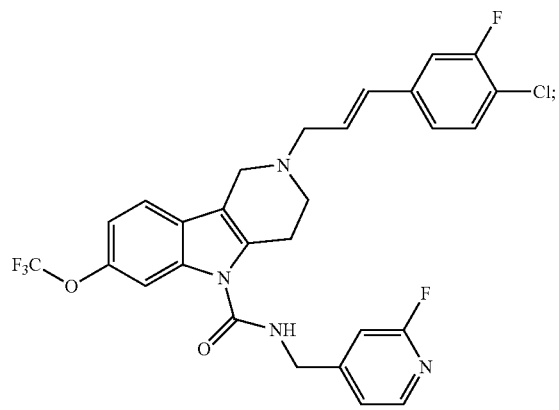 [SMILES: O=C(NCc1ccnc(F)c1)n1c2c(c3ccc(OC(F)(F)F)cc31)CN(C/C=C/c1ccc(Cl)c(F)c1)CC2]

Example 370, (E)-2-(3-(2,4-dichlorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-4);
Example 371, (E)-2-(3-(4-chloro-2-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-7);
Example 372, (E)-2-(3-(4-cyano-3-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-21);
Example 373, (E)-2-(3-(2-chloro-4-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-29);
Example 374, (E)-2-(3-(2,4-difluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-30);
Example 375, (E)-2-(3-(3-chloro-4-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-31);

Example 376, (E)-2-(3-(3,4-difluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-32);

Example 377, (E)-N-((2-fluoropyridin-4-yl)methyl)-7-(trifluoromethoxy)-2-(3-(3,4,5-trifluorophenyl)allyl)-1,2,3,4-tetrahydro-5H-pyrido[4,3-b]indole-5-carboxamide (I-33);

Example 378, (E)-2-(3-(3,5-difluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-34);

Example 379, (E)-2-(3-(4-chlorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-38);

Example 379a, (E)-2-(3-(4-chlorophenyl)allyl)-N-((2-fluoropyridin-4-yl)methyl)-9-(trifluoromethoxy)-1,2,3,4-tetrahydro-5H-pyrido[4,3-b]indole-5-carboxamide (I-40);

Example 380, (E)-2-(3-(3-chloro-5-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide (I-52);

Example 381, (E)-2-(3-(3-cyano-5-fluorophenyl)allyl)-N-((2-fluoropyridin-4-yl)methyl)-7-(trifluoromethoxy)-1,2,3,4-tetrahydro-5H-pyrido[4,3-b]indole-5-carboxamide HCl (I-54);

Example 382, (E)-2-(3-(4-chlorophenyl)allyl)-N-((2-chlorothiazol-5-yl)methyl)-7-(trifluoromethoxy)-1,2,3,4-tetrahydro-5H-pyrido[4,3-b]indole-5-carboxamide (I-38) and Example 383, (E)-2-(3-(4-chlorophenyl)allyl)-N-((2-chlorothiazol-5-yl)methyl)-9-(trifluoromethoxy)-1,2,3,4-tetrahydro-5H-pyrido[4,3-b]indole-5-carboxamide were prepared similarly to Example 145 but using (3-(trifluoromethoxy)phenyl)hydrazine, (2-chlorothiazol-5-yl)methanamine, and aldehyde intermediate, I-38.

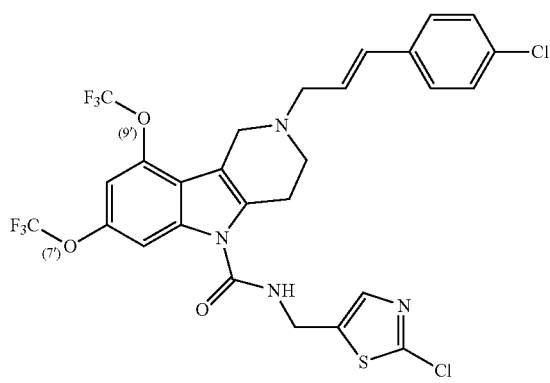 [SMILES: O=C(NCc1cnc(Cl)s1)n1c2c(c3c(OC(F)(F)F)cc(OC(F)(F)F)cc31)CN(C/C=C/c1ccc(Cl)cc1)CC2]

The following compounds were prepared similarly to Example 167 but using (4-(trifluoromethoxy)phenyl)hydrazine and the respective aldehyde intermediate:

Example 384, (E)-2-(3-(4-chloro-3-fluorophenyl)allyl)-N-((2-chloropyridin-4-yl)methyl)-8-(trifluoromethoxy)-1,2,3,4-tetrahydro-5H-pyrido[4,3-b]indole-5-carboxamide (I-3)

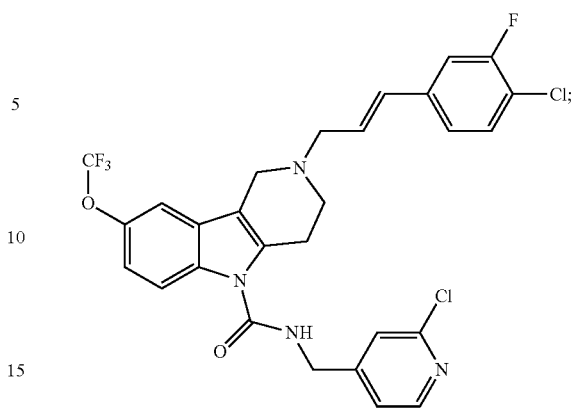

Example 385, (E)-N-((2-chloropyridin-4-yl)methyl)-8-(trifluoromethoxy)-2-(3-(5-(trifluoromethyl)pyridin-2-yl)allyl)-1,2,3,4-tetrahydro-5H-pyrido[4,3-b]indole-5-carboxamide (I-18);

Example 386, (E)-N-((2-chloropyridin-4-yl)methyl)-2-(3-(4-cyano-3-fluorophenyl)allyl)-8-(trifluoromethoxy)-1,2,3,4-tetrahydro-5H-pyrido[4,3-b]indole-5-carboxamide (I-21);

Example 387, (E)-N-((2-chloropyridin-4-yl)methyl)-2-(3-(2,4-difluorophenyl)allyl)-8-(trifluoromethoxy)-1,2,3,4-tetrahydro-5H-pyrido[4,3-b]indole-5-carboxamide (I-30);

Example 388, (E)-2-(3-(3-chloro-4-fluorophenyl)allyl)-N-((2-chloropyridin-4-yl)methyl)-8-(trifluoromethoxy)-1,2,3,4-tetrahydro-5H-pyrido[4,3-b]indole-5-carboxamide (I-31);

Example 389, (E)-N-((2-chloropyridin-4-yl)methyl)-2-(3-(3,4-difluorophenyl)allyl)-8-(trifluoromethoxy)-1,2,3,4-tetrahydro-5H-pyrido[4,3-b]indole-5-carboxamide (I-32);

Example 390, (E)-N-((2-chloropyridin-4-yl)methyl)-2-(3-(4-cyanophenyl)allyl)-8-(trifluoromethoxy)-1,2,3,4-tetrahydro-5H-pyrido[4,3-b]indole-5-carboxamide (I-37);

Example 391, (E)-2-(3-(4-chlorophenyl)allyl)-N-((2-chloropyridin-4-yl)methyl)-8-(trifluoromethoxy)-1,2,3,4-tetrahydro-5H-pyrido[4,3-b]indole-5-carboxamide (I-38);

Example 392, (E)-N-((2-chloropyridin-4-yl)methyl)-2-(3-(3,4-dichlorophenyl)allyl)-8-(trifluoromethoxy)-1,2,3,4-tetrahydro-5H-pyrido[4,3-b]indole-5-carboxamide (I-39);

Example 393, (E)-N-((2-chloropyridin-4-yl)methyl)-2-(3-(4-fluorophenyl)allyl)-8-(trifluoromethoxy)-1,2,3,4-tetrahydro-5H-pyrido[4,3-b]indole-5-carboxamide (I-40);

Example 394, (E)-N-((2-chloropyridin-4-yl)methyl)-2-(3-(4-methoxyphenyl)allyl)-8-(trifluoromethoxy)-1,2,3,4-tetrahydro-5H-pyrido[4,3-b]indole-5-carboxamide (I-44);

Example 395, (E)-N-((2-chloropyridin-4-yl)methyl)-8-(trifluoromethoxy)-2-(3-(4-(trifluoro-methoxy)phenyl)allyl)-1,2,3,4-tetrahydro-5H-pyrido[4,3-b]indole-5-carboxamide (I-45);

Example 396, (E)-N-((2-chloropyridin-4-yl)methyl)-8-(trifluoromethoxy)-2-(3-(4-(trifluoro-methyl)phenyl)allyl)-1,2,3,4-tetrahydro-5H-pyrido[4,3-b]indole-5-carboxamide (I-46);

Example 397, (E)-2-(3-(3-chloro-5-fluorophenyl)allyl)-N-((2-chloropyridin-4-yl)methyl)-8-(trifluoromethoxy)-1,2,3,4-tetrahydro-5H-pyrido[4,3-b]indole-5-carboxamide HCl (I-52);

Example 398, (E)-N-((2-chloropyridin-4-yl)methyl)-2-(3-(3-cyano-5-fluorophenyl)allyl)-8-(trifluoromethoxy)-1,2,3,4-tetrahydro-5H-pyrido[4,3-b]indole-5-carboxamide HCl (I-54);

Example 399, (E)-2-(3-(3-chloro-5-cyanophenyl)allyl)-N-((2-chloropyridin-4-yl)methyl)-8-(trifluoromethoxy)-1,2,3,4-tetrahydro-5H-pyrido[4,3-b] 5-carboxamide HCl (I-55); and Example 400, (E)-2-(3-(3-bromo-5-fluorophenyl)allyl)-N-((2-chloropyridin-4-yl)methyl)-8-(trifluoromethoxy)-1,2,3,4-tetrahydro-5H-pyrido[4,3-b]indole-5-carboxamide HCl (I-56).

The following compounds were prepared similarly to Example 167 but using (4-(trifluoromethoxy)phenyl)hydrazine, (2-fluoropyridin-4-yl)methanamine, and the respective aldehyde intermediate:

Example 401, (E)-2-(3-(4-chloro-3-fluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-3)

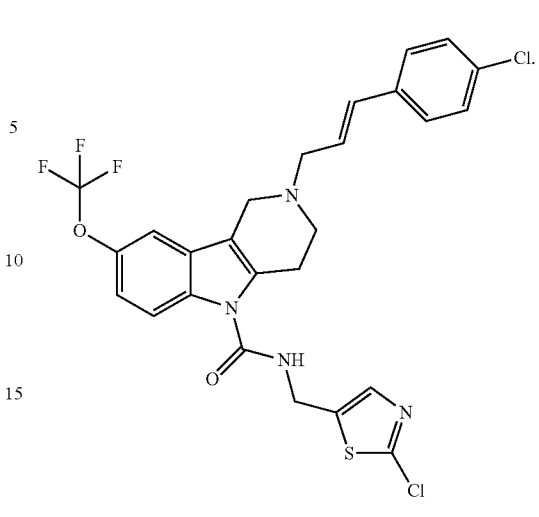

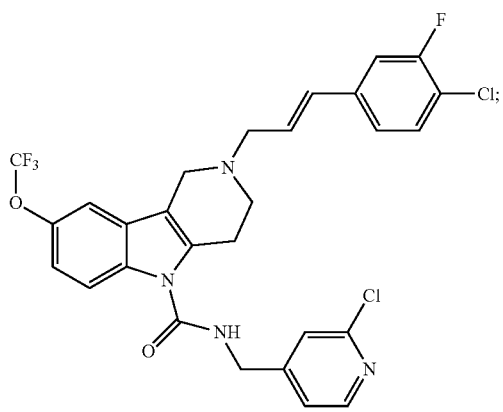 [SMILES: O=C(NCc1ccnc(Cl)c1)n1c2c(c3cc(OC(F)(F)F)ccc31)CN(C/C=C/c1ccc(Cl)c(F)c1)CC2]

The following compounds were prepared similarly to Example 167 but using (4-(trifluoromethyl)phenyl)hydrazine and the respective aldehyde intermediate:

Example 410, (E)-2-(3-(4-chloro-3-fluorophenyl)allyl)-N-((2-chloropyridin-4-yl)methyl)-8-(trifluoromethyl)-1,2,3,4-tetrahydro-5H-pyrido[4,3-b]indole-5-carboxamide (I-3)

Example 402, (E)-2-(3-(4-cyano-3-fluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-21);

Example 403, (E)-2-(3-(2,4-difluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-30);

Example 404, (E)-2-(3-(3-chloro-4-fluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-31);

Example 405, (E)-2-(3-(3,4-difluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-32);

Example 406, (E)-N-((2-fluoropyridin-4-yl)methyl)-8-(trifluoromethoxy)-2-(3-(3,4,5-trifluorophenyl)allyl)-1,2,3,4-tetrahydro-5H-pyrido[4,3-b]indole-5-carboxamide (I-33);

Example 407, (E)-2-(3-(3,5-difluorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-34); and Example 408, (E)-2-(3-(4-chlorophenyl)allyl)-N-((2-fluoropyridin-4-yl)methyl)-8-(trifluoromethoxy)-1,2,3,4-tetrahydro-5H-pyrido[4,3-b]indole-5-carboxamide (I-38).

Example 409, (E)-2-(3-(4-chlorophenyl)allyl)-N-((2-chlorothiazol-5-yl)methyl)-8-(trifluoromethoxy)-1,2,3,4-tetrahydro-5H-pyrido[4,3-b]indole-5-carboxamide, was prepared similarly to Example 167 but using (4-(trifluoromethoxy)phenyl)hydrazine, (2-chlorothiazol-5-yl)methanamine, and aldehyde intermediate, I-38

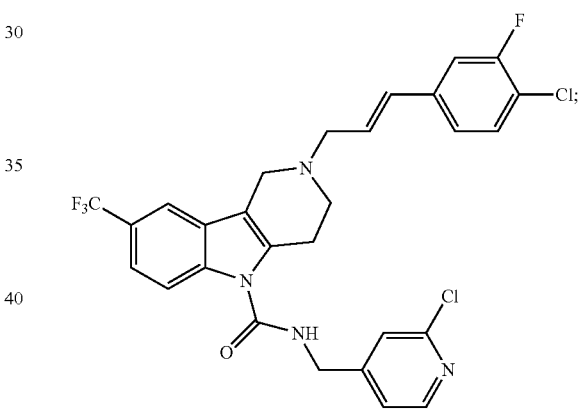

Example 411, (E)-N-((2-chloropyridin-4-yl)methyl)-2-(3-(4-cyano-3-fluorophenyl)allyl)-8-(trifluoromethyl)-1,2,3,4-tetrahydro-5H-pyrido[4,3-b]indole-5-carboxamide (I-21);

Example 412, (E)-N-((2-chloropyridin-4-yl)methyl)-2-(3-(2,4-difluorophenyl)allyl)-8-(trifluoromethyl)-1,2,3,4-tetrahydro-5H-pyrido[4,3-b]indole-5-carboxamide (I-30);

Example 413, (E)-2-(3-(3-chloro-4-fluorophenyl)allyl)-N-((2-chloropyridin-4-yl)methyl)-8-(trifluoromethyl)-1,2,3,4-tetrahydro-5H-pyrido[4,3-b]indole-5-carboxamide (I-31); and Example 414, (E)-N-((2-chloropyridin-4-yl)methyl)-2-(3-(3,4-difluorophenyl)allyl)-8-(trifluoromethyl)-1,2,3,4-tetrahydro-5H-pyrido[4,3-b]indole-5-carboxamide (I-32).

The following compounds were prepared similarly to Example 167 but using (4-(trifluoromethyl)phenyl)hydrazine, (2-fluoropyridin-4-yl)methanamine, and the respective aldehyde intermediate:

Example 415, (E)-2-(3-(4-chloro-3-fluorophenyl)allyl)-N-((2-fluoropyridin-4-yl)methyl)-8-(trifluoromethyl)-1,2,3,4-tetrahydro-5H-pyrido[4,3-b]indole-5-carboxamide (I-3)

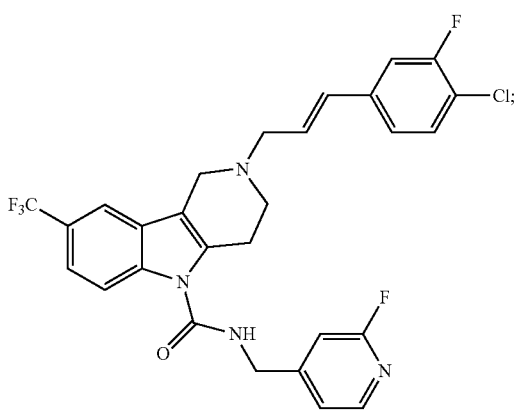 [SMILES: O=C(NCc1ccnc(F)c1)n1c2c(c3cc(C(F)(F)F)ccc31)CN(C/C=C/c1ccc(Cl)c(F)c1)CC2]

Example 416, (E)-2-(3-(4-cyano-3-fluorophenyl)allyl)-N-((2-fluoropyridin-4-yl)methyl)-8-(trifluoromethyl)-1,2,3,4-tetrahydro-5H-pyrido[4,3-b]indole-5-carboxamide (I-21);
Example 417, (E)-2-(3-(2,4-difluorophenyl)allyl)-N-((2-fluoropyridin-4-yl)methyl)-8-(trifluoromethyl)-1,2,3,4-tetrahydro-5H-pyrido[4,3-b]indole-5-carboxamide HCl (I-30);
Example 418, (E)-2-(3-(3-chloro-4-fluorophenyl)allyl)-N-((2-fluoropyridin-4-yl)methyl)-8-(trifluoromethyl)-1,2,3,4-tetrahydro-5H-pyrido[4,3-b]indole-5-carboxamide (I-31);
Example 419, (E)-2-(3-(3,4-difluorophenyl)allyl)-N-((2-fluoropyridin-4-yl)methyl)-8-(trifluoromethyl)-1,2,3,4-tetrahydro-5H-pyrido[4,3-b]indole-5-carboxamide (I-32);
Example 420, (E)-2-(3-(4-cyanophenyl)allyl)-N-((2-fluoropyridin-4-yl)methyl)-8-(trifluoromethyl)-1,2,3,4-tetrahydro-5H-pyrido[4,3-b]indole-5-carboxamide (I-37);
Example 421, (E)-2-(3-(4-chlorophenyl)allyl)-N-((2-fluoropyridin-4-yl)methyl)-8-(trifluoromethyl)-1,2,3,4-tetrahydro-5H-pyrido[4,3-b]indole-5-carboxamide (I-38); and
Example 422, (E)-2-(3-(3,4-dichlorophenyl)allyl)-N-((2-fluoropyridin-4-yl)methyl)-8-(trifluoromethyl)-1,2,3,4-tetrahydro-5H-pyrido[4,3-b]indole-5-carboxamide (I-39).

The following compounds were prepared similarly to Example 145 but using (3-(trifluoromethyl)phenyl)hydrazine and the respective aldehyde intermediate:
Example 423, (E)-2-(3-(3-chloro-4-fluorophenyl)allyl)-N-((2-chloropyridin-4-yl)methyl)-7-(trifluoromethyl)-1,2,3,4-tetrahydro-5H-pyrido[4,3-b]indole-5-carboxamide HCl (I-31)

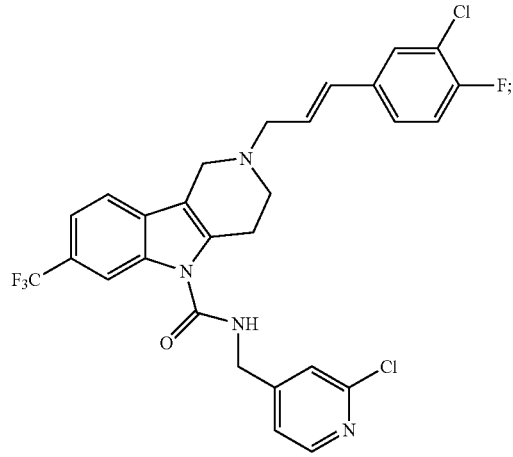 [SMILES: O=C(NCc1ccnc(Cl)c1)n1c2c(c3ccc(C(F)(F)F)cc31)CN(C/C=C/c1ccc(F)c(Cl)c1)CC2]

Example 424, (E)-N-((2-chloropyridin-4-yl)methyl)-2-(3-(2,4-difluorophenyl)allyl)-7-(trifluoromethyl)-1,2,3,4-tetrahydro-5H-pyrido[4,3-b]indole-5-carboxamide HCl (I-30); and Example 425, (E)-N-((2-chloropyridin-4-yl)methyl)-7-(trifluoromethyl)-2-(3-(4-(trifluoro-methyl)phenyl)allyl)-1,2,3,4-tetrahydro-5H-pyrido[4,3-b]indole-5-carboxamide (I-46).

The following compounds were prepared similarly to Example 145 but using (3-(trifluoromethyl)phenyl)hydrazine, (2-fluoropyridin-4-yl)methanamine, and the respective aldehyde intermediate:

Example 426, (E)-2-(3-(4-cyano-3-fluorophenyl)allyl)-N-((2-fluoropyridin-4-yl)methyl)-7-(trifluoromethyl)-1,2,3,4-tetrahydro-5H-pyrido[4,3-b]indole-5-carboxamide HCl (I-21)

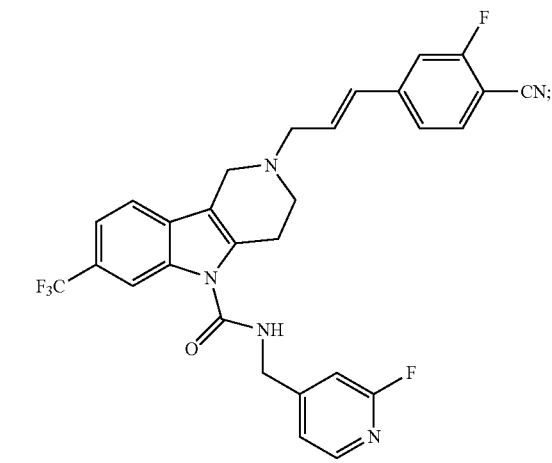 [SMILES: N#Cc1ccc(/C=C/CN2CCc3c(c4ccc(C(F)(F)F)cc4n3C(=O)NCc3ccnc(F)c3)C2)cc1F]

Example 427, (E)-2-(3-(2,4-difluorophenyl)allyl)-N-((2-fluoropyridin-4-yl)methyl)-7-(trifluoromethyl)-1,2,3,4-tetrahydro-5H-pyrido[4,3-b]indole-5-carboxamide HCl (I-30);

Example 428, (E)-2-(3-(3-chloro-4-fluorophenyl)allyl)-N-((2-fluoropyridin-4-yl)methyl)-7-(trifluoromethyl)-1,2,3,4-tetrahydro-5H-pyrido[4,3-b]indole-5-carboxamide HCl (I-31); and Example 429, (E)-2-(3-(3,4-difluorophenyl)allyl)-N-((2-fluoropyridin-4-yl)methyl)-7-(trifluoromethyl)-1,2,3,4-tetrahydro-5H-pyrido[4,3-b]indole-5-carboxamide HCl (I-32).

The following compounds were prepared similarly to Example 167 but using p-tolylhydrazine and the respective aldehyde intermediate:

Example 430, (E)-N-((2-chloropyridin-4-yl)methyl)-2-(3-(4-cyanophenyl)allyl)-8-methyl-1,2,3,4-tetrahydro-5H-pyrido[4,3-b]indole-5-carboxamide (I-37)

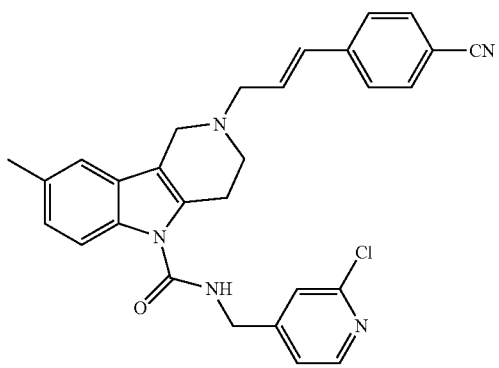 [SMILES: Cc1ccc2c(c1)c1c(n2C(=O)NCc2ccnc(Cl)c2)CCN(C/C=C/c2ccc(C#N)cc2)C1]

Example 431, (E)-2-(3-(4-chlorophenyl)allyl)-N-((2-chloropyridin-4-yl)methyl)-8-methyl-1,2,3,4-tetrahydro-5H-pyrido[4,3-b]indole-5-carboxamide (I-38);

Example 432, (E)-N-((2-chloropyridin-4-yl)methyl)-2-(3-(3,4-dichlorophenyl)allyl)-8-methyl-1,2,3,4-tetrahydro-5H-pyrido[4,3-b]indole-5-carboxamide (I-39);

Example 433, (E)-N-((2-chloropyridin-4-yl)methyl)-2-(3-(4-fluorophenyl)allyl)-8-methyl-1,2,3,4-tetrahydro-5H-pyrido[4,3-b]indole-5-carboxamide (I-40);

Example 434, (E)-N-((2-chloropyridin-4-yl)methyl)-8-methyl-2-(3-(4-(trifluoromethoxy)-phenyl)allyl)-1,2,3,4-tetrahydro-5H-pyrido[4,3-b]indole-5-carboxamide (I-45); and Example 435, (E)-N-((2-chloropyridin-4-yl)methyl)-8-methyl-2-(3-(4-(trifluoromethyl)-phenyl)allyl)-1,2,3,4-tetrahydro-5H-pyrido[4,3-b]indole-5-carboxamide (I-46).

Example 436, (E)-10-(3-(4-chlorophenyl)allyl)-N-((2-chloropyridin-4-yl)methyl)-8,9,10,11-tetrahydro-7H-benzo[e]pyrido[4,3-b]indole-7-carboxamide, was prepared similarly to Example 145, but using naphthalen-2-yl-hydrazine and aldehyde intermediate, I-38

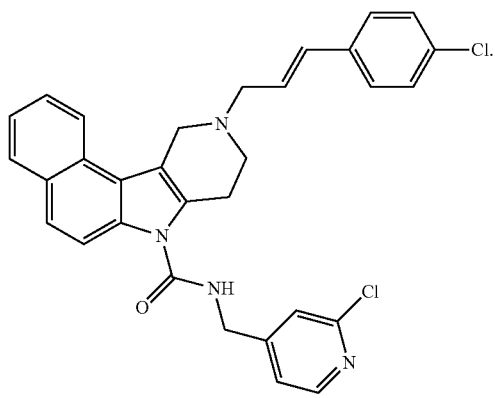 [SMILES: O=C(NCc1ccnc(Cl)c1)n1c2c(c3c4ccccc4ccc31)CN(C/C=C/c1ccc(Cl)cc1)CC2]

The following compounds were prepared similarly to Example 145 but using (3-bromophenyl)hydrazine and the respective aldehyde intermediate:

Example 437, (E)-7-bromo-2-(3-(4-chloro-3-fluorophenyl)allyl)-N-((2-chloropyridin-4-yl)methyl)-1,2,3,4-tetrahydro-5H-pyrido[4,3-b]indole-5-carboxamide (I-3)

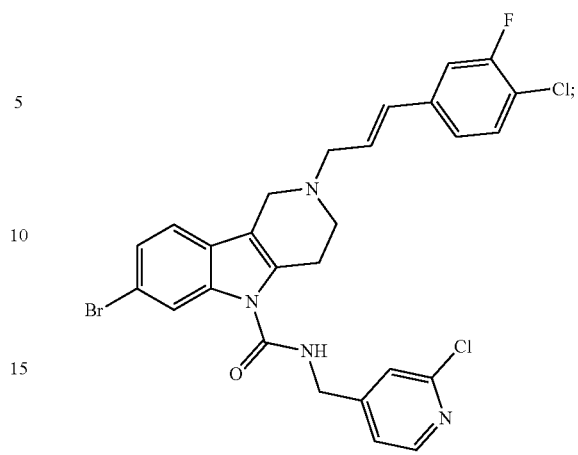

Example 438, (E)-7-bromo-N-((2-chloropyridin-4-yl)methyl)-2-(3-(4-cyano-3-fluorophenyl)allyl)-1,2,3,4-tetrahydro-5H-pyrido[4,3-b]indole-5-carboxamide (I-21);

Example 439, (E)-7-bromo-2-(3-(3-chloro-4-fluorophenyl)allyl)-N-((2-chloropyridin-4-yl)methyl)-1,2,3,4-tetrahydro-5H-pyrido[4,3-b]indole-5-carboxamide (I-31);

Example 440, (E)-7-bromo-N-((2-chloropyridin-4-yl)methyl)-2-(3-(3,4-difluorophenyl)allyl)-1,2,3,4-tetrahydro-5H-pyrido[4,3-b]indole-5-carboxamide (I-32);

Example 441, (E)-7-bromo-N-((2-chloropyridin-4-yl)methyl)-2-(3-(4-cyanophenyl)allyl)-1,2,3,4-tetrahydro-5H-pyrido[4,3-b]indole-5-carboxamide (I-37);

Example 442, (E)-9-bromo-N-((2-chloropyridin-4-yl)methyl)-2-(3-(4-cyanophenyl)allyl)-1,2,3,4-tetrahydro-5H-pyrido[4,3-b]indole-5-carboxamide (I-37);

Example 443, (E)-7-bromo-2-(3-(4-chlorophenyl)allyl)-N-((2-chloropyridin-4-yl)methyl)-1,2,3,4-tetrahydro-5H-pyrido[4,3-b]indole-5-carboxamide (I-38); and Example 444, (E)-9-bromo-2-(3-(4-chlorophenyl)allyl)-N-((2-chloropyridin-4-yl)methyl)-1,2,3,4-tetrahydro-5H-pyrido[4,3-b]indole-5-carboxamide (I-38).

The following compounds were prepared similarly to Example 167 but using (4-methylsulfanylphenyl)hydrazine and the respective aldehyde intermediate:

Example 445, (E)-2-(3-(4-chloro-3-fluorophenyl)allyl)-N-((2-chloropyridin-4-yl)methyl)-8-(methylthio)-1,2,3,4-tetrahydro-5H-pyrido[4,3-b]indole-5-carboxamide (I-3)

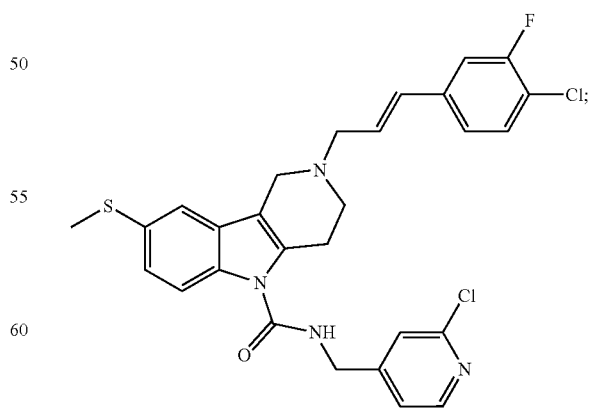

Example 446, (E)-N-((2-chloropyridin-4-yl)methyl)-2-(3-(3,4-difluorophenyl)allyl)-8-(methylthio)-1,2,3,4-tetrahydro-5H-pyrido[4,3-b]indole-5-carboxamide (I-32);

Example 447, (E)-2-(3-(4-chlorophenyl)allyl)-N-((2-chloropyridin-4-yl)methyl)-8-(methylthio)-1,2,3,4-tetrahydro-5H-pyrido[4,3-b]indole-5-carboxamide (I-38); and Example 448, (E)-N-((2-chloropyridin-4-yl)methyl)-2-(3-(4-fluorophenyl)allyl)-8-(methylthio)-1,2,3,4-tetrahydro-5H-pyrido[4,3-b]indole-5-carboxamide (I-40).

Example 449, (E)-8-cyano-2-(3-(3,4-dichlorophenyl)allyl)-N-((2-hydroxypyridin-4-yl)methyl)-1,2,3,4-tetrahydro-5H-pyrido[4,3-b]indole-5-carboxamide

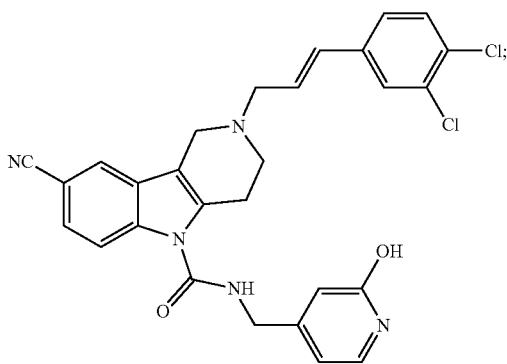 [SMILES: N#Cc1ccc2c(c1)c1c(n2C(=O)NCc2ccnc(O)c2)CCN(C/C=C/c2ccc(Cl)c(Cl)c2)C1]

was prepared in accordance with the following scheme and reaction:

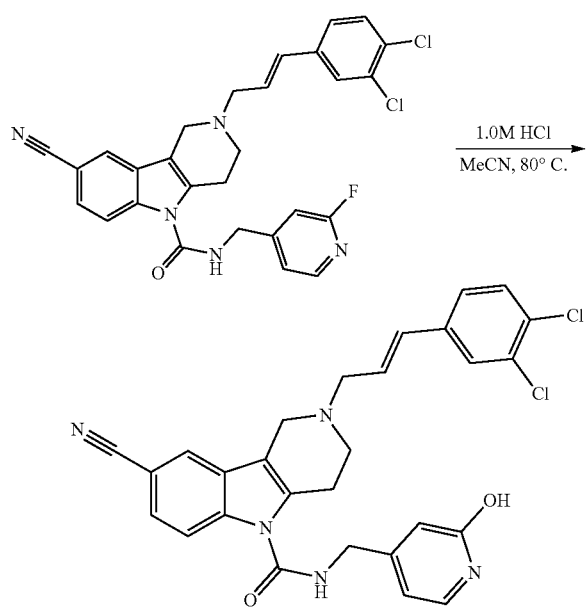

In a 5 mL vial, a suspension of 50 mg of (E)-8-cyano-2-(3-(3,4-dichlorophenyl)allyl)-N-((2-fluoropyridin-4-yl)methyl)-1,2,3,4-tetrahydro-5H-pyrido[4,3-b]indole-5-carboxamide in 1.0 mL of MeCN was treated with 1.0 mL of 1.0 M HCl and the resulting suspension was heated to 80° C. for 24 hours. Upon completion of the reaction monitored by LCMS the crude was cooled to room temperature and treated with 2.0 mL of 1.0 M HCl and the vial was placed in the freezer. The precipitate was collected by filtration. No further purification was required.

The following compounds were prepared similarly to Example 449 but using the respective aldehyde intermediate:

Example 450, (E)-2-(3-(4-chloro-3,5-difluorophenyl)allyl)-8-cyano-N-((2-hydroxypyridin-4-yl)methyl)-1,2,3,4-tetrahydro-5H-pyrido[4,3-b]indole-5-carboxamide HCl (I-1);

Example 451, (E)-2-(3-(4-bromo-2-fluorophenyl)allyl)-8-cyano-N-((2-hydroxypyridin-4-yl)methyl)-1,2,3,4-tetrahydro-5H-pyrido[4,3-b]indole-5-carboxamide HCl (I-5); and Example 452, (E)-8-cyano-2-(3-(3,5-dichloro-4-fluorophenyl)allyl)-N-((2-hydroxypyridin-4-yl)methyl)-1,2,3,4-tetrahydro-5H-pyrido[4,3-b]indole-5-carboxamide HCl (I-19).

Example 453, (E)-2-(3-(2,4-difluorophenyl)allyl)-N-((2-hydroxypyridin-4-yl)methyl)-8-(trifluoromethyl)-1,2,3,4-tetrahydro-5H-pyrido[4,3-b]indole-5-carboxamide was prepared similarly to Example 449 but using (E)-2-(3-(2,4-difluorophenyl)allyl)-N-((2-fluoropyridin-4-yl)methyl)-8-(trifluoromethyl)-1,2,3,4-tetrahydro-5H-pyrido[4,3-b]indole-5-carboxamide (Example 417)

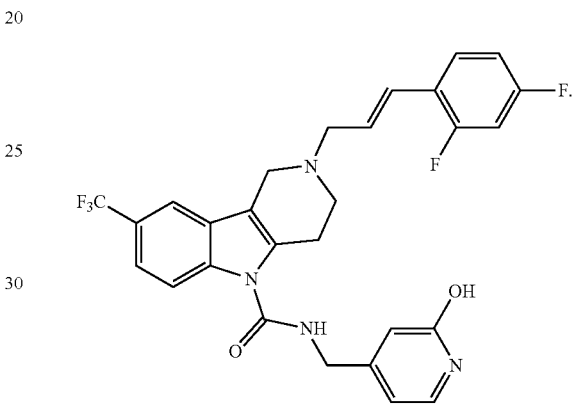

Example 454, (E)-2-(3-(4-cyanophenyl)allyl)-N-((2-hydroxypyridin-4-yl)methyl)-8-(trifluoromethyl)-1,2,3,4-tetrahydro-5H-pyrido[4,3-b]indole-5-carboxamide HCl, was prepared similarly to Example 449 but using (E)-2-(3-(4-cyanophenyl)allyl)-N-((2-fluoropyridin-4-yl)methyl)-8-(trifluoromethyl)-1,2,3,4-tetrahydro-5H-pyrido[4,3-b]indole-5-carboxamide (Example 420)

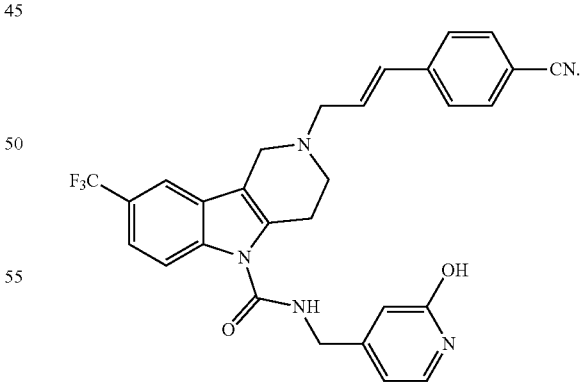

The following compounds were prepared similarly to Example 167 but using (4-(methylsulfonyl)phenyl)hydrazine and the respective aldehyde intermediate:

Example 455, (E)-2-(3-(4-chloro-3-fluorophenyl)allyl)-N-((2-chloropyridin-4-yl)methyl)-8-(methylsulfonyl)-1,2,3,4-tetrahydro-5H-pyrido[4,3-b]indole-5-carboxamide (I-3)

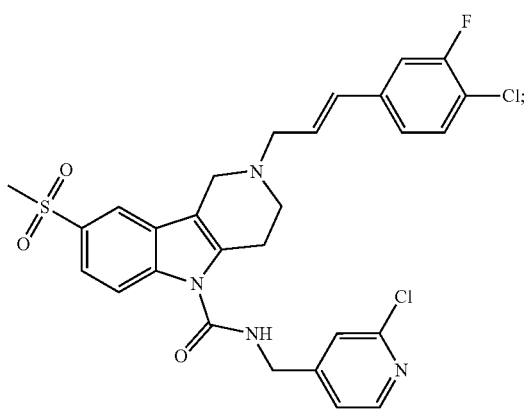 [SMILES: CS(=O)(=O)c1ccc2c(c1)c1c(n2C(=O)NCc2ccnc(Cl)c2)CCN(C/C=C/c2ccc(Cl)c(F)c2)C1]

Example 456, (E)-N-((2-chloropyridin-4-yl)methyl)-2-(3-(2,4-difluorophenyl)allyl)-8-(methylsulfonyl)-1,2,3,4-tetrahydro-5H-pyrido[4,3-b]indole-5-carboxamide (I-30);
Example 457, (E)-2-(3-(4-chlorophenyl)allyl)-N-((2-chloropyridin-4-yl)methyl)-8-(methylsulfonyl)-1,2,3,4-tetrahydro-5H-pyrido[4,3-b]indole-5-carboxamide (I-38);
Example 458, (E)-N-((2-chloropyridin-4-yl)methyl)-2-(3-(3,4-dichlorophenyl)allyl)-8-(methylsulfonyl)-1,2,3,4-tetrahydro-5H-pyrido[4,3-b]indole-5-carboxamide (I-39); and
Example 459, (E)-N-((2-chloropyridin-4-yl)methyl)-2-(3-(4-fluorophenyl)allyl)-8-(methylsulfonyl)-1,2,3,4-tetrahydro-5H-pyrido[4,3-b]indole-5-carboxamide (I-40).

Example 460, (E)-2-(3-(4-chlorophenyl)allyl)-8-(6-cyanopyridin-3-yl)-N-((2-fluoropyridin-4-yl)methyl)-1,2,3,4-tetrahydro-5H-pyrido[4,3-b]indole-5-carboxamide (I-38) was prepared according to the following process.

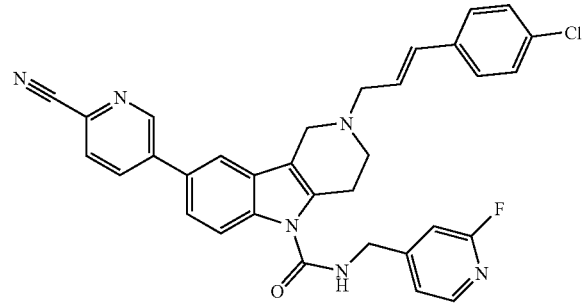 [SMILES: N#Cc1ccc(-c2ccc3c(c2)c2c(n3C(=O)NCc3ccnc(F)c3)CCN(C/C=C/c3ccc(Cl)cc3)C2)cn1]

(E)-8-bromo-2-(3-(4-chlorophenyl)allyl)-N-((2-fluoropyridin-4-yl)methyl)-1,2,3,4-tetrahydro-5H-pyrido[4,3-b]indole-5-carboxamide (100 mg) was dissolved in dioxane/water (6:1, 7.0 mL). KOAc (71 mg), 5-(4,4,5,5-tetramethyl-1,3,2-dioxaborolan-2-yl)picolinonitrile (44 mg) and Pd(PPh$_3$)$_4$ (5 mol %, 9.0 mg) were added and the resulting solution was degassed with argon. The resulting solution was heated at 120° C. for 60 minutes under low power millimeter wave irradiation and the progression of the reaction was monitored by LCMS. After cooling the mixture to room temperature, the crude solution was filtered through a Pd scavenging resin, water was removed and the crude material was purified on a preparatory HPLC to give the title compound as an off white solid after lyophilization.
Example 461, (E)-8-(4-chlorophenyl)-2-(3-(4-chlorophenyl)allyl)-N-((2-fluoropyridin-4-yl)methyl)-1,2,3,4-tetrahydro-5H-pyrido[4,3-b]indole-5-carboxamide (I-38), was prepared similarly to Example 460 but using using 2-(4-chlorophenyl)-4,4,5,5-tetramethyl-1,3,2-dioxaborolane

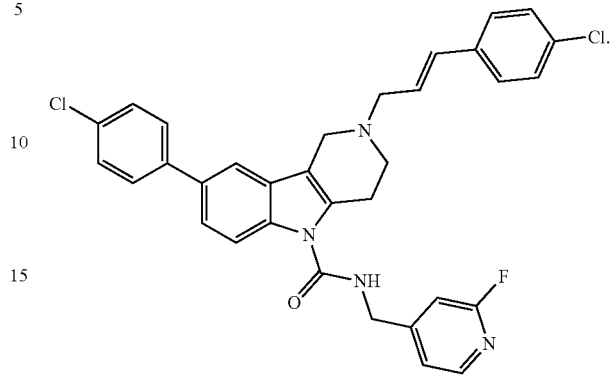

Example 462, (E)-8-(3-chlorophenyl)-2-(3-(4-chlorophenyl)allyl)-N-((2-fluoropyridin-4-yl)methyl)-1,2,3,4-tetrahydro-5H-pyrido[4,3-b]indole-5-carboxamide (I-38) was prepared similarly to Example 460 but using using 2-(3-chlorophenyl)-4,4,5,5-tetramethyl-1,3,2-dioxaborolane

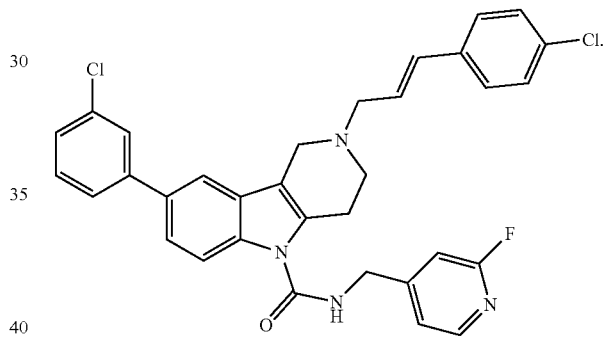 [SMILES: O=C(NCc1ccnc(F)c1)n1c2c(c3cc(-c4ccc(F)cc4)ccc31)CN(C/C=C/c1ccc(Cl)cc1)CC2]

Example 463, (E)-2-(3-(4-chlorophenyl)allyl)-8-(4-fluorophenyl)-N-((2-fluoropyridin-4-yl)methyl)-1,2,3,4-tetrahydro-5H-pyrido[4,3-b]indole-5-carboxamide, was prepared similarly to Example 460 but using 2-(4-fluorophenyl)-4,4,5,5-tetramethyl-1,3,2-dioxaborolane

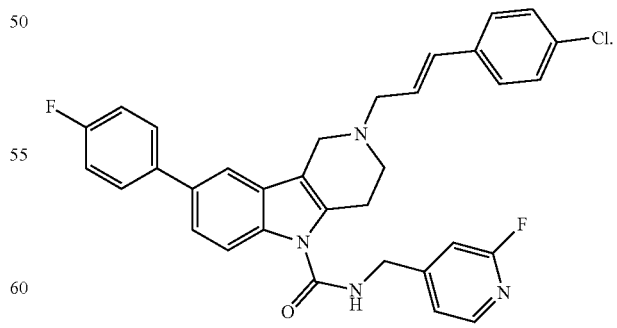

Example 464, (E)-2-(3-(4-chlorophenyl)allyl)-N$^5$-((2-chloropyridin-4-yl)methyl)-1,2,3,4-tetrahydro-5H-pyrido[4,3-b]indole-5,7-dicarboxamide (I-38) was prepared according to the following process

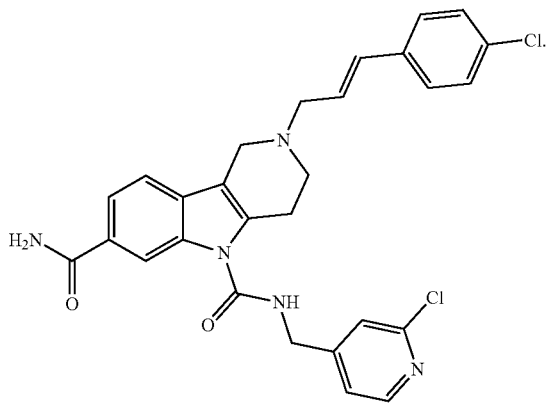 [SMILES: NC(=O)c1ccc2c3c(n(C(=O)NCc4ccnc(Cl)c4)c2c1)CCN(C/C=C/c1ccc(Cl)cc1)C3]

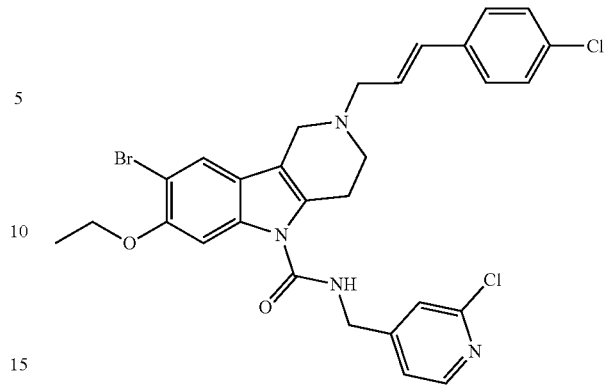

In a vial to the mixture of (E)-2-(3-(4-chlorophenyl)allyl)-N-((2-chloropyridin-4-yl)methyl)-7-cyano-1,2,3,4-tetrahydro-5H-pyrido[4,3-b]indole-5-carboxamide (60 mg, 0.117 mmol, 1 eq) and TMSCl (0.059 mL, 0.466 mmol, 4 eq) was added water (0.008 mL, 0.466 mmol, 4 eq). After stirring at room temperature for 16 hours, the crude material was purified by preparative HPLC to afford an off white solid. The hydrochloride salt of compound was made by using etheral HCl (2 mL), to afford an off white solid.

The following compounds were prepared similarly to Example 464 but using the respective aldehyde intermediate:

Example 465, (E)-2-(3-(4-chloro-3-fluorophenyl)allyl)-$N^5$-((2-chloropyridin-4-yl)methyl)-1,2,3,4-tetrahydro-5H-pyrido[4,3-b]indole-5,7-dicarboxamide (I-3); and Example 466, (E)-$N^5$-((2-chloropyridin-4-yl)methyl)-2-(3-(4-fluorophenyl)allyl)-1,2,3,4-tetrahydro-5H-pyrido[4,3-b]indole-5,7-dicarboxamide (I-40).

Example 467, (E)-2-(3-(4-chloro-3-fluorophenyl)allyl)-$N^5$-((2-chloropyridin-4-yl)methyl)-1,2,3,4-tetrahydro-5H-pyrido[4,3-b]indole-5,8-dicarboxamide, was prepared similarly to Example 464 but using (E)-2-(3-(4-chloro-3-fluorophenyl)allyl)-N-((2-chloropyridin-4-yl)methyl)-8-cyano-1,2,3,4-tetrahydro-5H-pyrido[4,3-b]indole-5-carboxamide and aldehyde intermediate, I-35

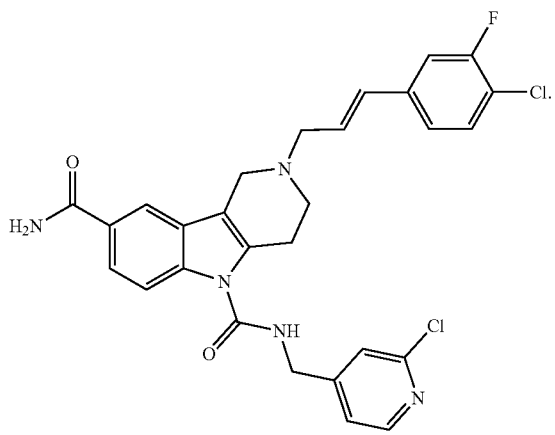 [SMILES: NC(=O)c1ccc2c(c1)c1c(n2C(=O)NCc2ccnc(Cl)c2)CCN(C/C=C/c2ccc(Cl)c(F)c2)C1]

Example 468, (E)-8-bromo-2-(3-(4-chlorophenyl)allyl)-N-((2-chloropyridin-4-yl)methyl)-7-ethoxy-1,2,3,4-tetrahydro-5H-pyrido[4,3-b]indole-5-carboxamide Step 1: Synthesis of (4-bromo-3-ethoxy-phenyl)-hydrazine HCl Salt:

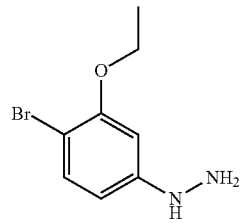

In 250 mL round bottom flask, to a stirred solution of commercially available 4-bromo-3-ethoxyaniline hydrochloride salt (5.0 gm, 23.14 mmol, 1 eq) was added concentrated HCl (35 mL) at −5° C. to 0° followed by sodium nitrite (1.756 gm, 25.45 mol, 1.1 eq) pre-dissolved in water (8 mL). Reaction mixture was stirred at −5° C. to 0° C. for 1 hour. After that solution of $SnCl_2.2H_2O$ (11.48 gm, 50.90 mmol, 2.2 eq) in concentrated HCl (15 mL) was added drop wise. The internal reaction temperature was maintained at −5° C. during the addition. The resulting suspension was stirred at 0° C. for 1 hour. Resulting precipitate was filtered, solid was dried under reduced pressure to afford off white solid (6.0 gm, HCl salt, crude). Crude was used as such for next Step. LC-MS (m/z): 231.9 (M+H).

Step 2: Synthesis of 8-bromo-7-ethoxy-2,3,4,5-tetrahydro-1H-pyrido[4,3-b]indole HCl Salt:

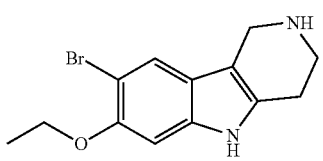 [SMILES: CCOc1cc2[nH]c3c(c2cc1Br)CNCC3]

In a 100 mL round bottom flask to the stirred solution of (4-bromo-3-ethoxy-phenyl)-hydrazine hydrochloride salt (2.0 gm, crude, 7.489 mmol, 1 equivalent) in acetic acid (20 mL) and 1,4-dioxane HCl (20 mL) was added piperidin-4-one hydrochloride (1.204 gm, 8.99 mmol, 1.2 equivalents) at room temperature. Reaction mixture was heated at 120° C. for 16 hours. Progress of reaction was monitored by LCMS. After completion of starting material, reaction mixture was evaporated under reduced pressure to afford brown solid (3 gm, crude). Crude compound was used as such for next Step. LC-MS (m/z): 295.2 (M+H).

Step 3: Synthesis of 8-bromo-7-ethoxy-1,3,4,5-tetrahydro-pyrido[4,3-b]indole-2-carboxylic Acid Tert-Butyl Ester

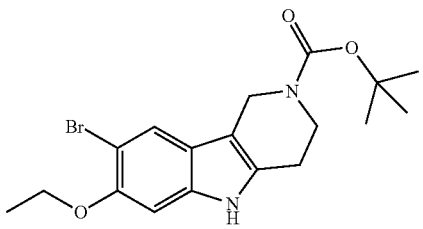 [SMILES: CCOc1cc2[nH]c3c(c2cc1Br)CN(C(=O)OC(C)(C)C)CC3]

In a 100 mL round bottom flask to the stirred solution of crude 8-bromo-7-ethoxy-2,3,4,5-tetrahydro-1H-pyrido[4,3-b]indole HCl salt (3.0 gm, crude, 9.059 mmol, 1 eq)) in THF (30 mL) was added TEA (10.082 ml, 72.468 mmol, 8 eq). After that BOC anhydride (3.291 mL, 13.588 mmol, 1.5 eq) was added drop wise at room temperature and stirring was continued at room temperature for 1 hour. Progress of reaction was monitored by TLC. After consumption of starting material, reaction mixture was quenched with water (100 mL). Aqueous layer was extracted with ethyl acetate (100 mL×3). Combined organic layer was dried over sodium sulfate, filtered and concentrated under reduced pressure to afford brown oil as crude compound 4g. Crude compound was purified by combiflash (40 gm, Redisep column). Compound was eluted using 16% ethyl acetate in hexane to afford 410 mg as off-white solid. 1H NMR (400 MHz, DMSO) δ: 1.38 (t, J=7.0 Hz, 3H), 1.43 (s, 9H), 2.72 (t, J=5.32 Hz, 2H), 3.66 (t, J=5.64 Hz, 2H), 4.05 (q, J=6.92 Hz, 2H), 4.46 (bs, 2H), 6.94 (s, 1H), 7.59 (s, 1H), 10.87 (s, 1H). LC-MS (m/z): 393.0 (M−H).

Step 4: Synthesis of 8-bromo-5-[(2-chloro-pyridin-4-ylmethyl)-carbamoyl]-7-ethoxy-1,3,4,5-tetrahydro-pyrido[4,3-b]indole-2-carboxylic Acid Tert-Butyl Ester

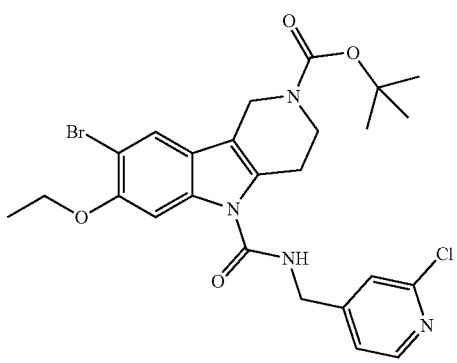 [SMILES: CCOc1cc2c(cc1Br)c1c(n2C(=O)NCc2ccnc(Cl)c2)CCN(C(=O)OC(C)(C)C)C1]

In a 25 mL round bottom flask to a stirred solution of NaH (60% in oil) (54.64 mg, 2.277 mmol, 3.0 eq) in THF (3 mL) was added drop wise 8-bromo-7-ethoxy-1,3,4,5-tetrahydro-pyrido[4,3-b]indole-2-carboxylic acid tert-butyl ester (300 mg, 0.759 mmol, 1.0 eq) in THF (1.5 mL) at 0° C. Resulting reaction mixture was allowed to room temperature stirred for 30 minutes. After that added 2-Chloro-4-isocyanatomethyl-pyridine (191.9 mg, 1.138 mmol, 1.5 eq) in THF (1.5 mL) at 0° C. The resulting reaction mixture was stirred at 0° C. for 15 minutes. Progress of reaction was monitored by TLC. Reaction mixture was quenched with cold 6N hydrochloric acid (5 mL) followed by water (15 mL). Aqueous was extracted with ethyl acetate (20 mL×3). Combined organic layer was dried over sodium sulfate, filtered and evaporated under reduced pressure to get brown oil (400 mg, crude). Purification was done by combiflash column chromatography (12 gm Redisep column). Compound was eluted by 35% ethyl acetate in hexane to afford off white solid (85 mg, 19.86%). 1H NMR (400 MHz, DMSO) δ: 1.37 (t, J=6.90 Hz, 3H), 1.44 (s, 9H), 2.97 (bs, 2H), 3.64 (t, J=5.48 Hz, 2H), 4.05 (q, J=6.84 Hz, 2H), 4.50-4.53 (m, 4H), 7.43-7.44 (m, 2H), 7.53 (s, 1H), 7.76 (s, 1H), 8.39 (d, J=5.08 Hz, 1H), 8.49 (t, J=5.60 Hz, 1H). LC-MS (m/z): 562.2 (M−H).

Step 5: Synthesis of 8-bromo-7-ethoxy-1,2,3,4-tetrahydro-pyrido[4,3-b]indole-5-carboxylic acid (2-chloro-pyridin-4-ylmethyl)-amide TFA Salt

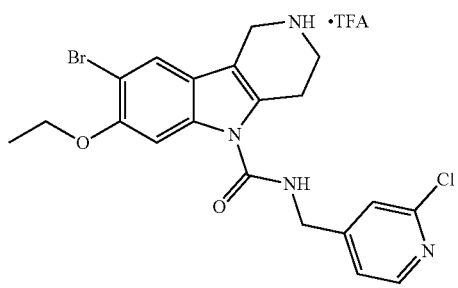 [SMILES: CCOc1cc2c(cc1Br)c1c(n2C(=O)NCc2ccnc(Cl)c2)CCNC1]

In a 10 mL vial to a stirred solution of 8-Bromo-5-[(2-chloro-pyridin-4-ylmethyl)-carbamoyl]-7-ethoxy-1,3,4,5-tetrahydro-pyrido[4,3-b]indole-2-carboxylic acid tert-butyl ester (150 mg, 0.266 mmol, 1 eq) in DCM (2 mL) was added trifluoroacetic acid (0.5 mL). Resulting reaction mixture was stirred at room temperature for 1 hour. Progress of reaction was monitored by TLC. After consumption of starting material, reaction mixture was concentrated under reduced pressure to afford 150 mg brown mass as TFA salt. Crude was used as such for next Step. LC-MS (m/z): 465.2 (M+H).

Step 6: Preparation of Example 468.

In a 10 mL vial to a stirred solution of 8-Bromo-7-ethoxy-1,2,3,4-tetrahydro-pyrido[4,3-b]indole-5-carboxylic acid (2-chloro-pyridin-4-ylmethyl)-amide TFA salt (150 mg, 0.26 mmol, 1 eq) in DMF (1.5 mL) was added TEA (0.181 mL, 1.298 mmol, 5 eq) at room temperature. After that added (E)-3-(4-chloro-phenyl)-propenal (51.90 mg, 0.312 mmol, 1.2 eq) followed by sodium triacetoxy borohydride (110.08 mg, 0.519 mmol, 2 eq). Resulting reaction mixture was stirred at room temperature for 2 hours. Progress of reaction was monitored by TLC and LCMS. After consumption of starting material, reaction mixture was evaporated under reduced pressure to afford brown mass. Purification was done by preparative HPLC using ammonia buffer to afford off white solid (31 mg). HCl salt of compound was made by using etheral HCl (3 mL) to afford off white solid.

The following compounds were prepared similarly to Example 468 but using commercially available 4-fluoro-3-(trifluoromethoxy)aniline and the respective aldehyde intermediate:

Example 469, (E)-2-(3-(4-chlorophenyl)allyl)-N-((2-chloro-pyridin-4-yl)methyl)-8-fluoro-7-(trifluoromethoxy)-1,2,3,4-tetrahydro-5H-pyrido[4,3-b]indole-5-carboxamide (I-38)

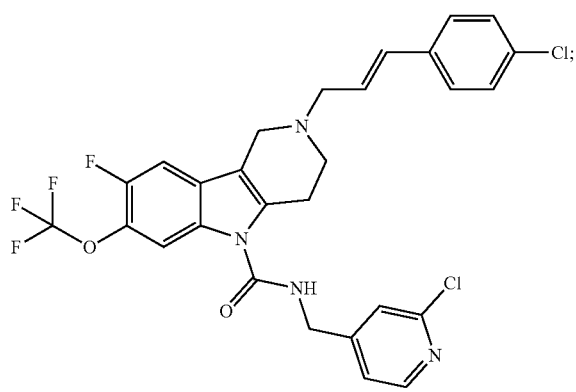 [SMILES: O=C(NCc1ccnc(Cl)c1)n1c2c(c3cc(F)c(OC(F)(F)F)cc31)CN(C/C=C/c1ccc(Cl)cc1)CC2]

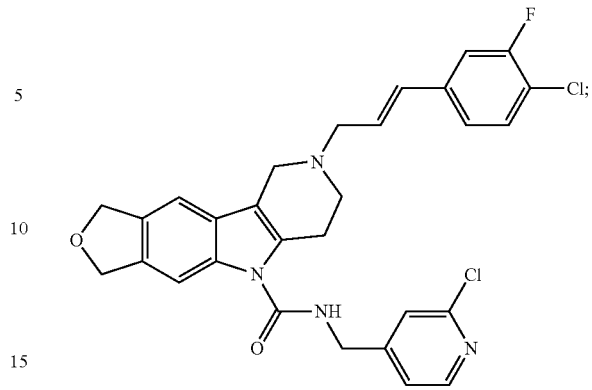

Example 470, (E)-N-((2-chloropyridin-4-yl)methyl)-2-(3-(4-cyanophenyl)allyl)-8-fluoro-7-(trifluoromethoxy)-1,2,3,4-tetrahydro-5H-pyrido[4,3-b]indole-5-carboxamide (I-37); and Example 471. (E)-N-((2-chloropyridin-4-yl)methyl)-8-fluoro-2-(3-(4-fluorophenyl)allyl)-7-(trifluoromethoxy)-1,2,3,4-tetrahydro-5H-pyrido[4,3-b]indole-5-carboxamide (I-40).

Example 472, (E)-2-(3-(4-chlorophenyl)allyl)-8-fluoro-N-((2-fluoropyridin-4-yl)methyl)-7-(trifluoromethoxy)-1,2,3,4-tetrahydro-5H-pyrido[4,3-b]indole-5-carboxamide, was prepared similarly to Example 468 but using using commercially available 4-fluoro-3-(trifluoromethoxy)aniline and (2-fluoropyridin-4-yl)methanamine

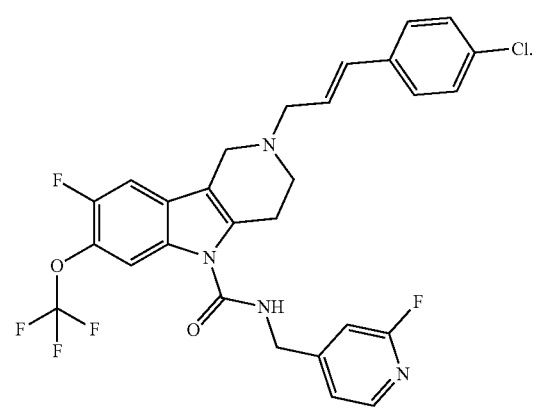 [SMILES: O=C(NCc1ccnc(F)c1)n1c2c(c3cc(F)c(OC(F)(F)F)cc31)CN(C/C=C/c1ccc(Cl)cc1)CC2]

The following compounds were prepared similarly to Example 468 but using commercially available 1,3-dihydroisobenzofuran-5-amine and the respective aldehyde intermediate:

Example 473, (E)-8-(3-(4-chloro-3-fluorophenyl)allyl)-N-((2-chloropyridin-4-yl)methyl)-1,3,6,7,8,9-hexahydro-5H-furo[3,4-f]pyrido[4,3-b]indole-5-carboxamide HCl (I-3)

Example 474, (E)-N-((2-chloropyridin-4-yl)methyl)-8-(3-(5-(trifluoromethyl)pyridin-2-yl)allyl)-1,3,6,7,8,9-hexahydro-5H-furo[3,4-f]pyrido[4,3-b]indole-5-carboxamide (I-18);

Example 475, (E)-N-((2-chloropyridin-4-yl)methyl)-8-(3-(4-cyano-3-fluorophenyl)allyl)-1,3,6,7,8,9-hexahydro-5H-furo[3,4-f]pyrido[4,3-b]indole-5-carboxamide HCl (I-21);

Example 476, (E)-N-((2-chloropyridin-4-yl)methyl)-8-(3-(2,4-difluorophenyl)allyl)-1,3,6,7,8,9-hexahydro-5H-furo[3,4-f]pyrido[4,3-b]indole-5-carboxamide HCl (I-30);

Example 477, (E)-8-(3-(3-chloro-4-fluorophenyl)allyl)-N-((2-chloropyridin-4-yl)methyl)-1,3,6,7,8,9-hexahydro-5H-furo[3,4-f]pyrido[4,3-b]indole-5-carboxamide, HCl (I-31);

Example 478, (E)-N-((2-chloropyridin-4-yl)methyl)-8-(3-(3,4-difluorophenyl)allyl)-1,3,6,7,8,9-hexahydro-5H-furo[3,4-f]pyrido[4,3-b]indole-5-carboxamide HCl ((I-32);

Example 479, (E)-N-((2-chloropyridin-4-yl)methyl)-8-(3-(4-cyanophenyl)allyl)-1,3,6,7,8,9-hexahydro-5H-furo[3,4-f]pyrido[4,3-b]indole-5-carboxamide (I-37);

Example 480, (E)-8-(3-(4-chlorophenyl)allyl)-N-((2-chloropyridin-4-yl)methyl)-1,3,6,7,8,9-hexahydro-5H-furo[3,4-f]pyrido[4,3-b]indole-5-carboxamide (I-38);

Example 481, (E)-N-((2-chloropyridin-4-yl)methyl)-8-(3-(4-fluorophenyl)allyl)-1,3,6,7,8,9-hexahydro-5H-furo[3,4-f]pyrido[4,3-b]indole-5-carboxamide (I-40); and Example 482. (E)-N-((2-chloropyridin-4-yl)methyl)-8-(3-(4-(trifluoromethyl)phenyl)allyl)-1,3,6,7,8,9-hexahydro-5H-furo[3,4-f]pyrido[4,3-b]indole-5-carboxamide (I-46).

The following compounds were prepared similarly to Example 468 but using commercially available 1,3-dihydroisobenzofuran-5-amine, (2-fluoropyridin-4-yl)methanamine, and the respective aldehyde intermediate:

Example 483, (E)-8-(3-(4-chlorophenyl)allyl)-N-((2-fluoropyridin-4-yl)methyl)-1,3,6,7,8,9-hexahydro-5H-furo[3,4-f]pyrido[4,3-b]indole-5-carboxamide (I-38)

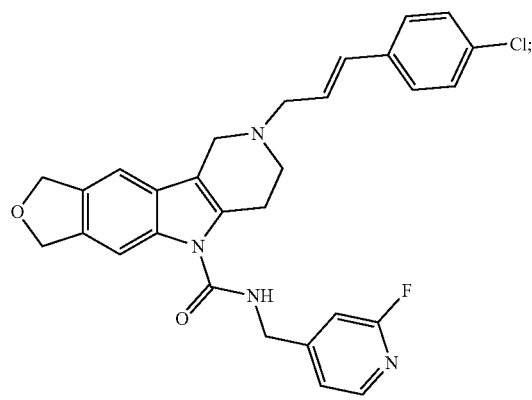 [SMILES: O=C(NCc1ccnc(F)c1)n1c2c(c3cc4c(cc31)COC4)CN(C/C=C/c1ccc(Cl)cc1)CC2]

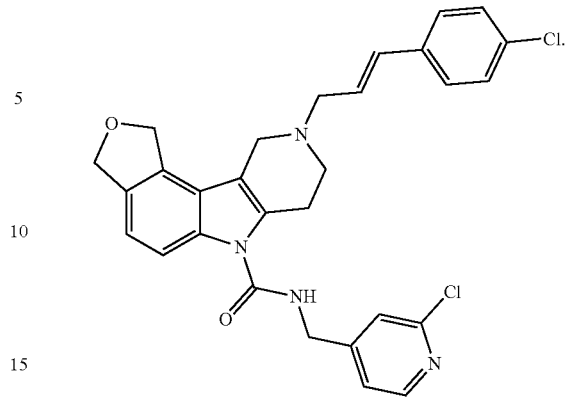

Example 484, (E)-8-(3-(4-chloro-3-fluorophenyl)allyl)-N-((2-fluoropyridin-4-yl)methyl)-1,3,6,7,8,9-hexahydro-5H-furo[3,4-f]pyrido[4,3-b]indole-5-carboxamide (I-3);

Example 485, (E)-8-(3-(4-cyano-3-fluorophenyl)allyl)-N-((2-fluoropyridin-4-yl)methyl)-1,3,6,7,8,9-hexahydro-5H-furo[3,4-f]pyrido[4,3-b]indole-5-carboxamide (I-21);

Example 486, (E)-8-(3-(2,4-difluorophenyl)allyl)-N-((2-fluoropyridin-4-yl)methyl)-1,3,6,7,8,9-hexahydro-5H-furo[3,4-f]pyrido[4,3-b]indole-5-carboxamide HCl (I-30);

Example 487, (E)-8-(3-(3-chloro-4-fluorophenyl)allyl)-N-((2-fluoropyridin-4-yl)methyl)-1,3,6,7,8,9-hexahydro-5H-furo[3,4-f]pyrido[4,3-b]indole-5-carboxamide HCl (I-31); and Example 488, (E)-8-(3-(3,4-difluorophenyl)allyl)-N-((2-fluoropyridin-4-yl)methyl)-1,3,6,7,8,9-hexahydro-5H-furo[3,4-f]pyrido[4,3-b]indole-5-carboxamide (I-32).

Example 489, (E)-8-(3-(4-chlorophenyl)allyl)-N-((2-chlorothiazol-5-yl)methyl)-1,3,6,7,8,9-hexahydro-5H-furo[3,4-f]pyrido[4,3-b]indole-5-carboxamide, was prepared similarly to Example 468 but using commercially available 1,3-dihydroisobenzofuran-5-amine and (2-chlorothiazol-5-yl)methanamine

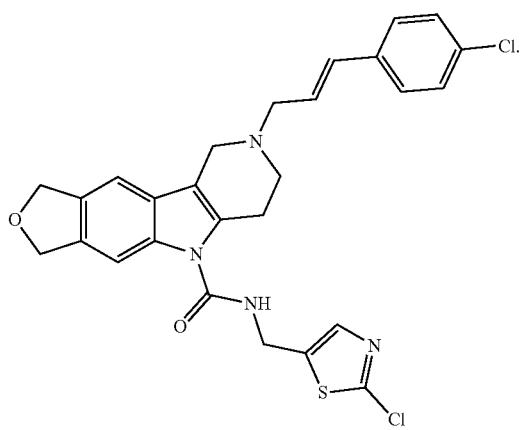 [SMILES: O=C(NCc1cnc(Cl)s1)n1c2c(c3cc4c(cc31)COC4)CN(C/C=C/c1ccc(Cl)cc1)CC2]

Example 490, (E)-9-(3-(4-chlorophenyl)allyl)-N-((2-chloropyridin-4-yl)methyl)-1,3,7,8,9,10-hexahydro-6H-furo[3,4-e]pyrido[4,3-b]indole-6-carboxamide was prepared similarly to Example 468 but using commercially available 1,3-dihydroisobenzofuran-5-amine Example 491, (E)-2-(3-(4-chlorophenyl)allyl)-N-((2-chloropyridin-4-yl)methyl)-7-cyano-8-(methylthio)-1,2,3,4-tetrahydro-5H-pyrido[4,3-b]indole-5-carboxamide, was prepared similarly to Example 468 but using commercially available 5-amino-2-(methylthio)benzonitrile

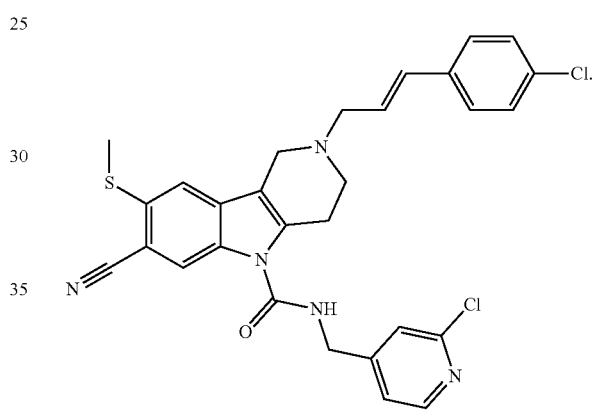

Example 492, (E)-8-bromo-2-(3-(4-chlorophenyl)allyl)-N-((2-chloropyridin-4-yl)methyl)-7-(trifluoromethoxy)-1,2,3,4-tetrahydro-5H-pyrido[4,3-b]indole-5-carboxamide, was prepared similarly to Example 468 but using commercially available 4-bromo-3-(trifluoromethoxy)aniline

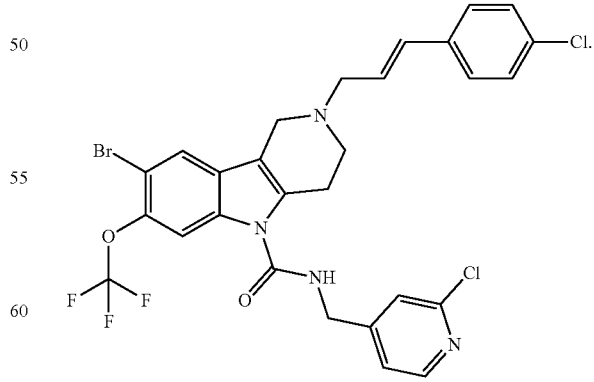

Example 493, (E)-2-(3-(4-chlorophenyl)allyl)-N-((2-chloropyridin-4-yl)methyl)-7-cyano-8-methoxy-1,2,3,4-tetrahydro-5H-pyrido[4,3-b]indole-5-carboxamide, was prepared similarly to Example 468 but using commercially available 5-amino-2-methoxybenzonitrile

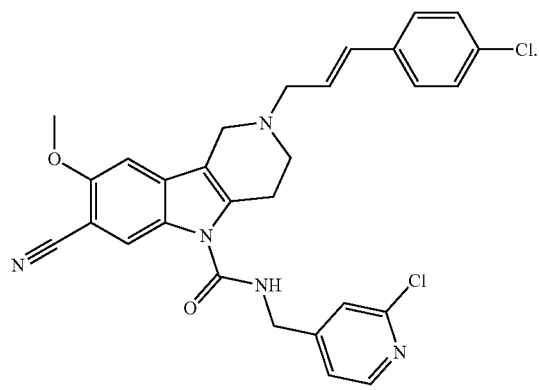 [SMILES: CSc1cc2c3c(n(C(=O)NCc4ccnc(Cl)c4)c2cc1C#N)CCN(C/C=C/c1ccc(Cl)cc1)C3]

Example 494, (E)-2-(3-(4-chlorophenyl)allyl)-N-((2-chloropyridin-4-yl)methyl)-7-methyl-8-(trifluoromethoxy)-1,2,3,4-tetrahydro-5H-pyrido[4,3-b]indole-5-carboxamide, was prepared similarly to Example 468 but using commercially available 3-methyl-4-(trifluoromethoxy)aniline

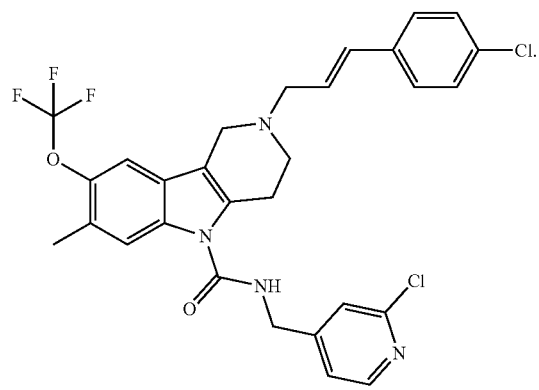 [SMILES: Cc1cc2c(cc1OC(F)(F)F)c1c(n2C(=O)NCc2ccnc(Cl)c2)CCN(C/C=C/c2ccc(Cl)cc2)C1]

Example 495, (E)-2-(3-(4-chlorophenyl)allyl)-N-((2-chloropyridin-4-yl)methyl)-7-fluoro-8-(trifluoromethoxy)-1,2,3,4-tetrahydro-5H-pyrido[4,3-b]indole-5-carboxamide, was prepared similarly to Example 468 but using commercially available 3-fluoro-4-(trifluoromethoxy)aniline

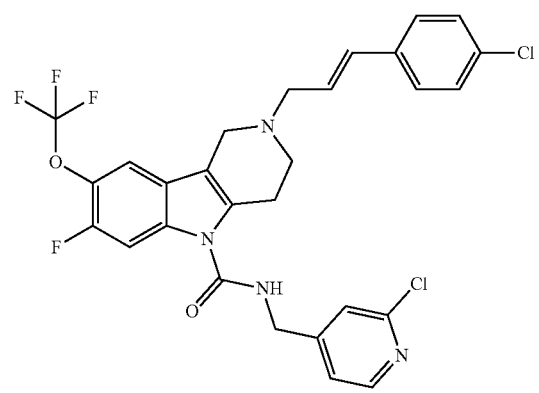 [SMILES: O=C(NCc1ccnc(Cl)c1)n1c2c(c3cc(OC(F)(F)F)c(F)cc31)CN(C/C=C/c1ccc(Cl)cc1)CC2]

Example 496, (E)-7-chloro-2-(3-(4-chlorophenyl)allyl)-N-((2-chloropyridin-4-yl)methyl)-8-(trifluoromethoxy)-1,2,3, 4-tetrahydro-5H-pyrido[4,3-b]indole-5-carboxamide, was prepared similarly to Example 468 but using commercially available 3-chloro-4-(trifluoromethoxy)aniline

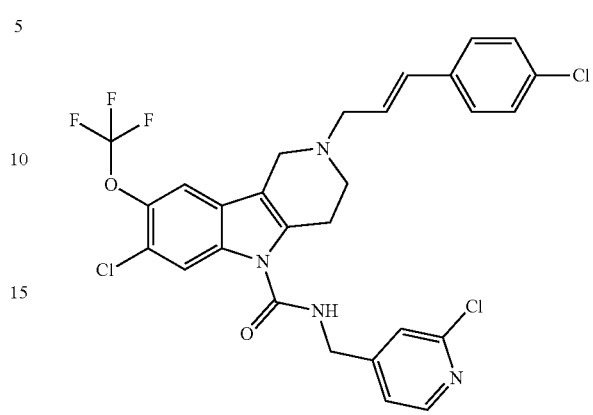

Example 497, (E)-7-bromo-2-(3-(4-chlorophenyl)allyl)-N-((2-chloropyridin-4-yl)methyl)-8-(trifluoromethoxy)-1,2,3,4-tetrahydro-5H-pyrido[4,3-b]indole-5-carboxamide, was prepared similarly to Example 468 but using commercially available 3-chloro-4-(trifluoromethoxy)aniline

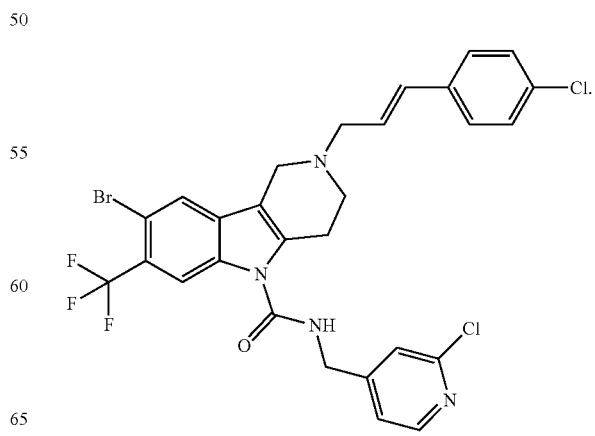

Example 498, (E)-8-bromo-2-(3-(4-chlorophenyl)allyl)-N-((2-chloropyridin-4-yl)methyl)-7-(trifluoromethyl)-1,2,3,4-tetrahydro-5H-pyrido[4,3-b]indole-5-carboxamide, was prepared similarly to Example 468 but using commercially available 4-bromo-3-(trifluoromethyl)aniline Example 499, (E)-8-chloro-2-(3-(4-chlorophenyl)allyl)-N-((2-chloropyridin-4-yl)methyl)-7-(trifluoromethoxy)-1,2,3,4-tetrahydro-5H-pyrido[4,3-b]indole-5-carboxamide, was prepared similarly to Example 468 but using commercially available 4-chloro-3-(trifluoromethyl)aniline

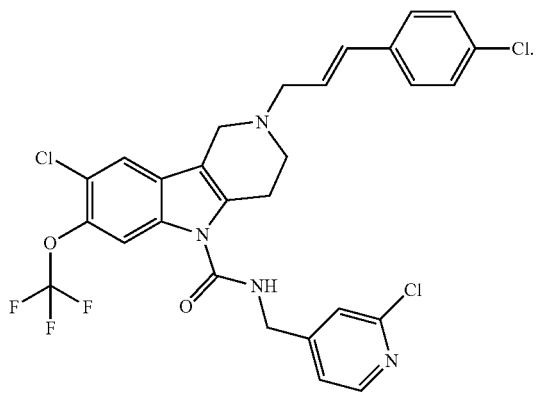 [SMILES: O=C(NCc1ccnc(Cl)c1)n1c2c(c3cc(Cl)c(OC(F)(F)F)cc31)CN(C/C=C/c1ccc(Cl)cc1)CC2]

Example 500, (E)-2-(3-(4-chlorophenyl)allyl)-N-((2-chloropyridin-4-yl)methyl)-8-(2-oxopyridin-1 (2H)-yl)-1,2,3,4-tetrahydro-5H-pyrido[4,3-b]indole-5-carboxamide, was prepared similarly to Example 468 but using commercially available 1-(4-aminophenyl)pyridin-2(1H)-one

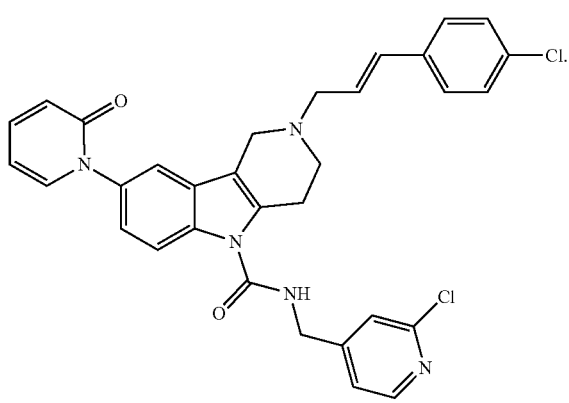 [SMILES: O=C(NCc1ccnc(Cl)c1)n1c2c(c3cc(-n4ccccc4=O)ccc31)CN(C/C=C/c1ccc(Cl)cc1)CC2]

Example 501, (E)-2-(3-(4-chlorophenyl)allyl)-8-cyclopropyl-N-((2-fluoropyridin-4-yl)methyl)-1,2,3,4-tetrahydro-5H-pyrido[4,3-b]indole-5-carboxamide, was prepared similarly to Example 468 but using commercially available 4-cyclopropylaniline

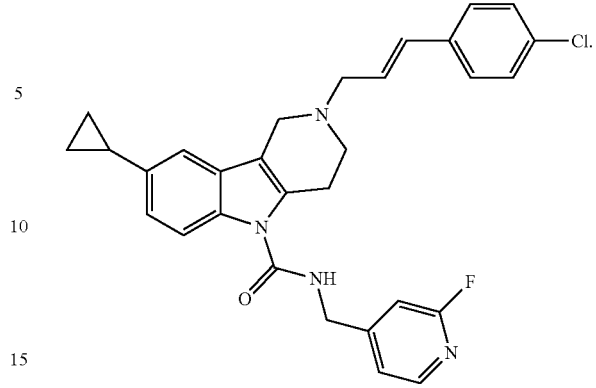

Example 502, (E)-2-(3-(4-chlorophenyl)allyl)-N-((2-chloropyridin-4-yl)methyl)-7-cyano-8-(trifluoromethoxy)-1,2,3,4-tetrahydro-5H-pyrido[4,3-b]indole-5-carboxamide, was prepared similarly to Example 468 but using commercially available 5-amino-2-(trifluoromethoxy)benzonitrile.

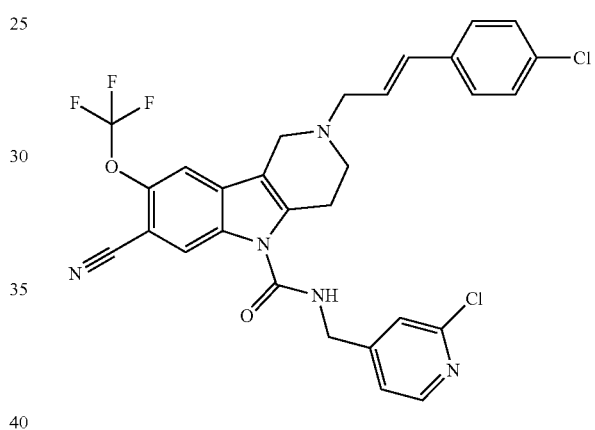

Example 503, (E)-2-(3-(4-chlorophenyl)allyl)-N-((2-chloropyridin-4-yl)methyl)-8-cyano-7-(trifluoromethoxy)-1,2,3,4-tetrahydro-5H-pyrido[4,3-b]indole-5-carboxamide, was prepared similarly to Example 468 but using commercially available 4-amino-2-(trifluoromethoxy)benzonitrile

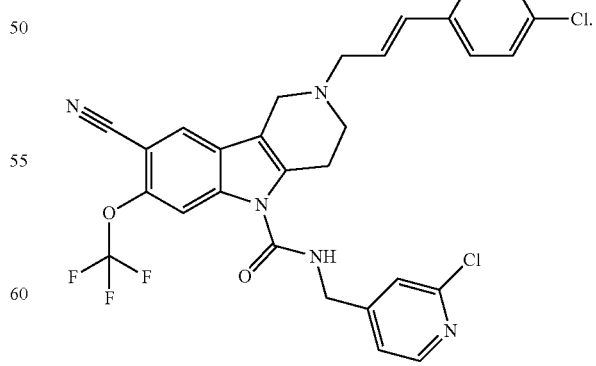

Example 504. (E)-2-(3-(4-chloro-3-fluorophenyl)allyl)-N-((2-chloropyridin-4-yl)methyl)-8-morpholino-1,2,3,4-tetrahydro-5H-pyrido[4,3-b]indole-5-carboxamide HCl

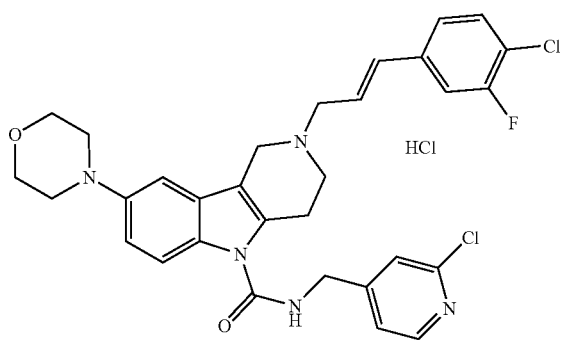 [SMILES: O=C(NCc1ccnc(Cl)c1)n1c2c(c3cc(N4CCOCC4)ccc31)CN(C/C=C/c1ccc(Cl)c(F)c1)CC2 ; Cl]

Step 1: tert-butyl 8-morpholino-1,3,4,5-tetrahydro-2H-pyrido[4,3-b]indole-2-carboxylate

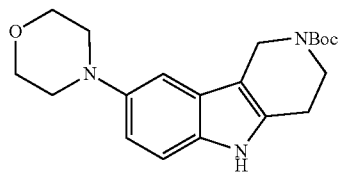

A teflon screw-cap 10 mL vial, equipped with a magnetic stir bar, was charged with XPhos (144 mg, 0.30 mmol) and XPhos Pd G2 precatalyst (224 mg, 0.30 mmol) and commercially available tert-butyl 8-bromo-1,3,4,5-tetrahydro-2H-pyrido[4,3-b]indole-2-carboxylate (1.05 g, 3.0 mmol). The vial was sealed with a teflon screw-cap, evacuated and backfilled with $N_2$ 3 times. Morpholine (315 µL, 3.6 mmol) was added via syringe followed by LiHMDS (1 M in THF, 7.2 mL, 7.2 mmol). The reaction mixture was heated at 65° C. overnight. The progress of the reaction was followed by LCMS. After consumption of all starting materials the reaction mixture was cooled down to RT and the crude mixture was diluted with 10 mL of EtOAc, then 5 mL of 1 N HCl was added to quench the reaction. The latter solution was poured into a saturated $NaHCO_3$ solution, diluted with EtOAc and the aq. layer extracted 3 times with EtOAc. The org layers were combined, dried over $MgSO_4$, filtered and the volatiles removed under reduced pressure. The crude material was purified by flash chromatography on silica using EtOAc in Hexanes (from 0 to 50%) to give the desired product as a pale yellow solid (632 mg, 71% yield). LC-Ms (m/z): [M+H]=358.2

Step 2: tert-butyl 5-(((2-chloropyridin-4-yl)methyl)carbamoyl)-8-morpholino-1,3,4,5-tetrahydro-2H-pyrido[4,3-b]indole-2-carboxylate

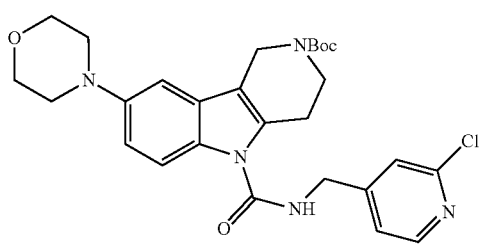 [SMILES: CC(C)(C)OC(=O)N1CCc2c(c3cc(N4CCOCC4)ccc3n2C(=O)NCc2ccnc(Cl)c2)C1]

A 10 mL Teflon cap vial was charged with tert-butyl 8-morpholino-1,3,4,5-tetrahydro-2H-pyrido[4,3-b]indole-2-carboxylate (179 mg, 0.50 mmol), DMAP (6 mg, 0.05 mmol) and CDI (164 mg, 1.0 mmol) and MeCN (0.6 mL). The resulting solution was heated to 65° C. for 1.5 hours. The reaction mixture was cooled to room temperature and (2-chloropyridin-4-yl)methanamine dihydrochloride (200 mg, 1.00 mmol) was added followed by 1.0 mL of MeCN and TEA (210 µL, 1.50 mmol). The resulting suspension was heated to 65° C. for 30 minutes. The progress of the reaction was monitored by LCMS. After cooling the reaction mixture to room temperature, the crude material was transferred into a separatory funnel, diluted with 50 mL DCM and 50 mL 15% citric acid in $H_2O$ and the layers were separated. The aqueous layer was extracted with DCM, the organic layers were combined, dried over $MgSO_4$ and the volatiles removed under reduced pressure. The crude material was purified by flash chromatography on a 25 g silica column with EtOAc in Hexanes (0 to 75%) to give the desired product as an amorphous white solid (198 mg, 0.652 mmol, 75%). LC-Ms (m/z): [M+H]=526.2.

Step 3: Preparation of Example 504.

In a 8 mL vial 98 mg of tert-butyl 5-(((2-chloropyridin-4-yl)methyl)carbamoyl)-8-morpholino-1,3,4,5-tetrahydro-2H-pyrido[4,3-b]indole-2-carboxylate was dissolved in 5.0 mL of DCM and 284 µL of TFA was added at room temperature. The resulting solution was stirred at room temperature for two hours. Upon completion of the reaction the volatiles were removed under reduced pressure. The crude was dissolved in 2.0 mL of DCM and 0.2 mL of MeOH after which 77 µL of TEA was added. The resulting solution was cooled to 0° C. and 41 mg of aldehyde intermediate I-3 was added. After stirring for 15 minutes at 0° C., 120 mg of sodium triacetoxyborohydride was added and the resulting solution was stirred for 3 hours. Upon completion of the reaction as monitored by LCMS, 3 mL of saturated $NaHCO_3$ solution were added and the resulting solution stirred for 1 hour at room temperature. The biphasic solution was passed through a phase separator cartridge and the aqueous layer washed with DCM. The organic volatiles were removed under a flow of $N_2$, and the crude material was purified on KP-NH silica using flash chromatography (EtOAc in Hexanes from 0 to 100%). The crystals were dissolved in DCM and $Et_2O$ and a stream of HCl gas was passed through the solution. 32 mg of the title HCl salt were retrieved by filtration as a white solid.

Example 505, (E)-2-(3-(4-chlorophenyl)allyl)-N-((2-chloropyridin-4-yl)methyl)-8-morpholino-1,2,3,4-tetrahydro-5H-pyrido[4,3-b]indole-5-carboxamide HCl, was prepared similarly to Example 504 but using aldehyde intermediate, I-38.

Example 506, (E)-2-(3-(4-chloro-3-fluorophenyl)allyl)-N-((2-chloropyridin-4-yl)methyl)-8-(pyrrolidin-1-yl)-1,2,3,4-tetrahydro-5H-pyrido[4,3-b]indole-5-carboxamide

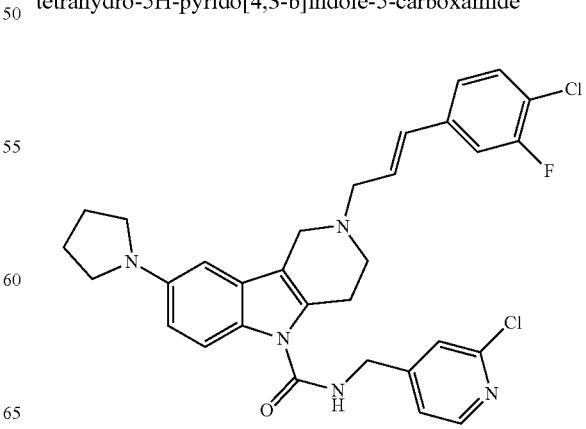

Step 1: tert-butyl 8-(pyrrolidin-1-yl)-1,3,4,5-tetrahydro-2H-pyrido[4,3-b]indole-2-carboxylate

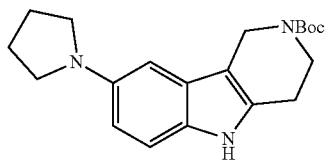 [SMILES: CC(C)(C)OC(=O)N1CCc2[nH]c3ccc(N4CCCC4)cc3c2C1]

A teflon screw-cap 10 mL vial, equipped with a magnetic stir bar, was charged with XPhos (144 mg, 0.30 mmol) and XPhos Pd G2 precatalyst (224 mg, 0.30 mmol) and commercially available tert-butyl 8-bromo-1,3,4,5-tetrahydro-2H-pyrido[4,3-b]indole-2-carboxylate (1.05 g, 3.0 mmol). The vial was sealed with a teflon screw-cap, evacuated and backfilled with $N_2$ 3 times. Pyrrolidine (347 µL, 4.2 mmol) was added via syringe followed by LiHMDS (1M in THF, 7.2 mL, 7.2 mmol). The reaction mixture was heated at 65° C. overnight. The progress of the reaction was followed by LCMS. After consumption of all starting materials the reaction mixture was cooled down to room temperature and the crude mixture was diluted with 10 mL of EtOAc, then 5 mL of 1 N HCl was added to quench the reaction. The latter solution was poured into a saturated $NaHCO_3$ solution, diluted with EtOAc and the aqueous layer extracted 3 times with EtOAc. The org layers were combined, dried over $MgSO_4$, filtered and the volatiles removed under reduced pressure. The crude material was purified by flash chromatography on silica using EtOAc in Hexanes (from 0 to 50%) to give the desired product as a pale yellow solid (890 mg, 87% yield). LC-Ms (m/z): [M+H]=342.3.

Step 2: tert-butyl 5-(((2-chloropyridin-4-yl)methyl)carbamoyl)-8-(pyrrolidin-1-yl)-1,3,4,5-tetrahydro-2H-pyrido[4,3-b]indole-2-carboxylate

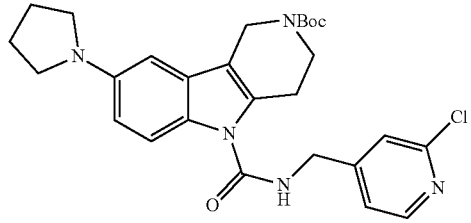 [SMILES: CC(C)(C)OC(=O)N1CCc2c(c3cc(N4CCCC4)ccc3n2C(=O)NCc2ccnc(Cl)c2)C1]

A 10 mL Teflon cap vial was charged with tert-butyl 8-(pyrrolidin-1-yl)-1,3,4,5-tetrahydro-2H-pyrido[4,3-b]indole-2-carboxylate (905 mg, 2.651 mmol), DMAP (33 mg, 0.2651 mmol) and CDI (868 mg, 5.302 mmol) and MeCN (3.0 mL). The resulting solution was heated to 65° C. for 1.5 hours. The reaction mixture was cooled to room temperature and (2-chloropyridin-4-yl)methanamine dihydrochloride (1.055 g, 5.302 mmol) was added followed by 5 mL of MeCN and TEA (1.11 mL, 7.953 mmol). The resulting suspension was heated to 65° C. for 30 minutes. The progress of the reaction was monitored by LCMS. After cooling the reaction mixture to room temperature, the crude material was transferred into a separatory funnel, diluted with 50 mL DCM and 50 mL 15% citric acid in $H_2O$ and the layers were separated. The aq. layer was extracted with DCM, the organic layers were combined, dried over $MgSO_4$ and the volatiles removed under reduced pressure. The crude material was purified by flash chromatography on a 25 g silica column with EtOAc in Hexanes (0 to 75%) to give the desired product as an amorphous white solid (314 mg, 0.616 mmol, 23%). LC-Ms (m/z): [M+H]=510.2

Step 3: Preparation of Example 506.

In a 8 mL vial 105 mg of tert-butyl 5-(((2-chloropyridin-4-yl)methyl)carbamoyl)-8-(pyrrolidin-1-yl)-1,3,4,5-tetrahydro-2H-pyrido[4,3-b]indole-2-carboxylate was dissolved in 5.0 mL of DCM and 157 µL of TFA was added at room temperature. The resulting solution was stirred at room temperature for two hours. Upon completion of the reaction the volatiles were removed under reduced pressure. The crude was dissolved in 2.0 mL of DCM and 0.2 mL of MeOH after which 86 µL of TEA was added. The resulting solution was cooled to 0° C. and 45 mg of aldehyde intermediate I-3 was added. After stirring for 15 minutes at 0° C., 133 mg of sodium triacetoxyborohydride was added and the resulting solution was stirred for 3 hours. Upon completion of the reaction as monitored by LCMS, 3 mL of saturated $NaHCO_3$ solution were added and the resulting solution stirred for 1 hour at room temperature. The biphasic solution was passed through a phase separator cartridge and the aqueous layer washed with DCM. The organic volatiles were removed under a flow of $N_2$, and the crude material was purified on KP-NH silica using flash chromatography (EtOAc in Hexanes from 0 to 100%) to give the title compound as a free amine as an off-white solid.

Example 507, (E)-N-((2-chloropyridin-4-yl)methyl)-2-(3-(3,4-dichlorophenyl)allyl)-8-(pyrrolidin-1-yl)-1,2,3,4-tetrahydro-5H-pyrido[4,3-b]indole-5-carboxamide, was prepared similarly to Example 506 but using aldehyde intermediate, I-39.

Example 508, (E)-N-((2-chloropyridin-4-yl)methyl)-2-(3-(3,4-dichlorophenyl)allyl)-7-morpholino-1,2,3,4-tetrahydro-5H-pyrido[4,3-b]indole-5-carboxamide HCl (I-39)

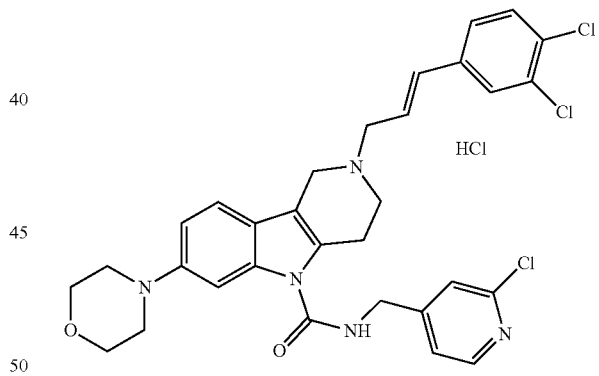

Step 1: tert-butyl 7-morpholino-1,3,4,5-tetrahydro-2H-pyrido[4,3-b]indole-2-carboxylate

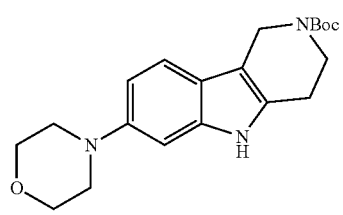 [SMILES: CC(C)(C)OC(=O)N1CCc2[nH]c3cc(N4CCOCC4)ccc3c2C1]

A teflon screw-cap 10 mL vial, equipped with a magnetic stir bar, was charged with SPhos (45 mg, 0.30 mmol) and SPhos Pd G2 precatalyst (58 mg, 0.30 mmol) and tert-butyl 7-bromo-1,3,4,5-tetrahydro-2H-pyrido[4,3-b]indole-2-carboxylate (1.05 g, 3.0 mmol). The vial was sealed with a teflon screw-cap, evacuated and backfilled with $N_2$ 3 times. Morpholine (315 μL, 3.6 mmol) was added via syringe followed by LiHMDS (1M in THF, 7.2 mL, 7.2 mmol). The reaction mixture was heated at 65° C. overnight. The progress of the reaction was followed by LCMS. After consumption of all starting materials the reaction mixture was cooled down to RT and the crude mixture was diluted with 10 mL of EtOAc, then 5 mL of 1 N HCl was added to quench the reaction. The latter solution was poured into a saturated $NaHCO_3$ solution, diluted with EtOAc and the aq. layer extracted 3 times with EtOAc. The org layers were combined, dried over $MgSO_4$, filtered and the volatiles removed under reduced pressure. The crude material was purified by flash chromatography on silica using EtOAc in Hexanes (from 0 to 50%) to give the desired product as a pale yellow solid (570 mg, 53% yield). LC-Ms (m/z): [M+H]=358.2

Step 2: tert-butyl 5-(((2-chloropyridin-4-yl)methyl)carbamoyl)-7-morpholino-1,3,4,5-tetrahydro-2H-pyrido[4,3-b]indole-2-carboxylate

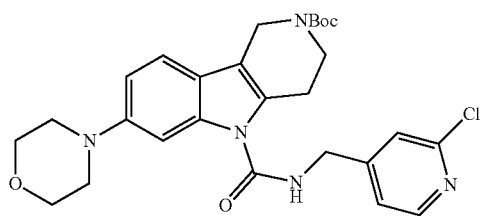 [SMILES: CC(C)(C)OC(=O)N1CCc2c(c3ccc(N4CCOCC4)cc3n2C(=O)NCc2ccnc(Cl)c2)C1]

A 100 mL Schlenk flask was charged with tert-butyl 7-morpholino-1,3,4,5-tetrahydro-2H-pyrido[4,3-b]indole-2-carboxylate (360 mg, 1.00 mmol) and anhydrous THF (10 mL). The resulting suspension was cooled to 0° C. with an ice bath and NaH (121 mg, 60% disp, 3.00 mmol) was added in small portions. Gas slowly evolves and the reaction mixture turned from an off white suspension to a rose pinkish-red suspension. The ice bath was removed after 2 hours, and the reaction was allowed to warm to RT for 10 minutes. Next, the mixture was cooled back to 0° C. (ice bath) and 2-chloro-4-(isocyanatomethyl)pyridine (255 mg, 1.50 mmol) in DCM (3.0 mL) was added quickly in one portion. After stirring for 5 minutes at 0° C., the reaction mixture was carefully quenched with addition of HCl (3 mL, 1.0 M) at 0° C. The reaction mixture diluted with water (10 mL) and saturated $NaHCO_3$ (10 mL) and extracted with EtOAc (2×15 mL). The combined organic phases were washed with brine, dried over $MgSO_4$, and concentrated under reduced pressure. The crude was purified by flash chromatography using EtOAc in Hexanes (0 to 70%) to give the desired compound as an amorphous off yellow solid (180 mg, 0.34 mmol, 34% yield). LC-Ms (m/z): [M+H]=526.2.

Step 3: Preparation of Example 508.

In a 8 mL vial 90 mg of tert-butyl 5-(((2-chloropyridin-4-yl)methyl)carbamoyl)-7-morpholino-1,3,4,5-tetrahydro-2H-pyrido[4,3-b]indole-2-carboxylate was dissolved in 5.0 mL of DCM and 131 μL of TFA was added at RT. The resulting solution was stirred at RT for two hours. Upon completion of the reaction the volatiles were removed under reduced pressure. The crude was dissolved in 2.0 mL of DCM and 0.2 mL of MeOH after which 72 μL of TEA was added. The resulting solution was cooled to 0° C. and 41 mg of aldehyde intermediate I-39 was added. After stirring for 15 minutes at 0° C., 111 mg of sodium triacetoxyborohydride was added and the resulting solution was stirred for 3 hours. Upon completion of the reaction as monitored by LCMS, 3 mL of saturated $NaHCO_3$ solution were added and the resulting solution stirred for 1 hour at RT. The biphasic solution was passed through a phase separator cartridge and the aqueous layer washed with DCM. The organic volatiles were removed under a flow of $N_2$, and the crude material was purified on KP-NH silica using flash chromatography (EtOAc in Hexanes from 0 to 100%). The crystals were dissolved in DCM and $Et_2O$ and a stream of HCl gas was passed through the solution. 30 mg of the title HCl salt were retrieved by filtration as a white solid.

Example 509, (E)-2-(3-(4-chloro-3-fluorophenyl)allyl)-N-((2-chloropyridin-4-yl)methyl)-7-morpholino-1,2,3,4-tetrahydro-5H-pyrido[4,3-b]indole-5-carboxamide, HCl was prepared similarly to Example 508 but using aldehyde intermediate, I-3.

Example 510, (E)-2-(3-(4-chloro-3-fluorophenyl)allyl)-N-((2-chloropyridin-4-yl)methyl)-8-(1,3-thiazinan-3-yl)-1,2,3,4-tetrahydro-5H-pyrido[4,3-b]indole-5-carboxamide, HCl (I-3)

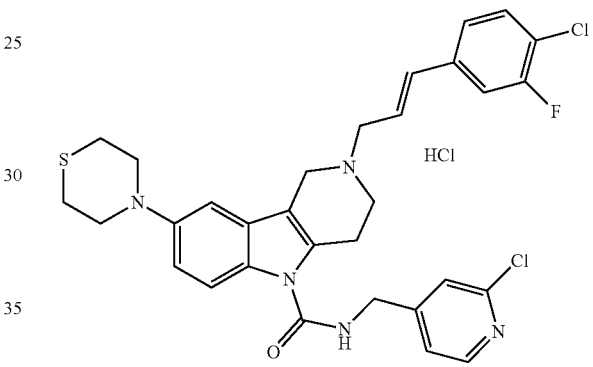

Step 1: tert-butyl 8-(1,3-thiazinan-3-yl)-1,3,4,5-tetrahydro-2H-pyrido[4,3-b]indole-2-carboxylate

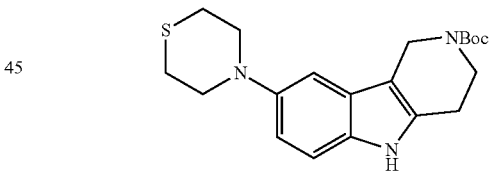

A teflon screw-cap 10 mL vial, equipped with a magnetic stir bar, was charged with XPhos (29 mg, 0.30 mmol) and XPhos Pd G2 precatalyst (45 mg, 0.30 mmol) and tert-butyl 8-bromo-1,3,4,5-tetrahydro-2H-pyrido[4,3-b]indole-2-carboxylate (1.05 g, 3.0 mmol). The vial was sealed with a teflon screw-cap, evacuated and backfilled with $N_2$ 3 times. Thiomorpholine (616 μL, 6.00 mmol) was added via syringe followed by LiHMDS (1M in THF, 7.2 mL, 7.2 mmol). The reaction mixture was heated at 65° C. overnight. The progress of the reaction was followed by LCMS. After consumption of all starting materials the reaction mixture was cooled down to RT and the crude mixture was diluted with 10 mL of EtOAc, then 5 mL of 1 N HCl was added to quench the reaction. The latter solution was poured into a saturated $NaHCO_3$ solution, diluted with EtOAc and the aq. layer extracted 3 times with EtOAc. The organic layers were combined, dried over MgSO4, filtered and the volatiles removed under reduced pressure. The crude material was purified by flash chromatography on silica using EtOAc in Hexanes (from 0 to 50%) to give the desired product as a pale yellow solid (510 mg, 46% yield). LC-Ms (m/z): [M+H]=374.2

Step 2: tert-butyl 5-(((2-chloropyridin-4-yl)methyl)carbamoyl)-8-(1,3-thiazinan-3-yl)-1,3,4,5-tetrahydro-2H-pyrido[4,3-b]indole-2-carboxylate

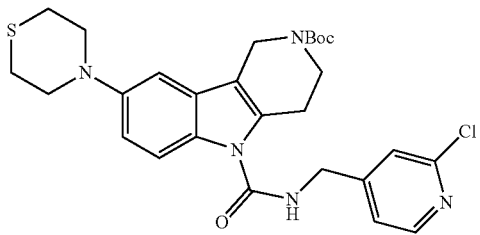 [SMILES: CC(C)(C)OC(=O)N1CCc2c(c3cc(N4CCSCC4)ccc3n2C(=O)NCc2ccnc(Cl)c2)C1]

A 100 mL Schlenk flask was charged with tert-butyl 8-thiomorpholino-1,3,4,5-tetrahydro-2H-pyrido[4,3-b]indole-2-carboxylate (510 mg, 1.365 mmol) and anhydrous THF (10 mL). The resulting suspension was cooled to 0° C. with an ice bath and NaH (164 mg, 60% disp, 4.096 mmol) was added in small portions. Gas slowly evolves and the reaction mixture turned from an off white suspension to a rose pinkish-red suspension. The ice bath was removed after 2 hours, and the reaction was allowed to warm to RT for 10 minutes. Next, the mixture was cooled back to 0° C. (ice bath) and 2-chloro-4-(isocyanatomethyl)pyridine (345 mg, 2.048 mmol) in DCM (4.0 mL) was added quickly in one portion. After stirring for 5 minutes at 0° C., the reaction mixture was carefully quenched with addition of HCl (4 mL, 1.0 M) at 0° C. The reaction mixture diluted with water (10 mL) and saturated NaHCO₃ (10 mL) and extracted with EtOAc (2×15 mL). The combined organic phases were washed with brine, dried over MgSO₄, and concentrated under reduced pressure. The crude was purified by flash chromatography using EtOAc in Hexanes (0 to 70%) to give the desired compound as an amorphous off yellow solid (180 mg, 0.33 mmol, 24% yield). LC-Ms (m/z): [M+H]=542.3.

Step 3: Preparation of Example 510.

In a 8 mL vial 90 mg of tert-butyl 5-(((2-chloropyridin-4-yl)methyl)carbamoyl)-8-(1,3-thiazinan-3-yl)-1,3,4,5-tetrahydro-2H-pyrido[4,3-b]indole-2-carboxylate was dissolved in 5.0 mL of DCM and 128 µL of TFA was added at RT. The resulting solution was stirred at RT for two hours. Upon completion of the reaction the volatiles were removed under reduced pressure. The crude was dissolved in 2.0 mL of DCM and 0.2 mL of MeOH after which 70 µL of TEA was added. The resulting solution was cooled to 0° C. and 37 mg of aldehyde intermediate I-3 was added. After stirring for 15 minutes at 0° C., 108 mg of sodium triacetoxyborohydride was added and the resulting solution was stirred for 3 hours. Upon completion of the reaction as monitored by LCMS, 3 mL of saturated NaHCO₃ solution were added and the resulting solution stirred for 1 hour at RT. The biphasic solution was passed through a phase separator cartridge and the aqueous layer washed with DCM. The organic volatiles were removed under a flow of N₂, and the crude material was purified on KP-NH silica using flash chromatography (EtOAc in Hexanes from 0 to 100%). The crystals were dissolved in DCM and Et₂O and a stream of HCl gas was passed through the solution. 45 mg of the title HCl salt were retrieved by filtration as a white solid.

Example 511, (E)-N-((2-chloropyridin-4-yl)methyl)-2-(3-(3,4-dichlorophenyl)allyl)-8-(1,3-thiazinan-3-yl)-1,2,3,4-tetrahydro-5H-pyrido[4,3-b]indole-5-carboxamide, HCl, was prepared similarly to Example 510 but using aldehyde intermediate, I-39.

Example 512, (E)-2-(3-(4-chlorophenyl)allyl)-N-((2-chloropyridin-4-yl)methyl)-8-methoxy-1,2,3,4-tetrahydro-5H-pyrido[4,3-b]indole-5-carboxamide was prepared similarly to Example 167 but using 8-methoxy-2,3,4,5-tetrahydro-1H-pyrido[4,3-b]indole hydrochloride in place of 8-fluoro-2,3,4,5-tetrahydro-1H-pyrido[4,3-b]indole and the aldehyde intermediate, I-38

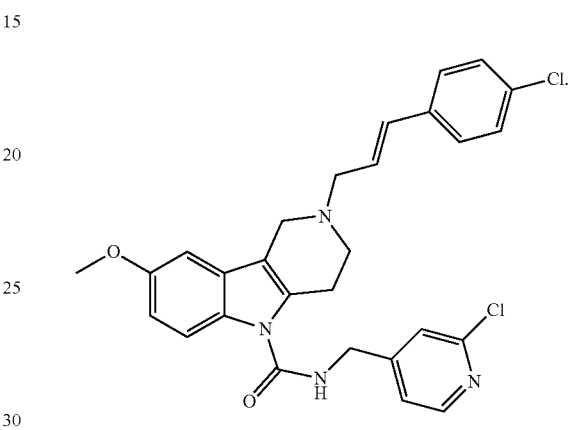

The following compounds were prepared similarly to Example 512 but using 8-ethoxy-2,3,4,5-tetrahydro-1H-pyrido[4,3-b]indole hydrochloride in place of 8-methoxy-2,3,4,5-tetrahydro-1H-pyrido[4,3-b]indole hydrochloride and the respective aldehyde intermediate:

Example 513, (E)-2-(3-(4-chlorophenyl)allyl)-N-((2-chloropyridin-4-yl)methyl)-8-ethoxy-1,2,3,4-tetrahydro-5H-pyrido[4,3-b]indole-5-carboxamide (I-38) and

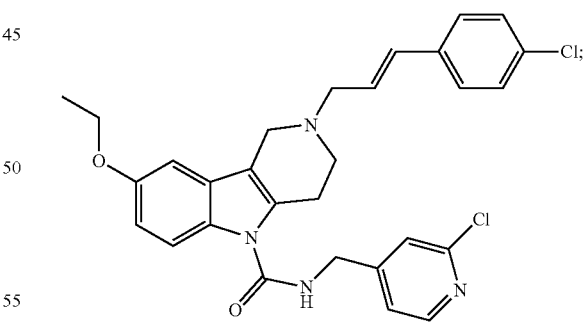

Example 514, (E)-N-((2-chloropyridin-4-yl)methyl)-8-ethoxy-2-(3-(4-fluorophenyl)allyl)-1,2,3,4-tetrahydro-5H-pyrido[4,3-b]indole-5-carboxamide (I-40).

Example 515, (E)-2-(3-(4-chloro-3-fluorophenyl)allyl)-7-cyano-N-((2-cyclopropylpyridin-4-yl)methyl)-1,2,3,4-tetrahydro-5H-pyrido[4,3-b]indole-5-carboxamide HCl, was prepared similarly to Example 1 but using (2-cyclopropylpyridin-4-yl)methanamine in place of (2-chloropyridin-4-yl) methanamine and aldehyde intermediate (I-3)

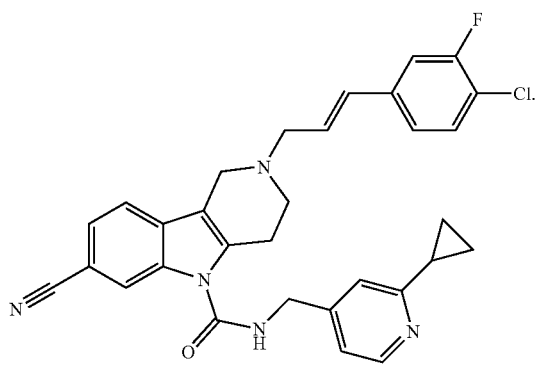 [SMILES: N#Cc1ccc2c3c(n(C(=O)NCc4ccnc(C5CC5)c4)c2c1)CCN(C/C=C/c1ccc(Cl)c(F)c1)C3]

Example 516, (E)-8-chloro-2-(3-(4-chlorophenyl)allyl)-N-((2-chloropyridin-4-yl)methyl)-1,2,3,4,4a,9b-hexahydro-5H-pyrido[4,3-b]indole-5-carboxamide (I-38)

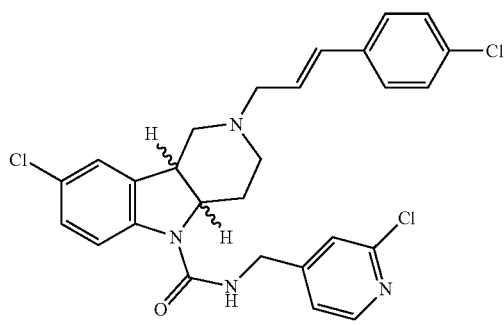 [SMILES: O=C(NCc1ccnc(Cl)c1)N1c2ccc(Cl)cc2C2CN(C/C=C/c3ccc(Cl)cc3)CCC21]

Step 1: tert-butyl 8-chloro-5-[(2-chloro-4-pyridyl)methylcarbamoyl]-3,4,4a,9b-tetrahydro-1H-pyrido[4,3-b]indole-2-carboxylate.

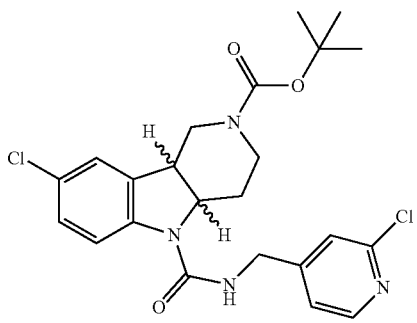 [SMILES: CC(C)(C)OC(=O)N1CCC2C(C1)c1cc(Cl)ccc1N2C(=O)NCc1ccnc(Cl)c1]

To a stirred solution of triphosgene (172 mg, 0.56 mmol) in CH$_2$Cl$_2$ (15 mL) at 0° C. was slowly added commercially available (Wuxi) tert-butyl 8-chloro-1,3,4,4a,5,9b-hexahydropyrido[4,3-b]indole-2-carboxylate (500 mg, 1.6 mmol) and N,N-diisopropylethylamine (1.2 mL, 6.5 mmol) as a solution in CH$_2$Cl$_2$ (10 mL). The reaction was allowed to warm to room temperature and stirred for 3 hours. 2-chloropyridin-4-yl)methanamine (0.37 g, 2.1 mmol) was next added and the reaction was stirred at room temperature for 18 hours. The reaction mixture was diluted with CH$_2$Cl$_2$ (75 mL) and water (75 mL). The organic phase was separated, dried (Na$_2$SO$_4$), and concentrated under vacuum. The crude material was chromatographed (40 g Redi-Sep column) eluting from 100 hexanes to 100% EtOAc to afford the intermediate as a solid. LC-Ms (m/z): [M+H-tbutyl]=421.

Step 2: 8-chloro-N-[(2-chloro-4-pyridyl)methyl]-1,2,3,4,4a,9b-hexahydropyrido[4,3-b]indole-5-carboxamide.

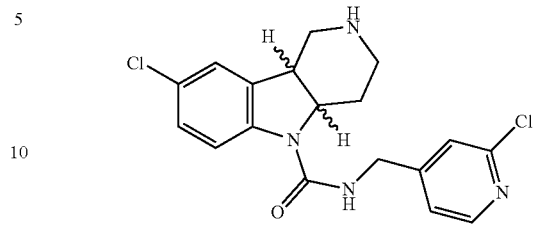

The title compound was synthesized following the same procedure as described in Example 145, Step-3, but using tert-butyl 8-chloro-5-[(2-chloro-4-pyridyl)methylcarbamoyl]-3,4,4a,9b-tetrahydro-1H-pyrido[4,3-b]indole-2-carboxylate in place of tert-butyl 5-[(2-chloro-4-pyridyl)methylcarbamoyl]-7-methyl-3,4-dihydro-1H-pyrido[4,3-b]indole-2-carboxylate. LC-MS (m/z): [M+H]=377.

Step 3: Preparation of Example 516.

The title compound was synthesized following the same procedure as for the synthesis of Example 145, Step 4, but using 8-chloro-N-[(2-chloro-4-pyridyl)methyl]-1,2,3,4,4a,9b-hexahydropyrido[4,3-b]indole-5-carboxamide in place of of N-[(2-chloro-4-pyridyl)methyl]-7-methyl-1,2,3,4-tetrahydropyrido[4,3-b]indole-5-carboxamide and aldehyde intermediate I-38.

Example 517, (E)-8-chloro-N-((2-chloropyridin-4-yl)methyl)-2-(3-(3,4-dichlorophenyl)allyl)-1,2,3,4,4a,9b-hexahydro-5H-pyrido[4,3-b]indole-5-carboxamide was prepared similarly to Example 516 with the aldehyde intermediate, I-39. The 8-chloro-N-[(2-chloro-4-pyridyl)methyl]-2-[(E)-3-(3,4-dichlorophenyl)allyl]-3,4,4a,9b-tetrahydro-1H-pyrido[4,3-b]indole-5-carboxamide was separated into single enantiomers (Prep SFC=Berger Thar MS100, column=AS-H 30×250 mm 5 um, MP A=CO$_2$ MP B=0.1% TEA in MeOH, Isocratic 30% B, 100 mL/min, 100bar, 33° C.) as Peak 1 and Peak 2, respectively.

Biology:

To identify novel parasiticides, compounds were screened for nematocidal activity using in vitro motility assays. The compounds described herein have demonstrated nematocidal activity against either *Haemonchus contortus* (L3) and/or *Dirofilaria immitis* (microfilariae) as determined by reductions in nematode motility either by paralysis or death. Active compounds were then subsequently investigated for in vivo efficacy using a jird infection model whereby clearance of *Trichostrongylus* colubriformus was determined.

The biological activity *Haemonchus contortus* (L3), *Dirofilaria immitis* (microfilariae) and jird efficacy of the compounds of the invention can be measured using the test methods described below.

*Haemonchus contortus*, Larvae Stage 3 (HcL3) In Vitro Assay

The *Haemonchus contortus* L3 strain was obtained from the University of Georgia and is a relatively recent multiple-resistant field isolate (International Journal for Parasitology 37 (2007) 795-804). Compounds were dissolved in DMSO to give an initial concentration of 30 mM. The stock concentration was subsequently titrated in basal media to give an eleven point half-log concentration curve for testing. Following the serial dilution, 250 nl of each compound solution was transferred to an assay plate (384-well) whereby 25 µL of exsheathed worms (100 larvae/well) were subsequently added. The final compound concentrations in the 384-well plate following worm addition ranged from 0.001-100 μM. Assay plates were incubated at 37° C. and observed at 96 hours for drug effect. Endpoint data (Table 2, HcL3) are recorded as a Minimal Effective Concentration (MEC) in μM, whereby worm motility is inhibited by approximately 70%.

*Dirofilaria immitis*, Microfilariae (DiMF) In Vitro Assay

Compounds were initially dissolved in DMSO. The stock concentration was subsequently diluted in basal media and serially diluted to give a concentration response curve starting at 100 μM (11 total concentrations). Following the serial dilution, compound solution was transferred to an assay plate (384-well) where *D. immitis* microfilariae (~200/well) that have been purified from microfilaremic canine blood were subsequently added. Assay plates were observed at 72 hours for drug effect. Each compound was evaluated for decrease in microfilariae motility by subjective visual assessment and endpoint data were recorded as minimally effective dose (MEC) in μM following the incubation period in Table 2.

Jird Efficacy Model

Compounds were evaluated for in vivo activity against *Trichostrongylus colubriformis* (T.c.) in a Mongolian gerbil (jird) infection model. Jirds were fed an immunosuppression diet containing 200 ppm (0.02%) hydrocortisone acetate before being infected by oral gavage with approximately 750 T.c. larvae suspended in 0.2 mL Earles balanced salt solution. Nine days post-infection, jirds were dosed (4/group) with test compound (10 mg/kg) by subcutaneous route of administration. Approximately four days after dosing, jirds were euthanized by carbon dioxide asphyxiation and necropsied whereby stomach and small intestine were removed for evaluation. Both stomach and small intestine were dissected to remove contents and placed in 20 mL scintillation vials filled with 15 mL tap water. Vials were then placed in a 37° C. incubator or water bath for approximately four hours before worms were counted. The mean and geometric means were calculated to determine percentage efficacy. A percentage efficacy (Table 2) was calculated against the geometric mean control burden as shown:

% Efficacy=100×(mean number of worms recovered from control untreated group−mean number of worms recovered from treated group)÷(mean number of worms recovered from control untreated group).

TABLE 2

| Biological Data | | | |
|---|---|---|---|
| Ex# | DiMF | HcL3 | Jird % |
| 1 | 0.2 | 0.2 | 100 |
| 2 | 4.8 | 1.6 | 100 |
| 3 | 18.2 | 1.0 | 99 |
| 4 | 10.0 | >100 | |
| 5 | 5.7 | 1.0 | |
| 6 | 18.2 | 2.4 | 99 |
| 7 | 10.0 | 2.4 | 100 |
| 8 | 18.2 | 0.5 | |
| 9 | 5.7 | 7.6 | 99 |
| 10 | >100 | 1.0 | |
| 11 | >100 | 1.8 | |
| 12 | 18.2 | 1.8 | |
| 13 | 10.0 | 1.8 | 100 |
| 14 | >100 | 0.5 | |
| 15 | >100 | 1.0 | |
| 16 | >100 | >100 | |
| 17 | >100 | 1.0 | |
| 24 | 7.6 | 5.7 | |
| 25 | 33.0 | >100 | |
| 26 | 5.7 | 2.4 | |
| 27 | 1.8 | 1.8 | |
| 28 | 4.4 | 1.8 | |
| 29 | 1.8 | 0.7 | 99 |
| 30 | 10.0 | 0.5 | 100 |
| 31 | >100 | 1.0 | |
| 32 | 18.2 | 1.8 | 100 |
| 33 | >100 | 3.3 | |
| 34 | 3.3 | 3.3 | |
| 35 | 33.0 | 3.3 | 100 |
| 36 | 3.3 | 5.7 | 100 |
| 37 | 33.0 | >100 | |
| 41 | 5.7 | 0.3 | 100 |
| 50 | 10.0 | 1.8 | |
| 51 | 5.7 | 3.3 | |
| 52 | 10.0 | 5.7 | |
| 53 | >100 | 5.7 | |
| 54 | 10.0 | >100 | |
| 55 | 10.0 | >100 | |
| 59 | 10.0 | 7.7 | |
| 60 | 13.5 | 4.4 | |
| 63 | 0.3 | | |
| 64 | 3.3 | 0.5 | |
| 65 | >100 | | |
| 66 | >100 | | |
| 67 | 0.01 | | |
| 68 | 0.03 | 0.01 | |
| 69 | 0.03 | 0.02 | |
| 71 | >100 | 0.2 | |
| 72 | 5.1 | 0.2 | |
| 73 | >100 | 0.1 | |
| 74 | >100 | 0.2 | |
| 75 | 10.2 | 0.1 | |
| 76 | >100 | 0.1 | |
| 77 | >100 | 0.3 | |
| 78 | >100 | 0.6 | |
| 79 | >100 | 0.3 | |
| 80 | >100 | 0.06 | |
| 81 | >100 | 0.2 | |
| 82 | >100 | 0.2 | |
| 83 | >100 | 0.1 | |
| 84 | >100 | 0.1 | |
| 85 | >100 | 0.1 | |
| 87 | 5.7 | 0.2 | |
| 88 | 3.3 | 0.1 | 99 |
| 89 | 1.0 | 0.1 | |
| 90 | 3.3 | 0.1 | |
| 91 | 13.5 | 0.4 | |
| 92 | 3.3 | 0.3 | |
| 93 | 2.4 | 0.7 | |
| 94 | >100 | 0.1 | |
| 96 | >100 | 0.2 | |
| 97 | >100 | 0.3 | |
| 98 | >100 | 0.3 | |
| 99 | 10.0 | 0.1 | 100 |
| 100 | >100 | >100 | |
| 101 | 24.0 | 0.2 | |
| 102 | 3.3 | 0.3 | 97 |
| 103 | 3.3 | 0.2 | |
| 104 | 3.2 | 0.1 | |
| 105 | >100 | 0.3 | |
| 106 | >100 | 0.3 | |
| 107 | 1.8 | 0.5 | |
| 108 | 3.2 | 2.4 | 100 |
| 109 | 18.2 | 1.22 | 99 |
| 110 | >100 | 0.3 | |
| 111 | >100 | 0.3 | |
| 112 | >100 | 0.5 | |
| 113 | >100 | 1.3 | |
| 114 | 10.0 | 0.1 | |
| 115 | 3.3 | 0.1 | 100 |
| 116 | 1.3 | 0.1 | |
| 117 | 1.8 | 0.2 | |
| 118 | 5.7 | 1.8 | |
| 119 | 18.2 | 3.3 | |

TABLE 2-continued

Biological Data

| Ex# | DiMF | HcL3 | Jird % |
|---|---|---|---|
| 120 | >100 | 0.5 | |
| 121 | 10.0 | 0.3 | |
| 122 | 18.2 | 1.0 | 100 |
| 123 | 10.0 | 0.3 | 100 |
| 124 | 33 | 100 | |
| 125 | >100 | 0.3 | |
| 126 | >100 | >100 | |
| 128 | 0.7 | 0.1 | 100 |
| 129 | 3.5 | 0.05 | |
| 145 | 33.0 | 1.0 | |
| 146 | 10.0 | 0.4 | |
| 147 | 10.0 | 2.8 | |
| 148 | 10.0 | 5.7 | |
| 149 | 10.0 | 4.4 | |
| 150 | 10.0 | 3.3 | |
| 151 | 13.5 | >100 | |
| 152 | 3.3 | 1.0 | 99 |
| 153 | 7.6 | 1.3 | |
| 155 | 22.6 | 1.0 | 100 |
| 156 | 33.0 | 0.5 | 99 |
| 157 | 11.9 | 3.8 | |
| 158 | 16.8 | 2.2 | |
| 159 | 10.0 | 18.2 | |
| 160 | 10.0 | 1.8 | |
| 161 | 10.0 | 2.1 | |
| 162 | 10.0 | >100 | |
| 163 | 5.7 | 1.8 | 100 |
| 164 | 10.0 | 3.3 | 100 |
| 165 | 3.3 | 3.3 | 100 |
| 166 | 5.7 | 10.0 | |
| 167 | 33.0 | 0.3 | |
| 168 | 10.0 | 0.5 | |
| 169 | 18.2 | 0.1 | |
| 170 | 1.0 | >100 | |
| 171 | 10.0 | 0.5 | |
| 172 | >100 | 10.0 | |
| 173 | >100 | 18.2 | |
| 174 | >100 | 57.4 | |
| 175 | 10.0 | 1.8 | |
| 176 | 3.3 | 0.2 | |
| 177 | 5.7 | 0.3 | |
| 178 | >100 | 0.3 | |
| 179 | 75.8 | 0.5 | |
| 180 | >100 | 0.5 | |
| 181 | 32.3 | 0.2 | |
| 182 | >100 | 1.0 | |
| 183 | 18.2 | 0.5 | |
| 184 | 57.4 | 1.0 | 100 |
| 185 | 7.7 | 0.7 | 100 |
| 186 | >100 | 1.0 | |
| 187 | >100 | 1.3 | |
| 188 | 3.3 | 0.3 | |
| 189 | 10.4 | 0.3 | |
| 190 | 5.7 | 1.0 | |
| 191 | 10.0 | 0.3 | |
| 192 | 11.5 | 0.7 | |
| 193 | 75.8 | 1.0 | |
| 194 | 5.7 | 0.4 | |
| 195 | 5.7 | 0.5 | |
| 196 | 5.7 | 0.3 | |
| 197 | 4.4 | 0.4 | |
| 198 | 5.7 | 1.0 | |
| 199 | 24.5 | 5.7 | |
| 205 | 18.2 | 1.0 | |
| 206 | 3.3 | 0.2 | |
| 207 | 10.0 | 0.3 | |
| 208 | >100 | 1.8 | |
| 209 | 33.0 | >100 | |
| 210 | 10.0 | 3.3 | |
| 211 | 10.0 | 1.0 | 100 |
| 212 | >100 | 1.0 | |
| 213 | 3.3 | 0.3 | |
| 214 | 18.2 | 0.5 | |
| 215 | 10.0 | 0.5 | |
| 216 | 18.2 | 1.0 | |
| 217 | 3.3 | 1.8 | |
| 218 | 10.0 | 1.0 | |
| 219 | 3.3 | 0.5 | |
| 220 | 10.0 | 3.3 | |
| 221 | 3.3 | >100 | |
| 222 | 10.0 | >100 | |
| 223 | 3.3 | 10.0 | |
| 224 | 3.3 | 1.8 | |
| 225 | 3.3 | 1.8 | |
| 226 | 1.8 | >100 | |
| 227 | 1.8 | 5.7 | |
| 228 | 3.3 | 1.8 | 98 |
| 229 | 10.0 | 3.3 | 100 |
| 230 | 10.0 | 1.8 | 100 |
| 231 | 13.5 | 3.3 | |
| 232 | 10.0 | 1.0 | |
| 233 | 1.8 | 0.01 | |
| 234 | 3.3 | 0.1 | |
| 235 | >100 | 0.1 | |
| 237 | 1.8 | 0.03 | |
| 238 | 5.7 | 1.0 | 100 |
| 239 | 3.3 | 0.3 | 98 |
| 240 | 3.3 | 0.2 | 98 |
| 241 | 13.5 | 0.4 | |
| 242 | 10.0 | 0.7 | |
| 243 | 10.0 | 1.3 | |
| 244 | 10.0 | 0.7 | |
| 245 | 11.9 | 3.3 | |
| 246 | 10.0 | 3.3 | |
| 247 | 1.8 | 1.0 | |
| 248 | 0.5 | 0.4 | |
| 254 | 100 | 3.3 | |
| 255 | 18.2 | 0.3 | |
| 256 | 10.0 | 0.2 | |
| 257 | 5.7 | 0.2 | |
| 258 | 100 | 10 | |
| 259 | 3.3 | 0.1 | |
| 260 | 10.0 | 0.4 | |
| 261 | 10.0 | 1.0 | |
| 266 | 18.2 | >100 | |
| 267 | 10.0 | >100 | |
| 268 | 10.0 | >100 | |
| 269 | 3.3 | >100 | |
| 270 | 10.0 | >100 | |
| 271 | 5.7 | >100 | |
| 272 | 10.0 | >100 | |
| 273 | 18.2 | >100 | |
| 274 | 33.0 | 1.8 | |
| 275 | >100 | 0.3 | |
| 276 | 18.2 | 0.3 | |
| 277 | >100 | 1.0 | |
| 278 | 18.2 | 1.8 | |
| 279 | >100 | 1.8 | |
| 280 | >100 | 0.3 | |
| 281 | >100 | 1.0 | |
| 282 | 3.3 | 0.3 | 100 |
| 283 | 3.3 | 0.5 | |
| 284 | 10.0 | >100 | |
| 285 | 10.0 | >100 | |
| 287 | 3.3 | 0.2 | |
| 292 | 5.7 | 3.3 | |
| 293 | 5.7 | 3.3 | |
| 294 | 10.0 | >100 | |
| 295 | 18.2 | >100 | |
| 296 | >100 | 1.0 | |
| 297 | >100 | 0.3 | |
| 298 | >100 | 1.8 | |
| 299 | 1.8 | 0.4 | |
| 300 | 10.0 | 0.5 | |
| 301 | 18.2 | 0.2 | |
| 302 | 5.7 | 0.3 | |
| 303 | 57.4 | 1.0 | |
| 304 | 18.2 | 0.3 | |
| 305 | 16.5 | 0.9 | |
| 306 | 12.7 | 0.5 | 98 |
| 307 | 3.3 | 0.5 | 100 |
| 308 | 32.1 | 10.3 | |

TABLE 2-continued

Biological Data

| Ex# | DiMF | HcL3 | Jird % |
|---|---|---|---|
| 309 | 1.8 | 0.3 | |
| 310 | 24.5 | 1.3 | |
| 311 | 5.7 | 0.5 | |
| 312 | 1.0 | 0.1 | |
| 313 | 3.3 | 0.5 | |
| 314 | 3.3 | 1.0 | 100 |
| 315 | 5.7 | 1.0 | |
| 316 | 5.7 | >100 | |
| 317 | 18.2 | 1.0 | 100 |
| 318 | 5.7 | 3.3 | |
| 319 | 10.0 | 10.0 | |
| 320 | 18.2 | 3.3 | |
| 321 | 5.7 | 2.4 | 100 |
| 322 | 10.0 | 5.7 | |
| 323 | 7.6 | >100 | |
| 324 | 10.0 | 3.3 | |
| 325 | 7.6 | 3.3 | |
| 326 | 10.0 | 7.6 | |
| 327 | 10.0 | >100 | |
| 328 | 33.0 | 0.3 | |
| 329 | 1.8 | 0.3 | |
| 330 | >100 | 0.5 | |
| 331 | 24.0 | 0.7 | |
| 332 | 13.5 | 1.0 | |
| 333 | >100 | 1.8 | |
| 334 | 10.0 | 1.0 | |
| 335 | 24.0 | 10.0 | |
| 336 | 33.0 | 1.0 | |
| 337 | 18.2 | 1.0 | |
| 338 | 10.0 | 0.3 | |
| 339 | 0.5 | 0.5 | |
| 340 | 5.7 | 0.3 | |
| 341 | 5.7 | 3.3 | |
| 342 | 10.0 | 1.8 | |
| 343 | 3.3 | 33.0 | |
| 344 | 10.0 | 0.5 | 100 |
| 345 | 18.2 | 0.5 | |
| 346 | 1.8 | 0.5 | |
| 347 | 2.4 | 2.4 | |
| 348 | 24.5 | 1.0 | |
| 349 | 10.0 | 1.0 | 99 |
| 350 | 1.3 | 0.2 | |
| 351 | 32.3 | 0.7 | |
| 352 | 5.7 | 33.0 | |
| 353 | 18.2 | 1.0 | |
| 354 | 18.2 | 57.4 | |
| 355 | 69.1 | 1.0 | |
| 356 | 3.8 | 0.6 | 100 |
| 357 | 3.3 | 10.0 | |
| 358 | 7.6 | 1.3 | |
| 359 | 3.3 | 3.3 | |
| 360 | 13.6 | 7.7 | |
| 361 | 57.4 | >100 | |
| 362 | 31.5 | >100 | |
| 363 | 33.0 | >100 | |
| 364 | 1.8 | >100 | |
| 365 | 4.4 | >100 | |
| 366 | 2.4 | >100 | |
| 367 | >100 | 10.0 | |
| 368 | 43.5 | >100 | |
| 369 | 10.0 | 1.0 | |
| 370 | 33.0 | 3.3 | |
| 371 | 24.5 | 1.3 | |
| 372 | 5.7 | 0.5 | |
| 373 | 10.0 | 1.8 | |
| 374 | 5.7 | 5.7 | 72 |
| 375 | 18.2 | 1.8 | |
| 376 | 10.0 | 0.5 | |
| 377 | 5.7 | 0.3 | 99 |
| 378 | 10.0 | 1.8 | |
| 379 | 5.7 | 1.0 | 100 |
| 379a | 3.3 | >100 | |
| 380 | 33.0 | >100 | |
| 382 | 10.0 | 3.3 | |
| 383 | 5.7 | >100 | |
| 384 | 18.2 | 1.0 | |
| 385 | 47.8 | 0.5 | |
| 386 | 3.3 | 0.2 | |
| 387 | 3.3 | 0.2 | |
| 388 | >100 | 1.8 | |
| 389 | 10.0 | 0.5 | |
| 390 | 18.2 | 0.5 | 100 |
| 391 | 32.1 | 1.0 | 100 |
| 392 | 22.2 | 1.0 | |
| 393 | 1.5 | 0.4 | |
| 394 | 6.9 | 1.0 | |
| 395 | 22.2 | 3.3 | |
| 396 | 1.0 | 3.3 | |
| 401 | 18.2 | 0.5 | |
| 402 | 5.7 | 0.3 | |
| 403 | 18.2 | 0.3 | |
| 404 | 18.2 | 1.0 | |
| 405 | 5.7 | 0.3 | |
| 406 | 13.5 | 0.4 | |
| 407 | 5.7 | 1.0 | |
| 408 | 10.0 | 1.0 | |
| 409 | 10.0 | 1.0 | |
| 410 | 10.0 | 1.8 | |
| 411 | 1.8 | 0.03 | |
| 412 | 10.0 | 1.8 | |
| 413 | >100 | 1.8 | |
| 414 | 10.0 | 1.0 | |
| 415 | 12.4 | 2.7 | |
| 416 | 57.4 | 1.8 | |
| 417 | 10.0 | 5.7 | 100 |
| 418 | 18.2 | 3.3 | 95 |
| 419 | 10.0 | 1.0 | 100 |
| 420 | 14.1 | 2.8 | 100 |
| 421 | 12.7 | 3.3 | 100 |
| 422 | 18.2 | 10.0 | |
| 425 | 15.8 | >100 | |
| 430 | >100 | 1.0 | |
| 431 | 3.3 | 1.0 | |
| 432 | 57.4 | 1.0 | |
| 433 | 5.7 | 0.5 | |
| 434 | 5.7 | 3.3 | |
| 435 | 5.7 | 5.7 | |
| 436 | 18.2 | >100 | |
| 437 | 10.0 | 1.0 | |
| 438 | 18.2 | >100 | |
| 439 | 18.2 | 1.8 | |
| 440 | 10.0 | 1.8 | |
| 441 | 4.4 | >100 | |
| 442 | 10.0 | 10.0 | |
| 443 | 3.3 | 0.5 | |
| 444 | 2.4 | 0.7 | 100 |
| 445 | 33.0 | 0.5 | |
| 446 | 3.3 | 0.5 | |
| 447 | 3.3 | 0.5 | |
| 448 | 3.3 | 1.3 | |
| 449 | >100 | >100 | |
| 450 | 100.0 | 0.5 | |
| 451 | 3.3 | >100 | |
| 452 | >100 | >100 | |
| 453 | 10.0 | >100 | |
| 454 | >100 | >100 | |
| 455 | 5.7 | 0.7 | |
| 456 | 10.0 | 1.3 | |
| 457 | 10.0 | 1.0 | |
| 458 | 3.3 | 5.7 | |
| 459 | 5.7 | 1.0 | 92 |
| 460 | 57.4 | >100 | |
| 461 | >100 | 33.0 | |
| 462 | >100 | >100 | |
| 463 | >100 | >100 | |
| 464 | 7.6 | 3.3 | |
| 465 | 10.0 | 3.3 | |
| 466 | 3.3 | >100 | |
| 467 | 1.0 | >100 | |
| 468 | 1.8 | 0.2 | |
| 469 | >100 | 1.0 | |
| 470 | 13.5 | 1.0 | 100 |

TABLE 2-continued

Biological Data

| Ex# | DiMF | HcL3 | Jird % |
|---|---|---|---|
| 471 | 10.0 | 0.3 | |
| 472 | 10.0 | 1.0 | |
| 474 | 10.0 | 0.2 | |
| 479 | >100 | 1.0 | |
| 480 | 3.3 | 0.3 | |
| 481 | 3.3 | 0.3 | 99 |
| 482 | 3.3 | 1.8 | |
| 483 | 3.3 | 0.5 | 100 |
| 489 | 3.3 | 3.3 | 100 |
| 490 | 10.0 | 0.2 | |
| 491 | 18.2 | 1.0 | |
| 492 | 0.5 | 1.8 | |
| 493 | 5.7 | 1.0 | |
| 494 | >100 | 1.0 | |
| 495 | 10.0 | 1.0 | |
| 496 | 5.7 | 1.0 | |
| 497 | 5.7 | 1.0 | |
| 498 | 5.7 | 1.8 | |
| 499 | >100 | 1.8 | |

TABLE 2-continued

Biological Data

| Ex# | DiMF | HcL3 | Jird % |
|---|---|---|---|
| 500 | 5.7 | >100 | |
| 501 | 18.2 | 3.3 | |
| 502 | >100 | 18.2 | |
| 503 | 3.3 | 33.0 | |
| 504 | 10.0 | 5.7 | 100 |
| 505 | 13.5 | 10.0 | 100 |
| 506 | >100 | 7.6 | |
| 507 | 13.5 | 10.0 | |
| 508 | 9.0 | 1.6 | |
| 509 | 18.2 | 1.0 | |
| 510 | >100 | >100 | |
| 511 | >100 | >100 | |
| 512 | 10.0 | 1.0 | |
| 513 | 3.3 | 7.6 | |
| 514 | 5.7 | 5.7 | |
| 515 | 13.5 | 1.8 | |
| 516 | 10.0 | 0.3 | |
| 517 | 10.0 | 0.5 | |

TABLE 3

Example Mass and NMR Data

| Ex# | Mass | 1H-NMR(400 MHz, DMSO-d6) δ ppm |
|---|---|---|
| 1 | 552 | 3.33-3.60(m, 3H), 3.74-3.82(m, 1H), 4.05-4.21(m, 2H), 4.39-4.44(m, 1H), 4.60(d, 2H), 4.71(d, 1H), 6.68-6.76(m, 1H), 6.91(d, 1H), 7.48(dd, 1H), 7.56-7.58(m, 3H) 7.64(dd, 1H), 7.77(d, 1H), 8.25-8.28(m, 1H), 8.38-8.42(m, 1H), 9.15(t, 1H), 11.60(bs, 1H). |
| 2 | 534 | 3.36-3.52(m, 3H), 3.74-3.84(m, 1H), 4.05-4.18(m, 2H), 4.39-4.44(m, 1H), 4.60(d, 2H), 4.70(d, 1H), 6.61-6.69(m, 1H), 6.92(d, 1H), 7.40(dd, 1H), 7.47(dd, 1H), 7.57(s, 1H), 7.61-7.66(m, 3H), 7.77(d, 1H), 8.25-8.27(m, 1H), 8.38-8.41(m, 1H), 9.15(t, 1H), 11.60(bs, 1H) |
| 3 | 552 | 3.35-3.53(m, 3H), 3.74-3.83(m, 1H), 4.15-4.24(m, 2H), 4.39-4.44(m, 1H), 4.60(d, 2H), 4.71(d, 1H), 6.60-6.68(m, 1H), 7.16(d, 1H), 7.47-7.53(m, 2H), 7.57(s, 1H), 7.63(dd, 1H), 7.70(d, 1H), 7.77(d, 1H), 7.83(d, 1H), 8.25-8.28(m, 1H), 8.38-8.41(m, 1H), 9.13(t, 1H), 11.60(bs, 1H) |
| 4 | 550 | 3.36-3.40(m, 2H), 3.48(bs, 1H), 3.81(bs, 1H), 4.25(bs, 2H), 4.57-4.65(m, 2H), 4.85(d, 1H), 6.59-6.63(m, 1H), 7.18(d, 1H), 7.45-7.55(m, 4H), 7.69-7.74(m, 2H), 7.82(d, 1H), 8.13(d, 1H), 8.40 (d, 1H), 9.18(bs, 1H), 11.12(bs, 1H). |
| 5 | 580 | 3.33-3.53(m, 3H), 3.75-3.84(m, 1H), 4.09-4.21(m, 2H), 4.37-4.43(m, 1H), 4.60(d, 2H), 4.69(d, 1H), 6.63-6.70(m, 1H), 6.99(d, 1H), 7.47-7.53(m, 2H), 7.57(s, 1H), 7.61-7.70(m, 3H), 7.78(d, 1H), 8.25-8.28(m, 1H), 8.38-8.41(m, 1H), 9.12(t, 1H), 11.50(bs, 1H) |
| 6 | 552 | 3.35-3.51(m, 3H), 3.75-3.82(m, 1H), 4.12-4.25(m, 2H), 4.35-4.40(m, 1H), 4.59-4.67(m, 3H), 6.69-6.77(m, 1H), 6.88(d, 1H), 7.46-7.51(m, 3H), 7.57(s, 1H), 7.62(dd, 1H), 7.78(d, 1H), 8.25-8.28(m, 1H), 8.38-8.41(m, 1H), 9.12(t, 1H), 11.67(bs, 1H) |
| 7 | 534 | 3.35-3.52(m, 3H), 3.76-3.82(m, 1H), 4.10-4.22(m, 2H), 4.37-4.43(m, 1H), 4.60(d, 2H), 4.69(d, 1H), 6.62-6.69(m, 1H), 7.00(d, 1H), 7.37(dd, 1H), 7.47(dd, 1H), 7.51(dd, 1H), 7.57(s, 1H), 7.62(dd, 1H), 7.72-7.79(m, 2H), 8.24-8.28(m, 1H), 8.38-8.41(m, 1H), 9.12(t, 1H), 11.51(bs, 1H) |
| 8 | 580 | 3.35-3.54(m, 3H), 3.75-3.83(m, 1H), 4.06-4.17(m, 2H), 4.38-4.44(m, 1H), 4.59(d, 2H), 4.70(d, 1H), 6.62-6.70(m, 1H), 6.91(d, 1H), 7.33(dd, 1H), 7.47(dd, 1H), 7.57-7.64(m, 3H), 7.73-7.78(m, 2H), 8.25-8.28(m, 1H), 8.38-8.41(m, 1H), 9.13(t, 1H), 11.50(bs, 1H) |
| 9 | 536 | 3.34-3.51(m, 3H), 3.74-3.81(m, 1H), 4.09-4.24(m, 2H), 4.35-4.40(m, 1H), 4.59-4.67(m, 3H), 6.64-6.72(m, 1H), 6.86(d, 1H), 7.29-7.36(m, 2H), 7.47(dd, 1H), 7.57(s, 1H), 7.63(dd, 1H), 7.79(d, 1H), 8.24-8.27(m, 1H), 8.38-8.41(m, 1H), 9.13(t, 1H), 11.66(bs, 1H) |
| 10 | 580 | 3.35-3.54(m, 3H), 3.78-3.84(m, 1H), 4.14-4.26(m, 2H), 4.40-4.45(m, 1H), 4.60(d, 2H), 4.73(d, 1H), 6.60-6.67(m, 1H), 7.11(d, 1H), 7.18-7.23(m, 1H), 7.47(dd, 1H), 7.57(s, 1H), 7.63(dd, 1H), 7.69-7.78(m, 3H), 8.25-8.28(m, 1H), 8.38-8.41(m, 1H), 9.13(t, 1H), 11.58(bs, 1H) |
| 11 | 580 | 3.35-3.54(m, 3H), 3.77-3.85(m, 1H), 4.11-4.23(m, 2H), 4.39-4.44(m, 1H), 4.60(d, 2H), 4.70(d, 1H), 6.67-6.74(m, 1H), 7.00(d, 1H), 7.25-7.30(m, 1H), 7.47(dd, 1H), 7.57-7.64(m, 4 H), 7.78(d, 1H), 7.94(dd, 1H), 8.25-8.28(m, 1H), 8.38-8.42(m, 1H), 9.13(t, 1H), 11.54(bs, 1H) |
| 12 | 580 | 3.34-3.54(m, 3H), 3.75-3.84(m, 1H), 4.05-4.14(m, 2H), 4.38-4.43(m, 1H), 4.59(d, 2H), 4.69(d, 1H), 6.53-6.61(m, 1H), 6.90(d, 1H), 7.40-7.48(m, 2H), 7.57-7.64(m, 3H), 7.78(d, 1H), 7.93(dd, 1H), 8.25-8.28(m, 1H), 8.38-8.42(m, 1H), 9.14(t, 1H), 11.53(bs, 1H) |
| 13 | 536 | 3.36-3.52(m, 3H), 3.75-3.83(m, 1H), 4.11-4.22(m, 2H), 4.37-4.43(m, 1H), 4.59(d, 2H), 4.68(d, 1H), 6.64-6.71(m, 1H), 7.01(d, 1H), 7.37-7.45(m, 1H), 7.47(dd, 1H), 7.54-7.65(m, 3H), 7.78(d, 1H), 8.24-8.27(m, 1H), 8.38-8.42(m, 1H), 9.15(t, 1H), 11.71(bs, 1H) |
| 14 | 596, 598 | 3.36-3.53(m, 3H), 3.75-3.83(m, 1H), 4.13-4.22(m, 2H), 4.38-4.43(m, 1H), 4.59(d, 2H), 4.69(d, 1H), 6.71-6.78(m, 1H), 7.02(d, 1H), 7.47-7.64(m, 5H), 7.78(d, 1H), 8.25-8.27(m, 1H), 8.38-8.42(m, 1H), 9.14(t, 1H), 11.70(bs, 1H) |
| 15 | 552 | 3.35-3.52(m, 3H), 3.76-3.84(m, 1H), 4.13-4.24(m, 2H), 4.36-4.45(m, 1H), 4.60(d, 2H), 4.66-4.73(m, 1H), 6.68-6.78(m, 1H), 7.03(d, 1H), 7.46-7.65(m, 5 H), 7.78(d, 1H), 8.25-8.28(m, 1H), 8.38-8.42(m, 1H), 9.13(t, 1H), 11.59(bs, 1H) |

TABLE 3-continued

Example Mass and NMR Data

| Ex# | Mass | 1H-NMR(400 MHz, DMSO-d6) δ ppm |
|---|---|---|
| 16 | 572 | 3.35-3.52(m, 3H), 3.72-3.83(m, 1H), 4.16-4.30(m, 2H), 4.35-4.44(m, 1H), 4.56-4.70(m, 3H), 6.76-6.95(m, 2H), 7.47(dd, 1H), 7.57-7.65(m, 2H), 7.77(d, 1H), 8.25-8.28(m, 1H), 8.38-8.42(m, 1H), 9.15(t, 1H), 11.90(bs, 1H) |
| 17 | 588 | 3.35-3.53 (m, 3H), 3.73-3.83 (m, 1H), 4.17-4.32 (m, 2H), 4.35-4.44 (m, 1H), 4.56-4.71 (m, 3H), 6.82-6.99 (m, 2H), 7.47 (dd, 1H), 7.57-7.65 (m, 2H), 7.77 (d, 1H), 8.25-8.28 (m, 1H), 8.38-8.42 (m, 1H), 9.14 (t, 1H), 11.85 (bs, 1H). |
| 18 | 584 | 11.82(br s, 1H), 9.18(m, 1H), 8.40(d, 1H), 8.26(s, 1H), 7.91-8.03(m, 1H), 7.72-7.80(m, 2H), 7.63(m, 1H), 7.57(m, 2H), 7.48(d, 1H), 6.96-7.05(m, 1H), 6.78-6.92(m, 1H), 4.71(br d, 1H), 4.60(br d, 2H), 4.37-4.48(m, 1H), 4.16(br s, 2H), 3.80(br s, 1H), 3.39-3.54(m, 3H). |
| 19 | 598 | 11.87(br s, 1H), 9.20(m, 1H), 8.40(d, 1H), 8.26(s, 1H), 8.12(m, 1H), 7.77(d, 1H), 7.62(m, 1H), 7.53-7.61(m, 2H), 7.48(d, 1H), 6.97(d, 1H), 6.64-6.76(m, 1H), 4.69(br d, 1H), 4.56-4.64(m, 2H), 4.35-4.47(m, 1H), 4.08-4.20(m, 2H), 3.73-3.82(m, 1H), 3.34-3.55(m, 3H). |
| 20 | 548 | 11.69(br s, 1H), 9.18(m, 1H), 8.40(d, 1H), 8.26(s, 1H), 7.77(m, 1H), 7.63(d, 1H), 7.57(s, 1H), 7.48(m, 1H), 7.33-7.41(m, 2H), 6.84(d, 1H), 6.52-6.63(m, 1H), 4.68(br d, 1H), 4.56-4.64(m, 2H), 4.40(br m, 1H), 4.05-4.17(m, 2H), 3.93-4.00(m, 3H), 3.77(br s, 1H), 3.36-3.54(m, 3H). |
| 21 | 564 | 11.80(br s, 1H), 9.17(m, 1H), 8.40(d, 1H), 8.26(s, 1H), 7.78(d, 1H), 7.53-7.67(m, 2H), 7.36-7.53(m, 3H), 7.02(d, 1H), 6.63-6.73(m, 1H), 4.68(br d, 1H), 4.55-4.63(m, 2H), 4.41(br s, 1H), 4.13-4.21(m, 2H), 3.84-3.96(m, 3H), 3.78(br s, 1H), 3.35-3.53(m, 3H). |
| 22 | 570 | 11.94(br s, 1H), 9.16(m, 1H), 8.40(d, 1H), 8.26(s, 1H), 7.77(d, 1H), 7.56-7.67(m, 3H), 7.43-7.52(m, 2H), 6.97(d, 1H), 6.68-6.80(m, 1H), 4.66(br d, 1H), 4.60(d, 2H), 4.40(br m, 1H), 4.20-4.31(m, 2H), 3.78(br s, 1H), 3.37-3.54(m, 3H). |
| 23 | 598 | 11.85(br s, 1H), 9.19(m, 1H), 8.39(d, 1H), 8.25(s, 1H), 7.72-7.87(m, 3H), 7.55-7.66(m, 2H), 7.48(d, 1H), 6.98(d, 1H), 6.70-6.83(m, 1H), 4.69(br d, 1H), 4.55-4.64(m, 2H), 4.35-4.46(m, 1H), 4.10-4.21(m, 2H), 3.73-3.82(m, 1H), 3.39-3.54(m, 3H). |
| 24 | 534 | 3.36-3.54(m, 3H), 3.77-3.83(m, 1H), 4.12-4.23(m, 2H), 4.38-4.44(m, 1H), 4.59(d, 2H), 4.70(d, 1H), 6.53-6.61(m, 1H), 7.16(d, 1H), 7.30-7.35(m, 1H), 7.47(dd, 1H), 7.52(dd, 1H), 7.57(s, 1H), 7.63(dd, 1H), 7.78(d, 1H), 7.85-7.89(m, 1H), 8.24-8.28(m, 1H), 8.38-8.41(m, 1H), 9.12(t, 1H), 11.51(bs, 1H) |
| 25 | 534 | 3.33-3.48(m, 3H), 3.82(bs, 1H), 4.24(bs, 2H), 4.57-4.58(m, 3H), 4.85(bs, 1H), 6.49-6.53(m, 1H), 7.17(d, 1H), 7.32(t, 1H), 7.45-7.55(m, 4H), 7.73(d, 1H), 7.85(t, 1H), 8.12(d, 1H), 8.40(d, 1H), 9.16(bs, 1H), 10.96(bs, 1H) |
| 26 | 518 | 3.36-3.52(m, 3H), 3.75-3.82(m, 1H), 4.10-4.22(m, 2H), 4.37-4.44(m, 1H), 4.60(d, 2H), 4.69(d, 1H), 6.55-6.62(m, 1H), 6.99(d, 1H), 7.16-7.33(m, 1H), 7.47(dd, 1H), 7.57(s, 1H), 7.62(dd, 1H), 7.74-7.80(m, 2H), 8.25-8.28(m, 1H), 8.38-8.41(m, 1H), 9.11(t, 1H), 11.40(bs, 1H) |
| 27 | 534 | 3.34-3.52(m, 3H), 3.76-3.81(m, 1H), 4.08-4.16(m, 2H), 4.38-4.44(m, 1H), 4.60(d, 2H), 4.70(d, 1H), 6.53-6.61(m, 1H), 6.90(d, 1H), 7.44-7.49(m, 2H), 7.54-7.57(m, 2H), 7.63(dd, 1H), 7.78(d, 1H), 7.83(dd, 1H) 8.25-8.28(m, 1H), 8.38-8.41(m, 1H), 9.12(t, 1H), 11.39(bs, 1H) |
| 28 | 518 | 3.35-3.53(m, 3H), 3.74-3.82(m, 1H), 4.06-4.15(m, 2H), 4.38-4.44(m, 1H), 4.60(d, 2H), 4.70(d, 1H), 6.52-6.59(m, 1H), 6.90(d, 1H), 7.36-7.40(m, 1H), 7.45-7.52(m, 2H), 7.57(s, 1H), 7.63(dd, 1H), 7.65-7.71(m 1H), 7.77(d, 1H), 8.25-8.28(m, 1H), 8.38-8.41(m, 1H), 9.13(t, 1H), 11.45(bs, 1H) |
| 29 | 536 | 3.35-3.54(m, 3H), 3.75-3.83(m, 1H), 4.05-4.17(m, 2H), 4.38-4.44(m, 1H), 4.59(d, 2H), 4.71(d, 1H), 6.60-6.67(m, 1H), 6.87(d, 1H), 7.47(dd, 1H), 7.53-7.61(m, 3H), 7.63(dd, 1H), 7.77(d, 1H), 8.25-8.28(m, 1H), 8.38-8.41(m, 1H), 9.14(t, 1H), 11.56(bs, 1H) |
| 30 | 518 | 3.35-3.54(m, 3H), 3.76-3.83(m, 1H), 4.07-4.19(m, 2H), 4.39-4.45(m, 1H), 4.60(d, 2H), 4.71(d, 1H), 6.65-6.72(m, 1H), 6.92(d, 1H), 7.20-7.26(m, 1H), 7.29-7.35(m, 2H), 7.47(dd, 1H), 7.57(s, 1H), 7.63(dd, 1H), 7.78(d, 1H), 8.25-8.28(m, 1H), 8.38-8.41(m, 1H), 9.14(t, 1H), 11.51(bs, 1H) |
| 31 | 534 | 3.35-3.53(m, 3H), 3.76-3.85(m, 1H), 4.11-4.24(m, 2H), 4.38-4.43(m, 1H), 4.59(d, 2H), 4.69(d, 1H), 6.66-6.74(m, 1H), 7.05(d, 1H), 7.29(t, 1H), 7.47(dd, 1H), 7.57-7.70(m, 4 H), 7.78(d, 1H), 8.25-8.28(m, 1H), 8.38-8.41(m, 1H), 9.13(t, 1H), 11.64(bs, 1H) |
| 32 | 518 | 3.35-3.53(m, 3H), 3.75-3.84(m, 1H), 4.12-4.23(m, 2H), 4.38-4.43(m, 1H), 4.60(d, 2H), 4.69(d, 1H), 6.66-6.74(m, 1H), 7.06(d, 1H), 7.24-7.30(m, 1H), 7.40-7.64(m, 5 H), 7.78(d, 1H), 8.25-8.28(m, 1H), 8.38-8.41(m, 1H), 9.12(t, 1H), 11.56(bs, 1H) |
| 33 | 507 | 3.36-3.54(m, 3H), 3.76-3.84(m, 1H), 4.10-4.21(m, 2H), 4.39-4.45(m, 1H), 4.59(d, 2H), 4.71(d, 1H), 6.71-6.78(m, 1H), 7.01(d, 1H), 7.47(dd, 1H), 7.57(s, 1H), 7.63(dd, 1H), 7.72-7.79(m, 3H), 7.86-7.91(m, 2H), 8.24-8.28(m, 1H), 8.38-8.41(m, 1H), 9.13(t, 1H), 11.54(bs, 1H) |
| 34 | 516 | 3.37-3.52(m, 3H), 3.75-3.82(m, 1H), 4.07-4.16(m, 2H), 4.38-4.43(m, 1H), 4.59(d, 2H), 4.69(d, 1H), 6.53-6.61(m, 1H), 6.92(d, 1H), 7.46-7.50(m, 3H), 7.55-7.58(m, 1H), 7.63(dd, 1H), 7.7(d, 1H), 8.25-8.27(m, 1H), 8.38-8.41(m, 1H), 9.14(t, 1H), 11.54(bs, 1H) |
| 35 | 552 | 3.36-3.54(m, 3H), 3.73-3.82(m, 1H), 4.05-4.17(m, 2H), 4.38-4.44(m, 1H), 4.59(d, 2H), 4.70(d, 1H), 6.62-6.70(m, 1H), 6.92(d, 1H), 7.47(dd, 1H), 7.53(dd, 1H), 7.57(s, 1H), 7.63(dd, 1H), 7.68(d, 1H), 7.77(d, 1H), 7.85(d, 1H), 8.25-8.28(m, 1H), 8.38-8.42(m, 1H), 9.16(t, 1H), 11.66(bs, 1H) |
| 36 | 500 | 3.36-3.53(m, 3H), 3.74-3.83(m, 1H), 4.04-4.16(m, 2H), 4.38-4.43(m, 1H), 4.59(d, 2H), 4.69(d, 1H), 6.45-6.53(m, 1H), 6.92(d, 1H), 7.22-7.28(m, 2H), 7.47(dd, 1H), 7.57-7.64(m, 4 H), 7.78(d, 1H), 8.25-8.28(m, 1H), 8.38-8.41(m, 1H), 9.13(t, 1H), 11.47(bs, 1H) |
| 37 | 483 | 3.43-3.49(m, 2H), 3.80-3.83(m, 1H), 4.11-4.19(m, 2H), 4.39-4.44(m, 1H), 4.60(d, 2H), 4.75-4.79(m, 1H), 6.76-6.83(m, 1H), 6.92(d, 1H), 7.47(d, 1H), 7.53-7.56(m, 3H), 7.62(d, 1H), 7.76(d, 1H), 8.26(s, 1H), 8.40(d, 1H), 8.61(d, 2H), 9.04(bs, 1H), 11.03(bs, 1H) |
| 38 | 530 | 11.75(br s, 1H), 9.20(m, 1H), 8.40(d, 1H), 8.26(s, 1H), 7.78(d, 1H), 7.62(d, 1H), 7.57(s, 1H), 7.48(m, 1H), 7.33(m, 1H), 7.24(m, 1H), 7.04-7.13(m, 1H), 6.90(d, 1H), 6.48-6.59(m, 1H), |

TABLE 3-continued

Example Mass and NMR Data

| Ex# | Mass | 1H-NMR(400 MHz, DMSO-d6) δ ppm |
|---|---|---|
| | | 4.68(br d, 1H), 4.60(d, 2H), 4.35-4.47(m, 1H), 4.10(br s, 2H), 3.89(s, 3H), 3.75-3.82(m, 1H), 3.37-3.54(m, 3H). |
| 39 | 568 | 3.45-3.47(m, 3H), 3.80-3.83(m, 1H), 4.10-4.13(m, 2H), 4.39-4.42(m, 1H), 4.61(d, 2H), 4.73(d, 1H), 6.56-6.64(m, 1H), 6.90(d, 1H), 7.41(d, 1H), 7.61-7.69(m, 5H), 7.76(d, 1H), 8.30(s, 1H), 9.05(bs, 1H), 10.86(bs, 1H), |
| 40 | 596 | 3.32-3.42(m, 2H), 3.46-3.50(m, 1H), 3.80-3.89(m, 1H), 4.11-4.13(m, 2H), 4.38-4.44(dd, 1H), 4.58(d, 2H), 4.72(d, 1H), 6.66-6.73(m, 1H), 6.89(d, 1H), 7.49-7.50(dd, 1H), 7.58(d, 2H), 7.63-7.65(dd, 1H), 7.70(s, 1H), 7.76(d, 1H), 8.27(s, 1H), 8.37(d, 1H), 9.11(t, 1H), 11.24(bs, 1H). |
| 41 | 578 | 3.38(bs, 2H), 3.51(bs, 1H), 3.80-3.83(m, 1H), 4.12-4.13(m, 2H), 4.39-4.44(m, 1H), 4.58(d, 2H), 4.72(d, 1H), 6.57-6.65(m, 1H), 6.90(d, 1H), 7.39-7.42(dd, 1H), 7.49(d, 1H), 7.61-7.70(m, 4H), 7.77(d, 1H), 7.27(s, 1H), 8.37(d, 1H), 9.09(t, 1H), 11.02(bs, 1H) |
| 42 | 578 | 3.47-3.49(m, 3H), 3.80-3.83(m, 1H), 4.14-4.17(m, 2H), 4.38-4.43(m, 1H), 4.58(d, 2H), 4.72(d, 1H), 6.57-6.64(m, 1H), 7.0(d, 1H), 7.36-7.39(m, 1H), 7.49-7.56(m, 2H), 7.62-7.64(m, 1H), 7.70-7.79(m, 3H), 8.27(s, 1H), 8.37(d, 1H), 9.08(t, 1H), 10.89(bs, 1H). |
| 43 | 580 | 3.34-3.48(m, 3H), 3.79-3.81(m, 1H), 4.14-4.17(m, 2H), 4.37-4.42(dd, 1H), 4.58(d, 2H), 4.70(d, 1H), 6.60-6.68(m, 1H), 7.00(d, 1H), 7.38-7.44(m, 1H), 7.50(d, 1H), 7.55-7.59(m, 1H), 7.62-7.64(m, 1H), 7.70(s, 1H), 7.78(d, 1H), 8.27(s, 1H), 8.37(d, 1H), 9.11(t, 1H), 11.33(bs, 1H). |
| 44 | 562 | 3.34-3.48(m, 3H), 3.77-3.80(m, 1H), 4.13-4.16(m, 2H), 4.37-4.43(m, 1H), 4.58(d, 2H), 4.70(d, 1H), 6.52-6.60(m, 1H), 6.99(d, 1H), 7.16-7.21(m, 1H), 7.31-7.37(m, 1H), 7.49(d, 1H), 7.62-7.64(m, 1H), 7.70(s, 1H), 7.75-7.81(m, 2H), 8.27(s, 1H), 8.37(d, 1H), 9.10(t, 1H), 11.10(bs, 1H) |
| 45 | 562 | 3.44-3.49(m, 3H), 3.79-3.81(m, 1H), 4.09-4.12(m, 2H), 4.40-4.42(m, 1H), 4.58(d, 2H), 4.72(d, 1H), 6.48-6.56(m, 1H), 6.88(d, 1H), 7.38-7.40(m, 1H), 7.45-7.52(m, 2H), 7.64(d, 1H), 7.68-7.78(m, 3H), 8.27(s, 1H), 8.37(d, 1H), 9.09(bs, 1H), 10.92(bs, 1H). |
| 46 | 580 | 3.38-3.49(m, 3H), 3.77-3.80(m, 1H), 4.11-4.12(m, 2H), 4.38-4.43(m, 1H), 4.58(d, 2H), 4.71(d, 1H), 6.57-6, 65(m, 1H), 6.85(d, 1H), 7.50(d, 1H), 7.56-7.60(m, 2H), 7.63-7.65(m, 1H), 7.70(s, 1H), 7.76(d, 1H), 8.27(s, 1H), 8.37(d, 1H), 9.12(t, 1H), 11.21(bs, 1H). |
| 47 | 562 | 3.38-3.40(m, 2H), 3.49-3.52(m, 1H), 3.81-3.83(m, 1H), 4.11-4.14(m, 2H), 4.39-4.45(m, 1H), 4.58(d, 2H), 4.73(d, 1H), 6.61-6.69(m, 1H), 6.90(d, 1H), 7.22-7.27(m, 1H), 7.33-7.7.34(m, 2H), 7.50(d, 1H), 7.63-7.65(m, 1H), 7.70(s, 1H), 7.77(d, 1H), 8.27(s, 1H), 8.37(d, 1H), 9.09(t, 1H), 10.99(bs, 1H). |
| 48 | 560 | 3.36-3.39(m, 2H), 3.48-3.52(m, 1H), 3.79-3.81(m, 1H), 4.09-4.12(m, 2H), 4.38-4.43(m, 1H), 4.58(d, 2H), 4.71(d, 1H), 6.49-6.57(m, 1H), 6.91(d, 1H), 7.47-7.50(m, 3H), 7.57(d, 2H), 7.62-7.64(dd, 1H), 7.70(s, 1H), 7.78(d, 1H), 8.27(s, 1H), 8.37(d, 1H), 9.09(t, 1H), 11.00(bs, 1H). |
| 49 | 544 | 3.42-3.45(m, 3H), 3.78-3.79(m, 1H), 4.07-4.10(m, 2H), 4.39-4.42(m, 1H), 4.57(d, 2H), 4.66-4.69(m, 1H), 6.42-6.49(m, 1H), 6.90(d, 1H), 7.24(t, 1H), 7.46-7.50(m, 2H), 7.57-7.63(m, 3H), 7.70(s, 1H), 7.77(d, 1H), 8.26(s, 1H), 8.37(d, 1H), 9.09(bs, 1H), 11.12(bs, 1H). |
| 50 | 536 | 3.38-3.52(m, 3H), 3.76-3.84(m, 1H), 4.07-4.18(m, 2H), 4.37-4.46(m, 1H), 4.63(d, 2H), 4.71(d, 1H), 6.67-6.76(m, 1H), 6.91(d, 1H), 7.22(s, 1H), 7.39-7.44(m, 1H), 7.54-7.66(m, 3H), 7.77(d, 1H), 8.21-8.28(m, 2H), 9.16(t, 1H), 11.56(bs, 1H) |
| 51 | 518 | 3.39-3.53(m, 3H), 3.77-3.84(m, 1H), 4.08-4.16(m, 2H), 4.38-4.46(m, 1H), 4.63(d, 2H), 4.70(d, 1H), 6.60-6.69(m, 1H), 6.92(d, 1H), 7.22(s, 1H), 7.38-7.44(m, 2H), 7.60-7.67(m, 3H), 7.77(d, 1H), 8.22-8.28(m, 2H), 9.14(t, 1H), 11.46(bs, 1H) |
| 52 | 518 | 3.38-3.52(m, 3H), 3.76-3.83(m, 1H), 4.10-4.18(m, 2H), 4.38-4.46(m, 1H), 4.63(d, 2H), 4.69(d, 1H), 6.60-6.69(m, 1H), 7.00(d, 1H), 7.22(s, 1H), 7.35-7.44(m, 2H), 7.52(dd, 1H), 7.62(dd, 1H), 7.73-7.80(m, 2H), 8.22-8.28(m, 2H), 9.14(t, 1H), 11.50(bs, 1H) |
| 53 | 536 | .35-3.52(m, 3H), 3.75-3.86(m, 1H), 4.11-4.24(m, 2H), 4.36-4.46(m, 1H), 4.60-4.73(m, 3H), 6.67-6.77(m, 1H), 7.03(d, 1H), 7.22(s, 1H), 7.39-7.43(m, 1H), 7.49-7.65(m, 3H), 7.78(d, 1H), 8.21-8.29(m, 2H), 9, 12(t, 1H), 11.45(bs, 1H) |
| 54 | 568 | 3.37-3.50(m, 3H), 3.80(bs, 1H), 4.03-4.24(m, 2H), 4.37-4.44(m, 1H), 4.62(d, 2H), 4.72(d, 1H), 6.66-6.74(m, 1H), 6.94(d, 1H), 7.22(s, 1H), 7.38-7.41(m, 2H), 7.45(s, 1H), 7.54(d, 1H), 7.63(dd, 1H), 7.7(d, 1H), 8.22(d, 1H), 8.27(s, 1H), 9.14-9.11(t, 1H), 11.22(s, 1H) |
| 55 | 500 | .38-3.51(m, 3H), 3.75-3.84(m, 1H), 4.07-4.17(m, 2H), 4.38-4.45(m, 1H), 4.63(d, 2H), 4.70(d, 1H), 6.51-6.61(m, 1H), 6.92(d, 1H), 7.22(s, 1H), 7.39-7.43(m, 1H), 7.46-7.50(m, 2H), 7.55-7.65(m, 3H), 7.78(d, 1H), 8.22-8.28(m, 2H), 9.13(t, 1H), 11.36(bs, 1H) |
| 56 | 500 | 3.28-3.39(m, 2H), 3.67-3.79(m, 2H), 4.11(bs, 2H), 4.42(bs, 1H), 4.63(d, 2H), 4.71(d, 1H), 6.57-6.65(m, 1H), 6.90(d, 1H), 7.39-7.41(dd, 1H), 7.61-7.68(m, 4H), 7.76(d, 1H), 8.12(d, 1H), 8.23(s, 1H), 8.63(s, 1H), 8.78(s, 1H), 9.12(t, 1H), 11.12(bs, 1H) |
| 57 | 514 | 2.57(s, 3H), 3.34-3.54(m, 3H), 3.82(bs, 1H), 4.12(bs, 2H), 4.41-4.45(m, 1H), 4.62(d, 2H), 4.69-4.73(m, 1H), 6.57-6.65(m, 1H), 6.90(d, 1H), 7.41(d, 1H), 7.47-7.52(m, 2H), 7.61-7.68(m, 3H), 7.77(d, 1H), 8.26(s, 1H), 8.54(d, 1H), 9.12(bs, 1H), 11.0(s, 1H). |
| 58 | 528 | 2.63(s, 6H), 3.35-3.54(m, 3H), 3.80(bs, 1H), 4.12(bs, 2H), 4.41-4.45(m, 1H), 4.65-4.73(m, 3H), 6.59-6.67(m, 1H), 6.91(d, 1H), 7.40(d, 1H), 7.52-7.67(m, 4H), 7.77(d, 1H), 8.28(s, 1H), 9.16(bs, 1H), 11.31(bs, 1H), 15.52(bs, 1H). |
| 59 | 530 | 3.36-3.40(m, 3H), 3.79-3.81(m, 1H), 3.84(s, 3H), 4.10-4.13(m, 2H), 4.39-4.43(m, 1H), 4.53(d, 2H), 4.71(d, 1H), 6.56-6.64(m, 1H), 6.82(s, 1H), 6.90(d, 1H), 7.03(d, 1H), 7.41(d, 1H), 7.62-7.69(m, 3H), 7.77(d, 1H), 8.15(d, 1H), 8.23(s, 1H), 9.06(t, 1H), 10.92(bs, 1H), |
| 60 | 568 | |
| 61 | 501 | |
| 62 | 504 | 3.37-3.41(m, 2H), 3.45-3.50(m, 1H), 3.77-3.78(m, 1H), 3.81(s, 3H), 4.07-4.13(m, 2H), 4.36(d, 2H), 4.40-4.42(m, 1H), 4.68(d, 1H), 6.60-6.67(m, 1H), 6.90(d, 1H), 7.40(d, 1H), 7.47(s, 1H), 7.58-7.61(m, 1H), 7.63-7.67(m, 2H), 7.71-7.75(m, 2H), 8.12(s, 1H), 8.90(t, 1H), 11.49(bs, 1H) |
| 63 | 532 | 3.29-3.46(m, 2H) 3.48-3.56(m, 1H) 3.79(br d, 1H) 3.85(s, 3H) 4.02-4.19(m, 2H) 4.39(br dd, 1H) 4.52(d, 2H) 4.68(br d, 1H) 6.62(dt, 1H) 6.85(br s, 1H) 6.88(d, 1H) 7.05(dd, 1H) |

TABLE 3-continued

Example Mass and NMR Data

| Ex# | Mass | 1H-NMR(400 MHz, DMSO-d6) δ ppm |
|---|---|---|
| | | 7.56(dd, 2H) 7.70(dd, 1H) 7.91(d, 1H) 8.15(d, 1H) 8.18(d, 1H) 9.20(br t, 1H) 11.47-11.63(m, 1H). |
| 64 | 530 | 3.36-3.44(m, 2H) 3.46-3.56(m, 1H) 3.74-3.82(m, 1H) 3.86(s, 3H) 4.05-4.17(m, 2H) 4.36-4.42(m, 1H) 4.52(br d, 2H) 4.66(br d, 1H) 6.64(dt, 1H) 6.86(d, 1H) 6.93(d, 1H) 7.06(dd, 1H) 7.40(dd, 1H) 7.61-7.64(m, 1H) 7.64(d, 1H) 7.70(dd, 1H) 7.91(dd, 1H) 8.15(dd, 1H) 8.18(d, 1H) 9.22(t, 1H) 11.71(br s, 1H). |
| 65 | 546 | 3.33-3.45(m, 2H) 3.46-3.58(m, 2H) 3.86(s, 3H) 4.19(br dd, 2H) 4.39(br dd, 1H) 4.53(d, 2H) 4.68(br d, 1H) 6.64(dt, 1H) 6.87(s, 1H) 7.06(dd, 1H) 7.17(d, 1H) 7.52(dd, 1H) 7.70(dd, 1H) 7.69(d, 1H) 7.83(d, 1H) 7.92(d, 1H) 8.16(dd, 1H) 8.19(d, 1H) 9.21(t, 1H) 11.74(br s, 1H). |
| 66 | 574 | 3.35-3.43(m, 2H) 3.46-3.51(m, 1H) 3.76-3.83(m, 1H) 3.86(s, 3H) 4.08-4.21(m, 1H) 4.38(br dd, 1H) 4.52(d, 2H) 4.67(br d, 1H) 6.66(dt, 1H) 6.84(s, 1H) 7.00(d, 1H) 7.05(dd, 1H) 7.50(dd, 1H) 7.64(dd, 1H) 7.68(t, 1H) 7.70(dd, 1H) 7.91(dd, 1H) 8.15(dd, 1H) 8.20(d, 1H) 9.17(t, 1H) 11.52(br s, 1H). |
| 67 | 514 | 3.31-3.43(m, 2H) 3.44-3.54(m, 1H) 3.75-3.83(m, 1H) 3.85(s, 3H) 4.11(br s, 2H, under H2O peak) 4.38(br dd, 1H) 4.52(d, 2H) 4.66(br d, 1H) 6.58(dt, 1H) 6.84(s, 1H) 6.99(d, 1H) 7.04(dd, 1H) 7.18(td, 1H) 7.33(ddd, 1H) 7.70(dd, 1H) 7.77(td, 1H) 7.91(dd, 1H) 8.15(dd, 1H) 8.20(d, 1H) 9.17(t, 1H) 11.49(br s, 1H). |
| 68 | 530 | 3.42(br s, 2H) 3.46-3.58(m, 1H) 3.72-3.82(m, 1H) 3.87(s, 3H) 4.01-4.18(m, 2H) 4.38(br dd, 1H) 4.52(br d, 2H) 4.65(br d, 1H) 6.58(dt, 1H) 6.89(s, 1H) 6.91(d, 1H) 7.07(dd, 1H) 7.42-7.50(m, 1H) 7.55(ddd, 1H) 7.69(dd, 1H) 7.80(dd, 1H) 7.91(d, 1H) 8.16(d, 1H) 8.19(d, 1H) 9.26(t, 1H) 11.83(br s, 1H). |
| 69 | 546 | 3.37-3.45(m, 2H) 3.47-3.56(m, 1H) 3.73-3.82(m, 1H) 3.87(s, 3H) 4.04-4.19(m, 2H) 4.39(br dd, 1H) 4.53(d, 2H) 4.66(br d, 1H) 6.66(dt, 1H) 6.89(s, 1H) 6.93(d, 1H) 7.52(dd, 1H) 7.68(d, 1H) 7.69(dd, 1H) 7.83(d, 1H) 7.91(d, 1H) 8, 16(dd, 1H) 8.18(d, 1H) 9.27(t, 1H) 11.88(br s, 1H). |
| 70 | 544 | 1.29(t, 3H), 3.36(bs, 2H), 3.52(bs, 1H), 3.74-3.84(m, 1H), 4.09-4.14(m, 2H), 4.29(q, 2H), 4.36-4.42(dd, 1H), 4.51(d, 2H), 4.70(d, , 1H), 6.56-6.63(m, 1H), 6.78(s, 1H), 6.91(d, 1H), 7.01(d, 1H), 7.41(d, 1H), 7.62-7.72(m, 3H), 7.91(d, 1H), 8.13(d, 1H), 8.19(s, 1H), 9.11(t, 1H), 11.06(bs, 1H). |
| 71 | 552 | 3.41(m, 2H), 3.51(br dd, 1H), 3.74(br s, 1H), 4.14(br d, 2H), 4.39(m, 1H), 4.57 (d, 2H) 4.67 (br d, 1H) 6.72 (m, 1H) 6.92 (d, 1H) 7.46 (dd, 1H) 7.55 (d, 2H) 7.56 (m, 1H) 7.69 (dd, 1H) 7.93 (d, 1H) 8.17 (d, 1H) 8.39 (d, 1H) 9.28 (t, 1H) 11.77 (br s, 1H) |
| 72 | 534 | 3.33-3.45(m, 3H) 3.77(br s, 1H) 4.04-4.20(m, 2H) 4.39(br dd, 1H) 4.58(br d, 2H) 4.67(br d, 1H) 6.65(dt, 1H) 6.94(br d, 1H) 7.40(br d, 1H) 7.47(br d, 1H) 7.56(s, 1H) 7.60-7.67(m, 2H) 7.70(dd, 1H) 7.94(d, 1H) 8.19(s, 1H) 8.40(d, 1H) 9.26(br t, 1H) 11.72(br s, 1H). |
| 73 | 578 | 3.41(m, 2H) 3.49(m, 1H) 3.77(m, 1H) 4.16(m, 2H) 4.37(br dd, 1H) 4.57(d, 2H) 4.64(br d, 1H) 6.68(m, 1H) 7.00(d, 1H) 7.47(dd, 1H) 7.49(m, 1H) 7.55(d, 1H), 7.66(m, 3H) 7.93(d, 1H) 8.19(d, 1H), 8.39(d, 1H) 9.27(t, 1H) 11.85 (br s, 1H) |
| 74 | 552 | 3.42 (m, 2H), 3.48(br s, 1H), 3.76(br d, 1H) 4.17(m, 2H), 4.36(br dd, 1H) 4.57 (br d, 2H), 4.60(m, 1H), 6.78(m, 1H), 6.89(m, 1H), 7.48(m, 3H), 7.56(s, 1H) 7.69 (dd, 1H) 7.93 (d, 1H) 8.21 (d, 1H) 8.40 (d, 1H) 9.30 (t, 1H) 12.03 (br s, 1H) |
| 75 | 534 | 3.40-3.50(m, 3H), 3.80(bs, 1H), 4.14-4.25(m, 2H), 4.40(bs, 1H), 4.58(d, 2H), 4.69(d, 1H), 6.59-6.64(m, 1H), 7.00(d, 1H), 7.38(d, 1H), 7.46(d, 1H), 7.51-7.55(m, 2H), 7.70-7.77(m, 2H), 7.94(d, 1H), 8.20(s, 1H), 8.40(d, 1H), 9.14(bs, 1H), 11.03(bs, 1H), |
| 76 | 536 | 3.42 (m, 3H) 3.77 (br d, 1H) 4.23 (m, 2H) 4.36 (br dd, 1H) 4.58 (d, 2H) 4.63 (br d, 1H) 6.71 (m, 1H) 6.87 (m, 1H) 7.32 (m, 2H) 7.47 (dd, 1H) 7.56 (d, 1H) 7.70 (dd, 1H) 7.94 (dd, 1H) 8.22 (d, 1H) 8.40 (dd, 1H) 9.25 (t, 1H) 11.84 (br s, 1H) |
| 77 | 578 | 3.42 (m, 2H), 3.53 (m, 1H) 3.80 (m, 1H) 4.19 (m, 2H) 4.40 (br dd, 1H) 4.58 (br s, 2H) 4.69 (br d, 1H) 6.64 (m, 1H) 7.11 (d, 1H) 7.20 (td, 1H) 7.47 (dd, 1H) 7.56 (d, 1H) 7.70 (m, 3H) 7.94 (d, 1H) 8.18 (d, 1H) 8.39 (d, 1H) 9.27 (t, 1H) 11.83 (br s, 1H) |
| 78 | 578 | 3.42 (m, 2H) 3.50 (m, 1H) 3.78 (m, 1H) 4.15 (m, 2H) 4.34 (m, 1H) 4.57 (d, 2H), 4.66(br d, 1H), 6.71(m, 1H), 7.00(d, 1H), 7.27(dd, 1H), 7.47(dd, 1H), 7.55(d, 1H), 7.58(m, 1H), 7.69 (dd, 1H), 7.93 (m, 2H), 8.19(d, 1H), 8.39(d, 1H) 9.27 (t, 1H) 11.84 (br s, 1H) |
| 79 | 578 | 3.52 (m, 3H) 3.80 (m, 1H) 4.11 (m, 2H) 4.40 (br s, 1H) 4.58 (br s, 2H) 4.67 (br d, 1H) 6.56 (m, 1H) 6.91 (br d, 1H) 7.46 (br s, 2H) 7.55 (br s, 2H) 7.70 (br d, 1H) 7.94 (m, 2H) 8.19 (br s, 1H) 8.40 (br s, 1H) 9.21 (br s, 1H) 11.48 (m, 1H) |
| 80 | 536 | 3.42 (m, 2H) 3.50 (m, 1H) 3.78 (m, 1H) 4.17 (m, 2H) 4.44 (m, 1H) 4.58 (d, 2H) 4.66 (br d, 1H) 6.69 (m, 1H) 7.02 (d, 1H) 7.41 (m, 1H) 7.47 (dd, 1H) 7.57 (m, 2H) 7.70 (dd, 1H) 7.94 (d, 1H) 8.20 (d, 1H) 8.40 (d, 1H) 9.28 (t, 1H) 11.88 (br s, 1H) |
| 81 | 596 | 3.42 (m, 2H) 3.50 (m, 1H) 3.78 (m, 1H) 4.18 (m, 2H) 4.38 (br s, 1H) 4.58 (d, 2H) 4.66 (br d, 1H) 6.76 (m, 1H) 7.04 (d, 1H) 7.47 (dd, 1H) 7.51 (ddd, 1H) 7.56 (d, 1H) 7.61 (m, 1H) 7.70 (m, 1H) 7.94 (d, 1H) 8.19 (d, 1H) 8.40 (d, 1H) 9.29 (t, 1H) 11.93 (br d, 1H) |
| 82 | 552 | 3.41 (m, 2H) 3.49 (br d, 1H) 3.78 (m, 1H) 4.17 (m, 2H) 4.38 (br dd, 1H) 4.57 (d, 2H) 4.65 (br d, 1H) 6.75 (m, 1H) 7.03 (d, 1H) 7.47 (dd, 1H) 7.51 (m, 1H) 7.55 (m, 2H) 7.69 (dd, 1H) 7.93 (d, 1H) 8.19 (d, 1H) 8.39 (d, 1H) 9.27 (t, 1H) 11.89 (br s, 1H) |
| 83 | 572 | 3.44 (br s, 2H) 3.49 (m, 1H) 3.76 (br d, 1H) 4.20 (m, 1H) 4.27 (m, 1H) 4.37 (br dd, 1H) 4.57 (d, 2H) 4.63 (br d, 1H) 6.85 (m, 1H) 6.92 (m, 1H) 7.47 (dd, 1H) 7.56 (s, 1H) 7.70 (dd, 1H) 7.94 (d, 1H) 8.20 (d, 1H) 8.39 (d, 1H) 9.29(t, 1H), 12.10(br s, 1H) |
| 84 | 588 | 3.44 (br s, 2H), 3.48 (br s, 1H), 3.76(br d, 1H), 4.23(m, 2H), 4.36(br s, 1H), 4.57(d, 2H), 4.62(br d, 1H), 6.90(m, 1H), 6.96(m, 1H), 7.47(dd, 1H), 7.55(d, 1H), 7.69(dd, 1H), 7.93(d, 1H), 8.19(d, 1H), 8.39(d, 1H), 9.30(t, 1H), 12.15(br s, 1H) |
| 85 | 578 | 3.41(m, 2H), 3.51(br dd, 1H), 3.77(m, 1H), 4.11(m, 2H), 4.39(br dd, 1H) 4.57 (d, 2H), 4.66 (br d, 1H), 6.67(m, 1H), 6.93(d, 1H), 7.33(dd, 1H), 7.47(dd, 1H), 7.55(d, 1H), 7.59(dd, 1H), 7.69(dd, 1H), 7.74(t, 1H), 7.93(d, 1H), 8.18(d, 1H), 8.39 (d, 1H) 9.28 (t, 1H) 11.81 (br s, 1H) |

TABLE 3-continued

Example Mass and NMR Data

| Ex# | Mass | 1H-NMR(400 MHz, DMSO-d6) δ ppm |
|---|---|---|
| 86 | 584 | 3.37-3.50(m, 3H), 3.80-3.83(m, 1H), 4.10-4.15(m, 2H), 4.37-4.43(m, 1H), 4.57(d, 2H), 4.70(d, 1H), 6.65-6.72(m, 1H), 6.95(d, 1H), 7.39-7.47(m, 3H), 7.54-7.55(m, 2H), 7.70-7.73(dd, 1H), 7.94(d, 1H), 8.19(s, 1H), 8.39(d, 1H), 9.18(t, 1H), 11.22(bs, 1H). |
| 87 | 534 | 3.34-3.51(m, 3H), 3.80(bs, 1H), 4.09-4.12(m, 2H), 4.40(bs, 1H), 4.58(d, 2H), 4.69(d, 1H), 6.49-6.57(m, 1H), 6.89(d, 1H), 7.45-7.49(m, 2H), 7.55-7.58(m, 2H), 7.71(d, 1H), 7.82-7.84(dd, 1H), 7.94(d, 1H), 8.19(s, 1H), 8.40(d, 1H), 9.16(bs, 1H), 11.11(bs, 1H), |
| 88 | 516 | 3.37-3.38(m, 2H), 3.45(bs, 1H), 3.79-3.82(m, 1H), 4.10-4.17(m, 2H), 4.35-4.40(m, 1H), 4.58(d, 2H), 4.67(d, 1H), 6.52-6.60(m, 1H), 6.99(d, 1H), 7.16-7.21(m, 1H), 7.31-7.37(m, 1H), 7.45-7.47(dd, 1H), 7.55(s, 1H), 7.69-7.72(dd, 1H), 7.74-7.80(m, 1H), 7.94(d, 1H), 8.20(s, 1H), 8.40(d, 1H), 9.17(t, 1H), 11.25(bs, 1H) |
| 89 | 536 | 3.40-3.51(m, 3H), 3.80-3.83(m, 1H), 4.10-4.14(m, 2H), 4.40(bs, 1H), 4.58(d, 2H), 4.70(d, 1H), 6.54-6.62(m, 1H), 6.86(d, 1H), 7.46(d, 1H), 7.55-7.60(m, 3H), 7.72(d, 1H), 7.94(d, 1H), 8.18(s, 1H), 8.40(d, 1H), 9.15(bs, 1H), 11.03(bs, 1H). |
| 90 | 518 | 3.38-3.54(m, 3H), 3.79-3.82(m, 1H), 4.09-4.15(m, 2H), 4.36-4.42(dd, 1H), 4.58(d, 2H), 4.70(d, 1H), 6.61-6.69(m, 1H), 6.91(d, 1H), 7.21-7.26(m, 1H), 7.31-7.34(m, 1H), 7.45-7.47(m, 1H), 7.55(s, 1H), 7.70-7.72(dd, 1H), 7.94(d, 1H), 8.19(d, 1H), 8.40(d, 1H), 9.18(t, 1H), 11.30(bs, 1H). |
| 91 | 507 | 3.33-3.44(m, 3H) 3.80(br s, 1H) 4.08-4.22(m, 2H) 4.40(br dd, 1H) 4.58(d, 2H) 4.69(br d, 1H) 6.73(dt, 1H) 7.01(d, 1H) 7.47(dd, 1H) 7.55(d, 1H) 7.68-7.73(m, 1H) 7.74(d, 2H) 7.89(d, 2H) 7.94(d, 1H) 8.19(d, 1H) 8.40(d, 1H) 9.19(t, 1H) 11.44(br s, 1H). |
| 92 | 516 | 3.41(br s, 2H) 3.50(br s, 1H) 3.77(br s, 2H) 4.13(br s, 1H) 4.38(br dd, 1H) 4.57(d, 2H) 4.67(br d, 1H) 6.56(dt, 1H) 6.93(d, 1H) 7.44-7.50(m, 3H) 7.55(s, 2H) 7.58(s, 1H) 7.70(dd, 1H) 7.94(d, 1H) 8.20(d, 1H) 8.40(d, 1H) 9.22(br t, 1H), 11.55(br s, 1H) |
| 93 | 550 | 3.36-3.46(m, 2H) 3.47-3.56(m, 1H) 3.75-3.82(m, 1H) 4.03-4.19(m, 2H) 4.39(br dd, 1H) 4.58(d, 2H) 4.67(br d, 1H) 6.65(dt, 1H) 6.92(d, 1H) 7.47(dd, 1H) 7.53(dd, 1H) 7.55(d, 1H) 7.68(d, 1H) 7.70(dd, 1H) 7.84(d, 1H) 7.94(dd, 1H) 8.19(d, 1H) 8.40(dd, 1H) 9.24(t, 1H), 11.66(br s, 1H) |
| 94 | 578 | 3.42 (m, 2H) 3.51 (m, 1H) 3.78 (m, 1H) 4.17 (m, 2H) 4.39 (br dd, 1H) 4.57 (br d, 2H) 4.66 (br d, 1H) 6.54 (m, 1H) 7.10 (d, 1H) 7.36 (td, 1H) 7.47 (dd, 1H) 7.55 (d, 1H) 7.66 (d, 1H) 7.69 (dd, 1H) 7.83 (dd, 1H) 7.93 (d, 1H) 8.19 (d, 1H) 8.39 (d, 1H) 9.28 (t, 1H) 11.89 (br s, 1H) |
| 95 | 541 | 3.35-3.43(m, 2H), 3.51-3.55(m, 1H), 3.79-3.82(m, 1H), 4.08-4.19(m, 2H), 4.37-4.42(dd, 1H), 4.58(d, 2H), 4.69(d, 1H), 6.72-6.79(m, 1H), 6.94(d, 1H), 7.46-7.47(dd, 1H), 7.55(s, 1H), 7.69-7.72(dd, 1H), 7.94(d, 1H), 8.00-8.02(m, 2H), 8.05(s, 1H), 8.18(d, 1H), 8.40(d, 1H), 9.23(t, 1H), 11.62(bs, 1H). |
| 96 | 530 | 2.35 (s, 3H) 3.41 (m, 2H) 3.49 (m, 1H) 3.76 (m, 1H) 4.10 (m, 2H) 4.31 (m, 1H) 4.57 (d, 2H) 4.64 (br d, 1H) 6.55 (m, 1H) 6.90 (d, 1H) 7.38 (m, 1H) 7.44 (m, 1H) 7.47 (dd, 1H) 7.51 (d, 1H) 7.56 (d, 1H) 7.69 (dd, 1H) 7.93 (d, 1H) 8.19 (d, 1H) 8.39 (d, 1H) 9.28 (t, 1H) 11.79 (br s, 1H) |
| 97 | 594 | 3.41 (m, 2H) 3.51 (br dd, 1H) 3.79 (br dd, 1H) 4.11 (m, 2H) 4.39 (br dd, 1H) 4.57 (d, 2H) 4.67 (br d, 1H) 6.64 (m, 1H) 6.92 (d, 1H) 7.47 (dd, 1H) 7.56 (m, 2H) 7.66 (d, 1H) 7.70 (d, 1H) 7.93 (d, 1H) 7.96 (d, 1H) 8.18 (d, 1H) 8.40 (d, 1H) 9.25 (t, 1H) 11.72 (br s, 1H) |
| 98 | 525 | 3.42 (m, 2H) 3.52 (br dd, 1H) 3.79 (m, 1H) 4.11 (m, 2H) 4.39 (br dd, 1H) 4.58 (d, 2H) 4.67 (br d, 1H) 6.65 (m, 1H) 6.96 (d, 1H) 7.47 (dd, 1H) 7.56 (d, 1H) 7.59 (t, 1H) 7.70 (dd, 1H) 7.95 (m, 2H) 8.15 (dd, 1H) 8.18 (d, 1H) 8.40 (d, 1H) 9.28 (t, 1H) 11.79 (br s, 1H) |
| 99 | 536 | 3.52-3.64(m, 3H) 3.79(br s, 1H) 4.13(br d, 2H) 4.42(br s, 1H) 4.62(br d, 2H) 4.69(br s, 1H) 6.56-6.74(m, 1H) 6.90(br d, 1H) 7.20(s, 1H) 7.40(br d, 1H) 7.57(d, 2H) 7.71(dd, 1H) 7.95(d, 1H) 8.17(d, 1H) 8.23(d, 1H) 9.16(br s, 1H) 11.00(br s, 1H) |
| 100 | 544 | 3.23 (s, 3H) 3.43 (m, 2H) 3.53 (m, 1H) 3.80 (m, 1H) 4.17 (m, 2H) 4.41 (br dd, 1H) 4.62 (d, 2H) 4.68 (br d, 1H) 6.75 (dt, 1H) 7.05 (d, 1H) 7.21 (s, 1H) 7.41 (dt, 1H) 7.70 (dd, 1H) 7.80 (d, 2H) 7.96 (m, 3H) 8.20 (d, 1H) 8.23 (d, 1H) 9.26 (t, 1H) 11.74 (br s, 1H) |
| 101 | 534 | 3.39-3.42(m, 2H), 3.47-3.53(m, 1H), 4.14-4.21(m, 2H), 4.36-4.42(dd, 1H), 4.61(d, 2H), 4.69(d, 1H), 6.58-6.65(m, 1H), 7.14-7.20(m, 2H), 7.41(d, 1H), 7.51-7.53(dd, 1H), 7.70-7.72(m, 2H), 7.83(d, 1H), 7.94(d, 1H), 8.19-8.23(m, 2H), 9.20(t, 1H), 11.41(bs, 1H). |
| 102 | 562 | 3.38-3.46(m, 2H) 3.49(br d, 1H) 3.78(br s, 1H) 4.15(br dd, 2H) 4.33-4.40(m, 1H) 4.61(d, 2H) 4.66(br d, 1H) 6.67(dt, 1H) 7.00(d, 1H) 7.21(s, 1H) 7.41(dt, 1H) 7.50(dd, 1H) 7.63(dd, 1H) 7.67(t, 1H) 7.70(dd, 1H) 7.94(dd, 1H) 8.20(d, 1H) 8.23(d, 1H) 9.23(t, 1H) 11.62(br s, 1H) |
| 103 | 536 | 3.41(br d, 2H) 3.46(br s, 1H) 3.78(br s, 1H) 4.16(br d, 1H) 4.21(br d, 1H) 4.29-4.43(m, 1H) 4.61(br d, 2H) 4.65(br s, 1H) 6.74(dt, 1H) 6.88(d, 1H) 7.20(s, 1H) 7.40(br d, 1H) 7.48(d, 2H) 7.70(dd, 1H) 7.94(d, 1H) 8.21(d, 1H) 8.23(d, 1H) 9.22(br t, 1H) 11.67(br s, 1H) |
| 104 | 518 | 3.37-3.52(m, 3H), 3.74-3.82(m, 1H), 4.13-4.18(m, 2H), 4.35-4.41(dd, 1H), 4.61(d, 2H), 4.68(d, 1H), 6.58-6.65(m, 1H), 7.00(d, 1H), 7.20(s, 1H), 7.36-7.40(m, 2H), 7.51-7.54(dd, 1H), 7.70-7.77(m, 2H), 7.94(d, 1H), 8.20-8.23(m, 2H), 9.17(t, 1H), 11.15(bs, 1H) |
| 105 | 562 | 3.43(br s, 2H) 3.48-3.57(m, 1H) 3.72-3.82(m, 1H) 4.01-4.20(m, 2H) 4.39(br dd, 1H) 4.60(d, 2H) 4.66(br d, 1H) 6.67(dt, 1H) 6.93(d, 1H) 7.21(s, 1H) 7.33(dd, 1H) 7.38-7.43(m, 1H) 7.59(dd, 1H) 7.67-7.71(m, 1H) 7.74(dd, 1H) 7.94(dd, 1H) 8.18(d, 1H) 8.22(d, 1H) 9.31(t, 1H) 11.86(br s, 1H). |
| 106 | 520 | 3.34-3.44(m, 2H) 3.45-3.53(m, 1H) 3.62(br s, 1H) 4.07-4.18(m, 1H) 4.18-4.28(m, 1H) 4.36(br dd, 1H) 4.61(d, 2H) 4.65(br s, 1H) 6.68(dt, 1H) 6.86(d, 1H) 7.20(s, 1H) 7.32(t, 2H) 7.38-7.43(m, 1H) 7.70(dd, 1H) 7.94(dd, 1H) 8.21(d, 1H) 8.23(d, 1H) 9.22(t, 1H) 11.64(br s, 1H). |
| 107 | 562 | 3.40-3.48(m, 2H) 3.48-3.58(m, 1H) 3.76-3.84(m, 1H) 4.10-4.28(m, 2H) 4.41(br dd, 1H) 4.61(d, 2H) 4.70(br d, 1H) 6.64(dt, 1H) 7.11(d, 1H) 7.16-7.24(m, 2H) 7.38-7.44(m, 1H) 7.66-7.72(m, 2H) 7.74(d, 1H) 7.95(dd, 1H) 8.18(d, 1H) 8.23(d, 1H) 9.25(t, 1H) 11.70(br s, 1H). |
| 108 | 562 | 3.42-3.47(m, 2H) 3.48-3.57(m, 1H) 3.79(br s, 1H) 4.07-4.25(m, 2H) 4.39(br dd, 1H) 4.61(d, 2H) 4.68(br d, 1H) 6.70(dt, 1H) 7.00(d, 1H) 7.21(s, 1H) 7.27(dd, 1H) 7.41(dt, 1H) |

TABLE 3-continued

Example Mass and NMR Data

| Ex# | Mass | 1H-NMR(400 MHz, DMSO-d6) δ ppm |
|---|---|---|
| | | 7.58(ddd, 1H) 7.70(dd, 1H) 7.91-7.94(m, 1H) 7.94(d, 1H) 8.19(d, 1H) 8.23(d, 1H) 9.24(t, 1H) 11.65(br s, 1H) |
| 109 | 562 | 3.43 (m, 2H) 3.51 (m, 1H) 3.79 (m, 1H) 4.10 (m, 2H) 4.39 (br dd, 1H) 4.61 (d, 2H) 4.67 (br d, 1H) 6.57 (dt, 1H) 6.92 (d, 1H) 7.21 (s, 1H) 7.42 (dd, 1H) 7.43 (t, 1H) 7.59 (ddd, 1H) 7.70 (dd, 1H) 7.93 (m, 2H) 8.19 (d, 1H) 8.23 (d, 1H) 9.27(t, 1H) 11.68 (br s, 1H) |
| 110 | 520 | 3.43(br dd, 2H) 3.47-3.55(m, 1H) 3.74-3.83(m, 1H) 4.08-4.25(m, 2H) 4.38(br dd, 1H) 4.61(d 2H) 4.65(br d, 1H) 6.68(dt, 1H) 7.01(d, 1H) 7.21(s, 1H) 7.36-7.45(m, 2H) 7.52-7.61(m, 1H) 7.69(dd, 1H) 7.94(d, 1H) 8.19(d, 1H) 8.23(d, 1H) 9.27(t, 1H) 11.81(br s, 1H). |
| 111 | 580 | 3.35-3.44(m, 2H) 3.49-3.55(m, 1H) 3.74-3.84(m, 1H) 4.08-4.27(m, 2H) 4.39(br dd, 1H) 4.61(d, 2H) 4.67(br d, 1H) 6.74(dt, 1H) 7.03(d, 1H) 7.21(s, 1H) 7.39-7.43(m, 1H) 7.48-7.55(m, 1H) 7.62(ddd, 1H) 7.70(dd, 1H) 7.95(d, 1H) 8.20(d, 1H) 8.23(d, 1H) 9.24(t, 1H) 11.71(br s, 1H). |
| 112 | 552 | 3.41(br s, 2H) 3.47-3.52(m, 1H) 3.80(br d, 1H) 4.01-4.20(m, 2H) 4.39(br dd, 1H) 4.61(d, 2H) 4.68(br d, 1H) 6.65(dt, 1H) 6.88(d, 1H) 7.21(s, 1H) 7.41(dt, 1H) 7.70(dd, 1H) 7.81(d, 2H) 7.94(dd, 1H) 8.18(d, 1H) 8.23(d, 1H) 9.24(t, 1H) 11.63(br s, 1H) |
| 113 | 509 | 3.42(br s, 2H) 3.48-3.57(m, 1H) 3.72-3.83(m, 1H) 4.10(br s, 2H) 4.39(br dd, 1H) 4.61(d, 2H) 4.67(br d, 1H) 6.59-6.70(m, 1H) 6.96(d, 1H) 7.21(s, 1H) 7.37-7.43(m, 1H) 7.59(t, 1H) 7.70(dd, 1H) 7.94(d, 1H) 7.94-7.97(m, 1H) 8.15(dd, 1H) 8.18(d, 1H) 8.23(d, 1H) 9.29(t, 1H) 11.79(br s, 1H). |
| 114 | 518 | 3.38-3.39(m, 3H), 3.80-3.83(m, 1H), 4.13-4.20(m, 2H), 4.37-4.42(dd, 1H), 4.61(d, 2H), 4.70(d, 1H), 6.53-6.57(m, 1H), 7.13-7.20(m, 2H), 7.31-7.36(m, 1H), 7.41(d, 1H), 7.52-7.55(dd, 1H), 7.70-7.72(m, 1H), 7.85-7.89(m, 1H), 7.95(d, 1H), 8.20-8.23(m, 2H), 9.18(t, 1H), 11.21(bs, 1H) |
| 115 | 500 | 3.33(s, 1H), 3.45-3.50(m, 2H), 3.79-3.82(m, 1H), 4.11-4.17(m, 2H), 4.35-4.41(m, 1H), 4.61(d, 2H), 4.68(d, 1H), 6.52-6.59(m, 1H), 6.99(d, 1H), 7.16-7.20(m, 2H), 7.31-7.37(m, 1H), 7.40(d, 1H), 7.70-7.72(dd, 1H), 7.74-7.81(m, 1H), 7.94(d, 1H), 8.20-8.22(m, 2H), 9.18(t, 1H), 11.16(bs, 1H) |
| 116 | 520 | 3.39(bs, 2H), 3.47-3.53(m, 1H), 3.78-3.81(m, 1H), 4.09-4.13(m, 2H), 4.36-4.41(dd, 1H), 4.61(d, 2H), 4.68(d, 1H), 6.57-6.64(m, 1H), 6.87(d, 1H), 7.20(s, 1H), 7.41(d, 1H), 7.55-7.59(m, 2H), 7.70-7.72(dd, 1H), 7.94(d, 1H), 8.18(d, 1H), 8.23(d, 1H), 9.23(t, 1H), 11.44(bs, 1H). |
| 117 | 502 | 3.38-3.48(m, 2H) 3.47-3.58(m, 1H) 3.74-3.85(m, 1H) 4.12(br dd, 2H) 4.39(d, 1H) 4.61(d, 2H) 4.68(br d, 1H) 6.68(dt, 1H) 6.92(d, 1H) 7.21(s, 1H) 7.22-7.27(m, 1H) 7.27-7.35(m, 2H) 7.41(dt, 1H) 7.70(dd, 1H) 7.94(dd, 1H) 8.19(d, 1H) 8.23(d, 1H) 9.24(t, 1H) 11.60(br s, 1H). |
| 118 | 518 | 3.40(br s, 2H) 3.49(br s, 1H) 3.79(br s, 1H) 4.16(br s, 2H) 4.40(br s, 1H) 4.61(d, 2H) 4.67(br s, 1H) 6.63-6.75(m, 1H) 7.05(d, 1H) 7.20(s, 1H) 7.29(t, 1H) 7.38-7.43(m, 1H) 7.54-7.62(m, 1H) 7.65-7.70(m, 1H) 7.70(dd, 1H) 7.94(dd, 1H) 8.20(d, 1H) 8.23(d, 1H) 9.22(br t, 1H) 11.64(br s, 1H). |
| 119 | 502 | 3.39-3.47(m, 2H) 3.47-3.54(m, 1H) 3.74-3.83(m, 1H) 4.07-4.18(m, 2H) 4.38(br dd, 1H) 4.61(d, 2H) 4.66(br d, 1H) 6.71(dt, 1H) 7.06(d, 1H) 7.21(s, 1H) 7.24-7.31(m, 1H) 7.38-7.47(m, 2H) 7.48-7.54(m, 1H) 7.70(dd, 1H) 7.94(dd, 1H) 8.20(d, 1H) 8.23(d, 1H) 9.27(t, 1H) 11.81(br s, 1H). |
| 120 | 491 | 3.42(br s, 2H) 3.47-3.57(m, 1H) 3.78(br s, 1H) 4.09-4.15(m, 2H) 4.41(br d, 1H) 4.61(br d, 2H) 4.68(br d, 1H) 6.70-6.80(m, 1H) 7.02(d, 1H) 7.21(s, 1H) 7.41(br d, 1H) 7.51(d, 1H) 7.74(d, 2H) 7.89(d, 2H) 7.92-7.97(m, 1H) 8.20(s, 1H) 8.23(d, 1H) 9.17(br t, 1H) 11.74(br s, 1H). |
| 121 | 500 | 3.44(br d, 2H) 3.48-3.55(m, 1H) 3.75(br s, 1H) 4.10(br dd, 2H) 4.38(br dd, 1H) 4.60(br d, 2H) 4.64(br d, 1H) 6.52-6.73(m, 1H) 6.94(d, 1H) 7.21(s, 1H) 7.41(br d, 1H) 7.44-7.50(m, 2H) 7.52-7.60(m, 2H) 7.67-7.73(m, 1H) 7.88-7.96(m, 1H) 8.19(d, 1H) 8.22(d, 1H) 9.31(t, 1H) 11.84(br s, 1H). |
| 122 | 534 | 3.34-3.46(m, 2H) 3.51(br dd, 1H) 3.78(br s, 1H) 4.03-4.20(m, 2H) 4.35-4.43(m, 1H) 4.61(br dd, 2H) 4.67(br d, 1H) 6.65(dt, 1H) 6.92(d, 1H) 7.21(s, 1H) 7.39-7.43(m, 1H) 7.53(dd, 1H) 7.68(d, 1H) 7.71(d, 1H) 7.84(d, 1H) 7.94(d, 1H) 8.19(d, 1H) 8.23(d, 1H) 9.25(t, 1H) 11.68(br s, 1H). |
| 123 | 484 | 3.33-3.44(m, 2H) 3.44-3.54(m, 1H) 3.74-3.78(m, 1H) 4.09(br dd, 2H) 4.39(br dd, 1H) 4.61(br d, 2H) 4.67(br d, 1H) 6.41-6.53(m, 1H) 6.92(d, 1H) 7.16-7.21(m, 1H) 7.21-7.32(m, 2H) 7.40(br d, 1H) 7.60(dd, 2H) 7.71(dd, 1H) 7.94(d, 1H) 8.20(d, 1H) 8.23(d, 1H) 9.20(t, 1H) 11.33(br s, 1H) |
| 124 | 467 | 3.47 (br s, 2H) 3.59 (br s, 1H) 3.80 (br d, 1H) 4.27 (br s, 2H) 4.40 (br d, 1H) 4.61 (d, 2H) 4.70 (br s, 1H) 7.21 (d, 2H) 7.26 (m, 1H) 7.42 (br d, 1H) 7.70 (dd, 1H) 7.94 (m, 1H) 8.15 (s, 1H) 8.17 (s, 2H) 8.23 (d, 1H) 8.93 (d, 2H) 9.36 (t, 1H) 12.28 (br s, 1H) |
| 125 | 562 | 3.39-3.47(m, 2H) 3.47-3.56(m, 1H) 3.76-3.84(m, 1H) 4.15-4.22(m, 2H) 4.39(br dd, 1H) 4.61(br d, 2H) 4.68(br d, 1H) 6.53(dt, 1H) 7.10(d, 1H) 7.21(s, 1H) 7.37(td, 1H) 7.41(br d, 1H) 7.66(dd, 1H) 7.70(dd, 1H) 7.84(dd, 1H) 7.94(d, 1H) 8.19(d, 1H) 8.23(d, 1H) 9.25(t, 1H) 11.76(br s, 1H). |
| 126 | 550 | 3.40(br d, 2H) 3.46(br s, 1H) 3.75(br s, 1H) 4.08(br dd, 2H) 4.36(br d, 1H) 4.61(d, 2H) 4.65(br s, 1H) 6.34(dt, 1H) 7.06(d, 1H) 7.21(s, 1H) 7.29(d, 1H) 7.38-7.43(m, 1H) 7.68(d, 1H) 7.70(dd, 1H) 7.94(d, 1H) 8.21(d, 1H) 8.23(d, 1H) 9.23(br t, 1H) 11.60(br s, 1H) |
| 127 | 509 | 3.38(bs, 2H), 3.51-3.58(m, 1H), 3.80-3.83(m, 1H), 4.09-4.17(m, 2H), 4.37-4.42(m, 1H), 4.61(d, 2H), 4.69(d, 1H), 6.70-6.77(m, 1H), 6.94(d, 1H), 7.21(s, 1H), 7.40(d, 1H), 7.70-7.73(dd, 1H), 7.83-7.86(m, 2H), 7.94(d, 2H), 8.18(bs, 1H), 8.23(d, 1H), 9.21(bs, 1H), 11.32(bs, 1H). |

TABLE 3-continued

Example Mass and NMR Data

| Ex# | Mass | 1H-NMR(400 MHz, DMSO-d6) δ ppm |
|---|---|---|
| 128 | 567 | |
| 129 | 551 | |
| 130 | 596 | 3.36-3.52)m, 3H), 3.80)bs, 1H), 4.11-4.15 (m, 2H), 4.40-4.42 (m, 1H), 4.56 (d, 2H), 4.70 (d, 1H), 6.64-6.71 (m, 1H), 6.90 (d, 1H), 7.48 (d, 1H), 7.58 (d, 2H), 6.69-7.73 (m, 2H), 7.93 (d, 1H), 8.18 (bs, 1H), 8.38 (d, 1H), 9.16 (t, 1H) 11.15 (bs, 1H) |
| 131 | 578 | 1H NMR(400 MHz, DMSO-d6) δ: 3.38-3.40(m, 2H), 3.46-3.53(m, 1H), 3.79-3.82(m, 1H), 4.08-4.14(m, 2H), 4.36-4.41(m, 1H), 4.56(d, 2H), 4.68(d, 1H), 6.57-6.64(m, 1H), 6.91(d, 1H), 7.41(dd, 1H), 7.48(dd, 1H), 7.62-7.92(m, 4H), 7.93(d, 1H), 8.19(d, 1H), 8.37(d, 1H), 9.17(t, 1H), 11.21(bs, 1H), |
| 132 | 578 | 3.37-3.54(m, 3H), 3.80-3.83(m, 1H), 4.13-4.19(m, 2H), 4.36-4.41(m, 1H), 4.56(d, 2H), 4.68(d, 1H), 6.57-6.64(m, 1H), 7.0(d, 1H), 7.38(dd, 1H), 7.48-7.54(m, 2H), 7.68-7.77(m, 3H), 7.93(d, 1H), 8.20(d, 1H), 8.38(d, 1H), 9.13(t, 1H), 11.02(bs, 1H), |
| 133 | 580 | 3.36-3.48(m, 3H), 3.80-3.83(m, 1H), 4.13-4.22(m, 2H), 4.35-4.41(m, 1H), 4.56(d, 2H), 4.68(d, 1H), 6.58-6.66(m, 1H), 7.0(d, 1H), 7.39-7.45(m, 1H), 7.49(d, 1H), 7.55-7.61(m, 1H), 7.69-7.73(m, 2H), 7.94(d, 1H), 8.2(d, 1H), 8.39(d, 1H), 9.15(t, 1H), 11.17(bs, 1H), |
| 134 | 569 | 3.36-3.40(m, 2H), 3.51-3.53(m, 1H), 3.80-3.83(m, 1H), 4.11-4.16(m, 2H), 4.37-4.42(m, 1H), 4.56(d, 2H), 4.70(d, 1H), 6.75-6.83(m, 1H), 6.99(d, 1H), 7.49(d, 1H), 7.58(d, 1H), 7.69-7.72(m, 2H), 7.76(d, 1H), 7.93(d, 1H), 7.98(t, 1H), 8.18(s, 1H), 8.37(d, 1H), 9.19(t, 1H), 11.41(bs, 1H), |
| 135 | 578 | 3.33-3.52(m, 3H), 3.82(bs, 1H), 4.16-4.20(m, 2H), 4.39-4.43(m, 1H), 4.57(d, 2H), 4.71(d, 1H), 6.47-6.55(m, 1H), 7.16(d, 1H), 7.32-7.36(m, 1H), 7.48-7.55(m, 2H), 7.68-7.73(m, 2H), 7.86-7.95(m, 2H), 8.19(s, 1H), 8.38(d, 1H), 9.11(bs, 1H), 10.87(bs, 1H), |
| 136 | 562 | .33-3.37(m, 2H), 3.45-3.50(m, 1H), 3.79-3.81(m, 1H), 4.11-4.18(m, 2H), 4.35-4.40(m, 1H), 4.56(d, 2H), 4.68(d, 1H), 6.54-6.60(m, 1H), 6.99(d, 1H), 7.16-7.21(m, 1H), 7.31-7.37(m, 1H), 7.48(dd, 1H), 7.69-7.72(m, 2H), 7.74-7.80(m, 1H), 7.93(d, 1H), 8.21(d, 1H), 8.37(d, 1H), 9.17(t, 1H), 11.28(bs, 1H) |
| 137 | 578 | 3.34-3.54(m, 3H), 3.80-3.84(m, 1H), 4.05-4.16(m, 2H), 4.39-4.45(m, 1H), 4.56(d, 2H), 4.71(d, 1H), 6.48-6.55(m, 1H), 6.90(d, 1H), 7.45-7.49(m, 2H), 7.55-7.58(m, 1H), 7.68-7.73(m, 2H), 7.84(d, 1H), 7.94(d, 1H), 8.19(s, 1H), 8.38(d, 1H), 9.12(bs, 1H), 10.79(bs, 1H). |
| 138 | 562 | 3.35-3.37(m, 2H), 3.49-3.52(m, 1H), 3.80-3.82(m, 1H), 4.10-4.17(m, 2H), 4.39-4.42(m, 1H), 4.56(d, 2H), 4.71(d, 1H), 6.46-6.53(m, 1H), 6.88(d, 1H), 7.39-7.41(m, 1H), 7.46-7.52(m, 2H), 7.68-7.73(m, 3H), 7.94(d, 1H), 8.19(s, 1H), 8.38(d, 1H), 9.13(bs, 1H), 10.79(bs, 1H), |
| 139 | 580 | 3.36-3.40(m, 2H), 3.46-3.53(m, 1H), 3.78-3.81(m, 1H), 4.06-4.13(m, 2H), 4.36-4.41(m, 1H), 4.56(d, 2H), 4.70(d, 1H), 6.56-6.63(m, 1H), 6.86(d, 1H), 7.48(dd, 1H), 7.56-7.60(m, 2H), 7.69-7.73(m, 2H), 7.94(d, 1H), 8.18(d, 1H), 8.37(d, 1H), 9.18(t, 1H), 11.25(bs, 1H), |
| 140 | 562 | 3.33-3.38(m, 2H), 3.50-3.54(m, 1H), 3.79-3.82(m, 1H), 4.09-4.16(m, 2H), 4.36-4.42(m, 1H), 4.56(d, 2H), 4.69(d1H), 6.61-6.69(m, 1H), 6.91(d, 1H), 7.21-7.27(m, 1H), 7.30-7.35(m, 2H), 7.49(dd, 1H), 7.69-7.72(m, 2H), 7.93(d, 1H), 8.19(d, 1H), 8.37(d, 1H), 9.19(t, 1H), 11.33(bs, 1H), |
| 141 | 560 | 3.34-3.51(m, 3H), 3.78-3.82(m, 1H), 4.05-4.15(m, 2H), 4.37-4.41(m, 1H), 4.56(d, 2H), 4.70(d, 1H), 6.47-6.55(m, 1H), 6.91(d, 1H), 7.47-7.49(m, 3H), 7.58(d, 2H), 7.68-7.72(m, 2H), 7.93(d, 1H), 8.20(bs, 1H), 8.38(d, 1H), 9.13(bs, 1H), 10.09(bs, 1H), |
| 142 | 544 | 3.37-3.52(m, 3H), 3.80-3.83(m, 1H), 4.07-4.13(m, 2H), 4.36-4.41(m, 1H), 4.56(d, 2H), 4.70(d, 1H), 6.39-6.47(m, 1H), 6.91(d, 1H), 7.24-7.28(m, 2H), 7.49(d, 1H), 7.59-7.62(m, 2H), 7.69-7.73(m, 2H), 7.94(d, 1H), 8.21(bs, 1H), 8.38(d, 1H), 9.13(t, 1H), 10.87(bs, 1H), |
| 143 | 534 | 3.38-3.44(m, 2H), 3.50-3.58(m, 2H), 4.39-4.44(m, 3H), 4.57(d, 2H), 4.64-4.68(m, 1H), 6.42(d, 1H), 7.46(d, 1H), 7.50-7.55(m, 3H), 7.60(d, 2H), 7.71(d, 1H), 7.93(d, 1H), 8.23(bs, 1H), 8.40(d, 1H), 9.21(bs, 1H), 11.45(bs, 1H). |
| 144 | 518 | 3.36-3.47(m, 3H), 3.85-3.89(m, 1H), 4.30-4.48(m, 3H), 4.60-4.65(m, 3H), 6.40(d, 1H), 7.20(s, 1H), 7.39(d, 1H), 7.51(d, 2H), 7.60(d, 2H), 7.70(d, 1H), 7.94(d, 1H), 8.23(d, 2H), 9.19(bs, 1H), 11.31(bs, 1H). |
| 145 | 539 | 2.40(s, 3H), 2.82(t, 2H), 2.96-3.03(m, 2H), 3.38(d, 2H), 3.62(s, 2H), 4.53(d, 2H), 6.52-6.68(m, 2H), 6.97(d, 1H), 7.29(d, 1H), 7.43(dd, 1H), 7.48-7.53(m, 2H) 7.57-7.61(m, 2H), 7.78(d, 1H), 8.38-8.41(m, 1H), 8.47(t, 1H). |
| 146 | 505 | 2.40(s, 3H), 2.81(t, 2H), 2.97-3.04(m, 2H), 3.38(d, 2H), 3.61(s, 2H), 4.52(d, 2H), 6.41-6.50(m, 1H), 6.63(d, 1H), 6.97(d, 1H), 7.29(d, 1H), 7.37-7.43(m, 3H), 7.49-7.53(m, 3H) 7.59(s, 1H), 8.38-8.41(m, 1H), 8.46(t, 1H). |
| 147 | 505 | 2.50(s, 3H), 2.78(t, 2H), 2.99(t, 2H), 3.40(d, 2H), 3.92(s, 2H), 4.52(d, 2H), 6.42-6.47(m, 1H), 6.64(d, 1H), 6.87(d, 1H), 7.05(t, 1H), 7.38-7.43(m, 3H), 7.50-7.53(m, 3H), 7.57(d, 1H), 8.38-8.41(m, 1H), 8.53(t, 1H) |
| 148 | 399 | 1.45(s, 9 H), 2.51(s, 3H), 2.97(t, 2H), 3.64(t, 2H), 4.52(d, 2H), 4.80(s, 2H), 6.91(d, 1H), 7.09(t, 1H), 7.42(d, 1H), 7.50(s, 1H), 7.58(d, 1H), 8.39, (d, 1H), 8.55(t, 1H). |
| 149 | 489 | 2.50(s, 3H), 2.78(t, 2H), 2.99(t, 2H), 3.39(d, 2H), 3.92(s, 2H), 4.52(d, 2H), 6.33-6.42(m, 1H), 6.64(d, 1H), 6.87(d, 1H), 7.05(t, 1H), 7.14-7.18(m, 2H), 7.48(d, 1H) 7.51-7.59(m, 4 H), 8.38-8.41(m, 1H), 8.53(t, 1H). |
| 150 | 539 | 2.40(s, 3H), 2.83(t, 2H), 2.98-3.05(m, 2H), 3.42(d, 2H), 3.63(s, 2H), 4.53(d, 2H), 6.57-6.65(m, 1H), 6.74(d, 1H), 6.97(d, 1H), 7.29(d, 1H), 7.41-7.61(m, 3H), 7.69-7.76(m, 4 H), 8.38-8.41(m, 1H), 8.47(t, 1H). |
| 151 | 603 | 3.23(s, 3H), 3.40-3.55(m, 3H), 3.80-3.86(m, 1H), 4.13-4.21(m, 2H), 4.41-4.47(m, 1H), 4.60(d, 2H), 4.72(d, 1H), 6.72-6.80(m, 1H), 7.05(d, 1H), 7.47(dd, 1H), 7.55-7.59(m, 2H), 7.78-7.83(m, 3H), 7.96(d, 2H), 8.10(s, 1H), 8.40(d, 1H), 9.14(t, 1H), 11.50(bs, 1H). |
| 152 | 577 | 2.86(t, 2H), 3.09(t, 2H), 3.41(d, 2H), 3.70(s, 2H), 4.57(d, 2H), 6.51-6.58(m, 1H), 6.65(d, 1H), 7.29(dd, 1H), 7.43-7.48(m, 2H) 7.52-7.66(m, 4 H), 8.07(s, 1H), 8.38-8.41(m, 1H), 8.70(t, 1H). |

TABLE 3-continued

Example Mass and NMR Data

| Ex# | Mass | 1H-NMR(400 MHz, DMSO-d6) δ ppm |
|---|---|---|
| 153 | 568 | 3.37-3.56(m, 3H), 3.77-3.86(m, 1H), 4.07-4.19(m, 2H), 4.41-4.47(m, 1H), 4.60(d, 2H), 4.74(d, 1H), 6.79-6.87(m, 1H), 7.01(d, 1H), 7.47(dd, 1H), 7.55-7.61(m, 3H), 7.75-7.82(m, 2H), 7.96-8.00(m, 1H), 8.10(s, 1H), 8.40(d, 1H), 9.14(t, 1H), 11.51(bs, 1H). |
| 154 | 561 | 3.33-3.51 (m, 3H), 3.83 (bs, 1H), 4.12 (bs, 2H), 4.43-4.44 (m, 1H), 4.60 (d, 2H), 4.74 (d, 1H), 6.48-6.55 (m, 1H), 6.89 (d, 1H), 7.40-7.58 (m, 5H), 7.70-7.81 (m, 2H), 8.09 (s, 1H), 8.40 (d, 1H), 9.08 (bs, 1H), 10.66 (bs, 1H). |
| 155 | 550 | 2.93-2.95(m, 2H), 3.12-3.14(m, 2H), 3.48(d, 2H), 3.72(s, 2H), 4.67(d, 2H), 5.94(t, 1H), 6.45-6.52(m, 1H), 6.65(d, 1H), 7.22-7.23(m, 1H), 7.33(s, 1H), 7.45-7.48(m, 4H), 7.60(d, 2H), 8.12(s, 1H), 8.38(d, 1H). |
| 156 | 559 | 2.86(t, 2H), 3.09(t, 2H), 3.40(d, 2H), 3.70(s, 2H), 4.56(d, 2H), 6.40-6.48(m, 1H), 6.65(d, 1H), 7.38-7.54(m, 7 H) 7.66(d, 1H), 8.07(s, 1H), 8.38-8.41(m, 1H), 8.69(t, 1H). |
| 157 | 559 | 2.85(t, 2H), 3.07(t, 2H), 3.39(d, 2H), 3.67(s, 2H), 4.57(d, 2H), 6.37-6.46(m, 1H), 6.63(d, 1H), 7.33-7.41(m, 3H), 7.44(d, 1H), 7.48-7.55(m, 4 H), 8.04(d, 1H), 8.40(d, 1H), 8.88(t, 1H). |
| 158 | 593 | 2.86(t, 2H), 3.09(t, 2H), 3.42(d, 2H), 3.70(s, 2H), 4.57(d, 2H), 6.52-6.66(m, 2H), 7.44-7.51(m, 3H) 7.54 (s, 1H), 7.59(d, 1H), 7.68(d, 1H), 7.78(d, 1H), 8.07(s, 1H), 8.38-8.41(m, 1H), 8.70(t, 1H). |
| 159 | 593 | 2.85(t, 2H), 3.07(t, 2H), 3.39(d, 2H), 3.68(s, 2H), 4.57(d, 2H), 6.48-6.57(m, 1H), 6.63(d, 1H), 7.35(t, 1H), 7.44-7.60(m, 5 H), 7.76(d, 1H), 8.04(d, 1H), 8.41(d, 1H), 8.88(t, 1H). |
| 160 | 543 | 2.86(t, 2H), 3.09(t, 2H), 3.41(d, 2H), 3.69(s, 2H), 4.56(d, 2H), 6.32-6.43(m, 1H), 6.64(d, 1H), 7.14-7.17(m, 2H) 7.42-7.55 (m, 5 H), 7.66(d, 1H), 8.07(s, 1H), 8.38-8.41(m, 1H), 8.69(t, 1H). |
| 161 | 543 | 2.85(t, 2H), 3.07(t, 2H), 3.38(d, 2H), 3.67(s, 2H), 4.57(d, 2H), 6.30-6.39(m, 1H), 6.63(d, 1H), 7.13-7.18(m, 2H), 7.36(t, 1H), 7.44(d, 1H), 7.49-7.55(m, 4 H), 8.04(d, 1H), 8.40(d, 1H), 8.88(t, 1H). |
| 162 | 593 | 2.87(t, 2H), 3.08(t, 2H), 3.43(d, 2H), 3.69(s, 2H), 4.57(d, 2H), 6.53-6.62(m, 1H), 6.74(d, 1H), 7.36(t, 1H), 7.44(d, 1H), 7.52-7.56(m, 2H), 7.69(s, 4 H), 8.04(d, 1H), 8.40(d, 1H), 8.88(t, 1H). |
| 163 | 561 | 2.86(t, 2H), 3.10(t, 2H), 3.41(d, 2H), 3.70(s, 2H), 4.60(d, 2H), 6.50-6.58(m, 1H), 6.65(d, 1H), 7.19(s, 1H), 7.32-7.42(m, 2H), 7.45(d, 1H), 7.52-7.66(m, 3H), 8.08(s, 1H), 8.23(d, 1H), 8.71(t, 1H). |
| 164 | 534 | 2.87(t, 2H), 3.11(t, 2H), 3.45(d, 2H), 3.71(s, 2H), 4.60(d, 2H), 6.62-6.77(m, 2H), 7.19(s, 1H), 7.37-7.41(m, 1H), 7.45(dd, 1H), 7.64-7.70(m, 3H), 7.77-7.82(m, 2H), 8.08(s, 1H), 8.23(d, 1H), 8.71(t, 1H). |
| 165 | 543 | 2.86(t, 2H), 3.10(t, 2H), 3.40(d, 2H), 3.70(s, 2H), 4.60(d, 2H), 6.40-6.48(m, 1H), 6.65(d, 1H), 7.19(s, 1H), 7.38-7.52(m, 6 H), 7.65(d, 1H), 8.08(s, 1H), 8.23(d, 1H), 8.70(t, 1H). |
| 166 | 577 | 2.86(t, 2H), 3.10(t, 2H), 3.41(d, 2H), 3.70(s, 2H), 4.60(d, 2H), 6.52-6.60(m, 1H), 6.65(d, 1H), 7.19(s, 1H), 7.38(d, 1H), 7.43-7.52(m, 2H), 7.59(d, 1H), 7.64(d, 1H), 7.78(d, 1H), 8.08(s, 1H), 8.23(d, 1H), 8.71(t, 1H). |
| 167 | 543 | 2.83(t, 2H), 3.04(t, 2H), 3.38(d, 2H), 3.63(s, 2H), 4.52(d, 2H), 6.52-6.66(m, 2H), 7.01-7.06(m, 1H), 7.22-7.26(m, 1H), 7.42-7.44(m, 1H), 7.47-7.52(m, 2H), 7.59(d, 1H), 7.75-7.79(m, 2H), 8.38(d, 1H), 8.51(t, 1H). |
| 168 | 500 | 3.35-3.40(m, 3H), 3.80-3.83(m, 1H), 4.12-4.20(m, 2H), 4.33-4.38(m, 1H), 4.55(d, 2H), 4.65(d, 1H), 6.65-6.73(m, 1H), 7.01(d, 1H), 7.15-7.20(m, 1H), 7.42-7.45(m, 2H), 7.53(s, 1H), 7.74(d, 2H), 7.78-7.82(m, 1H), 7.89(d, 2H), 8.39(d, 1H), 8.90(t, 1H), 10.88(bs, 1H). |
| 169 | 509 | 2.83(t, 2H), 3.04(t, 2H), 3.39(d, 2H), 3.62(s, 2H), 4.52(d, 2H), 6.40-6.48(m, 1H), 6.64(d, 1H), 6.99-7.04(m, 1H), 7.22-7.27(m, 1H), 7.37-7.42(m, 3H), 7.49-7.53(m, 3H), 7.75-7.79(m, 1H), 8.38(d, 1H), 8.50(t, 1H). |
| 170 | 492 | 2.9(2H, t), 3.1(2H, bs), 3.45(2H, d), 3.7(2H, s), 4.1(2H, d), 5.8(1h, bt), 6.35(1H, dt), 6.6(1H, d), 6.95(1H, dt), 7.0-7.15(3H, m), 7.25-7.45(6H, m), 7.75(1H, d). |
| 171 | 584 | 3.35-3.43(m, 3H), 3.50-3.53(m, 1H), 3.83(bs, 1H), 4.10-4.17(m, 2H), 4.41-4.45(m, 1H), 4.61(d, 2H), 4.76(d, 1H), 6.47-6.54(m, 1H), 6.92(d, 1H), 7.47-7.50(m, 3H), 7.57-7.60(m, 3H), 8.26(s, 1H), 8.41(d, 1H), 8.55(s, 1H), 9.34(bs, 1H), 11.12(bs, 1H), |
| 172 | 552 | 3.40(bs, 2H), 3.51(bs, 1H), 3.74-3.79(m, 1H), 4.10-4.12(m, 2H), 4.33-4.37(m, 1H), 4.59(d, 2H), 4.66(d, 1H), 6.55-6.63(m, 1H), 6.90(d, 1H), 7.39-7.41(dd, 1H), 7.46-7.47(m, 1H), 7.57(s, 1H), 7.62-7.67(m, 2H), 7.77(d, 1H), 8.33(d, 1H), 8.40(d, 1H), 9.12(t, 1H), 11.15(bs, 1H). |
| 173 | 525 | 3.40-3.48(m, 2H), 3.79(bs, 1H), 4.11-4.16(m, 3H), 4.33-4.38(dd, 1H), 4.59(d, 2H), 4.64(d, 1H), 6.68-6.76(m, 1H), 6.99(d, 1H), 7.47(d, 1H), 7.57(s, 1H), 7.71-7.79(m, 3H), 7.88(d, 2H), 8.32(d, 1H), 8.39(d, 1H), 9.16(t, 1H), 11.59(bs, 1H). |
| 174 | 518 | 3.39(bs, 2H), 3.47-3.49(m, 1H), 3.80(bs, 1H), 4.09-4.11(m, 2H), 4.35-4.37(m, 1H), 4.61-4.68(m, 3H), 6.46-6.53(m, 1H), 6.90(d, 1H), 7.21(s, 1H), 7.41(d, 1H), 7.48(d, 2H), 7.57(d, 2H), 7.78 (d, 1H), 8.23(d, 1H), 8.33(d, 1H), 9.11(bs, 1H), 10.90(bs, 1H) |
| 175 | 518 | 3.40(bs, 2H), 3.46-3.49(m, 1H), 3.79(bs, 1H), 4.06-4.11(m, 2H), 4.33-4.38(dd, 1H), 4.59(d, 2H), 4.65(d, 1H), 6.39-6.46(m, 1H), 6.90(d, 1H), 7.25(t, 2H), 7.47(d, 1H), 7.56-7.61(m, 3H), 7.79(d, 1H), 8.33(d, 1H), 8.40(d, 1H), 9.09-9.10(m, 1H), 10.96(bs, 1H). |
| 176 | 528 | 2.54(s, 3H), 3.34-3.48(m, 3H), 3.78(bs, 1H), 4.05-4.11(m, 2H), 4.33-4.38(m, 1H), 4.58(d, 2H), 4.64(d, 1H), 6.52-6.58(m, 1H), 6.91(d, 1H), 7.45-7.49(m, 3H), 7.58-7.61(m, 3H), 7.63(s, 1H), 8.19(s, 1H), 8.39(d, 1H), 9.02(t, 1H), 11.23(bs, 1H) |
| 177 | 550 | 3.49(bs, 2H), 3.82(bs, 1H), 4.07-4.14(m, 3H), 4.39(bs, 1H), 4.59(d, 2H), 4.70(d, 1H), 6.43-6.51(m, 1H), 6.91(d, 1H), 7.45-7.49(m, 3H), 7.56-7.58(m, 3H), 8.07(s, 1H), 8.35(s, 1H), 8.40(d, 1H), 9.16(bs, 1H), 10.63(bs, 1H). |
| 178 | 534 | 3.50(bs, 3H), 3.80(m, 1H), 4.07-4.15(m, 2H), 4.39(m, 1H), 4.57(d, 2H), 4.68(d, 1H), 6.46-6.54(m, 1H), 6.92(d, 1H), 7.45-7.49(m, 3H), 7.56-7.58(m, 3H), 7.89(d, 1H), 8.26(d, 1H), 8.40(d, 1H), 9.11(bs, 1H), 10.71(bs, 1H). |
| 179 | 589 | 3.38(bs, 2H), 3.49-3.52(bs, 1H), 3.79-3.81(bs, 1H), 4.10-4.13(m, 2H), 4.34-4.36(m, 1H), 4.56(d, 2H), 4.69(d, 1H), 6.56-6.62(m, 1H), 6.90(d, 1H), 7.40-7.46(m, 3H), 7.53(s, 1H), 7.65(q, 2H), 7.75(d, 1H), 7.83(s, 1H), 8.39(d, 1H), 8.93(s, 1H), 10.72(bs, 1H) |

TABLE 3-continued

Example Mass and NMR Data

| Ex# | Mass | 1H-NMR(400 MHz, DMSO-d6) δ ppm |
|---|---|---|
| 180 | 580 | 3.40(bs, 2H), 3.51(bs, 1H), 3.80(bs, 1H), 4.14-4.17(m, 2H), 4.33-4.37(m, 1H), 4.56(d, 2H), 4.69(d, 1H), 6.72-6.80(m, 1H), 6.96(d, 1H), 7.44-7.47(m, 2H), 7.53(s, 1H), 7.57-7.59(d, 1H), 7.74-7.82(m, 3H), 7.98(t, 1H), 8.39(d, 1H), 8.95(bs, 1H), 10.89(bs, 1H), |
| 181 | 573 | 3.48-3.49(m, 2H), 3.78(bs, 1H), 4.10-4.16(m, 2H), 4.31-4.36(m, 1H), 4.55(d, 2H), 4.67(d, 1H), 6.50-6.57(m, 1H), 6.99(d, 1H), 7.19(t, 1H), 7.31(t, 1H), 7.44-7.46(m, 2H), 7.53(s, 1H), 7.74-7.82(m, 2H), 7.85(s, 1H), 8.39(d, 1H), 8.94(bs, 1H), 10.80(bs, 1H), |
| 182 | 587 | 3.30(bs, 1H), 3.37(bs, 1H), 3.45-3.49(m, 1H), 3.79-3.81(m, 1H), 4.06-4.11(m, 2H), 4.32-4.38(m, 1H), 4.56(d, 2H), 4.68(d, 1H), 6.49-6.56(m, 1H), 6.89(d, 1H), 7.44-7.49(m, 3H), 7.53(s, 1H), 7.54-7.58(m, 1H), 7.75(d, 1H), 7.83-7.85(m, 2H), 8.39(d, 1H), 8.94(t, 1H), |
| 183 | 571 | 3.38(bs, 2H), 3.49(bs, 1H), 3.78(bs, 1H), 4.06-4.11(m, 2H), 4.32-4.37(m, 1H), 4.56(d, 2H), 4.68(d, 1H), 6.47-6.54(m, 1H), 6.88(d, 1H), 7.38-7.44(m, 1H), 7.45-7.50(m, 3H), 7.53(s, 1H), 7.68-7.73(m, 1H), 7.75(d, 1H), 7.84(d, 1H), 8.39(d, 1H), 8.94(t, 1H), 10.78(bs, 1H) |
| 184 | 560 | 2.92(t, 2H), 3.11(t, 2H), 3.46(d, 2H), 3.66(s, 2H), 4.64(d, 2H), 5.90(t, 1H), 6.44-6.51(m, 1H), 6.63(d, 1H), 7.22(dd, 1H), 7.31-7.33(m, 1H), 7.34(d, 1H), 7.46-7.50(m, 3H), 7.60(d, 2H), 7.67(d, 1H), 8.37(d, 1H). |
| 185 | 569 | 2.93(t, 2H) 3.12(t, 2H) 3.44(dd, 2H) 3.66(s, 2H) 4.63(d, 2H) 6.20(s, 1H) 6.33(dt, 1H) 6.59(d, 1H) 7.20-7.23(m, 1H) 7.28-7.36(m, 6 H) 7.49(t, 1H) 7.69(d, 1H) 8.36(dd, 1H). |
| 186 | 603 | 2.88(t, 2H) 3.07(t, 2H) 3.40(dd, 2H) 3.60(s, 2H) 4.60(d, 2H) 6.29(dt, 1H) 6.35(t, 1H) 6.52(d, 1H) 7.18(dd, 1H) 7.21(dd, 1H) 7.25-7.31(m, 2H) 7.38(d, 1H) 7.46(t, 2H) 7.64(d, 1H) 8.31(dd, 1H). |
| 187 | 619 | 2.87(t, 2H) 3.06(t, 2H) 3.40(dd, 2H) 3.58(s, 2H) 4.58(d, 2H) 6.30(dt, 2H) 6.59(d, 1H) 7.14-7.17(m, 2H) 7.18(s, 1H) 7.24-7.29(m, 2H) 7.38-7.42(m, 2H) 7.44(d, 1H) 7.62(d, 1H) 8.29(dd, 1H). |
| 188 | 571 | 3.36-3.37(m, 2H), 3.47(m, 1H), 3.78-3.80(m, 1H), 4.07-4.12(m, 2H), 4.32-4.37(m, 1H), 4.59(d, 2H), 4.66(d, 1H), 6.57-6.64(m, 1H), 6.91(d, 1H), 7.18(s, 1H), 7.38-7.46(m, 3H), 7.61-7.68(m, 2H), 7.76(d, 1H), 7.83(d, 1H), 8.22(d, 1H), 8.98(t, 1H), 11.05(s, 1H). |
| 189 | 562 | 3.36(m, 2H), 3.51(bs, 1H), 3.80(bs, 1H), 4.14-4.17(m, 2H), 4.35-4.39(m, 1H), 4.59(d, 2H), 4.69(d, 1H), 6.72-6.80(m, 1H), 6.98(d, 1H), 7.18(s, 1H), 7.39(d, 1H), 7.44-7.47(dd, 1H), 7.59(d, 1H), 7.75-7.82(m, 3H), 7.98(t, 1H), 8.22(d, 1H), 8.96(s, 1H), 10.88(s, 1H). |
| 190 | 571 | 3.36(bs, 2H), 3.49(m, 1H), 3.78-3.81(m, 1H), 4.06-4.11(m, 2H), 4.32-4.37(m, 1H), 4.58-4.68(m, 3H), 6.50-6.57(m, 1H), 6.89(d, 1H), 7.18(s, 1H), 7.39(d, 1H), 7.44-7.49(m, 2H), 7.54-7.58(m, 1H), 7.76(d, 1H), 7.82-7.84(m, 2H), 8.22 (d, 1H), 8.98(t, 1H), 11.0(s, 1H). |
| 191 | 555 | 3.43-3.49(m, 3H), 3.79-3.82(m, 1H), 4.08-4.10(m, 2H), 4.34-4.37(m, 1H), 4.59(d, 2H), 4.68(d, 1H), 6.46-6.53(m, 1H), 6.88(d, 1H), 7.18(s, 1H), 7.39-7.50(m, 4H), 7.69-7.77(m, 2H), 7.84(s, 1H), 8.22(d, 1H), 8.94(s, 1H), 10.63(s, 1H). |
| 192 | 553 | 2.90-2.97(m, 2H) 3.13(br t, 2H) 3.44(dd, 2H) 3.67(s, 2H) 4.69(d, 2H) 6.04(br t, 1H) 6.34(dt, 1H) 6.59(d, 1H) 6.93(dd, 1H) 7.18(dt, 1H) 7.29-7.34(m, 4 H) 7.34-7.36(m, 1H) 7.51(d, 1H) 7.70(d, 1H) 8.21(d, 1H). |
| 193 | 576 | 2.81(t, 2H), 2.98(s, 2H), 3.36(d, 2H), 3.61(s, 2H), 4.61(d, 2H), 6.39-6.47(m, 1H), 6.62(d, 1H), 7.32-7.34(dd, 1H), 7.38(d, 2H), 7.50(d, 2H), 7.62-7.69(m, 3H), 8.67(t, 1H). |
| 194 | 583 | 2.46(s, 3H), 3.32(bs, 2H), 3.44-3.48(m, 1H), 3.76-3.79(m, 1H), 4.05-4.12(m, 2H), 4.31-4.35(m, 1H), 4.56(d, 2H), 4.64(d, 1H), 6.50-6.55(m, 1H), 6.90(d, 1H), 7.44-7.49(m, 3H), 7.54-7.58(m, 3H), 7.79(s, 1H), 7.87(s, 1H), 8.39(d, 1H), 8.92(t, 1H), 10.92(s, 1H). |
| 195 | 599 | 3.31(bs, 2H), 3.39(m, 1H), 3.77-3.80(m, 1H), 3.87(s, 3H), 4.06-4.12(m, 2H), 4.32-4.34(m, 1H), 4.57-4.65(m, 3H), 6.46-6.54(m, 1H), 6.90(d, 1H), 7.44-7.49(m, 4H), 7.57-7.59(m, 3H), 7.86(s, 1H), 8.40(d, 1H), 8.90(t, 1H), 10.68(bs, 1H). |
| 196 | 603 | 3.55(bs, 2H), 3.46-3.47(m, 1H), 3.77(bs, 1H), 4.07-4.12(m, 2H), 4.31-4.34(m, 1H), 4.57(d, 2H), 4.66(d, 1H), 6.47-6.55(m, 1H), 6.90(d, 1H), 7.44-7.49(m, 3H), 7.55-7.58(m, 3H), 8.02(s, 1H), 8.07(s, 1H), 8.39(d, 1H), 9.01(t, 1H), 10.98(s, 1H). |
| 197 | 587 | 3.34(bs, 2H), 3.48(s, 1H), 3.80(m, 1H), 4.06-4.12(m, 2H), 4.31-4.36(m, 1H), 4.56(d, 2H), 4.65(d, 1H), 6.47-6.54(m, 1H), 6.91(d, 1H), 7.44-7.49(m, 3H), 7.56(m, 3H), 7.79(d, 1H), 7.99(d, 1H), 8.39(d, 1H), 8.94(t, 1H), 10.92(s, 1H). |
| 198 | 650 | 3.36(bs, 2H), 3.48(bs, 1H), 3.78-3.81(m, 1H), 4.06-4.12(m, 2H), 4.31-4.34(m, 1H), 4.57(d, 2H), 4.67(d, 1H), 6.48-6.53(m, 1H), 6.90(d, 1H), 7.44-7.49(m, 3H), 7.55-7.58(m, 3H), 8.07(s, 1H), 8.14(s, 1H), 8.39(d, 1H), 9.00(bs, 1H), 10.82(bs, 1H). |
| 199 | 573 | |
| 200 | 573 | 3.30 (bs, 2H), 3.47 (bs, 1H), 3.79 (bs, 1H), 4.12 (bs, 2H), 4.39 (bs, 1H), 4.60 (d, 2H), 4.67 (d, 1H), 6.56-6.64 (m, 1H), 6.90 (d, 1H), 7.19 (s, 1H), 7.38-7.42 (m, 3H), 7.54 (d, 1H), 7.61-7.69 (m, 2H), 7.97 (d, 1H), 8.23 (d, 1H), 8.99 (bs, 1H), 10.86 (bs, 1H), |
| 201 | 563 | 3.31 (bs, 2H), 3.47-3.49 (m, 1H), 3.80-3.83 (m, 1H), 4.17 (bs, 2H), 4.40 (bs, 1H), 4.60 (d, 2H), 4.69 (d, 1H), 6.73-6.81 (m, 1H), 6.97 (d, 1H), 7.19 (s, 1H), 7.38-7.42 (m, 2H), 7.52-7.59 (m, 2H), 7.78 (d, 1H), 7.96-8.00 (m, 2H), 8.23 (d, 1H), 8.98 (bs, 1H), 10.80 (bs, 1H), |
| 202 | 551 | 3.29 (bs, 2H), 3.45 (bs, 1H), 3.78 (bs, 1H), 4.14 (bs, 1H), 4.38 (bs, 2H), 4.59-4.68 (m, 3H), 6.51-6.58 (m, 1H), 6.98 (d, 1H), 7.16-7.19 (m, 2H), 7.31-7.41 (m, 3H), 7.55 (d, 1H), 7.78 (q, 1H), 7.97 (d, 1H), 8.22 (d, 1H), 8.98 (bs, 1H), 10.84 (bs, 1H), |
| 203 | 573 | 3.30-3.33 (m, 2H), 3.43-3.47 (m, 1H), 3.78-3.81 (m, 1H), 4.05-4.13 (m, 2H), 4.35-4.43 (m, 1H), 4.60 (d, 2H), 4.68 (d, 1H), 6.49-6.56 (m, 1H), 6.88 (d, 1H), 7.19 (s, 1H), 7.38-7.58 (m, 5H), 7.84 (d, 1H), 7.97 (d, 1H), 8.23 (d, 1H) 8.98 (t, 5 Hz, 1H), 10.66 (bs, 1H). |
| 204 | 555 | 3.30-3.33 (m, 2H), 3.43-3.47 (m, 1H), 3.78-3.81 (m, 1H), 4.05-4.13 (m, 2H), 4.35-4.40 (m, 1H), 4.60 (d, 2H), 4.68 (d, 1H), 6.48-6.55 (m, 1H), 6.89 (d, 1H), 7.19 (s, 1H), 7.38-7.73 (m, 5 H), 7.68-7.73 (m, 1H), 7.97 (d, 1H), 8.23 (d, 1H), 8.97 (t, 5 Hz, 1H), 10.81 (bs, 1H). |
| 205 | 543 | 3.33-3.37(m, 2H), 3.49(bs, 1H), 3.77-3.80(m, 1H), 4.09-4.12(m, 2H), 4.35-4.40(dd, 1H), 4.57(d, 2H), 4.66(d1H), 6.58-6.66(m, 1H), 6.90(d, 1H), 7.28-7.30(dd, 1H), 7.40-7.42(dd, 1H), 7.44-7.46(dd, 1H), 7.55(s, 1H), 7.59(d, 1H), 7.61-7.68(m, 2H), 7.83(d, 1H), 8.39(d, 1H), 8.99(t, 1H), 11.10(bs, 1H) |

TABLE 3-continued

Example Mass and NMR Data

| Ex# | Mass | 1H-NMR(400 MHz, DMSO-d6) δ ppm |
|---|---|---|
| 206 | 560 | 2.84(t, 2H), 3.04(bs, 2H), 3.48(d2H), 3.66(s, 2H), 4.54(d, 2H), 6.84(d, 1H), 6.99-7.06(m, 1H), 7.16-7.18(dd, 1H), 7.42-7.46(m, 2H), 7.52(s, 1H), 7.72(d, 1H), 7.79(d, 1H), 8.15-8.17(dd, 1H), 8.39(d, 1H), 8.58(t, 1H), 8.89(s, 1H) |
| 207 | 560 | 2.89(t, 2H), 3.09(t, 2H), 3.52(d, 2H), 4.07(s, 2H), 4.64(d, 2H), 6.03(t, 1H), 6.78(d, 1H), 6.94-7.01(m, 1H), 7.10-7.15(m, 2H), 7.20-7.22(dd, 1H), 7.31(s, 1H), 7.41(d, 1H), 7.68(dd, 1H), 7.85(dd1H), 8.37(d, 1H), 8.80(s, 1H) |
| 208 | 534 | 3.32-3.41(m, 3H), 3.79-3.82(m, 1H), 4.15-4.17(m, 2H), 4.36-4.41(dd, 1H), 4.57(d, 2H), 4.68(d, 1H), 6.75-6.82(m, 1H), 6.98(d, 1H), 7.28-7.30(dd, 1H), 7.44-7.45(dd, 1H), 7.54-7.60(m, 3H), 7.78(d, 1H), 7.83(d, 1H), 7.98(t, 1H), 8.40(d, 1H), 8.97(t, 1H), 11.04(bs, 1H). |
| 209 | 527 | 3.32(m, 2H), 3.47-3.48(m, 1H), 3.78-3.81(m, 1H), 4.14-4.15(m, 2H), 4.34-4.39(m, 1H), 4.57(d, 2H), 4.66(d, 1H), 6.51-6.58(m, 1H), 6.99(d, 1H), 7.15-7.20(m, 1H), 7.30-7.36(m, 2H), 7.45(d, 1H), 7.54(s, 1H), 7.60(d, 1H), 7.75-7.81(m, 1H), 7.83(d, 1H), 8.40(d, 1H), 8.96(t, 1H), 10.86(s, 1H). |
| 210 | 543 | 3.32-3.36(m, 2H), 3.41-3.48(m, 1H), 3.78-3.81(m, 1H), 4.08-4.11(m, 2H), 4.35-4.40(dd, 1H), 4.57(d, 2H), 4.67(d, 1H), 6.50-6.58(m, 1H), 6.89(d, 1H), 7.28-7.30(dd, 1H), 7.44-7.49(m, 2H), 7.54-7.61(m, 3H), 7.83-7.85(m, 2H), 8.40(d, 1H), 8.97(t, 1H), 10.93(bs, 1H). |
| 211 | 527 | 3.33-3.36(m, 2H), 3.42-3.48(m, 1H), 3.77-3.80(m, 1H), 4.07-4.10(m, 2H), 4.34-4.39(dd, 1H), 4.57(d, 2H), 4.65(d, 1H), 6.50-6.57(m, 1H), 6.89(d, 1H), 7.28-7.30(dd, 1H), 7.37-7.40(m, 1H), 7.44-7.52(m, 2H), 7.55(s, 1H), 7.60(d, 1H), 7.67-7.72(m, 1H), 8.39(d, 1H), 9.00(t, 1H), 11.10(bs, 1H). |
| 212 | 516 | 2.92(t, 2H), 3.10(t, 2H), 3.46(d, 2H), 3.68(s, 2H), 4.65(d, 2H), 5.91(t, 1H), 6.44-6.51(m, 1H), 6.64(d, 1H), 7.16-7.18(dd, 1H), 7.21-7.22(dd, 1H), 7.24-7.32(m, 2H), 7.46(d, 2H), 7.60(d, 2H), 7.84(d, 1H), 8.37(d, 1H). |
| 213 | 525 | 2.82-2.83(m, 2H), 3.02(bs, 2H), 3.38(d, 2H), 3.63(s, 2H), 4.53(d, 2H), 6.40-6.47(m, 1H), 6.63(d, 1H), 7.15-7.17(dd, 1H), 7.37-7.45(m, 4H), 7.50(d, 3H), 7.79(s, 1H), 8.38(d, 1H), 8.57(t, 1H). |
| 214 | 525 | 2.86(t, 2H), 3.07(t, 2H), 3.43(d, 2H), 4.04(s, 2H), 4.63(t, 2H), 5.98(t, 1H), 6.29-6.36(m, 1H), 6.57(d, 1H), 7.13-7.14(m, 2H), 7.20(d, 1H), 7.27-7.33(m, 5H), 7.66-7.68(dd1H), 8.37(d, 1H) |
| 215 | 559 | 2.82-2.83(m, 2H), 3.02(s, 2H), 3.39(d, 2H), 3.64(s, 2H), 4.53(d, 2H), 6.51-6.65(m, 2H), 7.16-7.18(dd, 1H), 7.42-7.51(m, 4H), 7.58(d, 1H), 7.77-7.79(dd, 2H), 8.39(d, 1H), 8.58(t, 1H). |
| 216 | 559 | 2.86(t, 2H), 3.08(t, 2H), 3.43(d, 2H), 4.04(s, 2H), 4.64(d, 2H), 5.96(t, 1H), 6.31-6.38(m, 1H), 6.52(d, 1H), 7.10-7.15(m, 2H), 7.20-7.24(m, 2H), 7.31(s, 1H), 7.37(d, 1H), 7.46(d, 1H), 7.66-7.68(m, 2H), 8.37(d, 1H). |
| 217 | 509 | 2.82(t, 2H), 3.02(bs, 2H), 3.37(d, 2H), 3.63(s, 2H), 4.53(d, 2H), 6.32-6.40(m, 1H), 6.63(d, 1H), 7.14-7.18(m, 3H), 7.42-7.45(m, 2H), 7.50-7.54(m, 3H), 7.79(d, 1H), 8.39(d, 1H), 8.58(t, 1H). |
| 218 | 509 | 2.86(t, 2H), 3.07(t, 2H), 3.42(d, 2H), 4.04(s, 2H), 4.63(d, 2H), 5.98(t, 2H), 6.22-6.30(m, 1H), 6.58(d, 1H), 7.00(t, 2H), 7.09-7.15(m, 2H), 7.20(d, 1H), 7.31(s, 1H), 7.34-7.37(m, 2H), 7.66-7.69(dd, 1H), 8.37(d, 1H). |
| 219 | 521 | 2.81(t, 2H), 3.01(bs, 2H), 3.35(d, 2H), 3.62(s, 2H), 3.74(s, 3H), 4.53(d, 2H), 6.20-6.27(m, 1H), 6.56(d, 1H), 6.89(d, 2H), 7.15-7.18(dd, 1H), 7.39-7.45(m, 4H), 7.51(s, 1H), 7.78(d, 1H), 8.39(d, 1H), 8.57(t, 1H) |
| 220 | 521 | 2.86(t, 2H), 3.06(d, 2H), 3.41(d, 2H), 3.80(s, 3H), 4.03(s, 2H), 4.63(d, 2H), 6.01(t, 1H), 6.17-6.24(m, 1H), 6.55(d, 1H), 7.09-7.14(m, 2H), 7.20(d, 1H), 7.31(s, 1H), 7.33(d, 2H), 7.67-7.70(dd, 1H), 8.37(d, 1H) |
| 221 | 575 | 2.82(t, 2H), 3.02(s, 2H), 3.39(d, 2H), 3.63(s, 2H), 4.53(d2H), 6.43-6.49(m, 1H), 6.67(d, 1H), 7.16-7.18(dd, 1H), 7.32(d, 2H), 7.41-7.45(m, 2H), 7.51(s, 1H), 7.60(d, 2H), 7.78(d, 1H), 8.39(d, 1H), 8.58(t, 1H). |
| 222 | 575 | 2.87(t, 2H), 3.08(t, 2H), 3.44(d2H), 4.05(s, 2H), 4.63(d, 1H), 5.96(t, 1H), 6.29-6.37(m, 1H), 6.60(d, 1H), 7.10-7.13(m, 2H), 7.16(d, 2H), 7.21(d, 1H), 7.31(s, 1H), 7.40(d, 2H), 7.66-7.68(dd, 1H), 8.37(d, 1H). |
| 223 | 559 | 2.83(t, 2H), 3.03(bs, 2H), 3.42(d, 2H), 3.65(s, 2H), 4.53(d, 2H), 6.56-6.63(m, 1H), 6.74(d, 1H), 7.16-7.18(dd, 1H), 7.42-7.45(m, 2H), 7.52(s, 1H), 7.66-7.71(m, 4H), 7.79(d, 1H), 8, 39(d, 1H), 8, 58(t, 1H). |
| 224 | 527 | 3.47(bs, 1H), 3.79(bs, 1H), 4.12(bs, 2H), 4.39(bs, 1H), 4.61(d, 2H), 4.68(d, 1H), 6.56-6.64(m, 1H), 6.90(d1H), 7.19(s, 1H), 7.29(d, 1H), 7.38-7.42(m, 2H), 7.58-7.69(m, 3H), 7.84(d, 1H), 8.23(d, 1H), 8.97(bs 1H), 10.79(bs, 1H). |
| 225 | 581 | 3.35(bs, 2H), 3.49(bs, 1H), 3.80(bs, 1H), 4.16(bs, 2H), 4.38-4.40(m, 1H), 4.61(d, 2H), 4.69(d, 1H), 6.74-6.82(m, 1H), 6.98(d, 1H), 7.19(s, 1H), 7.29(d, 1H), 7.58(d, 2H), 7.78(d, 1H), 7.84(d, 1H), 8.98(t, 1H), 8.23(d, 1H), 8.98(bs, 1H), 10.95(bs, 1H). |
| 226 | 511 | 3.44-3.47(m, 1H), 3.78(bs, 1H), 4.14(bs, 2H), 4.36-4.38(m, 1H), 4.59-4.68(m, 3H), 6.51-6.58(m, 1H), 6.98(d, 1H), 7.16-7.19(m, 2H), 7.27-7.39(m, 3H), 7.60(d, 1H), 7.75-7.84(m, 2H), 8.23(d, 1H), 8.97(bs, 1H), 10.85(bs, 1H). |
| 227 | 527 | 3.47(bs, 1H), 3.79(bs, 1H), 4.10(bs, 2H), 4.39(bs, 1H), 4.61(d, 2H), 4.67(d, 1H), 6.50-6.57(m, 1H), 6.88(d, 1H), 7.19(s, 1H), 7.29(d, 1H), 7.39(d, 1H), 7.46(t, 1H), 7.54-7.60(m, 2H), 7.84(bs, 2H), 8.23(d, 1H), 8.97(bs, 1H), 10.82(bs, 1H). |
| 228 | 511 | 3.30-3.34(m, 3H), 3.76-3.79(m, 1H), 4.09-4.10(m, 2H), 4.34-4.40(dd, 1H), 4.59-4.67(m, 3H), 6.50-6.58(m, 1H), 6.89(d, 1H), 7.19(s, 1H), 7.27-7.30(dd, 1H), 7.37-7.39(m, 2H), 7.45-7.52(q, 1H), 7.59(d, 1H), 7.67-7.72(m, 1H), 7.84(d, 1H), 8.23(d, 1H), 9.00(t, 1H), 11.16(bs, 1H). |
| 229 | 509 | 2.91(t, 2H), 3.08-3.09(m, 2H), 3.42(d, 2H), 3.67(s, 2H), 4.69(d, 2H), 5.91(t, 1H), 6.28-6.35(m, 1H), 6.57(d, 1H), 6.91(d, 1H), 7.15-7.18(m, 2H), 7.27-7.29(m, 3H), 7.31-7.33(m, 2H), 7.86(d, 1H), 8.21(d, 1H). |
| 230 | 509 | 2.87(t, 2H), 3.08(t, 2H), 3.43(d, 2H), 4.05(s, 2H), 4.68(d, 2H), 5.97(t, 1H), 6.30-6.36(m, 1H), 6.57(d, 3H), 6.91(s, 1H), 7.10-7.15(m, 2H), 7.17(d, 1H), 7.26-7.33(m, 4H), 7.67-7.69(dd, 1H), 8.21(d, 1H). |

TABLE 3-continued

Example Mass and NMR Data

| Ex# | Mass | 1H-NMR(400 MHz, DMSO-d6) δ ppm |
|---|---|---|
| 231 | 531 | 2.79(t, 2H), 2.96(t, 2H), 3.39(d, 2H), 3.91(s, 2H), 4.62(d, 2H), 6.39-6.47(m, 1H), 6.63(d, 1H), 7.13-7.19(m, 2H), 7.38(d, 2H), 7.50(d, 2H), 7.66-7.68(m, 2H), 8.81(t, 1H). |
| 232 | 543 | 11.69(br s, 1H), 9.06(m, 1H), 8.39(d, 1H), 7.81(d, 1H), 7.70(d, 1H), 7.60-7.68(m, 2H), 7.54(s, 1H), 7.36-7.48(m, 2H), 7.33(m, 1H), 6.93(d, 1H), 6.61-6.71(m, 1H), 4.63(br d, 1H), 4.53-4.59(m, 2H), 4.26-4.42(m, 1H), 4.00-4.20(m, 2H), 3.69-3.82(m, 1H), 3.44-3.55(m, 1H), 3.34-3.44(m, 2H). |
| 233 | 543 | 11.78(br s, 1H), 9.06(m, 1H), 8.39(d, 1H), 7.69-7.85(m, 3H), 7.44-7.56(m, 3H), 7.37(br m, 1H), 7.32(d, 1H), 7.01(d, 1H), 6.62-6.76(m, 1H), 4.62(br d, 1H), 4.56(d, 2H), 4.33(br m, 1H), 4.06-4.24(m, 2H), 3.66-3.85(m, 1H), 3.32-3.53(m, 3H). |
| 234 | 534 | 11.63(br s, 1H), 9.04(m, 1H), 8.39(d, 1H), 8.16(m, 1H), 7.90-8.01(m, 1H), 7.81(d, 1H), 7.69(d, 1H), 7.52-7.63(m, 2H), 7.46(m, 1H), 7.29-7.38(m, 1H), 6.95(d, 1H), 6.59-6.71(m, 1H), 4.64(br d, 1H), 4.52-4.60(m, 2H), 4.20-4.45(m, 1H), 4.01-4.20(m, 2H), 3.71-3.83(m, 1H), 3.34-3.54(m, 3H). |
| 235 | 534 | 11.82(br s, 1H), 9.07(m, 1H), 8.39(d, 1H), 7.97(m, 1H), 7.68-7.83(m, 3H), 7.51-7.61(m, 1H), 7.51-7.61(m, 1H), 7.46(d, 1H), 7.33(d, 1H), 6.97-7.05(m, 1H), 6.77-6.91(m, 1H), 4.65(br d, 1H), 4.52-4.60(m, 2H), 4.30-4.43(m, 1H), 4.04-4.24(m, 2H), 3.71-3.84(m, 1H), 3.33-3.55(m, 3H) |
| 236 | 593 | 3.37-3.52(m, 3H), 3.76-3.79(m, 1H), 4.08-4.14(m, 2H), 4.32-4.38(dd, 1H), 4.55(d, 2H), 4.65(d, 1H), 6.67-6.75(m, 1H), 6.95(d, 1H), 7.31-4.34(dd, 1H), 7.38(d1H), 7.44-7.46(m, 2H), 7.52-7.55(m, 2H), 7.70(d, 1H), 7.80(d, 1H), 8.39(d, 1H), 9.01(t, 1H), 11.48(bs, 1H). |
| 237 | 543 | 11.72(br s, 1H), 9.04(m, 1H), 8.39(d, 1H), 7.86(m, 1H), 7.81(d, 1H), 7.70(d, 1H), 7.48-7.58(m, 2H), 7.46(m, 1H), 7.26-7.40(m, 2H), 7.15(d, 1H), 6.53-6.65(m, 1H), 4.64(br d, 1H), 4.51-4.59(m, 2H), 4.35(br m, 1H), 4.07-4.14(m, 2H), 3.69-3.84(m, 1H), 3.33-3.54(m, 3H). |
| 238 | 527 | 11.72(br s, 1H), 9.05(m, 1H), 8.39(d, 1H), 7.68-7.84(m, 3H), 7.54(s, 1H), 7.46(m, 1H), 7.26-7.39(m, 2H), 7.18(m, 1H), 7.00(d, 1H), 6.55-6.65(m, 3H), 4.50-4.65(m, 3H), 4.26-4.50(m, 1H), 4.02-4.23(m, 2H), 3.66-3.85(m, 1H), 3.32-3.52(m, 3H). |
| 239 | 543 | 11.69(br s, 1H), 9.06(m, 1H), 8.39(d, 1H), 7.79-7.85(m, 2H), 7.70(d, 1H), 7.51-7.60(m, 2H), 7.44-7.51(m, 2H), 7.33(d, 1H), 6.92(d, 1H), 6.54-6.64(m, 1H), 4.63(br d, 1H), 4.56(d, 2H), 4.33(br d, 1H), 3.96-4.22(m, 2H), 3.67-3.84(m, 1H), 3.33-3.54(m, 3H). |
| 240 | 527 | 11.69(br s, 1H), 9.07(m, 1H), 8.39(d, 1H), 7.80(d, 1H), 7.64-7.73(m, 2H), 7.44-7.59(m, 3H), 7.25-7.44(m, 2H), 6.93(s, 1H), 6.52-6.67(m, 1H), 4.63(br d, 1H), 4.56(d, 2H), 4.26-4.51(m, 1H), 4.00-4.18(m, 2H), 3.66-3.84(m, 1H), 3.33-3.53(m, 3H). |
| 241 | 516 | 2.91(t, 2H) 3.09(t, 2H) 3.45(dd, 2H) 3.64(s, 2H) 4.60(d, 2H) 6.31(t, 1H) 6.47(dt, 1H) 6.64(d, 1H) 7.15(dd, 1H) 7.18(dd, 1H) 7.30(dd, 2H) 7.46(d, 2H) 7.58(d, 2H) 7.69(d, 1H) 8.31(d, 1H). |
| 242 | 525 | 2.97(t, 2H) 3.15(br t, 2H) 3.47(dd, 2H) 3.70(s, 2H) 4.65(d, 2H) 6.07(br t, 1H) 6.34(dt, 1H) 6.60(d, 1H) 7.18-7.24(m, 2H) 7.29-7.37(m, 6 H) 7.74(dd, 1H) 8.38(dd, 1H). |
| 243 | 559 | 2.83(br t, 2H) 3.03(br t, 2H) 3.38(br d, 2H) 3.64(s, 2H) 4.53(d, 2H) 6.54(dt, 1H) 6.62(d, 1H) 7.21(dd, 1H) 7.42(dd, 1H) 7.47-7.50(m, 1H) 7.50(d, 2H) 7.58(d, 1H) 7.76(d, 1H) 7.77(s, 1H) 8.39(d, 1H) 8.55(t, 1H). |
| 244 | 509 | 2.83(br t, 2H) 3.03(br s, 2H) 3.37(br d, 2H) 3.63(s, 2H) 4.53(d, 2H) 6.36(dt, 1H) 6.63(d, 1H) 7.16(t, 2H) 7.21(dd, 1H) 7.42(dd, 1H) 7.51(d, 2H) 7.52-7.56(m, 2H) 7.76(d, 1H) 8.38(dd, 1H) 8.55(t, 1H). |
| 245 | 575 | 2.92(t, 2H) 3.11(t, 2H) 3.44(dd, 2H) 3.65(s, 2H) 4.63(d, 2H) 6.13(br t, 1H) 6.33(dt, 1H) 6.62(d, 1H) 7.16-7.22(m, 4 H) 7.31(dd, 1H) 7.33(d, 1H) 7.40-7.44(m, 2H) 7.72(dd, 1H) 8.35(dd, 1H). |
| 246 | 559 | 2.95(t, 2H) 3.14(br t, 2H) 3.48(dd, 2H) 3.69(s, 2H) 4.66(d, 2H) 5.99(br t, 1H) 6.47(dt, 1H) 6.68(d, 1H) 7.19-7.24(m, 2H) 7.33(dd, 1H) 7.36(d, 1H) 7.51(d, 2H) 7.59(d, 2H) 7.74(d, 1H) 8.38(dd, 1H). |
| 247 | 550 | 11.59(br s, 1H), 9.12(m, 1H), 8.52(d, 1H), 8.39(d, 1H), 8.24(d, 1H), 8.12(d, 1H), 7.94(d, 1H), 7.87(m, 1H), 7.81(d, 1H), 7.66(d, 1H), 7.55(s, 1H), 7.47(m, 1H), 7.31(m, 1H), 4.91(s, 2H), 4.61(br s, 2H), 4.56(d, 2H), 3.78(br s, 2H), 3.37-3.54(m, 2H). |
| 248 | 492 | 12.26(br s, 1H), 9.14(br m, 1H), 8.92(d, 2H), 8.39(d, 1H), 8.15(d, 2H), 7.81(d, 1H), 7.68(d, 1H), 7.55(s, 1H), 7.43-7.50(m, 1H), 7.15-7.38(m, 3H), 4.66(br s, 1H), 4.49-4.61(m, 2H), 4.41(br s, 1H), 4.19-4.33(m, 2H), 3.78(br s, 1H), 3.56(br s, 1H), 3.45(br s, 2H). |
| 249 | 543 | 3.31(bs, 2H), 3.50(bs, 1H), 3.79(bs, 1H), 4.10-4.14(m, 2H), 4.33-4.37(m, 1H), 4.55(d, 2H), 4.68(d, 1H), 6.61-6.69(m, 1H), 6.89(d, 1H), 7.35(dd, 1H), 7.42-7.47(m, 3H), 7.53(s, 2H), 7.70(s, 1H), 7.80(d, 1H), 8.39(d, 1H), 8.95(bs, 1H), 10.92(brs, 1H). |
| 250 | 534 | 3.36(bs, 2H), 3.50-3.52(m, 1H), 3.79-3.82(m, 1H), 4.08-4.15(m, 2H), 4.33-4.38(m, 1H), 4.55(d, 2H), 4.69(d, 1H), 6.70-6.77(m, 1H), 6.93(d, 1H), 7.34(dd, 1H), 7.45(d, 1H), 7.54(s, 1H), 7.69(d, 1H), 7.79-7.85(m, 3H), 7.95(s, 1H), 8.39(d, 1H), 8.98(t, 1H), 11.19(bs, 1H) |
| 251 | 550 | 3.37-3.52(m, 3H), 3.77-3.80(m, 1H), 4.07-4.15(m, 2H), 4.32-4.38(dd, 1H), 4.55(d, 2H), 4.66(d, 1H), 6.72-6.79(m, 1H), 6.93(d, 1H), 7.32-4.34(dd, 1H), 7.44-7.46(dd, 1H), 7.54(s, 1H), 7.69(d, 1H), 7.80 (d, 1H), 8.01-8.05(m, 3H), 8.39(d, 1H), 9.01(t, 1H), 11.52(bs, 1H). |
| 252 | 589 | 3.35(bs, 2H), 3.50(bs, 1H), 3.78-3.81(m, 1H), 4.06-4.12(m, 2H), 4.32-4.38(m, 1H), 4.55(d, 2H), 4.66(d, 1H), 6.61-6.69(m, 1H), 6.89(d, 1H), 7.33(dd, 1H), 7.44-7.49(m, 2H), 7.53-7.55(m, 2H), 7.65(s, 1H), 7.69(d, 1H), 7.80(d, 1H), 8.39(d, 1H), 8.97(t, 1H), 11.13(bs, 1H), |
| 253 | 559 | 3.35(bs, 2H), 3.50(bs, 1H), 3.78-3.81(m, 1H), 4.07-4.12(m, 2H), 4.33-4.38(m, 1H), 4.55(d, 2H), 4.67(d, 1H), 6.63-6.71(m, 1H), 6.88(d, 1H), 7.33(d, 1H), 7.45(d, 1H), 7.53(s, 1H), 7.59(bs, 1H), 7.65(d, 2H), 7.69(d, 1H), 7.80(d, 1H), 8.40(d, 1H), 8.97(bs, 1H), 11.09(bs, 1H) |
| 254 | 527 | 11.54(br s, 1H), 9.04(m, 1H), 8.23(d, 1H), 7.81(d, 1H), 7.70(d, 1H), 7.57-7.68(m, 2H), 7.37-7.46(m, 2H), 7.33(m, 1H), 7.19(s, 1H), 6.92(d, 1H), 6.59-6.72(m, 1H), 4.53-4.69(m, 3H), 4.35(br d, 1H), 4.11(br s, 2H), 3.76(br s, 1H), 3.47(br d, 3H). |

TABLE 3-continued

Example Mass and NMR Data

| Ex# | Mass | 1H-NMR(400 MHz, DMSO-d6) δ ppm |
|---|---|---|
| 255 | 527 | 11.66(br s, 1H), 9.05(m, 1H), 8.22(d, 1H), 7.81(d, 1H), 7.67-7.78(m, 2H), 7.51(m, 1H), 7.30-7.45(m, 3H), 7.19(s, 1H), 7.01(d, 1H), 6.61-6.74(m, 1H), 4.54-4.68(m, 3H), 4.24-4.49(m, 1H), 3.99-4.24(m, 2H), 3.75(br s, 1H), 3.33-3.53(m, 3H). |
| 256 | 527 | 11.63(br s, 1H), 9.04(m, 1H), 8.23(d, 1H), 7.87(m, 1H), 7.78-7.84(m, 1H), 7.67-7.73(m, 1H), 7.52(m, 1H), 7.40(br d, 1H), 7.29-7.37(m, 2H), 7.11-7.22(m, 2H), 6.51-6.66(m, 1H), 4.54-4.68(m, 3H), 4.35(br m, 1H), 4.10-4.29(m, 2H), 3.73-3.82(m, 1H), 3.36-3.53(m, 3H). |
| 257 | 511 | 11.69(br s, 1H), 9.06(m, 1H), 8.22(d, 1H), 7.69-7.84(m, 3H), 7.40(br d, 1H), 7.26-7.37(m, 2H), 7.13-7.25(m, 2H), 7.00(d, 1H), 6.56-6.66(m, 1H), 4.55-4.67(m, 3H), 4.33(br m, 1H), 4.04-4.20(m, 2H), 3.75(br s, 1H), 3.33-3.52(m, 3H). |
| 258 | 527 | 11.63(br s, 1H), 9.06(m, 1H), 8.23(d, 1H), 7.81(d, 2H), 7.70(d, 1H), 7.55(m, 1H), 7.43-7.50(m, 1H), 7.37-7.42(m, 1H), 7.33(d, 1H), 7.19(s, 1H), 6.91(d, 1H), 6.53-6.64(m, 1H), 4.55-4.68(m, 3H), 4.35(br m, 1H), 4.02-4.10(m, 2H), 3.72-3.82(m, 1H), 3.34-3.54(m, 3H). |
| 259 | 511 | 11.50(br s, 1H), 9.04(m, 1H), 8.23(d, 1H), 7.81(d, 1H), 7.62-7.75(m, 2H), 7.48(m, 1H), 7.36-7.42(m, 2H), 7.33(m, 1H), 7.19(s, 1H), 6.91(d, 1H), 6.49-6.63(m, 1H), 4.56-4.67(m, 3H), 4.35(br m, 1H), 3.98-4.17(m, 2H), 3.76(br s, 1H), 3.33-3.46(m, 3H). |
| 260 | 509 | 2.83(t, 2H), 3.04(t, 2H), 3.38(d, 2H), 3.64(s, 2H), 4.56(d, 2H), 6.39-6.47(m, 1H), 6.64(d, 1H), 7.16(s, 1H), 7.22(d, 1H), 7.36-7.41(m, 3H), 7.48-7.53(m, 3H), 7.77(d, 1H), 8.22(d, 1H), 8.57(t, 1H). |
| 261 | 543 | 2.83(t, 2H), 3.04(t, 2H), 3.38(d, 2H), 3.64(s, 2H), 4.56(d, 2H), 6.50-6.65(m, 2H), 7.16(s, 1H), 7.22(d, 1H), 7.36-7.39(m, 1H), 7.47-7.53(m, 3H), 7.59(d, 1H), 7.75-7.79(m, 2H), 8.22(d, 1H), 8.57(t, 1H). |
| 262 | 527 | 3.35-3.50(m, 3H), 3.79(bs, 1H), 4.09-4.13(m, 2H), 4.34-4.38(m, 1H), 4.59(d, 2H), 4.67(d, 1H), 6.62-6.69(m, 1H), 6.89(d, 1H), 7.19(s, 1H), 7.32-7.35(dd, 1H), 7.38-7.46(m, 3H), 7.53(s, 1H), 7.70(d, 1H), 7.81(d, 1H), 8.23(d, 1H), 8.98(t, 1H), 11.05(bs, 1H). |
| 263 | 518 | 3.41-3.50(m, 3H), 3.79(bs, 1H), 4.11-4.15(m, 2H), 4.33-4.37(m, 1H), 4.59(d, 2H), 4.67(d, 1H), 6.70-6.77(m, 1H), 6.93(d, 1H), 7.19(s, 1H), 7.32-7.35(dd, 1H), 7.39(d, 1H), 7.69(d, 1H), 7.80-7.85(m, 3H), 7.95(s, 1H), 8.23(d, 1H), 9.00(t, 1H), 11.19(bs, 1H). |
| 264 | 571 | 3.40-3.50(m, 3H), 3.78-3.81(m, 1H), 4.09-4.11(m, 2H), 4.33-4.36(m, 1H), 4.59(d, 2H), 4.67(d, 1H), 6.61-6.69(m, 1H), 6.88(d, 1H), 7.19(s, 1H), 7.32-7.35(dd, 1H), 7.39(d, 1H), 7.48(d, 1H), 7.54(d, 1H), 7.65(s, 1H), 7.70(d, 1H), 7.81(d, 1H), 8.23(d, 1H), 8.98(t, 1H), 11.08(bs, 1H). |
| 265 | 543 | 3.32-3.40(m, 2H), 3.45-3.50(m, 1H), 3.78-3.80(m, 1H), 4.07-4.12(m, 2H), 4.32-4.38(dd, 1H), 4.59(d, 2H), 4.66(d, 1H), 6.66-6.72(m, 1H), 6.88(d, 1H), 7.19(s, 1H), 7.32-7.35(dd, 1H), 7.39(d, 1H), 7.59-7.60(m, 1H), 7.65(d, 2H), 7.70(d, 1H), 7.81(d, 1H), 8.23(d, 1H), 9.00(t, 1H), 11.26(bs, 1H). |
| 266 | 560 | |
| 267 | 525 | |
| 268 | 559 | |
| 269 | 509 | |
| 270 | 521 | |
| 271 | 575 | |
| 272 | 559 | |
| 273 | 531 | |
| 274 | 577 | 3.35-3.48(m, 3H), 3.78(bs, 1H), 4.09-4.13(m, 2H), 4.33-4.40(m, 1H), 4.57(d, 2H), 4.66(d, 1H), 6.55-6.62(m, 1H), 6.90(d, 1H), 7.39-7.46(m, 2H), 7.55(s, 1H), 7.61-7.68(m, 2H), 7.93(s, 1H), 8.02(s, 1H), 8.40(d, 1H), 9.01(bs, 1H), 11.00(bs, 1H). |
| 275 | 570 | 3.46-3.52(m, 3H), 3.80-3.83(m, 1H), 4.10-4.18(m, 2H), 4.37-4.40(m, 1H), 4.57(d, 2H), 4.69(d, 1H), 6.70-6.78(m, 1H), 6.97(d, 1H), 7.46(d, 1H), 7.55(s, 1H), 7.58(d, 1H), 7.78(d, 1H), 7.92(s, 1H), 7.98(t, 1H), 8.02(s, 1H), 8.40(d, 1H), 8.99(bs, 1H), 10.79(bs, 1H). |
| 276 | 562 | 3.35-3.36(m, 1H), 3.38-3.49(m, 2H), 3.76-3.80(m, 1H), 4.08-4.15(m, 2H), 4.31-4.35(m, 1H), 4.57(d, 2H), 4.65(d, 1H), 6.49-6.57(m, 1H), 6.98(d, 1H), 7.16-7.21(m, 1H), 7.31-7.36(m, 1H), 7.45(d, 1H), 7.55(s, 1H), 7.75-7.81(m, 1H), 7.95(s, 1H), 8.02(s, 1H), 8.39(d, 1H), 9.00(bs, 1H), 10.94(bs, 1H). |
| 277 | 577 | 3.38-3.49(m, 3H), 3.79-3.83(m, 1H), 4.06-4.12(m, 2H), 4.35-4.39(m, 1H), 4.57(d, 2H), 4.69(d, 1H), 6.46-6.53(m, 1H), 6.88(d, 1H), 7.44-7.49(m, 2H), 7.55-7.58(m, 2H), 7.84(d, 1H), 7.94(s, 1H), 8.02(s, 1H), 8.40(d, 1H), 8.98(bs, 1H), 10.64(bs, 1H) |
| 278 | 561 | 3.36-3.38(m, 2H), 3.41-3.50(m, 1H), 3.78(bs, 1H), 4.05-4.11(m, 2H), 4.31-4.35(m, 1H), 4.57(d, 2H), 4.66(d, 1H), 6.46-6.54(m, 1H), 6.88(d, 1H), 7.37-7.39(m, 1H), 7.44-7.52(m, 2H), 7.55(s, 1H), 7.67-7.72(m, 1H), 7.94(s, 1H), 8.02(s, 1H), 8.40(d, 1H), 9.01(t, 1H), 10.98(bs, 1H). |
| 279 | 550 | 2.92(t, 2H), 3.07-3.08(m, 2H), 3.46(d, 2H), 3.64(s, 2H), 4.63(d2H), 5.89(t, 1H), 6.44-6.50(m, 1H), 6.64(d, 1H), 7.20-7.22(m, 1H), 7.31(s, 1H), 7.42(s, 1H), 7.47(d, 2H), 7.60(d, 2H), 8.00(s, 1H), 8.38(d, 1H). |
| 280 | 559 | 2.82(t, 2H), 3.03(bs, 2H), 3.37(d, 2H), 3.63(s, 2H), 4.53(d, 2H), 6.39-6.46(m, 1H), 6.63(d, 1H), 7.38(d, 2H), 7.43(d, 1H), 7.49-7.52(m, 3H), 7.75(s, 1H), 7.96(s, 1H), 8.38(d, 1H), 8.61(t, 1H). |
| 281 | 593 | 2.82(t, 2H), 3.03(bs, 2H), 3.37(d, 2H), 3.63(s, 2H), 4.53(d, 2H), 6.51-6.64(m, 2H), 7.43(d, 1H), 7.47-7.52(m, 2H), 7.58(d, 1H), 7.75-7.78(m, 2H), 7.96(s, 1H), 8.38(d, 1H), 8.62(t, 1H). |
| 282 | 543 | 2.82-2.83(m, 2H), 3.03(bs, 2H), 3.36(d, 2H), 3.63(s, 2H), 4.53(d, 2H), 6.31-6.38(m, 1H), 6.62(d, 1H), 7.16(t, 2H), 7.43(d, 1H), 7.50-7.54(m, 3H), 7.75(s, 1H), 7.96(s, 1H), 8.38(d, 1H), 8.61(t, 1H). |
| 283 | 555 | 2.81(t, 2H), 3.03(bs, 2H), 3.33-3.35(m, 2H), 3.62(s, 2H), 3.75(s, 3H), 4.53(d, 2H), 6.21-6.26(m, 1H), 6.55(d, 1H), 6.90(d, 2H), 7.39-7.43(m, 3H), 7.52(s, 1H), 7.75(s, 1H), 7.96(s, 1H), 8.38(d, 1H), 8.61(t, 1H). |
| 284 | 609 | 2.82(t, 2H), 3.03(bs, 2H), 3.38(d, 2H), 3.63(s, 2H), 4.53(d, 2H), 6.40-6.48(m, 1H), 6.66(d, 1H), 7.32(d, 2H), 7.43(dd, 1H), 7.52(s, 1H), 7.60(d, 2H), 7.75(s, 1H), 7.96(s, 1H), 8.38(d, 1H), 8.61(t, 1H). |

TABLE 3-continued

Example Mass and NMR Data

| Ex# | Mass | 1H-NMR(400 MHz, DMSO-d6) δ ppm |
|---|---|---|
| 285 | 593 | 2.83(t, 2H), 3.04(bs, 2H), 3.41(d, 2H), 3.64(s, 2H), 4.53(d, 2H), 6.55-6.62(m, 1H), 6.73(d, 1H), 7.43(d, 1H), 7.52(s, 1H), 7.66-7.71(m, 4H), 7.75(s, 1H), 7.96(s, 1H), 8.38(d, 1H), 8.61(t, 1H). |
| 286 | 561 | 3.33-3.37 (m, 2H), 3.5 (bs, 1H), 3.79 (bs, 1H), 4.09-4.13 (m, 2H), 4.33-4.35 (m, 1H), 4.60 (d, 2H), 4.65-4.69 (m, 1H), 6.54-6.62 (m, 1H), 6.90 (d, 1H), 7.20 (s, 1H), 7.38-7.42 (m, 2H), 7.62-7.68 (m, 2H), 7.93 (s, 1H), 8.02 (s, 1H), 8.23 (d, 1H), 9.02 (bs, 1H), 10.92 (bs, 1H). |
| 287 | 594 | 2.84(t, 2H), 3.05(bs, 2H), 3.47(d, 2H), 3.66(s, 2H), 4.54(d, 2H), 6.84(d, 1H), 6.98-7.05(m, 1H), 7.43(dd, 1H), 7.52(s, 1H), 7.72(d, 1H), 7.75(s, 1H), 7.96(s, 1H), 8.16(dd, 1H), 8.39(d, 1H), 8.62(t, 1H), 8.89(s, 1H). |
| 288 | 552 | 3.30-3.32 (m, 2H), 3.45-3.50 (m, 1H), 3.78-3.80 (m, 1H), 4.10-4.18 (m, 2H), 4.35-4.43 (m, 1H), 4.60 (d, 2H), 4.68 (d, 1H), 6.72-6.80 (m, 1H), 6.98 (d, 1H), 7.20 (s, 1H), 7.39 (d, 1H), 7.58 (d, 1H), 7.77 (d, 1H), 7.93 (s, 1H), 7.96 (t, 1H), 8.02 (s, 1H), 8.23 (d, 1H), 9.03 (t, 1H), 11.06 (bs, 1H). |
| 289 | 545 | 3.33-3.48 (m, 3H), 3.78-3.80 (m, 1H), 4.05-4.18 (m, 2H), 4.35-4.43 (m, 1H), 4.60 (d, 2H), 4.69 (d, 1H), 6.48-6.55 (m, 1H), 6.99 (d, 1H), 7.17-7.40 (m, 4H), 7.75-7.81 (m, 1H), 7.95 (s, 1H), 8.02 (s, 1H), 8.23 (d, 1H), 9.00 (t, 1H), 10.75 (bs, 1H). |
| 290 | 561 | 3.35-3.38 (m, 2H), 3.47 (bs, 1H), 3.78 (bs, 1H), 4.06-4.11 (m, 2H), 4.33-4.35 (m, 1H), 4.60 (d, 2H), 4.64-4.68 (m, 1H), 6.49-6.56 (m, 1H), 6.88 (d, 1H), 7.20 (s, 1H), 7.39 (d, 1H), 7.47 (t, 1H), 7.54-7.58 (m, 1H), 7.82-7.84 (dd, 1H), 7.94 (s, 1H), 8.02 (s, 1H), 8.22 (d, 1H), 9.1 (bs, 1H), 11.06 (bs, 1H). |
| 291 | 545 | 3.35-3.40 (m, 2H), 3.40-3.50 (m, 1H), 3.78-3.80 (m, 1H), 4.05-4.18 (m, 2H), 4.35-4.43 (m, 1H), 4.60 (d, 2H), 4.69 (d, 1H), 6.45-6.52 (m, 1H), 6.89 (d, 1H), 7.20 (s, 1H), 7.38-7.52 (m, 3H), 7.68-7.73 (m, 1H), 7.94 (s, 1H), 8.02 (s, 1H), 8.23 (d, 1H), 9.01 (t, 1H), 10.72 (bs, 1H). |
| 292 | 543 | 2.82-2.83(m, 2H), 3.04(bs, 2H), 3.39(m, 2H), 3.63(s, 2H), 4.56(d, 2H), 6.40-6.46(m, 1H), 6.63(d, 1H), 7.17(s, 1H), 7.36-7.39(m, 3H), 7.50(d, 2H), 7.75(s, 1H), 7.96(s, 1H), 8.22(d, 1H), 8.62(t, 1H). |
| 293 | 543 | 2.80(bs, 2H), 3.03(bs, 2H), 3.40(d, 2H), 3.94(s, 2H), 4.56(d, 2H), 6.41-6.45(m, 1H), 6.63(d, H), 7.16(s, 1H), 7.36-7.39(m, 4H), 7.50(d, 2H), 7.71(d1H) 8.21(d, 1H), 8.78(t, 1H). |
| 294 | 565 | 2.80-2.81(m, 2H), 2.98(bs, 2H), 3.36(d, 2H), 3.61(s, 2H), 4.62(d, 2H), 6.38-6.46(m, 1H), 6.62(d, 1H), 7.38(d, 2H), 7.49(d, 2H), 7.66(s, 1H), 7.74(s, 1H), 7.94'(s, 1H), 8.72(t, 1H). |
| 295 | 565 | 2.78-2.79(m, 2H), 2.97(bs, 2H), 3.39(d, 2H), 3.92(s, 2H), 4.62(d, 2H), 6.41-6.46(m, 1H), 6.63(d, 1H), 7.37-7.39(m, 3H), 7.50(d, 2H), 7.66-7.69(m, 2H), 8.88(t, 1H), |
| 296 | 550 | |
| 297 | 561 | 3.35(bs, 2H), 3.41-3.49(m, 1H), 3.80(bs, 1H), 4.12(bs, 2H), 4.35(bs, 1H), 4.57(d, 2H), 4.64(d, 1H), 6.53-6.61(m, 1H), 6.90(d, 1H), 7.40-7.45(m, 2H), 7.55(s, 1H), 7.62-7.69(m, 3H), 7.96(d, 1H), 8.40(d, 1H), 8.95(bs, 1H), 10.72(bs, 1H). |
| 298 | 552 | 3.37-3.40(m, 2H), 3.45-3.50(m, 1H), 3.77-3.80(m, 1H), 4.11-4.16(m, 2H), 4.31-4.36(m, 1H), 4.55-4.64(m, 3H), 6.73-6.83(m, 1H), 6.99(d, 1H), 7.46(d, 1H), 7.55-7.58(m, 2H), 7.68(d, 1H), 7.76(d, 1H), 7.95-7.99(m, 2H), 8.39(d, 1H), 9.02(t, 1H), 11.52(s, 1H). |
| 299 | 545 | 3.35(m, 2H), 3.5(m, 1H), 3.79(m, 1H), 4.13-4.15(m, 2H), 4.32-4.34(m, 2H), 4.56-4.64(m, 3H), 6.50-6.56(m, 1H), 6.98(d, 1H), 7.13-7.21(m, 1H), 7.31-7.36(m, 1H), 7.44-7.45(dd, 1H), 7.55(s, 1H), 7.70(d, 1H), 7.75-7.81(m, 1H), 7.96(d, 1H), 8.39(d, 1H), 8.95(m, 1H), 10.83(s, 1H). |
| 300 | 545 | : 3.33-3.39(m, 2H), 3.48(bs, 1H), 3.80(bs, 1H), 4.10(bs, 2H), 4.36(bs, 1H), 4.57(d, 2H), 4.63(d, 1H), 6.45-6.53(m, 1H), 6.88(d, 1H), 7.38(d, 1H), 7.44-7.52(m, 2H), 7.55(s, 1H), 7.67-7.72(m, 2H), 7.96(d, 1H), 8.40(d, 1H), 8.96(bs, 1H), 10.78(bs, 1H). |
| 301 | 563 | 3.31-3.34(m, 2H), 3.41-3.51(m, 1H), 3.78-3.81(m, 1H), 4.08-4.11(m, 2H), 4.31-4.36(dd, 1H), 4.57(d, 2H), 4.63(d, 1H), 6.54-6.62(m, 1H), 6.85(d, 1H), 7.44-7.46(m, 1H), 7.55-7.60(m, 3H), 7.68(d, 1H), 7.96(d, 1H), 8.40(d, 1H), 8.98(t, 1H), 11.03(bs, 1H). |
| 302 | 545 | 3.35-3.50(m, 3H), 3.78(bs, 1H), 4.10-4.12(m, 2H), 4.31-4.37(dd, 1H), 4.56-4.65(m, 3H), 6.64-6.67(m, 1H), 6.90(d, 1H), 7.21-7.26(m, 1H), 7.31-7.34(m, 2H), 7.44-7.46(dd, 1H), 7.55(s, 1H), 7.68(d, 1H), 7.96(d, 1H), 8.40(d, 1H), 8.98(t, 1H), 11.12(bs, 1H), |
| 303 | 534 | 2.87(t, 2H), 3.08(t, 2H), 3.47(d, 2H), 4.05(s, 2H), 4.63(d, 2H), 5.92(t, 1H), 6.45-6.51(m, 1H), 6.64(d, 1H), 7.02(t, 1H), 7.19-7.21(dd, 1H), 7.30(s, 1H), 7.46(d, 2H), 7.60(d, 2H), 7.66-7.69(dd, 1H), 8.38(d, 1H). |
| 304 | 543 | 2.82(t, 2H), 3.03(s, 2H), 3.37(d, 2H), 3.61(s, 2H), 4.53(d, 2H), 6.39-6.46(m, 1H), 6.63(d, 3H), 7.38(d, 2H), 7.42(d, 1H), 7.51(d, 4H), 7.89(d, 1H), 8.38(d, 2H), 8.57(t, 1H). |
| 305 | 543 | 2.87(t, 2H), 3.06(t, 2H), 3.43(d, 2H), 4.04(s, 2H), 4.63(d, 2H), 5.91(t, 1H), 6.27-6.35(m, 1H), 6.57(d, 1H), 7.01(t, 1H), 7.20(dd, 1H), 7.27-7.33(m, 5H), 7.67-7.71(dd, 1H), 8.37(d, 1H). |
| 306 | 527 | 2.82(t, 2H), 3.03(s, 2H), 3.36(d, 2H), 3.61(s, 2H), 4.53(d, 2H), 6.31-6.39(m, 2H), 6.62(d, 1H), 7.16(s, 2H), 7.42(d, 1H), 7.50-7.54(m, 4H), 7.89(d, 1H), 8.38(d, 1H), 8.57(t, 1H). |
| 307 | 527 | 2.87(t, 2H), 3.06(t, 2H), 3.43(d, 2H), 4.03(s, 2H), 4.62(d, 2H), 5.96(t, 1H), 6.21-6.28(m, 1H), 6.58(d, 1H), 6.98-7.03(m, 3H), 7.20(dd, 1H), 7.30(s, 1H), 7.34-7.37(m, 2H), 7.67-7.70(dd, 1H), 8.37(d, 1H). |
| 308 | 577 | 2.88(t, 2H), 3.08(t, 2H), 3.47(d, 2H), 4.05(s, 2H), 4.63(d, 2H), 5.90(t, 1H), 6.40-6.48(m, 1H), 6.66(d, 1H), 7.02(t, 1H), 7.21(d, 1H), 7.30(s, 1H), 7.48(d, 2H), 7.57(d, 2H), 7.67-7.70(dd, 1H), 8.38(d, 1H). |
| 309 | 545 | 3.33(s, 2H), 3.48(bs, 1H), 3.79(bs, 1H), 4.10-4.11(m, 2H), 4.33-4.35(m, 1H), 4.60(d, 2H), 4.65(s, 1H), 6.55-6.62(m, 1H), 6.90(d, 1H), 7.19(s, 1H), 7.38-7.42(m, 2H), 7.61-7.69(m, 3H), 7.96(d, 1H), 8.22(d, 1H), 8.98(s, 1H), 10.94(s, 1H). |
| 310 | 543 | 3.30-3.35(m, 2H), 3.43-3.47(m, 1H), 3.78(bs, 1H), 4.12-4.16(m, 2H), 4.30-4.35(dd, 1H), 4.59-4.63(m, 3H), 6.57-6.65(m, 1H), 6.99(d, 1H), 7.20(s, 1H), 7.36-7.40(m, 2H), 7.51-7.54(dd, 1H), 7.70(d, 1H), 7.75(t, 1H), 7.96(d, 1H), 8.23(d, 1H), 8.99(t, 1H), 11.11(bs, 1H). |
| 311 | 536 | 3.35(bs, 3H), 3.81(m, 1H), 4.15-4.16(m, 2H), 4.36(m, 1H), 4.59-4.67(m, 3H), 6.73-6.78(m, 1H), 6.98(d, 1H), 7.19(s, 1H), 7.39(d, 1H), 7.58(d, 1H), 7.68(d, 1H), 7.78(d, 1H), 7.96-8.00(m, 2H), 8.23(d, 1H), 8.98(d, 1H), 10.80(bs, 1H). |

TABLE 3-continued

Example Mass and NMR Data

| Ex# | Mass | 1H-NMR(400 MHz, DMSO-d6) δ ppm |
|---|---|---|
| 312 | 529 | 3.46-3.49(m, 2H), 3.78(bs, 1H), 4.13-4.15(m, 2H), 4.32-4.33(m, 1H), 4.59-4.63(m, 3H), 6.49-6.57(m, 1H), 6.98(d, 1H), 7.16-7.19(m, 2H), 7.31-7.39(m, 2H), 7.70(d, 1H), 7.77-7.80(m, 1H), 7.97(d, 1H), 8.23(d, 1H), 10.91(bs, 1H), |
| 313 | 545 | 3.35-3.42(3, 3H), 3.78-3.80(m, 1H), 4.06-4.10(m, 2H), 4.31-4.35(m, 1H), 4.59-4.64(m, 3H), 6.53-6.56(m, 1H), 6.88(d, 1H), 7.20(s, 1H), 7.39(d, 1H), 7.47(t, 1H), 7.54-7.57(m, 1H), 7.69(d, 1H), 7.81-7.84(dd, 1H), 7.96(d, 1H), 8.22(d, 1H), 9.00(t, 1H), 11.06(s, 1H). |
| 314 | 529 | 3.51(bs, 3H), 3.79(bs, 1H), 4.10(bs, 2H), 4.35(bs, 1H), 4.59-4.64(m, 3H), 6.48-6.54(m, 1H), 6.88(d, 1H), 7.20(s, 1H), 7.39(bs, 2H), 7.45-7.52(q, 1H), 7.67-7.72(m, 2H), 7.97(d, 1H), 8.23(d, 1H), 8.98(s, 1H), 10.88(bs, 1H) |
| 315 | 547 | 3.36-3.49(m, 3H), 3.77-3.80(m, 1H), 4.07-4.10(m, 2H), 4.31-4.36(dd, 1H), 4.59-4.64(m, 3H), 6.55-6.63(m, 1H), 6.85(d, 1H), 7.20(s, 1H), 7.39(d, 1H), 7.55-7.59(m, 2H), 7.68(d, 1H), 7.96(d, 1H), 8.23(d, 1H), 9.00(t, 1H), 11.04(bs, 1H). |
| 316 | 529 | 3.45-3.49(m, 3H), 3.78(bs, 1H), 4.12(bs, 2H), 4.35(bs, 1H), 4.59-4.64(m, 3H), 6.60-6.67(m, 1H), 6.90(d, 1H), 7.18-7.26(m, 2H), 7.31-7.33(m, 2H), 7.39(d, 1H), 7.68(d, 1H), 7.96(d, 1H), 8.23(d, 1H), 8.99(t, 1H), 11.14(bs, 1H), |
| 317 | 527 | 2.82(t, 2H), 3.04(bs, 2H), 3.37(d, 2H), 3.61(s, 2H), 4.56(d, 2H), 6.41-6.47(m, 1H), 6.63(d, 1H), 7.17(s, 1H), 7.36-7.39(m, 3H), 7.49-7.52(m, 3H), 7.90(d, 1H), 8.21(d, 1H), 8.58(t, 1H). |
| 318 | 527 | 2.87(t, 2H), 3.07(t, 2H), 3.43(d, 2H), 4.04(s, 2H), 4.67(d, 2H), 5.92(t, 1H), 6.27-6.35(m, 1H), 6.57(d, 1H), 6.90(s, 1H), 7.02(t, 1H), 7.16(d, 1H), 7.29-7.33(m, 4H), 7.68-7.71(dd, 1H), 8.21(d, 1H). |
| 319 | 511 | 3.35-3.40(m, 2H), 3.45-3.49(m, 1H), 3.77-3.80(m, 1H), 4.05-4.12(m, 2H), 4.30-4.36(m, 1H), 4.59-4.63(m, 3H), 6.40-6.48(m, 1H), 6.90(d, 1H), 7.20(s, 1H), 7.25(t, 2H), 7.39(d, 1H), 7.57-7.61(m, 2H), 7.70(d, 1H), 7.96(d, 1H), 8.22(d, 1H), 8.99(t, 1H), 11.03(bs, 1H) |
| 320 | 568 | 3.30-3.32(m, 1H), 3.50(bs, 2H), 3.82(bs, 1H), 4.20-4.24(m, 2H), 4.41(bs, 1H), 4.49(d, 1H), 4.59(d2H), 6.64-6.71(m, 1H), 6.99(d, 1H), 7.46(d, 1H), 7.56(s, 1H), 7.61(d, 1H), 7.72(d, 2H), 7.88(d, 2H), 7.99(d, 1H), 8.40(d, 1H), 9.25(bs, 1H), 10.90(bs, 1H). |
| 321 | 568 | 3.34-3.45(m, 2H), 3.49(bs, 1H), 3.80(bs, 1H), 4.19(bs, 2H), 4.59-4.60(m, 3H), 4.76(d, 1H), 6.70-6.78(m, 1H), 6.99-7.03(d, 1H), 7.46-7.50(m, 2H), 7.57(s, 1H), 7.75(d, 2H), 7.88(d, 2H), 7.95(s, 1H), 8.40(d, 1H), 9.24(t, 1H), 11.21(bs, 1H) |
| 322 | 577 | 3.32-3.34(m, 1H), 3.46-3.50(m, 2H), 3.82(bs, 1H), 4.12-4.20(m, 2H), 4.34-4.37(m, 1H), 4.48(d, 1H), 4.59(d, 2H), 6.44-6.51(m, 1H), 6.90(d, 1H), 7.46-7.49(m, 3H), 7.55-7.57(m, 3H), 7.62(d, 1H), 7.99(d, 1H), 8.41(d, 1H), 9.23(bs, 1H), 10.68(bs, 1H). |
| 323 | 577 | 3.35-3.37(m, 2H), 3.41-3.47(m, 1H), 3.80(bs, 1H), 4.15(bs, 2H), 4.56-4.60(m, 3H), 4.76(d, 1H), 6.51-6.58(m, 1H), 6.92(d, 1H), 7.46-7.48(m, 4H), 7.57-7.59(m, 3H), 7.95(s, 1H), 8.41(d, 1H), 9.22(t, 1H), 10.94(bs, 1H), |
| 324 | 561 | 3.37(bs, 2H), 3.48-3.50(m, 1H), 3.81-3.84(m, 1H), 4.13-4.18(m, 2H), 4.37(bs, 1H), 4.48(d, 1H), 4.59(d, 2H), 6.37-6.45(m, 1H), 6.90(d, 1H), 7.25(t, 2H), 7.46(d, 1H), 7.56-7.63(m, 4H), 7.97-8.00(dd, 1H), 8.41(d, 1H), 9.25(d, 1H), 10.82(bs, 1H) |
| 325 | 561 | 3.35-3.41(m, 1H), 3.47(bs, 2H), 3.79(bs, 1H), 4.13(bs, 2H), 4.53-4.60(m, 3H), 4.74(d, 1H), 6.44-6.51(m, 1H), 6.93(d, 1H), 7.25(t, 2H), 7.46-7.50(m, 2H), 7.57-7.62(m, 3H), 7.95(s, 1H), 8.40(d, 1H), 9.22(t, 1H), 11.07(bs, 1H). |
| 326 | 561 | 3.28-3.30(m, 1H), 3.44-3.51(m, 2H), 3.82-3.85(m, 1H), 4.15-4.20(m, 2H), 4.35-4.38(m, 1H), 4.50(d, 1H), 4.63(d, 2H), 6.45-6.51(m, 1H), 6.90(d, 1H), 7.21(s, 1H), 7.40(d, 1H), 7.48(d, 2H), 8.54(d, 2H), 8.62(d, 1H), 8.00(d, 1H), 8.24(d, 1H), 9.24(bs, 1H), 10.57(bs, 1H). |
| 327 | 561 | 3.32(bs, 2H), 3.47(bs, 1H), 3.77(bs, 1H), 4.12(bs, 2H), 4.55-4.61(m, 3H), 4.74(d, 1H), 6.48-6.55(m, 1H), 6.89(d, 1H), 7.19(s, 1H), 7.38(d, 1H), 7.44(d, 3H), 7.55(d, 2H), 7.93(s, 1H), 8.20(d, 1H), 9.22(bs, 1H), 10.89(bs, 1H). |
| 328 | 593 | 3.39(bs, 2H), 3.50(bs, 1H), 3.82(m, 1H), 4.10(bs, 2H), 4.39(bs, 1H), 4.59(d, 2H), 4.72(d, 1H), 6.49-6.54(m, 1H), 6.91(d, 1H), 7.44-7.49(m, 3H), 7.56-7.59(m, 3H), 8.02(s, 1H), 8.18(s, 1H), 8.41(d, 1H), 9.12(bs, 1H), 10.75(bs, 1H). |
| 329 | 589 | 3.50-3.53(m, 2H), 3.82(bs, 2H), 3.90(s, 3H), 4.11-4.14(m, 2H), 4.35-4.40(m, 1H), 4.57(d, 2H), 4.67(d, 1H), 6.49-6.56(m, 1H), 6.92(d, 1H), 7.41(s, 1H), 7.44-7.49(m, 3H), 7.55-7.59(m, 3H), 8.00(s, 1H), 8.39(d, 1H), 8.96(t, 1H), 10.78(bs, 1H). |
| 330 | 573 | 2.49(s, 3H), 3.42-3.50(m, 3H), 3.82-3.85(m, 1H), 4.11-4.14(m, 2H), 4.30-4.39(m, 1H), 4.59(bs, 2H), 4.69(d, 1H), 6.47-6.55(m, 1H), 6.91(d, 1H), 7.45-7.49(m, 3H), 7.56-7.62(m, 4H), 8.06(s, 1H), 8.40(d, 1H), 9.01(bs, 1H), 10.64(bs, 1H). |
| 331 | 550 | 3.36-3.52(m, 3H), 3.74-3.84(m, 1H), 4.05-4.18(m, 2H), 4.39-4.44(m, 1H), 4.60(d, 2H), 4.70(d, 1H), 6.61-6.69(m, 1H), 6.92(d, 1H), 7.40(dd, 1H), 7.47(dd, 1H), 7.57(s, 1H), 7.61-7.66(m, 3H), 7.77(d, 1H), 8.25-8.27(m, 1H), 8.38-8.41(m, 1H), 9.15(t, 1H), 11.60(bs, 1H). |
| 332 | 559 | 3.04(br t, 2H) 3.22(br s, 2H) 3.54(br d, 1H) 3.83(s, 2H) 4.67(d, 2H) 6.20(br s, 1H) 6.38(dt, 1H) 6.64(d, 1H) 7.25(dd, 1H) 7.29-7.38(m, 5 H) 7.52(dd, 1H) 7.66(s, 1H) 7.93(d, 1H) 8.40(dd, 1H). |
| 333 | 593 | 8.71(s, 1H), 8.40(d, 1H), 7.94(d, 1H), 7.84(s, 1H), 7.78(d, 1H), 7.48-7.60(m, 4H), 7.44(d, 1H), 6.52-6.68(m, 2H), 4.56(d, 2H), 3.73(s, 2H), 3.41(br d, 2H), 3.06(br s, 2H), 2.86(br s, 2H). |
| 334 | 543 | 8.71(m, 1H), 8.40(d, 1H), 7.94(d, 1H), 7.81-7.88(m, 1H), 7.48-7.58(m, 4H), 7.44(m, 1H), 7.12-7.23(m, 2H), 6.64(d, 1H), 6.38(m, 1H), 4.56(d, 2H), 3.72(s, 2H), 3.39(br d, 2H), 3.06(br s, 2H), 2.85(br m, 2H) |
| 335 | 609 | 8.72(m, 1H), 8.40(d, 1H), 7.94(d, 1H), 7.85(s, 1H), 7.61(d, 1H), 7.49-7.56(m, 2H), 7.44(d, 1H), 7.33(d, 2H), 6.69(d, 1H), 6.47(m, 1H), 4.56(d, 2H), 3.72(s, 2H), 3.41(br d, 2H), 3.07(br s, 2H), 2.86(br m, 2H). |
| 336 | 593 | 3.37(bs, 2H), 3.49(bs, 1H), 3.79-3.82(m, 1H), 4.12(bs, 2H), 4.39-4.41(m, 1H), 4.58(d, 2H), 4.68(d, 1H), 6.57-6.65(m, 1H), 6.91(d, 1H), 7.26(d, 1H), 7.40-7.45(m, 2H), 7.54(s, 1H), 7.61-7.68(m, 3H), 7.75(s, 1H), 8.39(d, 1H), 8.96-8.97(m, 1H), 10.89(bs, 1H). |
| 337 | 611 | 3.35-3.53(m, 3H), 3.75-3.82(m, 1H), 4.14-4.23(m, 2H), 4.37-4.42(m, 1H), 4.58(d, 2H), 4.67(m, 1H), 6.62-6.69(m, 1H), 7.17(d, 1H), 7.22-7.27(m, 1H), 7.45(dd, 1H), 7.50- |

TABLE 3-continued

Example Mass and NMR Data

| Ex# | Mass | 1H-NMR(400 MHz, DMSO-d6) δ ppm |
|---|---|---|
| | | 7.56(m, 2H), 7.67-7.70(m, 2H), 7.74-7.77(m, 1H), 7.83(d, 1H), 8.38-8.41(m, 1H), 9.03(t, 1H), 11.65(bs, 1H). |
| 338 | 637, 639 | 3.35-3.52(m, 3H), 3.74-3.81(m, 1H), 4.10-4.20(m, 2H), 4.35-4.41(m, 1H), 4.57(d, 2H), 4.65(d, 1H), 6.64-6.72(m, 1H), 7.00(d, 1H), 7.22-7.27(m, 1H), 7.44-7.52(m, 2H), 7.55(s, 1H), 7.62-7.71(m, 3H), 7.73-7.77(m, 1H), 8.38-8.41(m, 1H), 9.03(t, 1H), 11.56(bs, 1H). |
| 339 | 611 | 3.37-3.50(m, 3H), 3.74-3.81(m, 1H), 4.15-4.23(m, 2H), 4.33-4.38(m, 1H), 4.57-4.66(m, 3H), 6.70-6.79(m, 1H), 6.88(d, 1H), 7.22-7.26(m, 1H), 7.45-7.52(m, 3H), 7.54-7.56(m, 1H), 7.69(d, 1H), 7.74-7.77(m, 1H), 8.38-8.42(m, 1H), 9.02(t, 1H), 11.67(bs, 1H). |
| 340 | 593 | 3.34-3.52(m, 3H), 3.75-3.81(m, 1H), 4.12-4.20(m, 2H), 4.35-4.41(m, 1H), 4.57(d, 2H), 4.65(d, 1H), 6.63-6.71(m, 1H), 7.01(d, 1H), 7.22-7.27(m, 1H), 7.37(dd, 1H), 7.46(dd, 1H), 7.50-7.56(m, 2H), 7.67-7.79(m, 3H), 8.38-8.41(m, 1H), 9.03(t, 1H), 11.57(bs, 1H). |
| 341 | 595 | 3.34-3.51(m, 3H), 3.73-3.81(m, 1H), 4.11-4.24(m, 2H), 4.33-4.38(m, 1H), 4.55-4.66(m, 3H), 6.65-6.73(m, 1H), 6.87(d, 1H), 7.21-7.36(m, 3H), 7.46(dd, 1H), 7.54-7.56(m, 1H), 7.67-7.77(m, 2H), 8.38-8.41(m, 1H), 9.02(t, 1H), 11.64(bs, 1H). |
| 342 | 610 | 3.35-3.40(m, 2H), 3.46-3.50(m, 1H), 3.78-3.81(m, 1H), 4.18-4.23(m, 2H), 4.37-4.43(dd, 1H), 4.58(d, 2H), 4.67(d, 1H), 7.11-7.13(m, 2H), 7.24(d, 1H), 7.46(d, 1H), 7.54(s, 1H), 7.69(d, 1H), 7.75-7.79(m, 2H), 8.26-8.28(dd, 1H), 8.39(d, 1H), 8.98-9.01(m, 2H), 11.38(bs, 1H). |
| 343 | 610 | 2.91(t, 2H), 3.09-3.10(m, 2H), 3.51(d, 2H), 3.89(s, 2H), 4.65(d, 2H), 5.96(t, 1H), 6.78(d, 1H), 6.93-6.98(m, 1H), 7.05-7.07(dd, 1H), 7.19-7.22(m, 2H), 7.32(s, 1H), 7.40(d, 1H), 7.72(d, 1H), 7.84-7.87(dd, 1H), 8.37(d, 1H), 8.81(s, 1H). |
| 344 | 584 | 3.36-3.55(m, 3H), 3.74-3.82(m, 1H), 4.07-4.17(m, 2H), 4.37-4.42(m, 1H), 4.57(d, 2H), 4.66(d, 1H), 6.62-6.70(m, 1H), 6.95(d, 1H), 7.23-7.28(m, 1H), 7.46(dd, 1H), 7.55-7.61(m, 2H), 7.67(d, 1H), 7.74-7.77(m, 1H), 7.93-7.97(m, 1H), 8.15-8.19(m, 1H), 8.38-8.42(m, 1H), 9.06(t, 1H), 11.65(bs, 1H). |
| 345 | 584 | 3.38(bs, 2H), 3.48-3.50(m, 1H), 3.80-3.82(m, 1H), 4.16(bs, 2H), 4.38-4.42(m, 1H), 4.58(d, 2H), 4.70(d, 1H), 6.76-6.84(m, 1H), 6.99(d, 1H), 7.26(d, 1H), 7.45(d, 1H), 7.54-7.59(m, 2H), 7.67(d, 1H), 7.75-7.79(m, 2H), 7.98(t, 1H), 8.39(d, 1H), 8.98(t, 1H), 11.16(bs, 1H). |
| 346 | 593 | 3.37-3.52(m, 3H), 3.75-3.81(m, 1H), 4.14-4.22(m, 2H), 4.37-4.42(m, 1H), 4.58(d, 2H), 4.67(d, 1H), 6.55-6.63(m, 1H), 7.16(d, 1H), 7.22-7.27(m, 1H), 7.29-7.36(m, 1H), 7.46(dd, 1H), 7.51-7.56(m, 2H), 7.68(d, 1H), 7.74-7.77(m, 1H), 7.84-7.88(m, 1H), 8.38-8.41(m, 1H), 9.04(t, 1H), 11.64(bs, 1H). |
| 347 | 577 | 3.35(bs, 2H), 3.80(bs, 2H), 4.16-4.17(m, 2H), 4.41(hump, 1H), 4.58(d, 2H), 4.70(d, 1H), 6.50-6.57(m, 1H), 6.99(d, 1H), 7.15-7.21(m, 1H), 7.26(d, 1H), 7.31-7.37(m, 1H), 7.45(d, 1H), 7.54(s, 1H), 7.69(d, 1H), 7.75-7.82(m, 2H), 8.39(d, 1H), 9.82-8.94(m, 1H), 10.61(s, 1H). |
| 348 | 593 | 3.37-3.38(m, 2H), 3.50(bs, 1H), 3.78-3.81(m, 1H), 4.08-4.11(m, 2H), 4.37-4.42(dd, 1H), 4.58(d, 2H), 4.68(d, 1H), 6.52-6.60(m, 1H), 6.89(d, 1H), 7.24-7.26(dd, 1H), 7.44-7.49(m, 2H), 7.54-7.58(m, 1H), 7.68(d, 1H), 7.75(s, 1H), 7.82-7.84(dd, 1H), 8.39(d, 1H), 8.98(t, 1H), 11.10(bs, 1H). |
| 349 | 577 | 3.35(bs, 2H), 3.38-3.49(m, 1H), 3.79-3.82(m, 1H), 4.11(bs, 2H), 4.37-4.41(m, 1H), 4.58(d, 2H), 4.68(d, 1H), 6.49-6.57(m, 1H), 6.89(d, 1H), 7.26(d, 1H), 7.37-7.40(m, 1H), 7.44-7.52(m, 2H) 7.54(s, 1H), 7.67-7.75(m, 3H), 8.39(d, 1H), 8.97(t, 1H), 10.90(bs, 1H). |
| 350 | 595 | 3.37-3.52(m, 3H), 3.74-3.82(m, 1H), 4.07-4.16(m, 2H), 4.37-4.42(m, 1H), 4.57(d, 2H), 4.67(d, 1H), 6.62-6.68(m, 1H), 6.88(d, 1H), 7.23-7.28(m, 1H), 7.45(dd, 1H), 7.53-7.61(m, 3H), 7.67(d, 1H), 7.74-7.77(m, 1H), 8.38-8.42(m, 1H), 9.05(t, 1H), 11.56(bs, 1H) |
| 351 | 566 | 2.92(t, 2H), 3.10(t, 2H), 3.47(d, 2H), 3.70(s, 2H), 4.65(d, 2H), 5.88(brs, 1H), 6.46-6.51(m, 1H), 6.64(d, 1H), 7.09(d, 1H), 7.21-7.22(m, 1H), 7.32-7.35(m, 2H), 7.47(d, 2H), 7.60(d, 1H), 7.77(s, 1H), 8.38(d, 1H) |
| 352 | 566 | 2.90(t, 2H), 3.09-3.11(m, 2H), 3.45(d, 2H), 3.86(s, 2H), 4.65(d2H), 5.95(t, 1H), 6.45-6.50(m, 1H), 6.64(d, 1H), 7.05-7.07(dd, 1H), 7.19-7.22(m, 2H), 7.32(s, 1H), 7.46(d, 2H), 7.60(d, 2H), 7.70(d, 1H), 8.37(d, 1H). |
| 353 | 575 | 2.83(t, 2H), 3.05(brs, 2H), 3.39(d, 2H), 3.66(s, 2H), 4.54(d, 2H), 6.41-6.48(m, 1H), 6.63(d, 1H), 7.13(d, 1H), 7.38(d, 2H), 7.43(d, 1H), 7.49-7.53(m, 4H), 7.72(s, 1H), 8.39(d, 1H), 8.56(t, 1H). |
| 354 | 575 | 2.89(t, 2H), 3.09(t, 2H), 3.41(d, 2H), 3.86(s, 2H), 4.64(d, 2H), 5.97(t, 1H), 6.27-6.34(m, 1H), 6.57(d, 1H), 7.05-7.07(dd, 1H), 7.18-7.22(m, 2H), 7.27-7.32(m, 5H), 7.72(d, 1H), 8.37(d, 1H). |
| 355 | 609 | 2.91(t, 2H), 3.08-3.10(m, 2H), 3.43(d, 2H), 3.69(s, 2H), 4.65(d, 2H), 5.88(t, 1H), 6.30-6.38(m, 1H), 6.53(d, 1H), 7.09(d, 1H), 7.20-7.24(m, 2H), 7.32(s, 1H), 7.34-7.36(m, 1H), 7.37-7.39(m, 1H), 7.46(d, 1H), 7.78(bs, 1H), 8.38(d, 1H). |
| 356 | 559 | 2.83(t, 2H), 3.05(bs, 2H), 3.38(d, 2H), 3.66(s, 2H), 4.54(d, 2H), 6.33-6.40(m, 1H), 6.63(d, 1H), 7.12-7.18(m, 3H), 7.42(d, 1H), 7.51-7.54(m, 4H), 7.72(s, 1H), 8.38(d, 1H), 8.56(t, 1H). |
| 357 | 559 | 2.89(t, 2H), 3.08-3.09(m, 2H), 3.41(d, 2H), 3.86(s, 2H), 4.64(d, 2H), 5.95(t, 1H), 6.22-6.28(m, 1H), 6.57(d, 1H), 7.00-7.04(m, 3H), 7.18-7.22(m, 2H), 7.31-7.37(m, 3H), 7.72(d, 1H), 8.37(d, 1H). |
| 358 | 571 | 2.82(t, 2H), 3.05(brs, 2H), 3.36(d, 2H), 3.65(s, 2H), 3.75(s, 3H), 4.54(d, 2H), 6.22-6.28(m, 1H), 6.56(d, 1H), 6.90(d, 2H), 7.12-7.14(dd, 1H), 7.39-7.43(m, 3H), 7.52(d, 2H), 7.72(s, 1H), 8.38(d, 1H), 8.56(t, 1H). |
| 359 | 571 | 2.88(t, 2H), 3.08(t, 2H), 3.39(d2H), 3.80(s, 3H), 3.86(s, 2H), 4.64(d, 2H), 5.99(t, 1H), 6.15-6.22(m, 1H), 6.55(d, 1H), 6.83-6.86(dd, 2H), 7.04-7.06(dd, 1H), 7.17-7.21(m, 2H), 7.31-7.50(m, 3H), 7.73(d, 1H), 8.36(d, 1H). |
| 360 | 625 | 2.92(t, 2H), 3.09(t, 2H), 3.42-3.44(m, 2H), 3.69(s, 2H), 4.65(d, 2H), 5.89(t, 1H), 6.29-6.36(m, 1H), 6.60(d, 1H), 7.08-7.10(dd, 1H), 7.17(d, 2H), 7.20-7.22(dd, 1H), 7.31-7.35(m, 2H), 7.41(d, 2H), 7.79(s, 1H), 8.37(d, 1H). |
| 361 | 625 | 2.89(t, 2H), 3.09(t, 2H), 3.41-3.43(m, 2H), 3.86(s, 2H), 4.64(d, 2H), 5.98(t, 1H), 6.28-6.35(m, 1H), 6.60(d, 1H), 7.05-7.07(dd, 1H), 7.15-7.22(m, 4H), 7.31(s, 1H), 7.38-7.41(m, 2H), 7.71(d, 1H), 8.36(d, 1H). |

TABLE 3-continued

Example Mass and NMR Data

| Ex# | Mass | 1H-NMR(400 MHz, DMSO-d6) δ ppm |
|---|---|---|
| 362 | 609 | 2.93(t, 2H), 3.10(t, 2H), 3.46(d, 2H), 3.70(s, 2H), 4.65(d, 2H), 5.89(t, 1H), 6.41-6.48(m, 1H), 6.66(d, 1H), 7.08-7.10(dd1H), 7.20-7.22(dd, 1H), 7.31-7.35(m, 2H), 7.48(d, 2H), 7.57(d, 2H), 7.78(s, 1H), 8.38(d, 1H). |
| 363 | 609 | 2.90(t, 2H), 3.10-3.11(m, 2H), 3.45(d, 2H), 3.88(s, 2H), 4.64(d, 2H), 5.98(t, 1H), 6.41-6.47(m, 1H), 6.65(d, 1H), 7.05-7.07(dd, 1H), 7.19-7.23(m, 2H), 7.31(d, 1H), 7.47(d, 2H), 7.56(d, 2H), 7.71(d, 1H), 8.37(d, 1H). |
| 364 | 645 | 3.38-3.40(m, 2H), 3.46-3.51(m, 1H), 3.78(bs, 1H), 4.38-4.43(m, 1H), 4.43-4.52(m, 1H), 4.57(d, 2H), 4.68-4.69(m, 2H), 7.20-7.22(m, 1H), 7.45(d, 1H), 7.54(s, 1H), 7.63(d, 1H), 7.71-7.74(m, 2H), 7.87-7.90(dd, 1H), 7.94(d, 1H), 8.04(d, 1H), 8.21(s, 1H), 8.31(d, 1H), 8.39(d, 1H), 8.99(t, 1H) 11.30(bs, 1H), |
| 365 | 600 | 3.46(bs, 2H), 3.78(bs, 2H), 4.58(d, 2H), 4.62-4.66(m, 2H), 4.92(s, 2H), 7.20-7.22(m, 1H), 7.45-7.46(m, 1H), 7.55(s, 1H), 7.64(d, 1H), 7.75(s, 1H), 7.84-7.88(m, 2H), 8.11(d, 1H), 8.24(d, 1H), 8.40(d, 1H), 8.51(d, 1H), 9.05(t, 1H), 11.33(bs, 1H), |
| 366 | 584 | 3.47(bs, 2H), 3.77(bs, 2H), 4.57(d, 2H), 4.65(bs, 2H), 4.91(s, 2H), 7.21(d, 1H), 7.45(d, 1H), 7.55(s, 1H), 7.64(d, 1H), 7.75-7.79(m, 2H), 7.88-7.91(m, 2H), 8.14-8.17(m, 1H), 8.39(d, 1H), 8.52(d, 1H), 9.12(t, 1H), 11.49(bs, 1H) |
| 367 | 600 | 3.38-3.41(m, 3H), 3.47-3.49(m, 1H), 3.77(bs, 1H), 4.56-4.57(m, 3H), 4.72-4.75(m, 2H), 7.20(d, 1H), 7.44(d, 1H), 7.54(s, 1H), 7.63(d, 1H), 7.69(d, 1H), 7.73(s, 1H), 8.07(d, 1H), 8.17(d, 1H), 8.32(s, 1H), 8.39(d, 1H), 8.51(d, 1H), 9.02(t, 1H), 11.50(bs, 1H). |
| 368 | 599 | 3.39(bs, 2H), 3.46-3.51(m, 1H), 3.76(hump, 1H), 4.38-4.44(m, 1H), 4.49-4.52(m, 1H), 4.58(d, 2H), 4.65-4.68(m, 1H), 7.21(d, 1H), 7.45(d, 1H), 7.54(s, 1H), 7.54(s, 1H), 7.61-7.65(m, 2H), 7.74(s, 1H), 7.88(d, 1H), 8.03(t, 2H), 8.15(d, 1H), 8.22(s, 1H), 8.39(d, 1H), 8.99(t, 1H), 11.23(bs, 1H). |
| 369 | 577 | 3.29(bs, 1H), 3.49(bs, 2H), 3.79(bs, 1H), 4.12(bs, 2H), 4.39-4.41(m, 1H), 4.62(d, 2H), 4.69(d, 1H), 6.58-6.65(m, 1H), 6.91(d, 1H), 7.19-7.27(m, 2H), 7.38-7.42(m, 2H), 7.61-7.75(m, 4H), 8.23(d, 1H), 8.99(s, 1H), 10.99(bs, 1H). |
| 370 | 593 | 3.35-3.49(m, 3H), 3.80(bs, 1H), 4.19(bs, 2H), 4.38-4.42(m, 1H), 4.61(d, 2H), 4.71(d, 1H), 6.56-6.64(m, 1H), 7.14-7.19(m, 2H), 7.26(d, 1H), 7.40(d, 1H), 7.51-7.53(dd, 1H), 7.66-7.70(m, 2H), 7.76(s, 1H), 7.85(d, 1H), 8.23(d, 1H), 8.97(bs, 1H), 10.90(bs, 1H), |
| 371 | 575 | 3.35-3.48(m, 3H), 3.78(bs, 1H), 4.16(bs, 2H), 4.38-4.40(m, 1H), 4.61(d, 2H), 4.67(d, 1H), 6.60-6.67(m, 1H), 7.00(d, 1H), 7.19(s, 1H), 7.25(d, 1H), 7.36-7.40(m, 2H), 7.50-7.54(dd, 1H), 7.68(d, 1H), 7.73-7.77(m, 2H), 8.23(d, 1H), 8.99(bs, 1H), 11.46(bs, 1H). |
| 372 | 566 | 3.27(bs, 1H), 3.51(bs, 2H), 3.80(bs, 1H), 4.17(bs, 2H), 4.40-4.42(m, 1H), 4.62(d, 2H), 4.71(d, 1H), 6.75-6.83(m, 1H), 6.98(d, 1H), 7.19(s, 1H), 7.26(d, 1H), 7.40(d, 1H), 7.58(d, 1H), 7.67(d, 1H), 7.75-7.79(m, 2H), 7.98(t, 1H), 8.23(d, 1H), 8.99(s, 1H), 11.03(bs, 1H). |
| 373 | 577 | 3.39-3.41(m, 3H), 3.78-3.79(m, 1H), 4.15-4.18(m, 2H), 4.40-4.42(m, 1H), 4.60-4.69(m, 3H), 6.57-6.60(m, 1H), 7.13-7.19(m, 2H), 7.23-7.26(dd, 1H), 7.30-7.35(m, 1H), 7.40(d, 1H), 7.51-7.54(dd, 1H), 7.68(d, 1H), 7.75(s, 1H), 7.85-7.88(m, 1H), 8.23(d, 1H), 9.02(t, 1H), 11.40(bs, 1H), |
| 374 | 559 | 3.30(bs, 1H), 3.42-3.48(m, 2H), 3.79(bs, 1H), 4.15(bs, 2H), 4.38-4.41(m, 1H), 4.62(d, 2H), 4.68(d, 1H), 6.51-6.59(m, 1H), 6.99(d, 1H), 7.16-7.19(m, 2H), 7.25(d, 1H), 7.31-7.39(m, 2H), 7.68(d, 1H), 7.75-7.81(m, 2H), 8.23(d, 1H), 8.97(bs, 1H), 10.84(bs, 1H). |
| 375 | 575 | 3.31(bs, 1H), 3.45-3.49(m, 2H), 3.79(bs, 1H), 4.10(bs, 2H), 4.39-4.41(m, 1H), 4.62(d, 2H), 4.69(d, 1H), 6.51-6.59(m, 1H), 6.89(d1H), 7.19(s, 1H), 7.26(d, 1H), 7.39(d, 1H), 7.47(t, 1H), 7.54-7.58(m, 1H), 7.68(d, 1H), 7.75(s, 1H), 7.83-7.85(dd, 1H), 8.23(d, 1H), 897-8.98(m, 1H), 10.95(bs, 1H). |
| 376 | 561 | 3.28(bs, 1H), 3.49(bs, 2H), 3.79(bs, 1H), 4.11(bs, 2H), 4.39-4.41(m, 1H), 4.62(d, 2H), 4.69(d, 1H), 6.49-6.56(m, 1H), 6.89(d, 1H), 7.19-7.27(m, 2H), 7.35-7.40(m, 2H), 7.45-7.56(m, 1H), 7.66-7.75(m, 3H), 8.23(d, 1H), 8.98(s, 1H), 10.88(bs, 1H). |
| 377 | 579 | 3.47-3.52(m, 3H), 3.78(m, 1H), 4.11(bs, 2H), 4.40-4.42(m, 1H), 4.60-4.70(m, 3H), 6.59-6.65(m, 1H), 6.86(d, 1H), 7.19(s, 1H), 7.26(d, 1H), 7.40(d, 1H), 7.56-7.60(m, 2H), 7.67(d, 1H), 7.75(s, 1H), 8.23 (d, 1H), 9.00(t, 1H), 11.11(bs, 1H). |
| 378 | 561 | 3.34-3.50(m, 3H), 3.81(bs, 1H), 4.14(bs, 2H), 4.40-4.42(m, 1H), 4.61(d, 2H), 4.71(d, 1H), 6.63-6.68(m, 1H), 6.90(d1H), 7.19(s, 1H), 7.21-7.27(m, 2H), 7.33(d, 2H), 7.40(d, 1H), 7.67(d, 1H), 7.75(s, 1H), 8.23(d, 1H), 8.97(bs, 1H), 10.82(bs, 1H). |
| 379 | 559 | 2.92(t, 2H), 3.10(t, 2H), 3.42-3.44(m, 2H), 3.69(s, 2H), 4.69(d, 2H), 5.89(t, 1H), 6.28-6.35(m, 1H), 6.57(d, 1H), 6.91(s, 1H), 7.09(dd, 1H), 7.17(d, 1H), 7.26-7.35(m, 5H), 7.79(s, 1H), 8.21(d, 1H). |
| 379a | 559 | 2.90(t, 2H), 3.10-3.11(m, 2H), 3.42(d, 2H), 3.87(s, 2H), 4.68(d, 2H), 5.96(brs, 1H), 6.29-6.34(m, 1H), 6.57(d, 1H), 6.92(s, 1H), 7.05-7.07(m, 1H), 7.16-7.24(m, 2H), 7.25-7.50(m, 4H), 7.72(d, 1H), 8.21(d, 1H). |
| 380 | 577 | 3.37-3.50(m, 3H), 3.78(bs, 1H), 4.12(bs, 2H), 4.39-4.42(m, 1H), 4.61(d, 2H), 4.68(d, 1H), 6.65-6.72(m, 1H), 6.90(d, 1H), 7.19(s, 1H), 7.25(d, 1H), 7.39-7.46(m, 3H), 7.52(s, 1H), 7.67(d, 1H), 7.75(s, 1H), 8.23(d, 1H), 9.00(bs, 1H), 11.26(bs, 1H), |
| 381 | 568 | 3.44-3.50 (m, 3H), 3.81 (bs, 1H), 4.15 (bs, 2H), 4.35-4.40 (m, 1H), 4.60 (d, 2H), 4.71 (d, J = 14.76 Hz, 1H), 6.70-6.77 (m, 1H), 6.93 (d, 1H), 7.19 (s, 1H), 7.31-7.40 (m, 2H), 7.63 (s, 1H), 7.83-7.90 (m, 3H), 7.96 (s, 1H), 8.23 (d, 1H), 9.02 (s, 1H), 10.95 (bs, 1H). |
| 382 | 581 | 2.90-2.94(m, 2H), 3.06(t, 2H), 3.40-3.42(dd, 2H), 3.67(s, 2H), 4.73(d, 2H), 5.81(t, 1H), 6.28-6.35(m, 1H), 6.57(d, 1H), 7.08(dd, 1H), 7.26-7.33(m, 5H), 7.48(s, 1H), 7.77(s, 1H). |
| 383 | 581 | 2.87(t, 2H), 3.07(t, 2H), 3.40(d, 2H), 3.83(s, 2H), 4.73(d, 2H), 5.92(t, 1H), 6.26-6.34(m, 1H), 6.56(d, 1H), 7.03-7.05(dd, 1H), 7.21(d, 1H), 7.26-7.32(m, 4H), 7.48(s, 1H), 7.69(d, 1H). |
| 384 | 593 | 3.36(bs, 2H), 3.46-3.51(m, 1H), 3.80-3.83(m, 1H), 4.09-4.12(m, 2H), 4.35-4.41(dd, 1H), 4.57(d, 2H), 4.68(d, 1H), 6.57-6.64(m, 1H), 6.91(d, 1H), 7.32(d, 1H), 7.40-7.42(dd, 1H), 7.46(d, 1H), 7.54(s, 1H), 7.62-7.69(m, 3H), 7.88(d, 1H), 8.40(d, 1H), 9.00(t, 1H), 10.91(bs, 1H). |

TABLE 3-continued

Example Mass and NMR Data

| Ex# | Mass | 1H-NMR(400 MHz, DMSO-d6) δ ppm |
|---|---|---|
| 385 | 610 | 2.85(bs, 2H), 3.06(bs, 2H), 3.48-3.49(m, 2H), 3.68(s, 2H), 4.54(d, H), 6.85(d, 1H), 7.00-7.07(m, 1H), 7.19(d, 1H), 7.43(d, 1H), 7.46(s, 1H), 7.51(s, 1H), 7.73(d, 1H), 7.83(d, 1H), 8.16(d, 1H), 8.39(d, 1H), 8.62(bs, 1H), 8.90(s, 1H). |
| 386 | 584 | 3.31(m, 1H), 3.38-3.50(m, 2H), 3.80-3.82(m, 1H), 4.14-4.16(m, 2H), 4.36-4.41(dd, 1H), 4.57(d, 2H), 4.69(d, 1H), 6.76-6.83(m, 1H), 6.99(d, 1H), 7.32(d, 1H), 7.44-7.46(dd1H), 7.54(s, 1H), 7.57-7.59(dd, 1H), 7.64(s, 1H), 7.76-7.79(dd, 1H), 7.88(d, 1H), 7.98(t, 1H), 8.40(d, 1H), 9.01(t, 1H), 11.17(bs, 1H), |
| 387 | 577 | 3.35(bs, 2H), 3.52(bs, 1H), 3.79-3.82(m, 1H), 4.13-4.15(m, 2H), 4.34-4.40(m, 1H), 4.56(d, 2H), 4.68(d, 1H), 6.51-6.58(m, 1H), 6.73-6.77(m, 1H), 6.99(d, 1H), 7.13-7.21(m, 1H), 7.30-7.36(m, 1H), 7.45(d, 1H), 7.54(s, 1H), 7.67(s, 1H), 7.75-7.81(m, 1H), 7.88(d, 1H), 8.39(d, 1H), 8.98(t, 1H), 10.84(s, 1H) |
| 388 | 593 | 3.34-3.39(m, 2H), 3.50(bs, 1H), 3.81(bs, 1H), 4.08-4.11(m, 2H), 4.38-4.40(m, 1H), 4.56(d, 2H), 4.70(d, 1H), 6.50-6.54(m, 1H), 6.89(d, 1H), 7.32(d, 1H), 7.44-7.49(m, 2H), 7.54-7.57(m, 2H), 7.65(s, 1H), 7.84-7.89(m, 2H), 8.39(d, 1H), 8.98(bs, 1H), 10.59(bs, 1H). |
| 389 | 577 | 3.30-3.39(m, 2H), 3.49(bs, 1H), 3.81-3.83(m, 1H), 4.10-4.11(m, 2H), 4.38-4.40(m, 1H), 4.56(d, 2H), 4.70(d, 1H), 6.46-6.54(m, 1H), 6.89(d, 1H), 7.32(d, 1H), 7.40(bs, 1H), 7.44-7.50(m, 2H), 7.54(s, 1H), 7.65(s, 1H), 7.69-7.74(m, 1H), 7.88(d, 1H), 8.40(d, 1H), 8.96-8.98(m, 1H), 10.57(bs, 1H). |
| 390 | 566 | 2.92(t, 2H), 3.12(bs, 2H), 3.46(d, 2H), 3.68(s, 2H), 4.65(d, 2H), 5.91(t, 1H), 6.44-6.52(m, 1H), 6.65(d, 1H), 7.12(d, 1H), 7.22-7.24(m, 2H), 7.31(s, 1H), 7.47(d, 2H), 7.60(d, 2H), 7.81(d, 1H), 8.37(d, 1H). |
| 391 | 575 | 2.80-2.81(m, 2H), 3.01(bs, 2H), 3.35(d, 2H), 3.62(s, 2H), 4.50(d, 2H), 6.38-6.45(m, 1H), 6.61(d, 1H), 7.15(d, 1H), 7.36(d, 2H), 7.35-7.42(m, 2H), 7.47-7.49(m, 3H), 7.80(d, 1H), 8.35(d, 1H), 8.59(t, 1H). |
| 392 | 609 | 2.83(t, 2H), 3.04(m, 2H), 3.39(d, 2H), 3.65(s, 2H), 4.53(d, 2H), 6.51-6.55(m, 2H), 7.18(d, 1H), 7.42-7.44(m, 2H), 7.47-7.51(m, 2H), 7.58(s, 1H), 7.78(d, 1H), 7.83(d, 1H), 8.39(d, 1H), 8.62(t, 1H). |
| 393 | 559 | 2.83(t, 2H), 3.03(bs, 2H), 3.33-3.38(m, 2H), 3.65(s, 2H), 4.53(d, 2H), 6.33-6.40(m, 1H), 6.63(d, 1H), 7.14-7.19(m, 3H), 7.42-7.45(m, 2H), 7.51-7.54(m, 3H), 7.83(d, 1H), 8.39(d, 1H), 8.61(t, 1H). |
| 394 | 571 | 2.82(t, 2H), 3.03(bs, 2H), 3.33-3.36(m, 2H), 3.64(s, 2H), 3.75(s, 3H), 4.53(d, 2H), 6.21-6.28(m, 1H), 6.56(d, 1H), 6.90(d, 2H), 7.18(d, 1H), 7.39-7.44(m, 4H), 7.51(s, 1H), 7.83(d, 1H), 8.39(d, 1H), 8.61(t, 1H). |
| 395 | 625 | 2.83(t, 2H), 3.04(bs, 2H), 3.40(d, 2H), 3.65(s, 2H), 4.53(d, 2H), 6.42-6.49(m, 1H), 6.67(d, 1H), 7.17-7.19(dd, 1H), 7.32(d, 2H), 7.42-7.44(m, 2H), 7.51(s, 1H), 7.61(d, 2H), 7.83(d, 1H), 8.39(d, 1H), 8.62(t, 1H). |
| 396 | 609 | 2.83-2.86(m, 2H), 3.05(bs, 2H), 3.43(d, 2H), 3.67(s, 2H), 4.53(d, 2H), 6.58-6.64(m, 1H), 6.75(d, 1H), 7.19(d, 1H), 7.42-7.45(m, 2H), 7.51(s, 1H), 7.67-7.72(m, 4H), 7.83(d, 1H), 8.39(d, 1H), 8.62(t, 1H). |
| 397 | 593 | 3.34-3.40 (m, 2H), 3.50 (bs, 1H), 3.80-3.83 (m, 1H), 4.09-4.14 (m, 2H), 4.36-4.41 (m, 1H), 4.56 (d, 2H), 4.69 (d, 1H), 6.62-6.70 (m, 1H), 6.89 (d, 1H), 7.32 (d, 1H), 7.42-7.47 (m, 3H), 7.54 (s, 2H), 7.65 (bs, 1H), 7.88 (d, 1H), 8.39 (d, 1H), 9.01 (t, 1H), 10.93 (bs, 1H). |
| 398 | 584 | 3.38 (bs, 2H), 3.50 (bs, 1H), 3.81 (bs, 1H), 4.15 (bs, 2H), 4.40.4.42 (m, 1H), 4.56 (d, 2H), 4.70 (d, 1H), 6.69-6.76 (m, 1H), 6.93 (d, 1H), 7.32 (d, 1H), 7.45 (d, 1H), 7.54 (s, 1H), 7.64 (bs, 1H), 7.84-7.89 (m, 3H), 7.96 (bs, 1H), 8.39 (d, 1H), 9.00 (bs, 1H), 10.87 (bs, 1H). |
| 399 | 600 | 3.32-3.40 (m, 2H), 3.49-3.51 (m, 1H), 3.81-3.83 (m, 1H), 4.11-4.14 (m, 2H), 4.36-4.42 (dd, 1H), 4.57 (d, 2H), 4.70 (d, 1H), 6.71-6.78 (m, 1H), 6.92 (d, 1H), 7.30-7.33 (m, 1H), 7.45-7.46 (dd, 1H), 7.54 (s, 1H), 7.63 (s, 1H), 7.88 (d, 1H), 8.03 (d, 2H), 8.07 (d, 1H), 8.40 (d, 1H), 9.01 (t, 1H), 11.04 (bs, 1H). |
| 400 | 637 | 3.40 (bs, 2H), 3.50 (bs, 1H), 3.80-3.83 (m, 1H), 4.11-4.12 (m, 2H), 4.36-4.41 (m, 1H), 4.56 (d, 2H), 4.70 (d, 1H), 6.61-6.69 (m, 1H), 6.88 (d, 1H), 7.32 (d, 1H), 7.45 (d, 1H), 7.49 (d, 1H), 7.54-7.56 (m, 2H), 7.65-7.66 (m, 2H), 7.88 (d, 1H), 8.39 (d, 1H), 9.01 (bs, 1H), 10.89 (bs, 1H). |
| 401 | 575 | 3.29(s, 1H), 3.49(hump, 2H), 3.81-3.84(m, 1H), 4.13(bs, 2H), 4.40-4.42(m, 1H), 4.60(d, 2H), 4.71(d, 1H), 6.55-6.62(m, 1H), 6.91(d, 1H), 7.19(s, 1H), 7.32(d, 1H), 7.39-7.43(m, 2H), 7.62-7.69(m, 3H), 7.89(d, 1H), 8.23(d, 1H), 9.00(bs, 1H), 10.60(bs, 1H). |
| 402 | 566 | 3.40-3.50(m, 2H), 3.72-3.84(m, 2H), 4.17(bs, 2H), 4.35-4.41(m, 1H), 4.60(d, 2H), 4.71(d, 1H), 6.75-6.80(m, 1H), 6.98(d, 1H), 7.19(s, 1H), 7.32(d, 1H), 7.59(d, 1H), 7.64(s, 1H), 7.79(d, 1H), 7.89(d, 1H), 7.98(t, 1H), 8.23(d, 1H), 9.00(bs, 1H), 10.77(bs, 1H). |
| 403 | 559 | 3.49(bs, 1H), 3.83(bs, 2H), 4.16(bs, 3H), 4.40(bs, 1H), 4.60(d, 2H), 4.70(d1H), 6.48-6.53(m, 1H), 6.99(d, 1H), 7.18(bs, 2H), 7.33(d, 2H), 7.39(d, 1H), 7.67(s, 1H), 7.77-7.81(m, 1H), 7.89(d, 1H), 8.23(d, 1H), 8.98(bs, 1H), 10.39(bs, 1H). |
| 404 | 577 | 3.49(bs, 2H), 3.84(bs, 2H), 4.12(bs, 2H), 4.40(bs, 1H), 4.60(d, 2H), 4.71(d, 1H), 6.50-6.54(m, 1H), 6.89(d, 1H), 7.19(s, 1H), 7.32(d, 1H), 7.40(d, 1H), 7.47(t, 1H), 7.57(bs, 1H), 7.65(s, 1H), 7.85(d, 1H), 7.89(d, 1H), 8.23(d, 1H), 8.99(bs, 1H), 10.52(bs, 1H), |
| 405 | 559 | 3.42-3.48(m, 2H), 3.84(bs, 2H), 4.11(bs, 2H), 4.35-4.40(m, 1H), 4.60(d, 2H), 4.70(d, 1H). 6.46-6.54(m, 1H), 6.89(d, 1H), 7.19(s, 1H), 7.32(d, 1H), 7.40(d, 2H), 7.46-7.52(q, 1H), 7.65(s, 1H), 7.71(t, 1H), 7.89(d, 1H), 8.23(d, 1H), 9.00(bs, 1H), 10.57(bs, 1H). |
| 406 | 579 | 3.34-3.49(m, 3H), 3.78-3.80(m, 1H), 4.08-4.11(m, 2H), 4.35-4.40(m, 1H), 4.60(d, 2H), 4.68(d, 1H), 6.57-6.65(m, 1H), 6.86(d, 1H), 7.19(s, 1H), 7.30-7.33(dd, 1H), 7.40(d, 1H), 7.56-7.63(m, 3H), 7.89(d, 1H), 8.23(d, 1H), 9.04(t, 1H), 11.21(bs, 1H). |
| 407 | 561 | 3.29(bs, 1H), 3.45-3.49(m, 2H), 3.79(bs, 1H), 4.12(bs, 2H), 4.38-4.41(m, 1H), 4.59(d, 2H), 4.69(d, 1H), 6.61-6.69(m, 1H), 6.90(d, 1H), 7.19-7.26(m, 2H), 7.30-7.34(m, 3H), 7.40(d, 1H), 7.64(s, 1H), 7.89(d, 1H), 8.19(s, 1H), 8.23 (d, 1H), 9.02(bs, 1H), 10.99(bs, 1H). |

TABLE 3-continued

Example Mass and NMR Data

| Ex# | Mass | 1H-NMR(400 MHz, DMSO-d6) δ ppm |
|---|---|---|
| 408 | 559 | 2.81-2.84(m, 2H), 3.03-3.06(m, 2H), 3.39(d, 2H), 3.65(s, 2H), 4.57(d, 2H), 6.41-6.49(m, 1H), 6.63(d, 1H), 7.16-7.19(m, 2H), 7.36-7.40(m, 3H), 7.45(s, 1H), 7.51(d, 2H), 7.83(d, 1H), 8.22(d, 1H), 8.63(t, 1H). |
| 409 | 581 | 2.81(t, 2H), 2.98-3.01(m, 2H), 3.38(d, 2H), 3.63(s, 2H), 4.63(d, 2H), 6.40-6.47(m, 1H), 6.63(d, 1H), 7.19(d, 1H), 7.39(d, 2H), 7.43(s, 1H), 7.51(d, 2H), 7.66(s, 1H), 7.80(d, 1H), 8.71(t, 1H). |
| 410 | 577 | 3.37(bs, 2H), 3.46(bs, 1H), 3.81-3.84(m, 1H), 4.06-4.15(m, 2H), 4.40-4.46(m, 1H), 4.59(d, 2H), 4.77(d, 1H), 6.57-6.64(m, 1H), 6.91(d, 1H), 7.42(d, 1H), 7.47(d, 1H), 7.55(s, 1H), 7.62-7.70(m, 3H), 7.98(d, 1H), 8.04(s, 1H), 8.41(d, 1H), 9.09(t, 1H), 10.83(bs, 1H). |
| 411 | 566 | 3.30(bs, 1H), 3.53-3.57(m, 2H), 3.82(bs, 1H), 4.15-4.19(m, 2H), 4.42-4.45(m, 1H), 4.58(d, 2H), 4.79(d, 1H), 6.74-6.82(m, 1H), 7.99(d, 1H), 7.46(d, 1H), 7.55-7.66(m, 3H). 7.78(d, 1H), 7.97-8.03(m, 3H), 8.40(d, 1H), 9.09(bs, 1H), 10.99(bs, 1H), |
| 412 | 559 | 3.28(bs, 1H), 3.50-3.51(m, 2H), 3.82-3.85(m, 1H), 4.14-4.18(m, 2H), 4.40-4.45(m, 1H), 4.59(d, 2H), 4.78(d, 1H), 6.50-6.57(m, 1H), 7.00(d, 1H), 7.19(t, 1H), 7.34(m, 1H), 7.46(d, 2H), 7.55(s, 1H), 7.64(d, 1H), 7.77-7.83(m, 1H), 7.98(d, 1H), 8.06(s, 1H), 8.40(d, 1H), 10.64(bs, 1H). |
| 413 | 577 | 3.37(bs, 2H), 3.47-3.55(bs, 1H), 3.80-3.83(m, 1H), 4.06-4.13(m, 2H), 4.40-4.45(dd, 1H), 4.58(d, 2H), 4.77(d, 1H), 6.51-6.59(m, 1H), 6.90(d, 1H), 7.45-7.49(m, 2H), 7.55-7.59(m, 2H), 7.63-7.65(m, 1H), 7.83-7.85(dd, 1H), 7.98(d, 1H), 8.05(s, 1H), 8.41(d, 1H), 9.11(t, 1H), 10.97(bs, 1H). |
| 414 | 561 | 3.38(bs, 2H), 3.46-3.53(m, 1H), 3.80-3.83(m, 1H), 4.09-4.14(m, 2H), 4.39-4.45(dd, 1H), 4.58(d, 2H), 4.75(d, 1H), 6.50-6.57(m, 1H), 6.90(d, 1H), 7.37-7.41(m, 1H), 7.45-7.52(m, 2H), 7.55(s, 1H), 7.63-7.65(m, 1H), 7.68-7.73(m, 1H), 7.98(d, 1H), 8.05(s, 1H), 8.41(d, 1H), 9.12(t, 1H), 11.07(bs, 1H). |
| 415 | 561 | 2.90(t, 2H) 3.10(t, 2H) 3.42(dd, 2H) 3.67(s, 2H) 4.66(d, 2H) 6.33(dt, 1H) 6.47(t, 1H) 6.55(d, 1H) 6.90(s, 1H) 7.10(dd, 1H) 7.13-7.19(m, 2H) 7.33(t, 1H) 7.44(dd, 1H) 7.61(d, 1H) 7.87(d, 1H) 8.13(d, 1H). |
| 416 | 552 | 3.35(bs, 2H), 3.53(bs, 1H), 3.82(bs, 1H), 4.15-4.19(m, 2H), 4.44(bs, 1H), 4.61(d, 2H), 4.78(d, 1H), 6.76-6.83(m, 1H), 6.99(d, 1H), 7.20(s, 1H), 7.40(d, 1H), 7.57-7.65(m, 2H), 7.78(d, 1H), 7.96-8.03(m, 3H), 8.23(d, 1H), 9.13(s, 1H), 11.16(bs, 1H). |
| 417 | 545 | 3.38-3.45(m, 2H) 3.47(br s, 1H) 3.80(br dd, 1H) 4.05-4.24(m, 2H) 4.41(br dd, 1H) 4.62(d, 2H) 4.73(br d, 1H) 6.60(dt, 1H) 7.00(d, 1H) 7.18(dd, 1H) 7.21(s, 1H) 7.33(ddd, 1H) 7.38-7.44(m, 1H) 7.63(dd, 1H) 7.78(td, 1H) 7.98(d, 1H) 8.06(s, 1H) 8.23(d, 1H) 9.16(t, 1H) 11.43(br s, 1H). |
| 418 | 561 | 3.38(bs, 2H), 3.51(bs, 1H), 3.81(bs, 1H), 4.08-4.13(m, 2H), 4.40-4.43(m, 1H), 4.62(d, 2H), 4.78(d, 1H), 6.51-6.58(m, 1H), 6.89(d, 1H), 7.20(s, 1H), 7.40-7.41(m, 1H), 7.47(t, 1H), 7.55-7.59(m, 1H), 7.64(d, 1H), 7.84(dd, 1H), 7.98(d, 1H), 8.04(s, 1H), 8.23(d, 1H), 9.12(bs, 1H), 10.94(bs, 1H). |
| 419 | 545 | 3.38(bs, 2H), 3.51(bs, 1H), 3.82(bs, 1H), 4.09-4.13(m, 2H), 4.40-4.44(m, 1H), 4.62(d, 2H), 4.78(d, 1H), 6.50-6.56(m, 1H), 6.92(d, 1H), 7.20(s, 1H), 7.40-7.41(m, 2H), 7.45-7.52(m, 1H), 7.64(d, 1H), 7.71(m, 1H), 7.98(d, 1H), 8.04(s, 1H), 8.23(d, 1H), 9.10(bs, 1H), 10.88(bs, 1H). |
| 420 | 534 | 2.92(br t, 2H) 3.08-3.15(m, 2H) 3.47(dd, 2H) 3.70(s, 2H) 4.67(d, 2H) 6.44-6.49(m, 1H) 6.50-6.57(m, 1H) 6.65(d, 1H) 6.91(s, 1H) 7.16(dt, 1H) 7.42-7.50(m, 3H) 7.54-7.59(m, 2H) 7.62(s, 1H) 7.88(d, 1H) 8.14(d, 1H) |
| 421 | 543 | 2.90(t, 2H) 3.04-3.13(m, 2H) 3.38-3.46(m, 2H) 3.64(s, 2H) 4.66(d, 2H) 6.31(dt, 1H) 6.50-6.62(m, 2H) 6.90(s, 1H) 7.15(dt, 1H) 7.27-7.35(m, 4 H) 7.44(dd, 1H) 7.60(s, 1H) 7.87(d, 1H) 8.14(d, 1H). |
| 422 | 577 | 2.91(t, 2H) 3.07-3.14(m, 2H) 3.43(dd, 2H) 3.68(s, 2H) 4.67(d, 2H) 6.34(dt, 1H) 6.46(br t, 1H) 6.54(d, 1H) 6.91(d, 1H) 7.16(dt, 1H) 7.22(dd, 1H) 7.38(d, 1H) 7.45(dd, 1H) 7.47(d, 1H) 7.62(s, 1H) 7.88(d, 1H) 8.15(d, 1H). |
| 423 | 577 | 3.34-3.39 (m, 2H), 3.50 (bs, 1H), 3.83 (bs, 1H), 4.12 (bs, 2H), 4.39-4.44 (m, 1H), 4.60 (d, 2H), 4.74 (d, 1H), 6.51-6.58 (m, 1H), 6.89 (d, 1H), 7.45-7.49 (m, 2H), 7.55-7.57 (m, 3H), 7.80 (d, 1H), 7.85 (d, 1H), 8.09 (s, 1H), 8.41 (d, 1H), 9.09 (bs, 1H), 10.81 (bs, 1H). |
| 424 | 561 | 3.38-3.45 (m, 3H), 3.81 (bs, 1H), 4.14-4.17 (bs, 2H), 4.39-4.45 (dd, 1H), 4.60 (d, 2H), 4.72 (d, 1H), 6.53-6.60 (m, 1H), 7.00 (d, 1H), 7.16-7.21 (m, 2H), 7.31-7.37 (m, 1H), 7.47 (d, 1H), 7.55-7.57 (m, 2H), 7.76-7.82 (m, 2H), 8.09 (s, 1H), 8.41 (d, 1H), 9.11 (t, 1H), 11.04 (bs, 1H). |
| 425 | 593 | 2.87 (t, 2H), 3.10 (t, 2H), 3.44 (d, 2H), 3.72 (s, 2H), 4.57 (d, 2H), 6.57-6.66 (m, 1H), 6.76 (d, 1H), 7.42-7.47 (m, 2H) 7.54 (s, 1H), 7.63-7.73 (m, 5 H), 8.07 (s, 1H), 8.38-8.41 (m, 1H), 8.70 (t, 1H). |
| 426 | 552 | 3.37-3.41 (m, 2H), 3.48-3.52 (m, 1H), 3.83 (bs, 1H), 4.17 (bs, 2H), 4.45 (bs, 1H), 4.63 (d, 2H), 4.75 (d, 1H), 6.76-6.84 (m, 1H), 6.99 (d, 1H), 7.22 (s, 1H), 7.41 (d, 1H), 7.55-7.60 (m, 2H), 7.77-7.80 (m, 2H), 7.98 (t, 1H), 8.10 (s, 1H), 8.24 (d, 1H), 9.12 (bs, 1H), 11.12 (bs, 1H). |
| 427 | 545 | 3.35-3.46 (m, 3H), 3.81 (bs, 1H), 4.16 (bs, 2H), 4.42-4.43 (m, 1H), 4.63 (d, 2H), 4.73 (d, 1H), 6.52-6.60 (m, 1H), 6.99 (d, 1H), 7.17-7.22 (m, 2H), 7.31-7.37 (m, 1H), 7.41 (d, 1H), 7.55 (d, 1H), 7.76-7.81 (m, 2H), 8.10 (s, 1H), 8.24 (d, 1H), 9.11 (bs, 1H), 10.96 (bs, 1H). |
| 428 | 561 | .36-3.40 (m, 2H), 3.47-3.51 (m, 1H), 3.81 (bs, 1H), 4.12 (bs, 2H), 4.41-4.46 (dd, 1H), 4.63 (d, 2H), 4.73 (d, 1H), 6.52-6.60 (m, 1H), 6.89 (d, 1H), 7.22 (s, 1H), 7.41 (d, 1H), 7.47 (t, 1H), 7.55-7.58 (m, 2H), 7.80 (d, 1H), 7.83-7.86 (dd, 1H), 8.10 (s, 1H), 8.24 (d, 1H), 9.12 (t, 1H), 11.02 (bs, 1H). |
| 429 | 545 | 3.35-3.40 (m, 2H), 3.45-3.50 (m, 1H), 3.82 (bs, 1H), 4.12 (bs, 2H), 4.44 (bs, 1H), 4.63 (d, 2H), 4.73 (d, 1H), 6.50-6.57 (m, 1H), 6.89 (d, 1H), 7.22 (s, 1H), 7.40-7.41 (m, 2H), 7.45-7.52 (m, 1H), 7.56 (d, 1H), 7.69-7.74 (m, 1H), 7.80 (d, 1H), 8.10 (s, 1H), 8.24 (d, 1H), 9.11 (bs, 1H), 10.92 (bs, 1H). |

TABLE 3-continued

Example Mass and NMR Data

| Ex# | Mass | 1H-NMR(400 MHz, DMSO-d6) δ ppm |
|---|---|---|
| 430 | 496 | 8.33-8.46(m, 2H), 7.79(d, 2H), 7.67(m, 3H), 7.50(s, 1H), 7.42(d, 1H), 7.19(s, 1H), 7.02(m, 1H), 6.61-6.78(m, 2H), 4.52(d, 2H), 3.55-3.66(m, 2H), 3.42(d, 2H), 3.02(br s, 2H), 2.75-2.90(m, 2H), 2.32-2.41(m, 3H). |
| 431 | 505 | 8.35-8.44(m, 2H), 7.66(d, 1H), 7.51(d, 3H), 7.37-7.49(m, 3H), 7.19(s, 1H), 7.02(d, 1H), 6.59-6.68(m, 1H), 6.45(m, 1H), 4.52(d, 2H), 3.61(s, 2H), 3.38(br d, 2H), 2.98-3.05(m, 2H), 2.77-2.89(m, 2H), 2.32-2.40(m, 3H). |
| 432 | 539 | 8.36-8.43(m, 2H), 7.78(d, 1H), 7.66(d, 1H), 7.55-7.61(m, 1H), 7.46-7.53(m, 2H), 7.42(m, 1H), 7.19(s, 1H), 7.02(m, 1H), 6.52-6.67(m, 2H), 4.52(d, 2H), 3.61(s, 2H), 3.38(d, 2H), 3.02(br s, 2H), 2.75-2.88(m, 2H), 2.31-2.41(m, 3H). |
| 433 | 489 | 8.33-8.45(m, 2H), 7.66(d, 1H), 7.47-7.57(m, 3H), 7.32-7.47(m, 1H), 7.12-7.24(m, 3H), 6.96-7.12(m, 1H), 6.63(d, 1H), 6.29-6.44(m, 1H), 4.52(d, 2H), 3.61(s, 2H), 3.37(br d, 2H), 3.01(br s, 2H), 2.72-2.92(m, 2H), 2.30-2.42(m, 3H). |
| 434 | 555 | 8.35-8.44(m, 2H), 7.58-7.68(m, 3H), 7.50(s, 1H), 7.42(m, 1H), 7.32(d, 2H), 7.20(s, 1H), 7.02(m, 1H), 6.68(d, 1H), 6.46(m, 1H), 4.52(d, 2H), 3.61(s, 2H), 3.39(br d, 2H), 3.02(br s, 2H), 2.74-2.91(m, 2H), 2.32-2.41(m, 3H). |
| 435 | 539 | 8.36-8.44(m, 2H), 7.63-7.75(m, 5H), 7.50(s, 1H), 7.42(m, 1H), 7.20(s, 1H), 7.02(m, 1H), 6.70-6.78(m, 1H), 6.56-6.67(m, 1H), 4.52(d, 2H), 3.63(s, 2H), 3.42(br d, 2H), 3.03(br s, 2H), 2.77-2.91(m, 2H), 2.32-2.41(m, 3H). |
| 436 | 541 | 3.39(bs, 1H), 3.47-3.49(m, 2H), 3.83(bs, 1H), 4.21-4.27(m, 2H), 4.61(d, 2H), 4.87-4.89(m, 1H), 5.16(d, 1H), 6.62-6.68(m, 1H), 6.90-6.99(m, 1H), 7.47-7.49(m, 3H), 7.52-7.54(m, 1H), 7.56(s, 1H), 7.61(d, 2H), 7.64-7.66(m, 1H), 7.78-7.83(m, 1H), 7.98(d, 1H), 8.03-8.10(m, 2H), 8.42(d, 1H), 9.17(bs, 1H), 10.68(bs, 1H). |
| 437 | 589 | 3.28-3.37(m, 2H), 3.42-3.47(m, 1H), 3.77-3.81(m, 1H), 4.08-4.11(m, 2H), 4.34-4.40(m, 1H), 4.57(d, 2H), 4.65(d, 1H), 6.59-6.66(m, 1H), 6.90(d, 1H), 7.39-7.45(m, 3H), 7.53-7.55(m, 2H), 7.61-7.67(m, 2H), 7.96(d, 1H), 8.39(d, 1H), 9.00(t, 1H), 11.23(bs, 1H). |
| 438 | 580 | 3.28-3.46(m, 3H), 3.79-3.82(m, 1H), 4.15-4.20(m, 2H), 4.36-4.41(dd, 1H), 4.57(d, 2H), 4.68(d, 1H), 6.75-6.82(m, 1H), 6.98(d, 1H), 7.39-7.45(m, 2H), 7.53-7.59(m, 3H), 7.78(d, 1H), 7.96-7.99(m, 2H), 8.40(d, 1H), 8, 98(t, 1H), 11.07(bs, 1H), |
| 439 | 588 | 3.36-3.39(m, 2H), 3.45-3.51(m, 1H), 3.77-3.80(m, 1H), 4.07-4.10(m, 2H), 4.34-4.40(dd, 1H), 4.57(d, 2H), 4.66(d, 1H), 6.51-6.59(m, 1H), 6.89(d, 1H), 7.39-7.41(dd, 1H), 7.44-7.49(m, 2H), 7.53-7.57(m, 3H), 7.82-7.84(dd, 1H), 7.97(d, 1H), 8.40(d, 1H), 8.98(t, 1H), 11.12(bs, 1H). |
| 440 | 571 | 3.28-3.32(m, 2H), 3.40-3.52(m, 1H), 3.77-3.80(m, 1H), 4.07-4.11(m, 2H), 4.34-4.39(dd, 1H), 4.57(d, 2H), 4.66(d, 1H), 6.50-6.57(m, 1H), 6.89(d, 1H), 7.36-7.41(m, 2H), 7.44-7.55(m, 4H), 7.67-7.72(m, 1H), 7.97(d, 1H), 8.40(d, 1H), 8.99(t, 1H), 11.08(bs, 1H). |
| 441 | 560 | 3.31-3.36(m, 2H), 3.47-3.49(m, 1H), 3.77-3.82(m, 1H), 4.12-4.16(m, 2H), 4.35-4.41(dd, 1H), 4.56(d, 2H), 4.67(d, 1H), 6.67-6.74(m, 1H), 6.99(d, 1H), 7.39-7.41(dd, 1H), 7.44-7.45(m, 1H), 7.53-7.55(m, 2H), 7.74(d, 2H), 7.89(d, 2H), 7.97(d, 1H), 8.40(d, 1H), 8.99(t, 1H), 10.99(bs, 1H), |
| 442 | 560 | 3.32-3.38(m, 2H), 3.40-3.44(m, 1H), 3.76-3.79(m, 1H), 4.18-4.23(m, 2H), 4.56(d, 2H), 4.63-4.68(dd, 1H), 4.93(d, 1H), 6.70-6.78(m, 1H), 7.01(d, 1H), 7.24(t, 1H), 7.41-7.45(m, 2H), 7.53(s, 1H), 7.74(d, 2H), 7.8(d, 1H), 7.88(d, 2H), 8.39(d, 1H), 9.14(t, 1H), 11.24(bs, 1H), |
| 443 | 569 | 3.32-3.36(m, 1H), 3.42-3.47(m, 1H), 3.76-3.79(m, 2H), 4.08-4.11(m, 2H), 4.34-4.39(m, 1H), 4.56(d, 2H), 4.65(d, 1H), 6.52-6.57(m, 1H), 6.91(d, 1H), 7.38-7.41(dd, 1H), 7.44-7.45(m, 1), 7.47(d, 2H), 7.54-7.58(m, 4H), 7.96(d, 1H), 8.40(d, 1H), 8.99(t, 1H), 11.06(bs, 1H) |
| 444 | 569 | 3.32-3, 35(m, 2H), 3.40-3.42(m, 1H), 3.74-3.76(m, 1H), 4.12-4.16(m, 2H), 4.56(d, 2H), 4.64(dd, 1H), 6.53-6.59(m, 1H), 6.93(d, 1H), 7.22(t, 1H), 7.41-7.48(m, 4H), 7.56(t, 3H), 7.80(d, 2H), 8.40(d, 1H), 9.14(t, 1H), 11.16(bs, 1H), |
| 445 | 555 | 2.50(s, 3H), 3.31-3.50(m, 3H), 3.74-3.81(m, 1H), 4.05-4.15(m, 2H), 4.33-4.38(m, 1H), 4.55(d, 2H), 4.64(d, 1H), 6.62-6.69(m, 1H), 6.92(d, 1H), 7.26(dd, 1H), 7.38-7.47(m, 2H), 7.50-7.55(m, 2H), 7.61-7.68(m, 2H), 7.75(d, 1H), 8.38-8.41(m, 1H), 8.91(t, 1H), 11.43(bs, 1H). |
| 446 | 539 | 2.49(s, 3H), 3.31-3.50(m, 3H), 3.72-3.80(m, 1H), 4.03-4.15(m, 2H), 4.32-4.38(m, 1H), 4.55(d, 2H), 4.65(d, 1H), 6.53-6.61(m, 1H), 6.90(d, 1H), 7.25(dd, 1H), 7.38-7.54(m, 5 H), 7.65-7.75(m, 2H), 8.38-8.42(m, 1H), 8.91(t, 1H), 11.39(bs, 1H). |
| 447 | 537 | 2.49(s, 3H), 3.31-3.49(m, 3H), 3.73-3.80(m, 1H), 4.04-4.14(m, 2H), 4.32-4.37(m, 1H), 4.55(d, 2H), 4.63(d, 1H), 6.54-6.62(m, 1H), 6.92(d, 1H), 7.25(dd, 1H), 7.44-7.58(m, 7 H), 7.75(d, 1H), 8.38-8.41(m, 1H), 8.91(t, 1H), 11.43(bs, 1H). |
| 448 | 521 | 2.49(s, 3H), 3.34-3.51(m, 3H), 3.75-3.80(m, 1H), 4.03-4.13(m, 2H), 4.32-4.38(m, 1H), 4.55(d, 2H), 4.64(d, 1H), 6.46-6.54(m, 1H), 6.92(d, 1H), 7.22-7.28(m, 3H), 7.45(dd, 1H), 7.51-7.53(m, 2H), 7.57-7.63(m, 2H), 7.75(d, 1H), 8.38-8.41(m, 1H), 8.90(t, 1H), 11.33(bs, 1H). |
| 449 | 532 | 3.39(br s under H2O peak, 2H) 3.53(br s, 1H) 3.79(br s, 1H) 4.11(br dd, 2H) 4.35(br d, 2H) 4.41(br s, 1H) 4.68(br d, 1H) 6.22(dd, 1H) 6.28(d, 1H) 6.58-6.71(m, 1H) 6.91(d, 1H) 7.36(d, 1H) 7.54(dd, 1H) 7.68(d, 1H) 7.70(dd, 1H) 7.85(d, 1H) 7.90(d, 1H) 8.19(d, 1H) 9.10(t, 1H) 11.53(br s, 1H) 11.57(br s, 1H). |
| 450 | 534 | 3.39(br s, 2H) 3.49-3.62(m, 1H) 3.79(br s, 1H) 4.03-4.23(m, 2H) 4.35(br d, 2H) 4.41(br s, 1H) 4.63-4.76(m, 1H) 6.22(dd, 1H) 6.28(d, 1H) 6.70(dt, 1H) 6.91(d, 1H) 7.36(dd, 1H) 7.53-7.59(m, 2H) 7.70(dd, 1H) 7.90(dd, 1H) 8.17(d, 1H) 9.10(t, 1H) 11.52(br s, 1H) 11.58(br s, 1H). |
| 451 | 560 | 3.43-3.48(m, 2H) 3.50-3.57(m, 1H) 3.71-3.86(m, 1H) 4.15(br dd, 2H) 4.35(br d, 2H) 4.39(br s, 1H) 4.66(br d, 1H) 6.23(dd, 1H) 6.29(s, 1H) 6.66(dt, 1H) 6.99(br d, 1H) 7.36(d, 1H) 7.50(dd, 1H) 7.63(dd, 1H) 7.67(br t, 1H) 7.70(dd, 1H) 7.90(d, 1H) 8.20(d, 1H) 9.10(br t, 1H) 11.59(br s, 2H). |
| 452 | 550 | 3.45-3.48(m, 1H) 3.53(br s, 2H) 3.80(br s, 1H) 4.00-4.20(m, 2H) 4.35(br d, 2H) 4.41(br s, 1H) 4.69(br d, 1H) 6.24(dd, 1H) 6.29(s, 1H) 6.59-6.71(m, 1H) 6.88(br d, 1H) 7.37(d, 1H) 7.71(dd, 1H) 7.82(d, 2H) 7.90(d, 1H) 8.18(s, 1H) 9.11(br t, 1H) 11.61(br s, 2H). |
| 453 | 543 | 3.38-3.40(m, 1H) 3.43-3.58(m, 2H) 3.80(br d, 1H) 4.14(br dd, 2H) 4.35(br d, 2H) 4.42(br s, 1H) 4.73(br d, 1H) 6.23(dd, 1H) 6.28(s, 1H) 6.60(dt, 1H) 6.99(d, 1H) 7.18(td, 1H) 7.28- |

TABLE 3-continued

Example Mass and NMR Data

| Ex# | Mass | 1H-NMR(400 MHz, DMSO-d6) δ ppm |
|---|---|---|
| | | 7.35(m, 1H) 7.36(d, 1H) 7.62(dd, 1H) 7.78(td, 1H) 7.94(d, 1H) 8.05(s, 1H) 9.03(br t, 1H) 11.50(br s, 2H). |
| 454 | 532 | 3.41(br s, 2H) 3.48-3.56(m, 1H) 3.78-3.87(m, 1H) 4.07-4.25(m, 2H) 4.35(br d, 2H) 4.43(br dd, 1H) 4.76(br d, 1H) 6.23(dd, 1H) 6.29(d, 1H) 6.74(dt, 1H) 7.01(d, 1H) 7.36(d, 1H) 7.63(dd, 1H) 7.72-7.77(m, 2H) 7.86-7.91(m, 2H) 7.94(d, 1H) 8.05(s, 1H) 9.01(t, 1H) 11.33(br s, 1H) 11.53(br s, 1H). |
| 455 | 587 | 3.21(s, 3H), 3.35-3.55(m, 3H), 3.78-3.84(m, 1H), 4.07-4.20(m, 2H), 4.42-4.47(m, 1H), 4.59(d, 2H), 4.76(d, 1H), 6.62-6.70(m, 1H), 6.94(d, 1H), 7.40-7.49(m, 2H), 7.54-7.58(m, 1H), 7.62-7.68(m, 2H), 7.84(dd, 1H), 8.00(d, 1H), 8.21-8.24(m, 1H), 8.38-8.42(m, 1H), 9.22(t, 1H), 11.49(bs, 1H). |
| 456 | 571 | 3.21(s, 3H), 3.35-3.54(m, 3H), 3.76-3.84(m, 1H), 4.08-4.22(m, 2H), 4.40-4.46(m, 1H), 4.58(d, 2H), 4.75(d, 1H), 6.57-6.65(m, 1H), 7.01(d, 1H), 7.15-7.22(m, 1H), 7.29-7.35(m, 1H), 7.47(dd, 1H), 7.54-7.58(m, 1H), 7.75-7.85(m, 2H), 8.00(d, 1H), 8.21-8.25(m, 1H), 8.38-8.42(m, 1H), 9.23(t, 1H), 11.56(bs, 1H). |
| 457 | 569 | 3.21(s, 3H), 3.34-3.54(m, 3H), 3.74-3.84(m, 1H), 4.04-4.19(m, 2H), 4.41-4.46(m, 1H), 4.58(d, 2H), 4.74(d, 1H), 6.55-6.63(m, 1H), 6.95(d, 1H), 7.45-7.51(m, 3H), 7.54-7.59(m, 3H), 7.84(dd, 1H), 8.00(d, 1H), 8.21-8.24(m, 1H), 8.38-8.42(m, 1H), 9.24(t, 1H), 11.58(bs, 1H). |
| 458 | 605 | 3.21(s, 3H), 3.35-3.56(m, 3H), 3.77-3.84(m, 1H), 4.06-4.18(m, 2H), 4.41-4.47(m, 1H), 4.58(d, 2H), 4.76(d, 1H), 6.64-6.71(m, 1H), 6.93(d, 1H), 7.47(dd, 1H), 7.52-7.57(m, 2H), 7.68(d, 1H), 7.83-7.87(m, 2H), 8.00(d, 1H), 8.21-8.24(m, 1H), 8.38-8.42(m, 1H), 9.24(t, 1H), 11.62(bs, 1H) |
| 459 | 553 | 3.21(s, 3H), 3.36-3.52(m, 3H), 3.76-3.82(m, 1H), 4.01-4.17(m, 2H), 4.41-4.46(m, 1H), 4.58(d, 2H), 4.75(d, 1H), 6.47-6.55(m, 1H), 6.94(d, 1H), 7.22-7.28(m, 2H), 7.46(dd, 1H), 7.53-7.66(m, 3H), 7.84(dd, 1H), 8.00(d, 1H), 8.21-8.25(m, 1H), 8.38-8.42(m, 1H), 9.23(t, 1H), 11.51(bs, 1H). |
| 460 | 577 | 3.45(br t, 2H) 3.68(br s, 2H) 4.11(br d, 2H) 4.55(br s, 2H) 4.71(s, 2H) 6.50(dt, 1H) 6.96(br d, 1H) 7.14(s, 1H) 7.36-7.44(m, 4 H) 7.54(d, 3H) 7.72(dd, 1H) 7.93-8.00(m, 2H) 8.20(d, 1H) 8.30(dd, 1H) 9.06(d, 1H). |
| 461 | 585 | 2.67(q, 2H) 2.91(t, 2H) 3.18(br t, 2H) 3.68(s, 2H) 4.68(d, 2H) 6.34(dt, 1H) 6.58(d, 1H) 6.98(s, 1H) 7.02(t, 1H) 7.22(dt, 1H) 7.28-7.38(m, 6 H) 7.40(dd, 1H) 7.47(d, 1H) 7.49-7.53(m, 2H) 7.87(dd, 1H) 8.16(d, 1H) |
| 462 | 585 | 3.37(br s, 2H) 3.44(br s, 2H) 3.86(br d, 2H) 4.26(br s, 2H) 4.67(d, 2H) 6.33(dt, 1H) 6.73(d, 1H) 6.98(s, 1H) 7.23(br d, 1H) 7.30-7.40(m, 7 H) 7.42-7.49(m, 2H) 7.51(dd, 1H) 7.55(t, 1H) 7.84(d, 1H) 8.19(d, 1H). |
| 463 | 569 | 3.04(br t, 2H) 3.22(br s, 2H) 3.54(br d, 2H) 3.83(br s, 2H) 4.70(d, 2H) 6.36(dt, 1H) 6.41(br s, 1H) 6.62(d, 1H) 6.96(s, 1H) 7.12(t, 2H) 7.21(br d, 1H) 7.33(q, 4 H) 7.44(dd, 1H) 7.49(d, 1H) 7.51-7.58(m, 2H) 7.83(d, 1H) 8.21(d, 1H) |
| 464 | 534 | 3.34(m, 2H), 3.51(m, 1H), 3.80-3.83(m, 1H), 4.12(bs, 2H), 4.38-4.34(m, 1H), 4.60(d, 2H), 4.69(d, 1H), 6.49-6.56(m, 1H), 6.91(d, 1H), 7.38(s, 1H), 7.46-7.49(m, 3H), 7.56-7.62(m, 4H), 7.75-7.78(dd, 1H), 8.03(s, 1H), 8.35(s, 1H), 8.39(d, 2H), 9.02(t, 1H), 10.69(s, 1H). |
| 465 | 550 | 3.34(m, 2H), 3.42-3.49(m, 1H), 3.80-3.83(m, 1H), 4.12-4.14(m, 2H), 4.37-4.43(m, 1H), 4.60(d, 2H), 4.69(d, 1H), 6.58-6.66(m, 1H), 6.91(d, 1H), 7.38-7.47(m, 3H), 7.56(s, 1H), 7.59-7.65(m, 2H), 7.66-7.69(m, 1H), 7.77(d, 1H), 8.04(s, 1H), 8.35-8.40(m, 2H), 9.05(t, 1H), 10.92(s, 1H). |
| 466 | 518 | 3.34-3.41(m, 2H), 3.49-3.50(m, 1H), 3.79-3.82(m, 1H), 4.11(m, 2H), 4.37-4.42(m, 1H), 4.60(d, 2H), 4.68(d, 1H), 6.42-6.49(m, 1H), 6.91(d, 1H), 7.25(t, 2H), 7.38(s, 1H), 7.47(d, 1H), 7.56(s, 1H), 7.59-7.62(m, 3H), 7.76(d, 1H), 8.04(s, 1H), 8.35(s, 1H), 8.39(d, 1H), 9.04(t, 1H), 10.77(s, 1H). |
| 467 | 552 | 3.33-3.42(m, 2H), 3.50-3.53(m, 1H), 3.80-3.82(m, 1H), 4.13-4.16(m, 2H), 4.40-4.44(m, 1H), 4.58(d, 2H), 4.73(d, 1H), 6.57-6.65(m, 1H), 6.91(d, 1H), 7.33(s, 1H), 7.42-7.46(m, 2H), 7.54(s, 1H), 7.62-7.71(m, 2H), 7.80-7.88(m, 2H), 7.97(s, 1H), 8.15(s, 1H), 8.40(d, 1H), 8.97(t, 1H), 10.62(s, 1H). |
| 468 | 613 | 1.38(t, 3H), 3.31(bs, 2H), 3.45(d, 1H), 3.76-3.79(m, 1H), 4.07-4.12(m, 4H), 4.32(bs, 1H), 4.56-4.65(m, 3H), 6.47-6.54(m, 1H), 6.90(d, 1H), 7.42(s, 1H), 7.46-7.49(m, 3H), 7.56-7.59(m, 3H), 7.85(s, 1H), 8.40(d, 1H), 8.89(t, 1H), 10.79(s, 1H). |
| 469 | 593 | 3.43-3.50(m, 3H), 3.75-3.76(m, 1H), 4.04-4.12(m, 2H), 4.31-4.36(m, 1H), 4.55-4.61(m, 3H), 6.54-6.59(m, 1H), 6.92(d, 1H), 7.45-7.48(m, 3H), 7.54-7.57(m, 3H), 7.78(d, 1H), 7.89(d, 1H), 8.39(d, 1H), 9.08(t, 1H), 11.61(bs, 1H). |
| 470 | 584 | 3.41(bs, 2H), 3.47-3.51(m, 1H), 3.77-3.79(m, 1H), 4.11-4.16(m, 2H), 4.32-4.38(m, 1H), 4.57(d, 2H), 4.62(d, 1H), 6.70-6.76(m, 1H), 7.00(d, 1H), 7.45(d, 1H), 7.55(s, 1H), 7.72-7.78(m, 3H), 7.89(d, 3H), 8.39(d, 1H), 9.05(t, 1H), 11.51(bs, 1H). |
| 471 | 577 | 3.38-3.41(m, 3H), 3.76(bs, 1H), 4.05-4.12(m, 2H), 4.35-4.37(m, 1H), 4.56-4.62(m, 3H), 6.43-6.50(m, 1H), 6.91(d, 1H), 7.25(t, 2H), 7.45-7.46(m, 1H), 7.55-7.60(m, 3H), 7.78(d, 1H), 7.89(d, 1H), 8.39(d, 1H), 9.04(t, 1H), 11.36(bs, 1H). |
| 472 | 577 | 3.41(bs, 2H), 3.51(bs, 1H), 3.78(bs, 1H), 4.09-4.12(m, 2H), 4.34-4.36(m, 1H), 4.60-4.65(m, 3H), 6.50-6.55(m, 1H), 6.91(d, 1H), 7.20(s, 1H), 7.39(d, 1H), 7.48(d, 2H), 7.57(d, 2H), 7.77(d, 1H), 7.90(d, 1H), 8.22(d, 1H), 9.00(bs, 1H), 11.03(bs, 1H). |
| 473 | 551 | |
| 474 | 568 | 2.85(d, 2H), 3.04(s, 2H), 3.48(d, 2H), 3.65(s, 2H), 4.52(d, 2H), 5.03(d, 4H), 6.85(d, 1H), 7.00-7.07(m, 1H), 7.30(s, 1H), 7.42(s, 1H), 7.50(s, 1H), 7.69-7.73(m, 2H), 8.16(dd, 1H), 8.38(d, 1H), 8.49(t, 1H), 8.89(s, 1H). |
| 475 | 542 | 3.34-3.50(m, 3H), 3.77-3.80(m, 1H), 4.13-4.16(m, 2H), 4.34-4.39(m, 1H), 4.54(d, 2H), 4.64(d, 1H), 5.07(d, 4H), 6.79-6.85(m, 1H), 6.99(d, 1H), 7.44-7.45(m, 2H), 7.53(s, 1H), 7.56-7.59(m, 1H), 7.74(s, 1H), 7.76-7.81(m, 1H), 7.97(t, 1H), 8.39(d, 1H), 8.92(t, 1H), 11.35(bs, 1H). |

TABLE 3-continued

Example Mass and NMR Data

| Ex# | Mass | 1H-NMR(400 MHz, DMSO-d6) δ ppm |
|---|---|---|
| 476 | 535 | 3.37-3.50(m, 3H), 3.75-3.78(m, 1H), 4.11-4.16(m, 2H), 4.31-4.36(m, 1H), 4.54(d, 2H), 4.59(d, 1H), 5.07(d, 4H), 6.59-6.63(m, 1H), 6.98(d, 1H), 7.15-7.20(m, 1H), 7.30-7.36(m, 1H), 7.45(bs, 2H), 7.53(s, 1H), 7.73-7.80(m, 2H), 8.38(d, 1H), 8.92(t, 1H), 11.40(bs, 1H), |
| 477 | 551 | 3.32-3.33(m, 2H), 3.43-3, 50(m, 1H), 3.76-3, 79(m, 1H), 4.07-4, 12(m, 2H), 4.32-4.41(m, 1H), 4.54(d, 2H), 4.62(d, 1H), 5.06(d, 4H), 6.53-6.60(m, 1H), 6.89(d, 1H), 7.44-7.48(m, 3H), 7.53-7.57(m, 2H), 7.74(s, 1H), 7.82(dd, 1H), 8.39(d, 1H), 8.91(t, 1H), 11.23(bs, 1H), |
| 478 | 535 | 3.32-3.36(m, 2H), 3.48(bs, 1H), 3.78-3.81(m, 1H), 4.08-4.11(m, 2H), 4.33-4.39(m, 1H), 4.55(d, 2H), 4.64(d, 1H), 5.07(d, 4H), 6.49-6.57(m, 1H), 6.89(d, 1H), 7.38-7.53(m, 5H), 7.68-7.74(m, 2H), 8.38(d, 1H), 8.89(t, 1H), 10.92(bs, 1H), |
| 479 | 524 | 2.93(t, 2H), 3.12(t, 2H), 3.46(d, 2H), 3.69(s, 2H), 4.64(d, 2H), 5.14(d, 4H), 5.91(t, 1H), 6.45-6.53(m, 1H), 6.64(d, 1H), 7.19(s, 1H), 7.21(dd, 1H), 7.31(d, 1H), 7.47(d, 2H), 7.60(d, 2H), 7.69(s, 1H), 8.37(d, 1H). |
| 480 | 533 | 2.82(t, 2H), 3.02(s, 2H), 3.38(d, 2H), 3.62(s, 2H), 4.52(d, 2H), 5.03(d, 4H), 6.40-6.48(m, 1H), 6.63(d, 1H), 7.29(s, 1H), 7.37-7.42(m, 3H), 7.51(d, 3H), 7.69(s, 1H), 8.38(d, 1H), 8.48(t, 1H). |
| 481 | 517 | 2.82(s, 2H), 3.02(s, 2H), 3.37(d, 2H), 3.62(s, 2H), 4.52(d, 2H), 5.03(d, 4H), 6.32-6.40(m, 1H), 6.63(d, 1H), 7.16(t, 2H), 7.29(s, 1H), 7.42(d, 1H), 7.50-7.54(m, 3H), 7.69(s, 1H), 8.38(d, 1H), 8.48(t, 1H). |
| 482 | 567 | 2.85(d, 2H), 3.03(s, 2H), 3.42(d, 2H), 3.64(s, 2H), 4.52(d, 2H), 5.03(d, 4H), 6.56-6.64(m, 1H), 6.74(d, 1H), 7.29(s, 1H), 7.42(d, 1H), 7.50(s, 1H), 7.67-7.74(m, 5H), 8.38(d, 1H), 8.50(t, 1H). |
| 483 | 517 | 2.82(t, 2H), 3.03(s, 2H), 3.38(d, 2H), 3.62(s, 2H), 4.55(d, 2H), 5.03(d, 4H), 6.41-6.48(m, 1H), 6.63(d, 1H), 7.15(s, 1H), 7.29(s, 1H), 7.35-7.39(m, 3H), 7.51(d, 2H), 7.69(s, 1H), 8.21(d, 1H), 8.49(t, 1H). |
| 484 | 535 | 3.31-3.33(m, 2H), 3.46-3.48(m, 1H), 3.79-3.81(m, 1H), 4.12-4.13(m, 2H), 4.34-4.39(m, 1H), 4.58(d, 2H), 4.64(d, 1H), 5.07(d, 4H), 6.57-6.64(m, 1H), 6.90(d, 1H), 7.17(s, 1H), 7.38-7.42(m, 2H), 7.45(s, 1H), 7.62(d, 1H), 7.65-7.70(m, 1H), 7.75(s, 1H), 8.22(d, 1H), 8.89(t, 1H), 10.82(bs, 1H), |
| 485 | 526 | 3.33-3.36(m, 2H), 3.50-3.52(m, 1H), 3.79-3.82(m, 1H), 4.16-4.19(m, 2H), 4.37-4.38(m, 1H), 4.58(d, 2H), 4.66(d, 1H), 5.07(d, 4H), 6.75-6.82(m, 1H), 6.98(d, 1H), 7.17(s, 1H), 7.38(d, 1H), 7.44(s, 1H), 7.58(d, 1H), 7.75(s, 1H), 7.78(d, 1H), 7.98(t, 1H), 8.22(d, 1H), 8.90(bs, 1H), 10.95(bs, 1H). |
| 486 | 519 | 3.32-3.35(m, 2H), 3.42-3.45(m, 1H), 3.75-3.78(m, 1H), 4.13-4.16(m, 2H), 4.32-4.35(m, 1H), 4.58(d, 2H), 4.61-4.63(m, 1H), 5.07(d, 4H), 6.57-6.61(m, 1H), 6.98(d, 1H), 7.16-7.20(m, 2H), 7.30-7.39(m, 2H), 7.45(s, 1H), 7.74(s, 1H), 7.77-7.81(m, 1H), 8.22(d, 1H), 8.91(t, 1H), 11.16(bs, 1H). |
| 487 | 535 | 3.33-3.39(m, 2H), 3.41-3.49(m, 1H), 3.79-3.81(m, 1H), 4.11-4.12(m, 2H), 4.34-4.39(m, 1H), 4.58(d, 2H), 4.65(d, 1H), 5.07(d, 4H), 6.50-6.58(m, 1H), 6.88(d, 1H), 7.17(s, 1H), 7.38(d, 1H), 7.45-7.49(m, 2H), 7.56-7.58(m, 1H), 7.74(s, 1H), 7.83-7.86(dd, 1H), 8.22(d, 1H), 8.89(t, 1H), 10.82(bs, 1H). |
| 488 | 519 | 3.33-3.37(m, 2H), 3.46-3.349(m, 1H), 3.78-3.81(m, 1H), 4.10-4.11(m, 2H), 4.34-4.39(m, 1H), 4.58(d, 2H), 4.64(d, 1H), 5.07(d, 4H), 6.49-6.56(m, 1H), 6.88(d, 1H), 7.17(s, 1H), 7.38(d, 2H), 7.45-7.52(m, 2H), 7.69-7.75(m, 2H), 8.22(d, 1H), 8.90(t, 1H), 10.86(bs, 1H). |
| 489 | 539 | 2.78(t, 2H), 2.95(s, 2H), 3.34(d, 2H), 3.57(s, 2H), 4.57(d, 2H), 4.98(s, 2H), 5.03(s, 2H), 6.37-6.44(m, 1H), 6.60(d, 1H), 7.25(s, 1H), 7.36(d, 2H), 7.48(d, 2H), 7.63(d, 2H), 8.54(t, 1H). |
| 490 | 533 | 2.78(t, 2H), 3.01(bs, 2H), 3.36(d, 2H), 3.70(s, 2H), 4.52(d, 2H), 5.05(s, 2H), 5.25(s, 2H), 6.40-6.47(m, 1H), 6.63(d, 1H), 7.12(d, 1H), 7.38(d, 2H), 7.42(d, 1H), 7.51(d, 3H), 7.69(d, 1H), 8.38(d, 1H), 8.55(t, 1H). |
| 491 | 562 | 2.61(s, 3H), 3.36(s, 2H), 3.48(bs, 1H), 3.79(bs, 1H), 4.11(bs, 2H), 4.39(bs, 1H), 4.58(d, 2H), 4.70(d, 1H), 6.50-6.57(m, 1H), 6.91(d, 1H), 7.43-7.49(m, 3H), 7.56-7.58(m, 3H), 7.71(s, 1H), 8.24(s, 1H), 8.39(d, 1H), 9.03(bs, 1H), 11.11(bs, 1H), |
| 492 | 653 | 3.39-3.50(m, 3H), 3.78(bs, 1H), 4.06-4.12(m, 2H), 4.33-4.38(m, 1H), 4.56-4.57(m, 2H), 4.67(d, 1H), 6.48-6.55(m, 1H), 6.91(d, 1H), 7.45-7.49(m, 3H), 7.55-7.58(m, 3H), 7.88(s, 1H), 8.10(s, 1H), 8.39(d, 1H), 9.02(t, 1H), 11.04(s, 1H). |
| 493 | 546 | 3.37-3.43(m, 3H), 3.77(bs, 1H), 3.92(s, 3H), 4.11(bs, 2H), 4.31-4.36(m, 1H), 4.56-4.65(m, 3H), 6.52-6.60(m, 1H), 6.91(d, 1H), 7.39(s, 1H), 7.45-7.48(m, 3H), 7.55-7.58(m, 3H), 8.13(s, 1H), 8.38(d, 1H), 8.96(t, 1H), 11.39(s, 1H). |
| 494 | 589 | 2.39(s, 3H), 3.32-3.48(m, 3H), 3.77-3.80(m, 1H), 4.07-4.10(m, 2H), 4.33-4.39(m, 1H), 4.56(d, 2H), 4.66(d, 1H), 6.49-6.57(m, 1H), 6.93(d, 1H), 7.45-7.49(m, 3H), 7.53-7.60(m, 4H), 7.78(s, 1H), 8.39(d, 1H), 8.97(t, 1H), 10.92(bs, 1H). |
| 495 | 593 | 3.31(bs, 1H), 3.47(bs, 2H), 3.78-3.81(m, 1H), 4.07-4.12(m, 2H), 4.34-4.39(m, 1H), 4.56(d, 2H), 4.67(d, 1H), 6.49-6.55(m, 1H), 6.91(d, 1H), 7.44-7.49(m, 3H), 7.55-7.58(m, 3H), 7.88-7.90(m, 2H), 8.39(d, 1H), 8.99-9.00(m, 1H), 10.87(bs, 1H). |
| 496 | 609 | 3.35(bs, 2H), 3.48(bs, 1H), 3.79-3.82(m, 1H), 4.09-4.11(m, 2H), 4.35-4.40(m, 1H), 4.55(d, 2H), 4.70(d, 1H), 6.49-6.54(m, 1H), 6.91(d, 1H), 7.44-7.49(m, 3H), 7.55-7.58(m, 3H), 7.89(s, 1H), 8.04(s, 1H), 8.40(d, 1H), 9.04(bs, 1H), 10.76(bs, 1H). |
| 497 | 653 | 3.29(bs, 1H), 3.45-3.49(m, 2H), 3.79(bs, 1H), 4.11(bs, 2H), 4.35-4.39(m, 1H), 4.57(d, 2H), 4.70(d, 1H), 6.49-6.54(m, 1H), 6.91(d, 1H), 7.45-7.49(m, 3H), 7.55-7.58(m, 3H), 7.86(s, 1H), 8.15(s, 1H), 8.40(d, 1H), 9.04(bs, 1H), 10.75(bs, 1H). |
| 498 | 637 | 3.40(bs, 2H), 3.50(bs, 1H), 3.81(bs, 1H), 4.09-4.13(m, 2H), 4.33-4.39(m, 1H), 4.60(d, 2H), 4.73(d, 1H), 6.46-6.54(m, 1H), 6.91(d, 1H), 7.46-7.49(m, 3H), 7.57-7.59(m, 3H), 8.19(s, 2H), 8.41(d, 1H), 9.13(bs, 1H), 10.82(bs, 1H). |
| 499 | 609 | 3.39-3.50(m, 3H), 3.78(bs, 1H), 4.08-4.12(m, 2H), 4.34-4.37(m, 1H), 4.56-4.58(m, 2H), 4.66(d, 1H), 6.48-6.56(m, 1H), 6.91(d, 1H), 7.45-7.49(m, 3H), 7.55-7.58(m, 3H), 7.90(s, 1H), 7.98(s, 1H), 8.40(d, 1H), 9.04(bs, 1H), 11.15(bs, 1H). |
| 500 | 584 | 3.38-3.40(m, 2H), 3.46-3.50(m, 1H), 3.78-3.79(m, 1H), 4.06-4.14(m, 2H), 4.31-4.36(m, 1H), 4.57(d, 2H), 4.62(s, 1H), 6.31-6.33(m, 1H), 6.48(d, 1H), 6.53-6.57(m, 1H), 6.91(d, 1H), 7.30- |

TABLE 3-continued

Example Mass and NMR Data

| Ex# | Mass | 1H-NMR(400 MHz, DMSO-d6) δ ppm |
|---|---|---|
| | | 7.32(dd, 1H), 7.45-7.47(m, 3H), 7.50-7.53(m, 1H), 7.54-7.57(m, 3H), 7.64-7.66(m, 2H), 7.87(d, 1H), 8.40(d, 1H), 9.06(t, 1H), 11.36(bs, 1H). |
| 501 | 515 | |
| 502 | 600 | |
| 503 | 600 | |
| 504 | 595 | 3.17(br s, 4 H) 3.26-3.41(m, 3H) 3.76(br s, 1H) 3.81(br s, 4 H) 4.11(br s, 2H) 4.32(br dd, 1H) 4.54(br d, 2H) 4.59(br d, 1H) 6.66(dt, 1H) 6.92(br d, 1H) 7.16(br s, 2H) 7.41(dd, 1H) 7.44(d, 1H) 7.52(s, 1H) 7.63(br t, 1H) 7.66(dd, 1H) 7.72(br d, 1H) 8.39(d, 1H) 8.78(br t, 1H) 11.35(br s, 1H). |
| 505 | 576 | 3.40(br s, 4 H) 3.41-3.61(m, 3H) 3.77(br d, 1H) 3.97(br s, 4 H) 4.07-4.18(m, 2H) 4.34(br dd, 1H) 4.55(br d, 2H) 4.58(br s, 1H) 6.60(dt, 1H) 6.93(d, 1H) 7.43-7.50(m, 3H) 7.54(d, 1H) 7.55-7.59(m, 2H) 7.68(br s, 1H) 7.82(br d, 1H) 8.39(d, 1H) 8.97(br s, 1H) 11.67(br s, 1H). |
| 506 | 578 | 2.00-2.03(m, 4 H) 2.86-2.92(m, 2H) 3.12(br t, 2H) 3.27-3.31(m, 4 H) 3.42(dd, 2H) 3.65(s, 2H) 4.58(d, 2H) 6.15-6.19(m, 1H) 6.32-6.41(m, 1H) 6.42(d, 1H) 6.53(s, 1H) 6.53-6.57(m, 1H) 7.09-7.13(m, 1H) 7.17-7.21(m, 2H) 7.28-7.30(m, 1H) 7.33(t, 1H) 7.57(d, 1H) 8.32(d, 1H). |
| 507 | 578 | 2.02(dt, 4 H) 2.88-2.93(m, 2H) 3.13(br t, 2H) 3.30(br t, 4 H) 3.44(br dd, 2H) 3.66(s, 2H) 4.61(d, 2H) 6.11(t, 1H) 6.34-6.41(m, 1H) 6.43(d, 1H) 6.52(s, 1H) 6.54-6.58(m, 1H) 7.19-7.22(m, 1H) 7.24(dd, 1H) 7.31(dd, 1H) 7.39(d, 1H) 7.48(d, 1H) 7.57(d, 1H) 8.34(dd, 1H). |
| 508 | 610 | 3.32-3.40(m, 2H) 3.45(br s, 4 H) 3.48-3.57(m, 1H) 3.72-3.79(m, 1H) 3.99(br s, 4 H) 4.06-4.14(m, 2H) 4.32-4.40(m, 1H) 4.57(br d, 2H) 4.63(br s, 1H) 6.67(dt, 1H) 6.92(d, 1H) 7.43-7.49(m, 1H) 7.49-7.54(m, 2H) 7.59(d, 1H) 7.61(br d, 1H) 7.67(d, 1H) 7.84(d, 1H) 7.92(br s, 1H) 8.40(dd, 1H) 9.16(br t, 1H) 11.74(br s, 1H) |
| 509 | 594 | 3.32-3.38(m, 4 H) 3.41-3.49(m, 1H) 3.71-3.79(m, 1H) 3.92(br s, 4 H) 4.08-4.14(m, 2H) 4.25(br dd, 2H) 4.35(br dd, 1H) 4.57(br d, 2H) 4.60-4.65(m, 1H) 6.66(dt, 1H) 6.92(d, 1H) 7.28-7.34(m, 1H) 7.40(dd, 1H) 7.49(dd, 1H) 7.55(br d, 1H) 7.58(d, 1H) 7.63(br t, 1H) 7.65(br dd, 1H) 7.68-7.74(m, 1H) 8.40(dd, 1H) 9.05(br t, 1H) 11.54(br s, 1H). |
| 510 | 610 | 3.13-3.22(m, 2H) 3.39-3.44(m, 2H) 3.46-3.53(m, 2H) 3.73(br s, 6 H, under H2O peak) 4.14(br s, 2H) 4.37(br dd, 1H) 4.57(br d, 2H) 4.60(br s, 1H) 6.63-6.74(m, 1H) 6.94(br d, 1H) 7.46(dd, 1H) 7.51-7.56(m, 2H) 7.68(d, 1H) 7.71-7.78(m, 2H) 7.83-7.91(m, 2H) 7.98(br d, 1H) 8.40(dd, 1H) 9.08(br t, 1H) 11.81(br s, 1H). |
| 511 | 626 | 2.95-3.04(m, 1H) 3.28(br dd, 1H) 3.35-3.45(m, 2H) 3.46-3.52(m, 1H) 3.61(br d, 1H) 3.75(br s, 3H) 3.88-3.98(m, 1H) 4.14(br s, 2H) 4.31-4.42(m, 2H) 4.52-4.63(m, 4 H) 6.61-6.75(m, 1H) 6.89-7.00(m, 1H) 7.40(dd, 1H) 7.44-7.48(m, 1H) 7.52-7.56(m, 1H) 7.60-7.67(m, 2H) 7.80(br d, 1H) 7.89(d, 1H) 7.99-8.11(m, 1H) 8.40(d, 1H) 9.12(br t, 1H) 11.87(br s, 1H). |
| 512 | 521 | 2.91(t, 2H) 3.12(br t, 2H) 3.43(dd, 2H) 3.65(s, 2H) 3.83(s, 3H) 4.62(d, 2H) 6.10-6.17(m, 1H) 6.35(dt, 1H) 6.58(d, 1H) 6.81(d, 1H) 6.84(dd, 1H) 7.18-7.22(m, 1H) 7.28-7.36(m, 5 H) 7.66(d, 1H) 8.34(dd, 1H). |
| 513 | 535 | 8.32-8.43(m, 2H), 7.67(d, 1H), 7.46-7.55(m, 3H), 7.36-7.44(m, 3H), 6.91(d, 1H), 6.80(m, 1H), 6.60-6.69(m, 1H), 6.37-6.52(m, 1H), 4.51(d, 2H), 3.98-4.06(m, 2H), 3.61(br s, 2H), 3.39(br d, 2H), 3.02(br s, 2H), 2.74-2.89(m, 2H), 1.32(m, 3H). |
| 514 | 519 | 8.31-8.43(m, 2H), 7.67(d, 1H), 7.47-7.56(m, 3H), 7.42(m, 1H), 7.10-7.22(m, 2H), 6.91(d, 1H), 6.80(m, 1H), 6.63(d, 1H), 6.37(m, 1H), 4.51(d, 2H), 4.02(m, 2H), 3.61(s, 2H), 3.37(br d, 2H), 3.02(br s, 2H), 2.72-2.90(m, 2H), 1.32(m, 3H). |
| 515 | 540 | 1.08 (bs, 2H), 1.14-1.23 (m, 2H), 2.32 (bs, 1H), 3.40-3.49 (m, 3H), 3.80 (bs, 1H), 4.12 (bs, 2H), 4.41-4.43(m, 1H), 4.64-4.74 (m, 3H), 6.54-6.66 (m, 1H), 6.92 (d, 1H), 7.41 (d, 1H), 7.55-7.68 (m, 5H), 7.78 (d, Hz, 1H), 8.27 (s, 1H), 8.53 (bs, 1H), 9.16 (bs, 1H), 11.22 (bs, 1H). |
| 516 | 527 | 1.21-1.36(m, 1H), 1.89(t, 1H), 2.09-2.18(m, 1H), 2.35-2.44(m, 1H), 2.72-2.81(m, 1H), 3.03-3.10(m, 1H), 3.17-3.25(m, 1H), 3.46-3.55(m, 2H), 4.33-4.46(m, 3H), 6.31-6.39(m, 1H), 6.55(d, 1H), 7.14(dd, 1H), 7.25(s, 1H), 7.31-7.42(m, 4 H), 7.46-7.57(m, 3H), 7.78(d, 1H), 8.34(d, 1H). |
| 517 | 563 | Peak 1: 1.22-1.37(m, 1H), 1.89(t, 1H), 2.10-2.19(m, 1H), 2.36-2.45(m, 1H), 2.72-2.80(m, 1H), 3.04-3.11(m, 1H), 3.17-3.25(m, 1H), 3.46-3.55(m, 2H), 4.34-4.47(m, 3H), 6.42-6.56(m, 2H), 7.14(dd, 1H), 7.26(s, 1H), 7.31-7.34(m, 1H), 7.40(s, 1H), 7.44-7.49(m, 1H), 7.52-7.58(m, 2H), 7.73-7.80(m, 2H), 8.34(d, 1H). |
| 517 | 563 | Peak 2: 1.22-1.37(m, 1H), 1.89(t, 1H), 2.10-2.19(m, 1H), 2.36-2.45(m, 1H), 2.72-2.80(m, 1H), 3.04-3.11(m, 1H), 3.17-3.25(m, 1H), 3.46-3.55(m, 2H), 4.34-4.47(m, 3H), 6.42-6.56(m, 2H), 7.14(dd, 1H), 7.26(s, 1H), 7.31-7.34(m, 1H), 7.40(s, 1H), 7.44-7.49(m, 1H), 7.52-7.58(m, 2H), 7.73-7.80(m, 2H), 8.34(d, 1H). |

We claim:

1. A Formula (1) compound

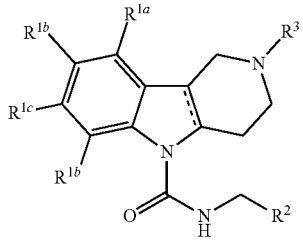

(1)

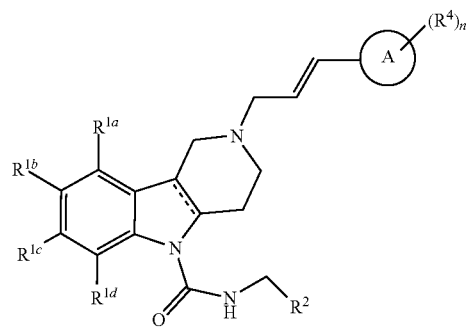

(1.1)

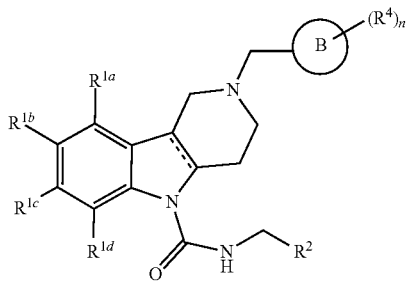

(1.2)

wherein $R^{1a}$, $R^{1b}$, $R^{1c}$, and $R^{1d}$ are each independently selected from the group consisting of hydrogen, halo, $C_1$-$C_6$alkyl, $C_2$-$C_6$alkenyl, $C_3$-$C_6$cycloalkyl, $C_1$-$C_6$alkoxy, $C_1$-$C_6$haloalkyl, $C_1$-$C_6$haloalkoxy, —C(O)NR$^a$R$^b$, cyano, —S(O)$_p$R, phenyl, pyridinyl, saturated or partially saturated 5- or 6-membered heterocyclic ring containing at least one heteroatom selected from the group consisting of N, S, and O, and wherein said heterocyclic ring, phenyl, or pyridinyl moiety are each optionally and independently substituted with at least one substituent selected from the group consisting of oxo, cyano, halo, and $C_1$-$C_6$alkyl; or $R^{1a}$ and $R^{1b}$ or $R^{1b}$ and $R^{1c}$ or $R^{1c}$ and $R^{1d}$ together form a tetrahydrofuran ring or phenyl ring;

$R^2$ is phenyl or a 5- or 6-membered heteroaryl ring containing at least one heteroatom selected from the group consisting of N, S, or O, and wherein said phenyl or heteroaryl ring is optionally and independently substituted with at least one $R^5$ substituent selected from the group consisting of halo, $C_1$-$C_6$alkyl, $C_1$-$C_6$haloalkyl, hydroxyl, $C_1$-$C_6$alkoxy, and $C_3$-$C_6$cycloalkyl;

$R^3$ is $C_1$-$C_4$alkylaryl, $C_1$-$C_4$alkylheteroaryl, $C_2$-$C_6$alkenylaryl, or $C_2$-$C_6$alkenylheteroaryl; and wherein each aryl and heteroaryl moiety is optionally and independently substituted with at least one $R^4$ substituent selected from the group consisting of halo, cyano, $C_1$-$C_6$alkoxy, $C_1$-$C_6$haloalkyl, $C_1$-$C_6$alkyl, $C_1$-$C_6$haloalkoxy, and —S(O)$_p$R; and wherein the alkenyl moiety is optionally substituted with halo;

$R^a$ and $R^b$ are each independently selected from the group consisting of H and $C_1$-$C_6$alkyl;

R is H or $C_1$-$C_6$alkyl;

p is the integer 0, 1, or 2; and wherein the solid line accompanied by the dotted line "- - - -" represents a single or double bond, and veterinary acceptable salts thereof, and stereoisomers thereof.

2. A veterinary composition comprising a Formula (1) compound of claim 1, and further comprising a veterinary acceptable carrier, and optionally, at least one additional antiparasitic agent.

3. A method for treating an animal with a parasitic infection comprising administering a therapeutically effective amount of a Formula (1) compound of claim 1 to an animal in need thereof.

4. A Formula (1.1) or Formula (1.2) compound of Formula (1) of claim 1 wherein

Ring A is phenyl, pyridinyl, or thiophene;

Ring B is naphthyl, quinolinyl, or isoquinolinyl;

each of Ring A and Ring B moieties are optionally and independently substituted with at least one $R^4$ substituent selected from halo, cyano, $C_1$-$C_6$alkyl, $C_1$-$C_6$haloalkyl, $C_1$-$C_6$alkoxy, $C_1$-$C_6$haloalkoxy, and —S(O)$_2$CH$_3$;

$R^2$ is phenyl, pyridinyl, thiazolyl, pyridazinyl, or pyrrolyl, each optionally and independently substituted with at least one $R^5$ substituent selected from the group consisting of halo, $C_1$-$C_6$alkyl, $C_1$-$C_6$haloalkyl, $C_1$-$C_6$alkoxy, hydroxyl, and cyclopropyl;

n is the integer 0, 1, 2, 3, 4, or 5, and when n is 2 or more, then each $R^4$ can be the same or different from each other; and veterinary acceptable salts thereof, and stereoisomers thereof.

5. A Formula (1.1) compound of claim 4 wherein Ring A is phenyl optionally substituted with at least one $R^4$ substituent selected from halo, cyano, $C_1$-$C_6$haloalkyl, $C_1$-$C_6$alkoxy, $C_1$-$C_6$alkyl, $C_1$-$C_6$haloalkoxy, and —S(O)$_2$CH$_3$; $R^2$ is pyridinyl or thiazolyl, each optionally and independently substituted with at least one $R^5$ substituent selected from the group consisting of halo, methyl, —CF$_3$, —OCH$_3$, —OCH$_2$CH$_3$, hydroxyl, and cyclopropyl, and veterinary acceptable salts thereof, and stereoisomers thereof.

6. A compound of claim 5 wherein $R^2$ is pyridinyl optionally substituted with at least one $R^5$ substituent selected from the group consisting of fluoro, chloro, bromo, methyl, hydroxyl, —CF$_3$, —OCH$_3$, —OCH$_2$CH$_3$, and cyclopropyl, and veterinary acceptable salts thereof, and stereoisomers thereof.

7. A Formula (1.2) compound of claim 4 wherein $R^2$ is pyridinyl optionally substituted with at least one $R^5$ substituent selected from the group consisting of fluoro, chloro, bromo, methyl, —CF$_3$, —OCH$_3$, —OCH$_2$CH$_3$, hydroxyl, and cyclopropyl, and veterinary acceptable salts thereof, and stereoisomers thereof.

8. A Formula (1.1a) compound of Formula (1.1) of claim 4

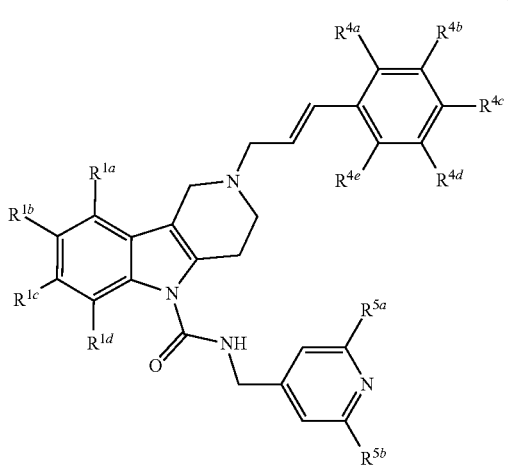
(1.1a)

wherein
$R^{1a}$, $R^{1b}$, $R^{1c}$, and $R^{1d}$, are each independently selected from the group consisting of H, chloro, fluoro, bromo, cyano, methyl, —OCH$_3$, —OCH$_2$CH$_3$, —OCF$_3$, —CF$_3$, —SCH$_3$, —S(O)$_2$CH$_3$, —C(O)NH$_2$, phenyl, pyridinyl, morpholinyl, azathienyl, and pyrrolidinyl; and wherein the phenyl and pyridinyl is optionally substituted with at least one substituent selected from halo, cyano, or oxo; or $R^{1a}$ and $R^{1b}$ or $R^{1b}$ and $R^{1c}$ or $R^{1c}$ and $R^{1d}$ together form a phenyl ring or tetrahydrofuran ring;

$R^{4a}$, $R^{4b}$, $R^{4c}$, $R^{4d}$ and $R^{4e}$ are each independently selected from the group consisting of H, fluoro, chloro, bromo, methyl, —CF$_3$, cyano, —OCF$_3$, —OCH$_3$, and —S(O)$_2$CH$_3$; and $R^{5a}$ and $R^{5b}$ are each independently selected from the group consisting of H, chloro, fluoro, bromo, —CF$_3$, methyl, hydroxyl, cyclopropyl, —OCH$_3$, and —OCH$_2$CH$_3$; and veterinary acceptable salts thereof, and stereoisomers thereof.

9. A Formula (1.1a) compound of claim 8 wherein at least two of $R^{1a}$, $R^{1b}$, $R^{1c}$, and $R^{1d}$ are H; and wherein one of $R^{5a}$ or $R^{5b}$ is hydrogen and the other is chloro, fluoro, bromo, —CF$_3$, methyl, hydroxyl, cyclopropyl, —OCH$_3$ or —OCH$_2$CH$_3$; and veterinary acceptable salts thereof, and stereoisomers thereof.

10. A Formula (1.1a) compound of claim 8 selected from the group consisting of
(E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, and veterinary acceptable salts thereof, and stereoisomers thereof.

11. A veterinary composition comprising a Formula (1.1a) compound

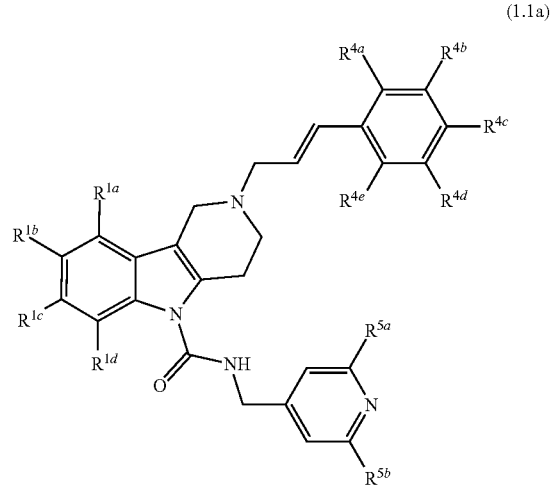
(1.1a)

wherein
$R^{1a}$, $R^{1b}$, $R^{1c}$, and $R^{1d}$, are each independently selected from the group consisting of H, chloro, fluoro, bromo, cyano, methyl, —OCH$_3$, —OCH$_2$CH$_3$, —OCF$_3$, —CF$_3$, —SCH$_3$, —S(O)$_2$CH$_3$, —C(O)NH$_2$, phenyl, pyridinyl, morpholinyl, azathienyl, and pyrrolidinyl; and wherein the phenyl and pyridinyl is optionally substituted with at least one substituent selected from halo, cyano, or oxo; or $R^{1a}$ and $R^{1b}$ or $R^{1b}$ and $R^{1c}$ or $R^{1c}$ and $R^{1d}$ together form a phenyl ring or tetrahydrofuran ring;

$R^{4a}$, $R^{4b}$, $R^{4c}$, $R^{4d}$ and $R^{4e}$ are each independently selected from the group consisting of H, fluoro, chloro, bromo, methyl, —CF$_3$, cyano, —OCF$_3$, —OCH$_3$, and —S(O)$_2$CH$_3$; and $R^{5a}$ and $R^{5b}$ are each independently selected from the group consisting of H, chloro, fluoro, bromo, —CF$_3$, methyl, hydroxyl, cyclopropyl, —OCH$_3$, and —OCH$_2$CH$_3$; and veterinary acceptable salts thereof, and stereoisomers thereof; and further comprising a veterinary acceptable carrier, and optionally, at least one additional antiparasitic agent.

12. The veterinary composition of claim 11 further comprising at least one additional antiparasitic agent selected from the group consisting of pyrantel, praziquantel, moxidectin, milbemycin, milbemycin oxime, doramectin, abamectin, ivermectin, selamectin, eprinomectin, levamisole, spinosad, emodepside, albendazole, mebendazole, derquantel, or mixtures thereof.

13. A method of treating a parasitic infection in an animal comprising administering a therapeutically effective amount of a Formula (1.1a) compound (1.1a)

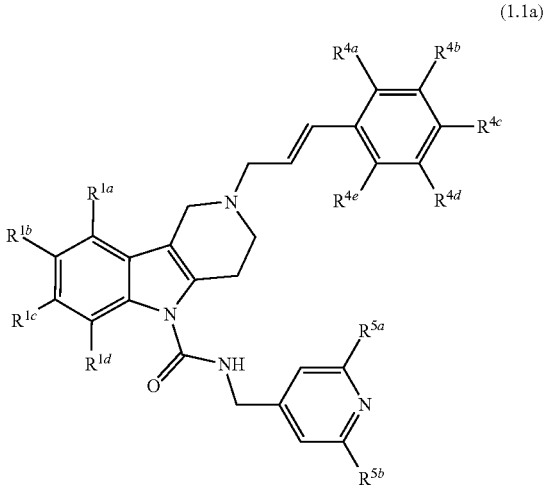

wherein
$R^{1a}$, $R^{1b}$, $R^{1c}$, and $R^{1d}$, are each independently selected from the group consisting of H, chloro, fluoro, bromo, cyano, methyl, —OCH$_3$, —OCH$_2$CH$_3$, —OCF$_3$, —CF$_3$, —SCH$_3$, —S(O)$_2$CH$_3$, —C(O)NH$_2$, phenyl, pyridinyl, morpholinyl, azathienyl, and pyrrolidinyl; and wherein the phenyl and pyridinyl is optionally substituted with at least one substituent selected from halo, cyano, or oxo;

$R^{4a}$, $R^{4b}$, $R^{4c}$, $R^{4d}$ and $R^{4e}$ are each independently selected from the group consisting of H, fluoro, chloro, bromo, methyl, —CF$_3$, cyano, —OCF$_3$, —OCH$_3$, and —S(O)$_2$CH$_3$; and $R^{5a}$ and $R^{5b}$ are each independently selected from the group consisting of H, chloro, fluoro, bromo, —CF$_3$, methyl, hydroxyl, cyclopropyl, —OCH$_3$, and —OCH$_2$CH$_3$; and veterinary acceptable salts thereof, and stereoisomers thereof.

14. The method of claim 13, wherein the animal is a companion animal and said parasitic infection is an endoparasitic infection, and wherein the Formula (1.1a) compound is administered orally, topically, or parenterally.

15. A Formula (1.1a) compound of claim 10 selected from the group consisting of
(E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide; and
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide; and veterinary acceptable salts thereof, and stereoisomers thereof.

16. A Formula (1.1a) compound of claim 15 that is (E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide, and veterinary acceptable salts thereof, and stereoisomers thereof.

17. The veterinary composition of claim 11 comprising a Formula (1.1a) compound selected from the group consisting of
(E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, and veterinary acceptable salts thereof, and stereoisomers thereof.

18. The veterinary composition of claim 17 comprising the Formula (1.1a) compound, (E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide; and veterinary acceptable salts thereof, and stereoisomers thereof.

19. The method of claim 13 comprising administering a therapeutically effective amount of a Formula (1.1a) compound selected from the group consisting of
(E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3-fluorophenyl)allyl)-N-((2-chloropyridin-4-yl)methyl)-7-cyano-1,2,3,4-tetrahydro-5H-pyrido[4,3-b]indole-5-carboxamide;
(E)-N-((2-chloropyridin-4-yl)methyl)-7-cyano-2-(3-(2,3,4-trifluorophenyl)allyl)-1,2,3,4-tetrahydro-5H-pyrido[4,3-b]indole-5-carboxamide;
(E)-2-(3-(4-chloro-2,3-difluorophenyl)allyl)-N-((2-chloropyridin-4-yl)methyl)-7-cyano-1,2,3,4-tetrahydro-5H-pyrido[4,3-b]indole-5-carboxamide;
(E)-2-(3-(4-chloro-3,5-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-N-((2-fluoropyridin-4-yl)methyl)-2-(3-(2,3,4-trifluorophenyl)allyl)-1,2,3,4-tetrahydro-5H-pyrido[4,3-b]indole-5-carboxamide
(E)-2-(3-(4-bromo-2,3-difluorophenyl)allyl)-8-cyano-N-((2-fluoropyridin-4-yl)methyl)-1,2,3,4-tetrahydro-5H-pyrido[4,3-b]indole-5-carboxamide
(E)-8-cyano-2-(3-(4-fluorophenyl)allyl)-N-((2-fluoropyridin-4-yl)methyl)-1,2,3,4-tetrahydro-5H-pyrido[4,3-b]indole-5-carboxamide, and veterinary acceptable salts thereof, and stereoisomers thereof.

20. The method of claim 19 comprising administering a therapeutically effective amount of a Formula (1.1a) compound that is (E)-2-(3-(4-chloro-3,5-difluorophenyl)allyl)-N-((2-chloropyridin-4-yl)methyl)-7-cyano-1,2,3,4-tetrahydro-5H-pyrido[4,3-b]indole-5-carboxamide; and veterinary acceptable salts thereof, and stereoisomers thereof.

* * * * *